US010065994B2

(12) United States Patent
Settembre et al.

(10) Patent No.: US 10,065,994 B2
(45) Date of Patent: Sep. 4, 2018

(54) NOROVIRUS DERIVED IMMUNOGENIC COMPOSITIONS AND METHODS

(71) Applicant: Novartis AG, Basel (CH)

(72) Inventors: Ethan Settembre, Lexington, MA (US); Angelica Medina-Selby, San Francisco, CA (US); Doris Coit, Petaluma, CA (US); Philip R. Dormitzer, Weston, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/946,324

(22) Filed: Nov. 19, 2015

(65) Prior Publication Data

US 2016/0222066 A1 Aug. 4, 2016

Related U.S. Application Data

(63) Continuation of application No. 13/808,157, filed as application No. PCT/US2011/042979 on Jul. 5, 2011, now abandoned.

(60) Provisional application No. 61/361,581, filed on Jul. 6, 2010.

(51) Int. Cl.

| | |
|---|---|
| ***A61K 39/00*** | (2006.01) |
| ***A61K 39/12*** | (2006.01) |
| ***C12N 7/00*** | (2006.01) |
| ***A61K 39/125*** | (2006.01) |
| ***C12N 15/86*** | (2006.01) |
| ***C07K 14/005*** | (2006.01) |
| ***A61K 39/295*** | (2006.01) |
| ***C07K 14/08*** | (2006.01) |

(52) U.S. Cl.

CPC ............ *C07K 14/005* (2013.01); *A61K 39/12* (2013.01); *A61K 39/295* (2013.01); *C07K 14/08* (2013.01); *C12N 7/00* (2013.01); *C07K 2319/00* (2013.01); *C12N 2770/16022* (2013.01); *C12N 2770/16023* (2013.01)

(58) Field of Classification Search

CPC ............ A61K 39/12; A61K 2039/5258; C07K 14/005; C07K 2319/00; C12N 7/00

See application file for complete search history.

(56) References Cited

U.S. PATENT DOCUMENTS

| | | | |
|---|---|---|---|
| 6,183,985 | B1 | 2/2001 | Shuster |
| 6,491,907 | B1 | 12/2002 | Rabinowitz et al. |
| 7,172,893 | B2 | 2/2007 | Rabinowitz et al. |
| 7,465,583 | B2 | 12/2008 | Samulski et al. |
| 7,527,801 | B2 | 5/2009 | Coit et al. |
| 7,790,154 | B2 | 9/2010 | Samulski et al. |
| 2005/0152911 | A1 | 7/2005 | Hardy |
| 2005/0175588 | A1 | 8/2005 | Mosca |
| 2006/0188483 | A1 | 8/2006 | Rabinowitz et al. |
| 2008/0248528 | A1 | 10/2008 | Nguyen et al. |

FOREIGN PATENT DOCUMENTS

| | | | |
|---|---|---|---|
| EP | 1290205 | B1 | 3/2006 |
| EP | 1135468 | B1 | 1/2010 |
| JP | 2006505255 | | 2/2006 |
| WO | 2004/026329 | | 4/2004 |
| WO | 2007053188 | A2 | 5/2007 |
| WO | 2007081447 | A2 | 7/2007 |
| WO | WO2007081447 | * | 7/2007 |
| WO | 2008016391 | A2 | 2/2008 |
| WO | 2008145400 | A2 | 12/2008 |
| WO | 2009/039229 | A2 | 3/2009 |
| WO | 2010/006238 | A2 | 1/2010 |
| WO | 2010017542 | A1 | 2/2010 |
| WO | 2010/033736 | A1 | 3/2010 |
| WO | 2010/053716 | A1 | 5/2010 |
| WO | 2010/060095 | A1 | 5/2010 |
| WO | 2010/062383 | A2 | 6/2010 |

OTHER PUBLICATIONS

Xia, M. et al., "Norovirus Capsid Protein Expressed in Yeast Forms Virus-like Particles and Stimulates Systemic and Mucosal Immunity in Mice Following an Oral Administration of Raw Yeast Extracts", J. Med. Virol. 79: 74-83, 2007.

Extended European Search Report dated Feb. 21, 2017, issued in EP Patent Application No. 16199523.8.

Pothier, Pierre, "Aeres Report on the Research Unit Agents Pathgenes et Inflammation", from the University of Franche-Comte, Nov. 1, 2010, Project Team 3 (Pierre Pothier): pp. 1-28.

Chen, et al,"Inter-and Instragenus Structural Variations in Calciviruses and Their Functional Implications", J. Virol. 78(12): 6469-6479 (2004).

Lobue D et al, "Multivalent Norovirus Vaccines Induce Strong Mucosal and Systemic Blocking Against Multiple Strains", Vaccine 24(24): 5220-5234 (2006).

Zvrbliene A et al, "Generation of Monoclonal Antibodies od Desired Specificity Using Chimeric Polyomavirus-Derived Virus-Like Particles", J. Immunolo. Methods 311(1-2): 57-70 (2006).

Chakravarty, Sugoto, et al., "Evolutionary Trace Residues in Noroviruses: Importance in Receptor Binding, Antigenicity, Virion Assembly, and Strain Diversity," J. Virol. 79(1): 554-568 (2005).

Donaldson, Eric F., et al., "Viral shape-shifting: norovirus evasion of the human immune system," Nature Reviews 8: 231-241 (2010).

Hansman, Grant S., et al., "Genetic and antigenic diversity among noroviruses," J. Gen. Virol. 87: 909-919 (2006).

Huang, Pengwei, et al., "Norovirus and Histo-Biood Group Antigens: Demonstration of a Wide Spectrum of Strain Specificities and Classification of Two Major Binding Groups among Multiple Binding Patterns," J. Virol., 79(11): 6714-6722 (2005).

(Continued)

*Primary Examiner* — Barry A Chestnut

(74) *Attorney, Agent, or Firm* — McDermott Will & Emery LLP

(57) ABSTRACT

The invention relates to chimeric norovirus VP1 proteins containing the S-domain of VP1 of a first norovirus strain and a P-domain that contains at least a portion of the P-domain of VP1 of a second norovirus strain. The invention also relates to nucleic acids that encode the chimeric VP1 proteins, virus-like particles that contain a chimeric norovirus VP1 protein, and to immunogenic compositions.

8 Claims, 17 Drawing Sheets

Specification includes a Sequence Listing.

(56) References Cited

OTHER PUBLICATIONS

Lindesmith, Lisa C., et al., "Heterotypic Humoral and Cellular Immune Responses following Norwalk Virus Infection," J. Virol. 84(4): 1800-1815 (2010).
Lochridge, Vance P., et al., "Epitopes in the P2 domain of norovirus VP1 recognized by monoclonal antibodies that block cell interactions," J. Gen. Virol. 86: 2799-2806 (2005).
Shiota, Tomoyuki, et al., "Characterization of a Broadly Reactive Monoclonal Antibody against Norovirus Genogroups I and II: Recognition of a Novel Conformational Epitope," J. Virol. 81(22): 12298-12306 (2007).
Tan, Ming, et al., "Mutations within the P2 Domain of Norovirus Capsid Affect Binding to Human Histo-Biood Group Antigens: Evidence for a Binding Pocket," J. Virol. 77(23): 12562-12571 (2003).
White, Laura J., et. al., "Attachment and Entry of Recombinant Norwalk Virus Capsids to Cultured Human and Animal Cell Lines," J. Virol. 70(10): 6589-6597 (1996).

* cited by examiner

```
norw    MMMASKDATSSVDGASGAGQLVPEVNASDPLAMDPVAGSSTAVATAGQVNPIDPWIINNF 60
snow    MKMASNDAAPSTDGAAG---LVPESNN-EVMALEPVAGAALAAPVTGQTNIIDPWIRANF 56
g2.4    MKMASSDANPSDGSTAN---LVPEVNN-EVMALEPVVGAAIAAPVAGQQNVIDPWIRNNF 56
        * ***.** .* ..:.:.  **** *   : :*.:**.*:: *...:** * *****  **

norw    VQAPQGEFTISPNNTPGDVLFDLSLGPHLNPFLLHLSQMYNGWVGNMRVRIMLAGNAFTA 120
snow    VQAPNGEFTVSPRNAPGEVLLNLELGPELNPYLAHLARMYNGYAGGMEVQVMLAGNAFTA 116
g2.4    VQAPGGEFTVSPRNAPGEILWSAPLGPDLNPYLSHLARMYNGYAGGFEVQVILAGNAFTA 116
        **** ****:**.*:**::* .   ***.***:* **::****:.*.:.*:::********

norw    GKIIVSCIPPGFGSHNLTIAQATLFPHVIADVRTLDPIEVPLEDVRNVLFHNNDRNQQTM 180
snow    GKLVFAAVPPHFPVENLSPQQITMFPHVIIDVRTLEPVLLPLPDVRNNFFHYNQKDDPKM 176
g2.4    GKIVFAAVPPNFPTEGLSPSQVTMFPHIIVDVRQLEPVLIPLPDVRNNFYHYNQSNDPTI 176
        **:::.:.:** *   ..*:  * *:***:* *** *:*: :** **** ::* *: :: .:

norw    RLVCMLYTPLRTGGGTGDSFVVAGRVMTCPSPDFNFLFLVPPTVEQKTRPFTLPNLPLSS 240
snow    RIVAMLYTPLRSNGSGDDVFTVSCRVLTRPSPDFDFTYLVPPTVESKTKPFTLPILTLGE 236
g2.4    KLIAMLYTPLRANNAGEDVFTVSCRVLTRPSPDFDFIFLVPPTVESRTKPFSVPILTVEE 236
        :::.*******:...  * *.*: **:* *****:* :*******.:*:**::* *.: .

norw    LSNSRAPLPISSMGISPDNVQSVQFQNGRCTLDGRLVGTTPVSLSHVAKIRGTSNGTV-- 298
snow    LSNSRFPVSIDQMYTSPNEVISVQCQNGRCTLDGELQGTTQLQVSGICAFKGEVTAHLQD 296
g2.4    MTNSRFPIPLEKLFTGPSSTIVVQPQNGRCTTDGVLLGTTQLSPVNICTFRGDVTHIAGT 296
        ::*** *:.:..:  .*...  ** ****** ** * *** :.   :. ::*  .

norw    ------INLTELDGTPFHPFEG-PAPIGFPDLGG-CDWHINMTQFGHSS---------QTQ 342
snow    NDHLYNITITNLNGSPFDPSEDIPAPLGVPDFQGRVFGVITQRDKQNAAGQSQPANRGHD 356
g2.4    QEYTMNLASQNWNN--YDPTEEIPAPLGTPDFVGKIQGVLTQTTRRDGS------TRGHK 348
              :   : :.  :.* *  ***:* **: *       :.      ..:        .

norw    YDVDTTPDTFVPHLGSIQANGIGSGNY-VGVLSWISPPSHP---SGSQVD---LWKIPNY 395
snow    AVVPTYTAQYTPKLGQVQIGTWQTDDLKVNQPVKFTPVGLN---DTEHFN---QWVVPRY 410
g2.4    ATVSTGSVNFTPKLGRIQFSTDTSNDFETGQSTRFTPVGVVQDGSTTHQNEPQQWVLPDY 408
          * *  .   :.*:** :*  .    :.:   ..    ::* .      .  : :     * :* *

norw    GSSITEATHLAPSVYPPGFGEVLVFFMSKMPGPGAY---NLPCLLPQEYISHLASEQAPT 452
snow    AGALNLNTNLAPSVAPVFPGERLLFFRSYLPLKGGYGNPAIDCLLPQEWVQHFYQEAAPS 470
g2.4    SGRDSHNVHLAPAVAPSFPGEQLLFFRSTMPGCSGYPNMNLDCLLPQEWVQHFYQEAAPA 468
        ..  .  .:***:* *   ** *:** * :*  ..*     : ******::.*: .* **:

norw    VGEAALLHYVDPDTGRNLGEFKAYPDGFLTCVPNGASSGPQQLPINGVFVFVSWVSRFYQ 512
snow    MSEVALVRYINPDTGRALFEAKLHRAGFMTVSSN--TSAPVVVPANGYFRFDSWVNQFYS 528
g2.4    QSDVALLRFVNPDTGRVLFECKLHKSGYVTVAHT--GQHDLVIPPNGYFRSDSWVNQFYT 526
         .:.**::::::***** * * * :  *::*   .   .    :* ** *   ***.:**

norw    LKPVGTASSARGRLGLRR 530
snow    LAPMGTGNGRRRIQ---- 542
g2.4    LAPMGNGTGRRRAL---- 540
        * *:*....  *
```

FIG. 3

Snow Mountain virus ORF2 cDNA encoding VP1 protein
Nucleotide residues 1..1629 corresponding to
GENE BANK ACCESSION No. AY134748 (REGION: 5085..6713)

```
   1 atgaagatgg cgtcgaatga cgccgctcca tctactgatg gtgcagccgg cctcgtgcca
  61 gaaagtaata atgaggtcat ggctcttgag cccgtggctg gtgctgcctt ggcagccccg
 121 gtcaccggtc aaacaaatat tatagaccct tggattagag caaattttgt ccaggcccct
 181 aatggtgaat ttacagtttc tccccgtaat gcccctggtg aagtgctatt aaatctagaa
 241 ttgggtccag aattaaatcc ttatctggca catttagcaa gaatgtacaa cgggtatgcc
 301 ggtgggatgg aggtgcaggt catgctagct gggaacgcgt tcacagctgg caaattggtc
 361 ttcgctgctg taccacctca tttcccggtt gaaaacctta gtccacagca aattaccatg
 421 ttccctcatg tgattataga tgttaggact ttggaacctg ttttattgcc actccccgat
 481 gttagaaata atttcttcca ttataatcaa aaagatgatc ctaagatgag aattgtggct
 541 atgctttata ctcccctcag gtccaatggt tctggtgatg atgtgttcac agtctcttgc
 601 agggtgttga ctagaccctc ccctgatttt gattttacat acctggtacc accaacagtg
 661 gaatccaaaa caaaaccatt caccttcca attcttacac ttggggagct ttccaattct
 721 agatttccag tgtccataga tcagatgtac actagcccca atgaagtcat atctgtgcag
 781 tgccagaatg gaaggtgcac actggatggg gagctccaag gaacaacaca gctccaagtt
 841 agtggcattt gtgcattcaa aggagaagtg accgctcact tgcaggacaa tgatcaccta
 901 tacaacatca ccatcacaaa cttgaatggg tccccttttg atccctctga ggacatcccc
 961 gcccccctgg gtgtgcccga ctttcaggga agagtctttg gtgtcatcac tcaaagagac
1021 aaacagaatg ccgctgggca aagccagccg gcaaacaggg gacacgatgc tgtggtcccc
1081 acttacacag cccagtatac cccaaaattg ggtcaggttc aaattggcac atggcagacc
1141 gacgatctta aagtcaacca accagtcaaa ttcaccccag tcggtctcaa tgacacagaa
1201 catttcaatc agtgggtggt ccctaggtac gctggtgctt taaatctaaa cacaaatctt
1261 gcccctctg ttgctccagt gtttccaggg gagcgtctgc tcttctttag atcatacctc
1321 ccccttaagg gtggttatgg aaacccagct attgattgcc tgctaccaca agagtgggtg
1381 cagcattttt atcaggaagc agccccctca atgagtgagg tagcccttgt cagatacatc
1441 aatccggaca ctggccgggc gctgtttgag gccaaactcc acagagctgg tttcatgaca
1501 gtctcgagta acaccagtgc tccggtggtt gtgcctgcca acggatactt cagatttgac
1561 tcttgggtga accaatttta ttctcttgcc cccatgggaa ctggaaatgg gcgtagaagg
1621 attcagtga
```

FIG. 4A

Snow Mountain virus, major capsid protein; VP1
Amino acid residues 1..542
PROTEIN ACCESSION No. AAN08112

```
              1 MKMASNDAAP STDGAAGLVP ESNNEVMALE PVAGAALAAP VTGQTNIIDP WIRA
NFVQAP
     61 NGEFTVSPRN APGEVLLNLE LGPELNPYLA HLARMYNGYA GGMEVQVMLA GNAFTAGKLV
    121 FAAVPPHFPV ENLSPQQITM FPHVIIDVRT LEPVLLPLPD VRNNFFHYNQ KDDPKMRIVA
    181 MLYTPLRSNG SGDDVFTVSC RVLTRPSPDF DFTYLVPPTV ESKTKPFTLP ILTLGELSNS
    241 RFPVSIDQMY TSPNEVISVQ CQNGRCTLDG ELQGTTQLQV SGICAFKGEV TAHLQDNDHL
    301 YNITITNLNG SPFDPSEDIP APLGVPDFQG RVFGVITQRD KQNAAGQSQP ANRGHDAVVP
    361 TYTAQYTPKL GQVQIGTWQT DDLKVNQPVK FTPVGLNDTE HFNQWVVPRY AGALNLNTNL
    421 APSVAPVFPG ERLLFFRSYL PLKGGYGNPA IDCLLPQEWV QHFYQEAAPS MSEVALVRYI
    481 NPDTGRALFE AKLHRAGFMT VSSNTSAPVV VPANGYFRFD SWVNQFYSLA PMGTGNGRRR
    541 IQ
```

FIG. 4B

Chimera

SMV.S.NV.OPTI.P

AAGCTTACAAAACAAAATGAAGATGGCGTCGAATGACGCCGCTCCATCTACTGATGGTGC
AGCTGGTCTCGTGCCAGAAACTAATAATGAGGTCATGGCTCTTGAGCCCGTGGCTGGTGC
TGCCTTGGCAGCCCCGGTCACCGGTCAAACAAATATTATAGACCCTTGGATTAGAGCAAA
TTTTGTCCAGGCCCCTAATGGTGAATTTACAGTTTCTCCCCGTAATGCCCCTGGTGAAGT
GCTATTAAATCTAGAATTGGGTCCAGAATTAAATCCTTATCTGGCACATTTAGCAAGAAT
GTACAACGGGTATGCCGGTGGATGGAGGTGCAGGTCATGTTAGCTGGGAACGCGTTCAC
AGCTGGCAAATTGGTCTTCGCTGCTGTACCACCTCATTTCCCGGTTGAAAACCTTAGTCC
ACAGCAAATTACCATGTTCCCTCATGTGATTATAGATGTTAGGACTTTGGAACCTGTTTT
ATTGCCACTCCCCGATGTTAGAAATAATTTCTTCCATTATAATCAAAAAGATGATCCTAA
GATGAGAATTGTGGCTATGCATTATACTCCCCTCAGGTCCAATGGTTCTGGTGATGATGT
GTTCACAGTCTCTTGCAGGGTGTTGACTAGACCCTCCCCTGATTTTGATTTTACATACCT
GGTACCACCAACAGTGGAATCCAAAACAAAACCATTTACTTTGCCAAATTTACCTTTGTC
ATCTTTATCTAATTCTAGAGCACCCTTGCCAATTTCTTCTATGGGTATTTCTCCTGATAA
TGTTCAATCTGTTCAATTTCAAAACGGTAGATGTACTTTAGATGGTAGATTGGTTGGTAC
TACTCCCGTTTCTTTATCTCATGTTGCTAAAATTAGAGGTACTTCTAACGGTACTGTTAT
TAACTTGACTGAATTAGATGGTACTCCATTTCATCCTTTTGAAGGTCCCGCTCCAATTGG
TTTTCCTGATTTGGGTGGTTGTGATTGGCATATTAACATGACTCAATTCGGTCATTCTTC
TCAAACTCAATACGATGTTGATACTACACCCGATACTTTTGTTCCACATTTAGGTTCTAT
TCAAGCTAATGGTATTGGTTCTGGTAATTATGTTGGTGTTTTGTCTTGGATTTCTCCTCC
CTCTCATCCATCTGGTTCTCAAGTTGATTTATGGAAAATTCCTAATTACGGTTCTTCTAT
TACTGAAGCTACTCATTTGGCTCCCTCTGTTTATCCACCTGGTTTCGGTGAAGTTTTAGT
TTTTTTCATGTCTAAAATGCCAGGTCCCGGTGCTTACAATTTGCCATGTTTATTGCCTCA
AGAATACATTTCTCATTTAGCTTCAGAACAAGCTCCCACTGTTGGTGAAGCTGCTTTGTT
ACATTATGTTGATCCAGATACTGGTAGAAATTTGGGTGAATTTAAAGCTTATCCTGATGG
TTTTTTAACTTGTGTTCCCAATGGTGCTTCTTCTGGTCCACAACAATTGCCTATTAATGG
TGTTTTTGTTTTCGTTTCTTGGGTTTCTAGATTTTACCAATTAAAACCCGTTGGTACTGC
TTCTTCTGCTAGAGGTAGATTGGGTTTGAGAAGATAATGAGTCGAC

*FIG. 5*

Chimera

SMV.S.GII.4.2006a.P

AAGCTTACAAAACAAAATGAAGATGGCGTCGAATGACGCCGCTCCATCTACTGATGGTGC
AGCTGGTCTCGTGCCAGAAAGTAATAATGAGGTCATGGCTCTTGAGCCCGTGGCTGGTGC
TGCCTTGGCAGCCCCGGTCACCGGTCAAACAAATATTATAGACCCTTGGATTAGAGCAAA
TTTTGTCCAGGCCCCTAATGGTGAATTTACAGTTTCTCCCCGTAATGCCCCTGGTGAAGT
GCTATTAAATCTAGAATTGGGTCCAGAATTAAATCCTTATCTGGCACATTTAGCAAGAAT
GTACAACGGGTATGCCGGTGGGATGGAGGTGCAGGTCATGTTAGCTGGGAACGCGTTCAC
AGCTGGCAAATTGGTCTTCGCTGCTGTACCACCTCATTTCCCGGTTGAAAACCTTAGTCC
ACAGCAAATTACCATGTTCCCTCATGTGATTATAGATGTTAGGACTTTGGAACCTGTTTT
ATTGCCACTCCCCGATGTTAGAAATAATTTCTTCCATTATAATCAAAAAGATGATCCTAA
GATGAGAATTGTGGCTATGCATTATACTCCCCTCAGGTCCAATGGTTCTGGTGATGATGT
GTTCACAGTCTCTTGCAGGGTGTTGACTAGACCCTCCCCTGATTTTGATTTTACATACCT
GGTACCACCAACAGTGGAATCCAAAACAAAACCCTTTTCTGTTCCAATTTTAACTGTTGA
AGAAATGACTAATTCTAGATTCCCTATTCCCTTGGAAAAATTGTTTACTGGTCCATCTTC
TACTATTGTTGTTCAACCTCAAAATGGTAGATGTACTACTGATGGTGTTTTGTTAGGTAC
TACTCAATTGTCTCCCGTTAACATTTGTACTTTCAGAGGTGATGTTACTCATATTGCTGG
TACTCAAGAATATACTATGAACTTAGCTTCTCAAAATTGGAACAATTACGATCCAACTGA
AGAAATTCCTGCTCCCTTAGGTACACCAGATTTTGTTGGTAAAATTCAAGGTGTTTTGAC
TCAAACTACTAGAAGAGATGGTTCTACAAGAGGTCATAAAGCTACTGTTTCTACTGGTTC
TGTTAATTTCACTCCTAAGTTGGGTAGAATTCAATTTTCTACTGATACTTCTAACGATTT
TGAAACTGGTCAATCTACTAGATTTACTCCCGTTGGTGTTGTTCAAGATGGTTCAACTAC
TCATCAAAATGAACCACAACAATGGGTTTTACCTGATTATTCTGGTAGAGATTCTCATAA
TGTTCATTTGGCTCCCGCTGTTGCTCCATCTTTTCCAGGTGAACAATTATTGTTTTTCAG
ATCTACTATGCCCGGTTGTTCTGGTTATCCAAATATGAACTTAGATTGTTTGTTACCTCA
AGAATGGGTTCAACATTTTTATCAAGAAGCTGCTCCCGCTCAATCTGATGTTGCTTTGTT
AAGATTTGTTAATCCAGATACTGGTAGAGTTTTGTTCGAATGTAAATTACATAAATCTGG
TTATGTTACTGTTGCTCATACTGGTCAACATGATTTGGTTATTCCTCCCAATGGTTACTT
TAGATCTGATTCTTGGGTTAATCAATTTTACACTTTAGCTCCAATGGGTAATGGTACTGG
TAGAAGAAGAGCTTTGTAATGAGTCGAC

FIG. 6

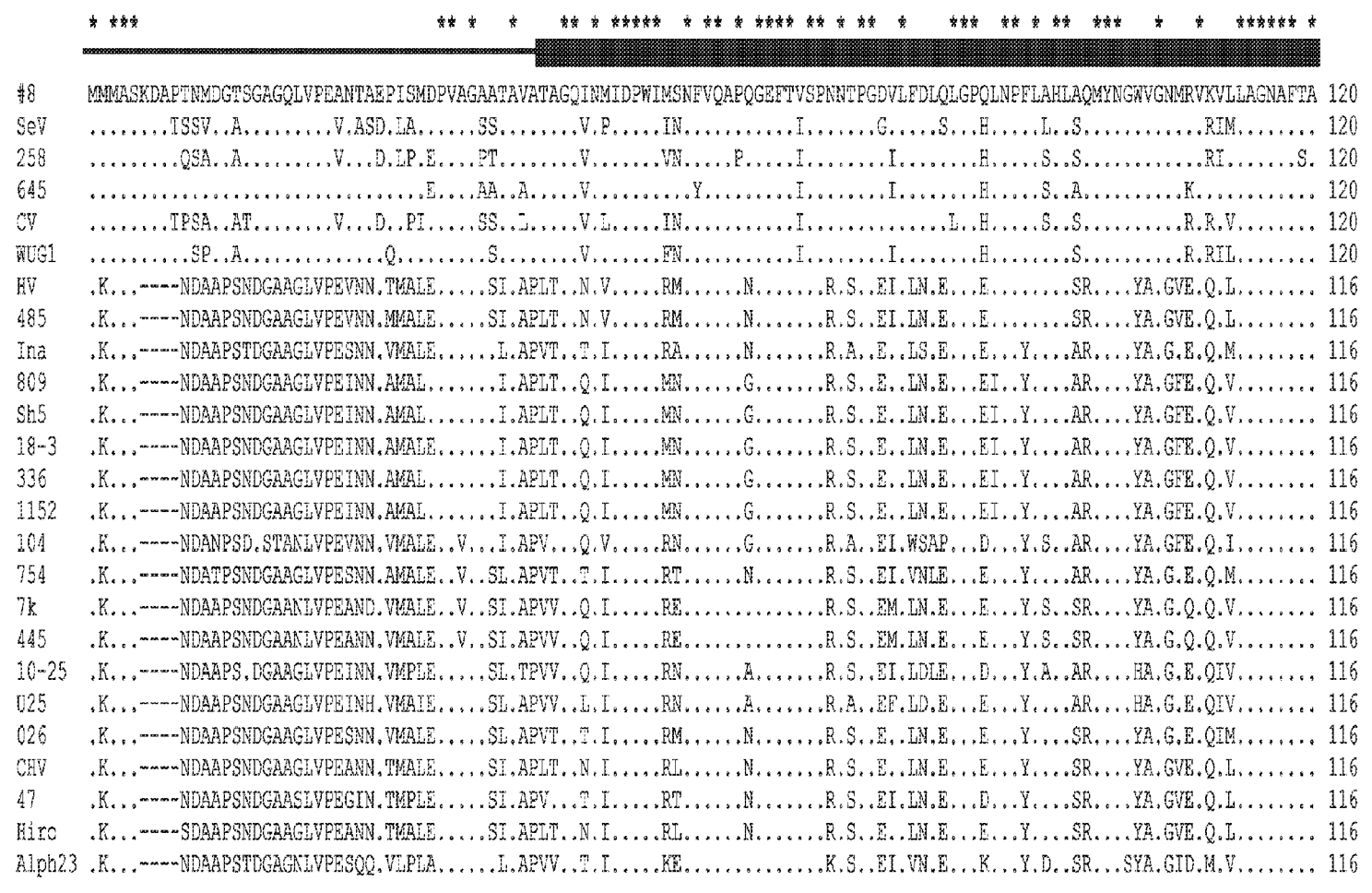

```
        * ***                                     ** *   *   ** * *****  * ** * **** ** * **  *    ***  ** * **  ***   *   *   ****** *
#8     MMMASKDAPTNMDGTSGAGQLVPEANTAEPISMDPVAGAATAVATAGQINMIDPWIMSNFVQAPQGEFTVSPNNTPGDVLFDLQLGPQLNPFLAHLAQMYNGWVGNMRVKVLLAGNAFTA 120
SeV    .......TSSV..A........V.ASD.LA.....SS.......V.P....IN..........I......G.....S...H.....L..S...........RIM....... 120
258    ........QSA..A........V...D.LP.E....PT.......V......VN....P....I.......I.......H.....S..S...........RI......S. 120
645    ..............................E....AA..A.....V.........Y........I.......I.......H.....S..A.........K........... 120
CV     .......TPSA..AT.......V...D..PI....SS..L.....V.L....IN..........I.............L..H.....S..S.........R.R.V....... 120
WUG1   .........SP..A.............Q........S.......V......FN..........I.......I.......H.......S.........R.RIL....... 120
HV     .K...----NDAAPSNDGAAGLVPEVNN.TMALE.....SI.APLT..N.V.....RM......N.......R.S..EI.LN.E...E........SR....YA.GVE.Q.L........ 116
485    .K...----NDAAPSNDGAAGLVPEVNN.MMALE.....SI.APLT..N.V.....RM......N.......R.S..EI.LN.E...E........SR....YA.GVE.Q.L........ 116
Ina    .K...----NDAAPSTDGAAGLVPESNN.VMALE......L.APVT..T.I.....RA......N.......R.A..E..LS.E...E...Y....AR....YA.G.E.Q.M........ 116
809    .K...----NDAAPSNDGAAGLVPEINN.AMAL.......I.APLT..Q.I.....MN......G.......R.S..E..LN.E...EI..Y....AR....YA.GFE.Q.V........ 116
Sh5    .K...----NDAAPSNDGAAGLVPEINN.AMAL.......I.APLT..Q.I.....MN......G.......R.S..E..LN.E...EI..Y....AR....YA.GFE.Q.V........ 116
18-3   .K...----NDAAPSNDGAAGLVPEINN.AMALE......I.APLT..Q.I.....MN......G.......R.S..E..LN.E...EI..Y....AR....YA.GFE.Q.V........ 116
336    .K...----NDAAPSNDGAAGLVPEINN.AMAL.......I.APLT..Q.I.....MN......G.......R.S..E..LN.E...EI..Y....AR....YA.GFE.Q.V........ 116
1152   .K...----NDAAPSNDGAAGLVPEINN.AMAL.......I.APLT..Q.I.....MN......G.......R.S..E..LN.E...EI..Y....AR....YA.GFE.Q.V........ 116
104    .K...----NDANPSD.STAKLVPEVNN.VMALE..V...I.APV...Q.V.....RN......G.......R.A..EI.WSAP...D...Y.S..AR....YA.GFE.Q.I........ 116
754    .K...----NDATPSNDGAAGLVPESNN.AMALE..V..SL.APVT..T.I.....RT......N.......R.S..EI.VNLE...E...Y....AR....YA.G.E.Q.M........ 116
7k     .K...----NDAAPSNDGAAKLVPEAND.VMALE..V..SI.APVV..Q.I.....RE..............R.S..EM.LN.E...E...Y.S..SR....YA.G.Q.Q.V........ 116
445    .K...----NDAAPSNDGAAKLVPEANN.VMALE..V..SI.APVV..Q.I.....RE..............R.S..EM.LN.E...E...Y.S..SR....YA.G.Q.Q.V........ 116
10-25  .K...----NDAAPS.DGAAGLVPEINN.VMPLE.....SL.TPVV..Q.I.....RN......A.......R.S..EI.LDLE...D...Y.A..AR....HA.G.E.QIV........ 116
U25    .K...----NDAAPSNDGAAGLVPEINH.VMAIE.....SL.APVV..L.I.....RN......A.......R.A..EF.LD.E...E...Y....AR....HA.G.E.QIV........ 116
026    .K...----NDAAPSNDGAAGLVPESNN.VMALE.....SL.APVT..T.I.....RM......N.......R.S..E..LN.E...E...Y....SR....YA.G.E.QIM........ 116
CHV    .K...----NDAAPSNDGAAGLVPEANN.TMALE.....SI.APLT..N.I.....RL......N.......R.S..E..LN.E...E...Y....SR....YA.GVE.Q.L........ 116
47     .K...----NDAAPSNDGAASLVPEGIN.TMPLE.....SI.APV...T.I.....RT......N.......R.S..EI.LN.E...D...Y....SR....YA.GVE.Q.L........ 116
Hirc   .K...----SDAAPSNDGAAGLVPEANN.TMALE.....SI.APLT..N.I.....RL......N.......R.S..E..LN.E...E...Y....SR....YA.GVE.Q.L........ 116
Alph23 .K...----NDAAPSTDGAGKLVPESQQ.VLPLA......L.APVV..T.I.....KE..............K.S..EI.VN.E...K...Y.D..SR...SYA.GID.M.V........ 116
```

FIG. 8A

```
         XXXXXXXXXXXXXXXXXXXXXXXXXXXXXXXXXXXXXXXXXXX
#8       FAPHLGTIHYTTDDYSPNTSIICTLDMLSQTTGQNN-VDFWQIPTYGSTITEAAQLAPPIFPGFGETLVFFLSDFPISNGNG..SVPCTLPQEFVTHPVNEQAPIRGEAALLHYVDP  447
SeV      IQANGIGSGNVIGVLSWVSPP.HPSGSQVDLWKIPNYGSSITEATHLAP.VYPPGFGEVLVF.MSKIPGFGAYS.PCLLPQEYISH.AS----------....TV............  333
258      .V....S.QFDEVFNHPTGDVIGTIEWISQPS.PPGTDINLWEIPDYGS.LSQA.NLAP.VFP.GFGEALVY.VSAFPGPN.RSAPND...L.....YI....S.....TM.D....  469
645      .A......QADGLSDVSVNTNM.AKLGWVSPVSD.HRGD....V..R........V....AI..M.....AH.T......I..................T..............L.  333
CV       .V...SS.TLDENVSSG-GDYIGTIQWTSPPSDS.GA.TNFWKIPDYGS.LAEASQLAPAVYP.GFNEVIVY.MA.IPGPNQSGSPNL....L.....YI.....IS.....Q.....  470
WUG1     ----FVPYLGSISPHNGGDTHAGDIIGSLGWISAPSD.TQLNVWTIPKYGSSLQMSLITHLLCS.RLW.VILY.Y.T..G.GQPSQ.Q...L.....I....C........A......  465
HV       ATWSPKFTP-------------KLGSVI.GTWEESDLDL.QPTRFTPVGLEN.DHFDQWAL.SYSGRLTLNMNLAPSVSPLFPGFGQLLFFRSHIPLKGGTSDGAIDCLLPQEWIQHFYQESA  460
485      ATWSPKFTP-------------KLGSVV.GTWEDRDFDI.QPTRFTPVGLYD.DHFNQWAL.NYSGALILNMNLAPSVAPLFPGEQLLFFRSHIPLKGGTSNGAIDCLLPQEWVQHFYQESA  461
Ina      RGHDAVPTK----Y.AQYTPKLGQVIGTWQIDDL.V.QPVKFTPVGLND.EHFNQWHV.RYAGALNLN.NLAPSVAPVFPGERLLFFRSIVPLKGGVGNPAIDCLLPQEWVQHFYQEAA   468
809      STTRAEEAKVD.AGRFT.KLGSLEISTDSDFDDQNQPTKFTPVGIGVDNEARFQQWSL.DYSGQFTHNMNLAPSVAPVAPNFPGEQLLFFRSQLPSSGGRSNGVLDCLVPQEWVQHFYQESA  474
Sh5      STTRAEEAKVD.AGRFT.KLGSLEISTES.DFDQNCPTKFTPVGIGVDNEARFQQ#SL.DYSGQFTHNMNLAPSVAPVAPNFPGEQLLFFRSQLPSSGGRSNGVLDCLVPQEWVQHFYQESA  474
18-3     STTRAEEAKVD.SGRFT.KLGSLEITTESDDFDTNQSTKFTPVGIGVDNEARFQQWSL.NYSGQFTHNMNLAPSVAPVAPNFPGEQLLFFRSQLPSSGGRSNGVLDCLVPQEWVQHFYQESA  474
336      GTTRAETAKVD.SGRFT.KLGSLEITTESDDFDMQNKPTRFTPVGIGVDNEADFQQWII.DYSGQFTHNMNLAPSVAPVAPNFPGEQLLFFRSQLPSSGGRSNGIILDCLVPQEWVQHFYQESA  474
1152     STTRAEEAKVD.SGRFT.KLGSLEISIESDDFDDQNCPTRFTPVGIGVDNEAGFQQWSL.DYSGQFTHNMNLAPSVAPVAPNFPGEQLLFFRSQLPSSGGRSNGIILDCLVPQEWVQHFYQESA  474
104      SVHFTPKLGSVQYT..TNNDFQTGQNTKETPVGVI.EGMNHQNEPQQWVLPNYSGRTGHNVHLA.AVAPT.PGEQLL.FR.TMPGCSGY.NMNLDCLLPQEWVQHFQCEAAP.QSDVALL  474
754      AVVRIYSDK-----Y..PKLG-.LVQIGTWNTNDVEN.PTKFT.IGLNEVANGRFEQWTL.RYSGALILNMNLAPAVAPLFPGERLLFFRSIVPLKGGFGNPAIDCSVFPQEWVQHFYQ.  467
7k       QQBQQGEYATRAHEAHIDTTDEKYAPK.GTILIKS..SDDFNTNQP.RFTPVGMCDNNWRQMELPDYSGRL..NMNLAPAVSPSFPGERILFFRSIVPBAGGYGSGY.DCLIPQEWVQHFYQ  456
445      PQEQGEYATRAHEAHIDTTDEKYAPK.GTILIKSES.DFITNQP.RFTPVGMCDNNWRQMELPDYSGRL..NMNLAPAVSPSFPGERILFFRSIVPBAGGYGSGY.DCLIPQEWQCHFYQ  456
10-25    IINTG.DHLCPQISSEIYL..PNILRCTNP.PLP.SGLRGTIL.RSDNGHCHDMVGTS.TTPTWPQQWRCSRG.NCCS.GHRYPVP.VMNRVTWI.LSHKSGETSTRKLPQ.NLRW.    474
U25      NTNDPTFAP-------------QIAQVRFKSPSNDFFDNEPIKFTPVGISVD.QNSYNQW.L.RYGGHLTNN.HLAPSVSPMFPGEQILFFRSTMPGASGH.DGAIDCLLPQEWV.HFYQEAA  462
026      NRA.EAV.ATYSPKFTPKLGNIQFS.WETQDVSS..PTKFT.VGLASVDANSHFDQWTL.SYSGALTLNMNLAPSVAPVFPGBCLLFFRSFIPLKGGYGNPAIDCLMPQEWVQH.YQESA  473
CHV      ATNSAKFTP---------------KLGAIQIGWEEDDVHL.QPTKFTPVGLFENEGFNQWTL.NYSGALINMGLAPGSLALMTNLAPAVAPT..GEQLLFFRSRVPCVQGLQGQDAFIDCLLPQEWGQH.YQESA  460
47       GIYIST.SG-----KFTPKIGSIGLHSITEHVHPNQ.SRFTPVGVAVDENTFFQQWVLPHYAGSLALMTNLAPAVAPT..GEQLLFFRSRVPCVQGLQGQDAFIDCLLPQEWGQH.YQESA  467
Hiro     ATNSAKFTP---------------KLGAIQIGWEEDDVHL.QPTKFTPVGLFEDGGFNQWTL.NYSGALTNMGLAPPVAPTFPGEQILFFRSHIPLKGG.ADP.IDCLLPQEWIQH.YQESA  460
Alph23   Y.NEAYVNTTASDYAPATG.MRFTVRNGTGHISANKYWEFKSEGVEGEGEHINIQY.EVELPDYS.QVASNENLAPPVAPRMPGES.LLFQSSMPVWEDGHGESTPKKIHCLLPQEFIGH  473
```

*FIG. 8D*

```
#8      DTHRNLGEFKLYPEGFMTCVPNTSGGGPQTLPINGVFVFVSWVSRFYQLKPVGTAGAARRLGLRRS----------------- 543
SeV     ..G.T.....A..D..L.....GASS...Q.........................SS..GRLGL.R----------------- 530
258     ..N..........G.YL.....GV.A...Q..L......................ST..SRLGV.RI---------------- 546
645     ......................S..T..............................P.C------------------------ 540
CV      ..N..........G.YL.....S.ST...Q..LD......................P..GRLGV.R----------------- 544
WUG1    ..G..........D.FM.....SVSS.............................S.....L..I------------------ 539
HV      PSPTDVALIRYTNPDTGRVLFEAKLHRQGFITVANSGSRPIV.PPNGYFRFDSWVNQFYS.APMGTGNGRRRVQ--------- 535
485     PSSTDVALIRYTNPDTGRVLFEAKLHRQGFITVANSGSRPIV.PPNGYFRFDSWVNQFYS.APMGTGNGRRRVQ--------- 535
Ina     PSMSEVALVRYINPDTGRALFEAKLHRAGFVTVSSNTSAPVV.PANGYFRFDSWVNQFYS.APMGAGNGRRRVQ--------- 542
809     PAQTQVALVRYVNPDTGKVLFEAKLHKLGFMT.ANNGDSPIT.PPNGYFRFESWVNPFYT.APMGTGNGRRRIQ--------- 548
Sh5     PAQTQVALVRYVNPDTGRVLFGAKLHKLGFMT.AKNGDSPIT.PPNGYFRFESWVNPFYT.APMGTGNGRRRIQ--------- 548
18-3    PAQTQVALVKYVNPDTGRVLFEAKLHKLGFMT.AKNGDSPIT.PPNGYFRFESWVNPFYT.APMGTGNGRRRIQ--------- 548
336     PAQTQVALVRYVNPDTGRVLFEAKLHKMGFMT.AKNGDSPIT.PPNGYFRFESWVNPFYT.APMGTGKGRRRIQ--------- 548
1152    PAQTQVALVRYVNPDTGRVLFEAKLHKLGFMT.SKNGDSPIT.PPNGYFRFESWVNPFYT.APMGTGNGRRRIQ--------- 548
104     RFVNPDTGRV.FECKLHKSGYV.VAHTGPHDLVIPPNGYFRFD.WVN.FYTLAPM.NGAGRRRAL------------------ 539
754     PSLGDVALVRYVNPDTGRVLFEAKLHKGGF.TVSSTSTGPVV.PANGYF.FDSWVNQFYS.APMGTGNGRRVQGIRRS----- 545
7k      EAAPSQSAVA.VRYVNPDTGR.IFEAKLHREGFLT.ANCGNNPIVVPPNGYFRFEAWGNQFYTLAPMGSGQGRRRAQ------ 550
445     EAAPSQSAVA.VRYVNPDTGR.IFEAKLHREGFLT.ANSGNNPIVVPPNGYFRFEAWVNQFYTLAPMGSGQGRRRA------- 550
10-25   LIRFINPDTGRVLFEARLHKQGFITVAHTGDNPIVMPPNGYFRFEAWVNQFYSL.PVGTGKG.R..VQ--------------- 541
U25     TAQTDVALIRFVNPDTGRVLFEGKLHKQGFIT.SNSGDHPIVMPANGYFRFEAWVNQFYS.APVGTGSGRRRIQ--------- 537
026     PSLSDVALVRYVNPETGRTLFEAKLHRNGF.TVARNSAGPVVAPTNGYFRFDSWVNQFYT.APMGNGSGRRRMQ--------- 548
CHV     PSQSDVALIRFTNPDTGRVLFEAKLHRSGYITVANTGSRPIVVPANGYFRFDTWVNQFYS.APMGTGNGRRRVQ--------- 535
47      PSQADVALIRYVNPDTGRTLFEAKLHRSGFITVSHTGAYPLVVPPNGHFRFDSWVNQFYS.APMGTGNGRRRIQ--------- 542
Hiro    PSQSDVALIRFTNPDTGRVLFEAKLHRSGYITVANTGSRPIVVPANGYFRFDSWVNQFYS.APMGTGNGRRRVQ--------- 535
Alph23  FFDKQAPSLGDAALLRYVNQETNRVLFECK.YRD.YIITVAASSGLLDFPLDGFFRFDSWVSSFYILSPVGSGQGRRGRVRFQ 556
```

FIG. 8E

| Partitions | Evolutionary class Total | ID | Sequence clusters in class | Antigenic norovirus strains in class | Class-specific residues and insertions that occur in the different evolutionary classes corresponding to the first few partitions |
|---|---|---|---|---|---|
| P01 | 1 | | S1–S56 | DSV, SOV, NV, MXV, HV, SMV, LSV | |
| P02, P03, P04 | 2 | GI | S1–S10 | DSV, SOV, NV | 44A, 70I, 104V, 106N, 163E, 201V, 203A, 204G, **226Q, 329H, 375W, 377S, 397S, 414F, 434P, 460H, 463D, 471G, 485P *,486N*, 500V, 514K, 519A, 527G*** |
| | | GII | S12–S56 | MXV, HV, SMV, LSV | 44P, 70V, 104A, 106G, 163P, 201T, 203S, 204C, **226S, 329G, 375P, 377G, 397G, 414P, 434D, 460R, 463N, 471F, 500Y, 514A, 519G** |
| P05 | 3 | GIa | S1–S10 | DSV, SOV, NV | GI + [83L, 181R, **227K, 306G, 492P**] |
| | | GIIa | S12–S42 | MXV, HV, SMV | GII + [83L, 181R, **227K, 306G, 492P**] |
| | | GIIb | S43–S56 | LSV | GII + [83A, 181K, **227R, 306W, 492D**] |
| P06 | 7 | GIb | S1–S3 | DSV | GIa + [46A, **229K, 232S, 236L, 241L**] |
| | | GIc | S4–S6 | SOV | GIb: [199S, **229R, 232T, 236I, 310M**] |
| | | GId | S7–S9 | NV | GIb: [84S, 197G*, **229R, 232T, 241L,**] |
| | | GIIc | S12–S23 | MXV | GIIa + [46T, 195G*, 199V, **229K, 232T**] |
| | | GIId | S25–S37 | HV, SMV | GIIa: [65N, 241L, **509Q**] |
| | | GIIe | S39–S42 | HV, SMV | GIIa: [46V, **250V, 509Q**] |
| | | GIIf | S43–S56 | LSV | GIIa: [46A, **250L, 275V, 306W, 310D**] |
| P07 | 8 | GIb | S1–S3 | DSV | P06 + 43A, 65Q, 82D, 125I, 133A, 142A, 149I, 156E, 160V, 203C, 223N, **239N, 240T, 246V, 253M, 259H, 288C, 301L, 347*, 356L, 389P, 401E, 422M, 446V, 452T, 504V** |
| | | GIe | S4–S5 | DSV | P06+ 43L, 65Q, 82D, 125I, 133Q, 142A, 149I, 156D, 160V, 203C, 223T, **239K, 240Y, 246I, 253M, 259Q, 288C, 301L, 347P, 356L, 389F, 401E, 422M, 446I, 452I, 504A** |
| | | GId | S7–S9 | NV | P06+ 43V, 65Q, 82D, 125V, 133G, 142A, 149I, 156D, 160V, 203C, 223T, **239S, 240S, 246A, 253M, 259N, 288A, 301L, 347T, 356L, 389L, 401E, 422M, 446A, 452T, 504V** |
| | | GIIc | S12–S23 | MXV | P06+ 43A, 65G, 82N, 125F, 133P, 142I, 149I, 156E, 160L, 203R, 223T, **239S, 240E, 246F, 253L, 259E, 288C, 301L, 347T, 356L, 389Q, 401H, 422R, 446Y, 452A, 504E** |
| | | GIIg | S25–S32 | HV | P06+ 43A, 65N, 82N, 125F, 133P, 142I, 149I, 156E, 160L, 203R, 223T, **239G, 240E, 246F, 253L, 259E, 288C, 301V, 347T, 356L, 389Q, 401L, 422R, 446Y, 452S, 504D** |
| | | GIIh | S33 S37 | SMV | P06+ 43A, 65N, 82N, 125F, 133P, 142I, 149I, 156E, 160L, 203R, 223T, **239G, 240E, 246F, 253M, 259E, 288C, 301I, 347T, 356L, 389Q, 401L, 422R, 446Y, 452S, 504D** |
| | | GIIi | S39–S41 | SMV | P06+ 43A, 65A, 82D, 125F, 133P, 142L, 149V, 156E, 160L, 203R, 223S, **239S, 240E, 246F, 253M, 259E, 288C, 301L, 347T, 356I, 389Q, 401N, 422R, 446Y, 452A, 504E** |
| | | GIIf | S43–S56 | LV | P06+ 43A, 65G, 82S, 125F, 133P, 142V, 149I, 156E, 160I, 203R, 223T, **239E, 240E, 246F, 253L, 259S, 288C, 301L, 347T, 356L, 389Q, 401R, 422R, 446Y, 452A, 504D** |

Residue numbers correspond to that of NV. The hinge region residues and the P domain residues are boldfaced in contrast to the S domain class-specific residues. *, insertions; P0n+, including all class specific residues of the previous class denoted by the number *n*.

FIG. 9

SEQUENCE LISTING

```
<160> NUMBER OF SEQ ID NOS: 41

<210> SEQ ID NO 1
<211> LENGTH: 8
<212> TYPE: PRT
<213> ORGANISM: Snow Mountain virus

<400> SEQUENCE: 1

Trp Thr Arg Gly Ser His Asn Leu
1               5


<210> SEQ ID NO 2
<211> LENGTH: 8
<212> TYPE: PRT
<213> ORGANISM: Snow Mountain virus

<400> SEQUENCE: 2

Trp Thr Arg Gly Gly His Gly Leu
1               5


<210> SEQ ID NO 3
<211> LENGTH: 8
<212> TYPE: PRT
<213> ORGANISM: Snow Mountain virus

<400> SEQUENCE: 3

Trp Thr Arg Gly Gln His Gln Leu
1               5


<210> SEQ ID NO 4
<211> LENGTH: 9
<212> TYPE: PRT
<213> ORGANISM: Snow Mountain virus

<400> SEQUENCE: 4

Trp Leu Pro Ala Pro Ile Asp Lys Leu
1               5
```

```
<210> SEQ ID NO 5
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(10)
<223> OTHER INFORMATION: /note="This sequence may encompass 2, 3, 4, 5,
      6, 7, 8, 9, or 10 residues"

<400> SEQUENCE: 5

Gly Gly Gly Gly Gly Gly Gly Gly Gly Gly
1               5                   10


<210> SEQ ID NO 6
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(16)
<223> OTHER INFORMATION: /note="This sequence may encompass 1, 2, 3, or
      4 'Gly-Gly-Gly-Ser' repeating units"

<400> SEQUENCE: 6

Gly Gly Gly Ser Gly Gly Gly Ser Gly Gly Gly Ser Gly Gly Gly Ser
1               5                   10                  15


<210> SEQ ID NO 7
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(16)
<223> OTHER INFORMATION: /note="This sequence may encompass 1, 2, 3, or
      4 'Ser-Arg-Ser-Lys' repeating units"

<400> SEQUENCE: 7

Ser Arg Ser Lys Ser Arg Ser Lys Ser Arg Ser Lys Ser Arg Ser Lys
1               5                   10                  15


<210> SEQ ID NO 8
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic His tag"
<220> FEATURE:
<221> NAME/KEY: misc_feature
<222> LOCATION: (1)..(10)
<223> OTHER INFORMATION: /note="This sequence may encompass 3, 4, 5, 6,
      7, 8, 9, or 10 residues"

<400> SEQUENCE: 8

His His His His His His His His His His
1               5                   10
```

<210> SEQ ID NO 9
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(1)
<223> OTHER INFORMATION: Inosine
<220> FEATURE:
<221> NAME/KEY: modified_base
<222> LOCATION: (3)..(3)
<223> OTHER INFORMATION: Inosine
<220> FEATURE:
<221> NAME/KEY: modified_base
<222> LOCATION: (5)..(5)
<223> OTHER INFORMATION: Inosine
<220> FEATURE:
<221> NAME/KEY: modified_base
<222> LOCATION: (7)..(7)
<223> OTHER INFORMATION: Inosine
<220> FEATURE:
<221> NAME/KEY: modified_base
<222> LOCATION: (9)..(9)
<223> OTHER INFORMATION: Inosine
<220> FEATURE:
<221> NAME/KEY: modified_base
<222> LOCATION: (11)..(11)
<223> OTHER INFORMATION: Inosine
<220> FEATURE:
<221> NAME/KEY: modified_base
<222> LOCATION: (13)..(13)
<223> OTHER INFORMATION: Inosine
<220> FEATURE:
<221> NAME/KEY: modified_base
<222> LOCATION: (15)..(15)
<223> OTHER INFORMATION: Inosine
<220> FEATURE:
<221> NAME/KEY: modified_base
<222> LOCATION: (17)..(17)
<223> OTHER INFORMATION: Inosine
<220> FEATURE:
<221> NAME/KEY: modified_base
<222> LOCATION: (19)..(19)
<223> OTHER INFORMATION: Inosine
<220> FEATURE:
<221> NAME/KEY: modified_base
<222> LOCATION: (21)..(21)
<223> OTHER INFORMATION: Inosine
<220> FEATURE:
<221> NAME/KEY: modified_base
<222> LOCATION: (23)..(23)
<223> OTHER INFORMATION: Inosine
<220> FEATURE:
<221> NAME/KEY: modified_base
<222> LOCATION: (25)..(25)
<223> OTHER INFORMATION: Inosine

<400> SEQUENCE: 9
ncncncncnc ncncncncnc ncncnc 26

<210> SEQ ID NO 10
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 10

Lys Leu Lys Leu Leu Leu Leu Leu Lys Leu Lys 1 5 10

<210> SEQ ID NO 11
<211> LENGTH: 530
<212> TYPE: PRT
<213> ORGANISM: Norwalk virus

<400> SEQUENCE: 11

Met Met Met Ala Ser Lys Asp Ala Thr Ser Ser Val Asp Gly Ala Ser
1 5 10 15

Gly Ala Gly Gln Leu Val Pro Glu Val Asn Ala Ser Asp Pro Leu Ala
20 25 30

Met Asp Pro Val Ala Gly Ser Ser Thr Ala Val Ala Thr Ala Gly Gln
35 40 45

Val Asn Pro Ile Asp Pro Trp Ile Ile Asn Asn Phe Val Gln Ala Pro
50 55 60

Gln Gly Glu Phe Thr Ile Ser Pro Asn Asn Thr Pro Gly Asp Val Leu
65 70 75 80

Phe Asp Leu Ser Leu Gly Pro His Leu Asn Pro Phe Leu Leu His Leu
85 90 95

Ser Gln Met Tyr Asn Gly Trp Val Gly Asn Met Arg Val Arg Ile Met
100 105 110

Leu Ala Gly Asn Ala Phe Thr Ala Gly Lys Ile Ile Val Ser Cys Ile
115 120 125

Pro Pro Gly Phe Gly Ser His Asn Leu Thr Ile Ala Gln Ala Thr Leu
130 135 140

Phe Pro His Val Ile Ala Asp Val Arg Thr Leu Asp Pro Ile Glu Val
145 150 155 160

Pro Leu Glu Asp Val Arg Asn Val Leu Phe His Asn Asn Asp Arg Asn
165 170 175

Gln Gln Thr Met Arg Leu Val Cys Met Leu Tyr Thr Pro Leu Arg Thr
180 185 190

Gly Gly Gly Thr Gly Asp Ser Phe Val Val Ala Gly Arg Val Met Thr
195 200 205

Cys Pro Ser Pro Asp Phe Asn Phe Leu Phe Leu Val Pro Pro Thr Val
210 215 220

Glu Gln Lys Thr Arg Pro Phe Thr Leu Pro Asn Leu Pro Leu Ser Ser
225 230 235 240

Leu Ser Asn Ser Arg Ala Pro Leu Pro Ile Ser Ser Met Gly Ile Ser
245 250 255

Pro Asp Asn Val Gln Ser Val Gln Phe Gln Asn Gly Arg Cys Thr Leu
260 265 270

Asp Gly Arg Leu Val Gly Thr Thr Pro Val Ser Leu Ser His Val Ala
275 280 285

Lys Ile Arg Gly Thr Ser Asn Gly Thr Val Ile Asn Leu Thr Glu Leu
290 295 300

Asp Gly Thr Pro Phe His Pro Phe Glu Gly Pro Ala Pro Ile Gly Phe
305 310 315 320

Pro Asp Leu Gly Gly Cys Asp Trp His Ile Asn Met Thr Gln Phe Gly
325 330 335

His Ser Ser Gln Thr Gln Tyr Asp Val Asp Thr Thr Pro Asp Thr Phe
340 345 350

Val Pro His Leu Gly Ser Ile Gln Ala Asn Gly Ile Gly Ser Gly Asn
355 360 365

-continued

```
Tyr Val Gly Val Leu Ser Trp Ile Ser Pro Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
        515                 520                 525

Arg Arg
    530


<210> SEQ ID NO 12
<211> LENGTH: 542
<212> TYPE: PRT
<213> ORGANISM: Snow Mountain virus

<400> SEQUENCE: 12

Met Lys Met Ala Ser Asn Asp Ala Ala Pro Ser Thr Asp Gly Ala Ala
1               5                   10                  15

Gly Leu Val Pro Glu Ser Asn Asn Glu Val Met Ala Leu Glu Pro Val
            20                  25                  30

Ala Gly Ala Ala Leu Ala Ala Pro Val Thr Gly Gln Thr Asn Ile Ile
        35                  40                  45

Asp Pro Trp Ile Arg Ala Asn Phe Val Gln Ala Pro Asn Gly Glu Phe
    50                  55                  60

Thr Val Ser Pro Arg Asn Ala Pro Gly Glu Val Leu Leu Asn Leu Glu
65                  70                  75                  80

Leu Gly Pro Glu Leu Asn Pro Tyr Leu Ala His Leu Ala Arg Met Tyr
                85                  90                  95

Asn Gly Tyr Ala Gly Gly Met Glu Val Gln Val Met Leu Ala Gly Asn
            100                 105                 110

Ala Phe Thr Ala Gly Lys Leu Val Phe Ala Ala Val Pro Pro His Phe
        115                 120                 125

Pro Val Glu Asn Leu Ser Pro Gln Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Lys Asp Asp Pro Lys Met
                165                 170                 175

Arg Ile Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205
```

Asp Phe Asp Phe Thr Tyr Leu Val Pro Pro Thr Val Glu Ser Lys Thr
210 215 220

Lys Pro Phe Thr Leu Pro Ile Leu Thr Leu Gly Glu Leu Ser Asn Ser
225 230 235 240

Arg Phe Pro Val Ser Ile Asp Gln Met Tyr Thr Ser Pro Asn Glu Val
245 250 255

Ile Ser Val Gln Cys Gln Asn Gly Arg Cys Thr Leu Asp Gly Glu Leu
260 265 270

Gln Gly Thr Thr Gln Leu Gln Val Ser Gly Ile Cys Ala Phe Lys Gly
275 280 285

Glu Val Thr Ala His Leu Gln Asp Asn Asp His Leu Tyr Asn Ile Thr
290 295 300

Ile Thr Asn Leu Asn Gly Ser Pro Phe Asp Pro Ser Glu Asp Ile Pro
305 310 315 320

Ala Pro Leu Gly Val Pro Asp Phe Gln Gly Arg Val Phe Gly Val Ile
325 330 335

Thr Gln Arg Asp Lys Gln Asn Ala Ala Gly Gln Ser Gln Pro Ala Asn
340 345 350

Arg Gly His Asp Ala Val Val Pro Thr Tyr Thr Ala Gln Tyr Thr Pro
355 360 365

Lys Leu Gly Gln Val Gln Ile Gly Thr Trp Gln Thr Asp Asp Leu Lys
370 375 380

Val Asn Gln Pro Val Lys Phe Thr Pro Val Gly Leu Asn Asp Thr Glu
385 390 395 400

His Phe Asn Gln Trp Val Val Pro Arg Tyr Ala Gly Ala Leu Asn Leu
405 410 415

Asn Thr Asn Leu Ala Pro Ser Val Ala Pro Val Phe Pro Gly Glu Arg
420 425 430

Leu Leu Phe Phe Arg Ser Tyr Leu Pro Leu Lys Gly Gly Tyr Gly Asn
435 440 445

Pro Ala Ile Asp Cys Leu Leu Pro Gln Glu Trp Val Gln His Phe Tyr
450 455 460

Gln Glu Ala Ala Pro Ser Met Ser Glu Val Ala Leu Val Arg Tyr Ile
465 470 475 480

Asn Pro Asp Thr Gly Arg Ala Leu Phe Glu Ala Lys Leu His Arg Ala
485 490 495

Gly Phe Met Thr Val Ser Ser Asn Thr Ser Ala Pro Val Val Val Pro
500 505 510

Ala Asn Gly Tyr Phe Arg Phe Asp Ser Trp Val Asn Gln Phe Tyr Ser
515 520 525

Leu Ala Pro Met Gly Thr Gly Asn Gly Arg Arg Arg Ile Gln
530 535 540

<210> SEQ ID NO 13
<211> LENGTH: 540
<212> TYPE: PRT
<213> ORGANISM: Snow Mountain virus

<400> SEQUENCE: 13

Met Lys Met Ala Ser Ser Asp Ala Asn Pro Ser Asp Gly Ser Thr Ala
1 5 10 15

Asn Leu Val Pro Glu Val Asn Asn Glu Val Met Ala Leu Glu Pro Val
20 25 30

Val Gly Ala Ala Ile Ala Ala Pro Val Ala Gly Gln Gln Asn Val Ile

```
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Val Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Glu Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Ile Leu Thr Val Glu Glu Met Thr Asn Ser
225                 230                 235                 240

Arg Phe Pro Ile Pro Leu Glu Lys Leu Phe Thr Gly Pro Ser Ser Thr
                245                 250                 255

Ile Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Thr Gln Glu Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Arg Asp Gly Ser Thr Arg Gly His Lys Ala Thr Val Ser
            340                 345                 350

Thr Gly Ser Val Asn Phe Thr Pro Lys Leu Gly Arg Ile Gln Phe Ser
        355                 360                 365

Thr Asp Thr Ser Asn Asp Phe Glu Thr Gly Gln Ser Thr Arg Phe Thr
    370                 375                 380

Pro Val Gly Val Val Gln Asp Gly Ser Thr Thr His Gln Asn Glu Pro
385                 390                 395                 400

Gln Gln Trp Val Leu Pro Asp Tyr Ser Gly Arg Asp Ser His Asn Val
                405                 410                 415

His Leu Ala Pro Ala Val Ala Pro Ser Phe Pro Gly Glu Gln Leu Leu
            420                 425                 430

Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
    450                 455                 460
```

```
Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Ser Asp Ser Trp Val Asn Gln Phe Tyr Thr Leu Ala
        515                 520                 525

Pro Met Gly Asn Gly Thr Gly Arg Arg Arg Ala Leu
    530                 535                 540


<210> SEQ ID NO 14
<211> LENGTH: 1629
<212> TYPE: DNA
<213> ORGANISM: Snow Mountain virus

<400> SEQUENCE: 14

atgaagatgg cgtcgaatga cgccgctcca tctactgatg gtgcagccgg cctcgtgcca     60

gaaagtaata atgaggtcat ggctcttgag cccgtggctg gtgctgcctt ggcagccccg    120

gtcaccggtc aaacaaatat tatagaccct tggattagag caaattttgt ccaggcccct    180

aatggtgaat ttacagtttc tccccgtaat gcccctggtg aagtgctatt aaatctagaa    240

ttgggtccag aattaaatcc ttatctggca catttagcaa gaatgtacaa cgggtatgcc    300

ggtgggatgg aggtgcaggt catgctagct gggaacgcgt tcacagctgg caaattggtc    360

ttcgctgctg taccacctca tttcccggtt gaaaacctta gtccacagca aattaccatg    420

ttccctcatg tgattataga tgttaggact ttggaacctg ttttattgcc actccccgat    480

gttagaaata atttcttcca ttataatcaa aaagatgatc ctaagatgag aattgtggct    540

atgctttata ctcccctcag gtccaatggt tctggtgatg atgtgttcac agtctcttgc    600

agggtgttga ctagaccctc ccctgatttt gattttacat acctggtacc accaacagtg    660

gaatccaaaa caaaaccatt cacccttcca attcttacac ttggggagct ttccaattct    720

agatttccag tgtccataga tcagatgtac actagcccca atgaagtcat atctgtgcag    780

tgccagaatg gaaggtgcac actggatggg gagctccaag gaacaacaca gctccaagtt    840

agtggcattt gtgcattcaa aggagaagtg accgctcact tgcaggacaa tgatcaccta    900

tacaacatca ccatcacaaa cttgaatggg tccccttttg atccctctga ggacatcccc    960

gcccccctgg gtgtgcccga ctttcaggga agagtctttg gtgtcatcac tcaaagagac   1020

aaacagaatg ccgctgggca aagccagccg gcaaacaggg gacacgatgc tgtggtcccc   1080

acttacacag cccagtatac ccccaaaattg ggtcaggttc aaattggcac atggcagacc   1140

gacgatctta aagtcaacca accagtcaaa ttcaccccag tcggtctcaa tgacacagaa   1200

catttcaatc agtgggtggt ccctaggtac gctggtgctt taaatctaaa cacaaatctt   1260

gcccccctctg ttgctccagt gtttccaggg gagcgtctgc tcttctttag atcatacctc  1320

ccccttaagg gtggttatgg aaacccagct attgattgcc tgctaccaca agagtgggtg   1380

cagcattttt atcaggaagc agccccctca atgagtgagg tagcccttgt cagatacatc   1440

aatccggaca ctggccgggc gctgtttgag gccaaactcc acagagctgg tttcatgaca   1500

gtctcgagta acaccagtgc tccggtggtt gtgcctgcca acggatactt cagatttgac   1560

tcttgggtga accaatttta ttctcttgcc cccatgggaa ctggaaatgg gcgtagaagg   1620

attcagtga                                                           1629
```

<210> SEQ ID NO 15
<211> LENGTH: 1606
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15
aagcttacaa aacaaaatga agatggcgtc gaatgacgcc gctccatcta ctgatggtgc 60
agctggtctc gtgccagaaa gtaataatga ggtcatggct cttgagcccg tggctggtgc 120
tgccttggca gccccggtca ccggtcaaac aaatattata gacccttgga ttagagcaaa 180
ttttgtccag gcccctaatg gtgaatttac agtttctccc cgtaatgccc ctggtgaagt 240
gctattaaat ctagaattgg gtccagaatt aaatccttat ctggcacatt tagcaagaat 300
gtacaacggg tatgccggtg ggatggaggt gcaggtcatg ttagctggga acgcgttcac 360
agctggcaaa ttggtcttcg ctgctgtacc acctcatttc ccggttgaaa accttagtcc 420
acagcaaatt accatgttcc ctcatgtgat tatagatgtt aggactttgg aacctgtttt 480
attgccactc cccgatgtta gaaataattt cttccattat aatcaaaaag atgatcctaa 540
gatgagaatt gtggctatgc attatactcc cctcaggtcc aatggttctg gtgatgatgt 600
gttcacagtc tcttgcaggg tgttgactag accctcccct gattttgatt ttacatacct 660
ggtaccacca acagtggaat ccaaaacaaa accatttact ttgccaaatt tacctttgtc 720
atctttatct aattctagag caccccttgcc aatttcttct atgggtattt ctcctgataa 780
tgttcaatct gttcaatttc aaaacggtag atgtacttta gatggtagat tggttggtac 840
tactcccgtt tctttatctc atgttgctaa aattagaggt acttctaacg gtactgttat 900
taacttgact gaattagatg gtactccatt tcatcctttt gaaggtcccg ctccaattgg 960
ttttcctgat ttgggtggtt gtgattggca tattaacatg actcaattcg gtcattcttc 1020
tcaaactcaa tacgatgttg atactacacc cgatactttt gttccacatt taggttctat 1080
tcaagctaat ggtattggtt ctggtaatta tgttggtgtt ttgtcttgga tttctcctcc 1140
ctctcatcca tctggttctc aagttgattt atggaaaatt cctaattacg gttcttctat 1200
tactgaagct actcatttgg ctccctctgt ttatccacct ggtttcggtg aagttttagt 1260
ttttttcatg tctaaaatgc caggtcccgg tgcttacaat ttgccatgtt tattgcctca 1320
agaatacatt tctcatttag cttcagaaca agctcccact gttggtgaag ctgctttgtt 1380
acattatgtt gatccagata ctggtagaaa tttgggtgaa tttaaagctt atcctgatgg 1440
ttttttaact tgtgttccca atggtgcttc ttctggtcca caacaattgc ctattaatgg 1500
tgtttttgtt ttcgtttctt gggtttctag attttaccaa ttaaaacccg ttggtactgc 1560
ttcttctgct agaggtagat tgggtttgag aagataatga gtcgac 1606

<210> SEQ ID NO 16
<211> LENGTH: 1648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 16

-continued

```
aagcttacaa aacaaaatga agatggcgtc gaatgacgcc gctccatcta ctgatggtgc     60
agctggtctc gtgccagaaa gtaataatga ggtcatggct cttgagcccg tggctggtgc    120
tgccttggca gccccggtca ccggtcaaac aaatattata gacccttgga ttagagcaaa    180
ttttgtccag gcccctaatg gtgaatttac agtttctccc cgtaatgccc ctggtgaagt    240
gctattaaat ctagaattgg gtccagaatt aaatccttat ctggcacatt tagcaagaat    300
gtacaacggg tatgccggtg ggatggaggt gcaggtcatg ttagctggga acgcgttcac    360
agctggcaaa ttggtcttcg ctgctgtacc acctcatttc ccggttgaaa accttagtcc    420
acagcaaatt accatgttcc ctcatgtgat tatagatgtt aggactttgg aacctgtttt    480
attgccactc cccgatgtta gaaataattt cttccattat aatcaaaaag atgatcctaa    540
gatgagaatt gtggctatgc attatactcc cctcaggtcc aatggttctg gtgatgatgt    600
gttcacagtc tcttgcaggg tgttgactag accctcccct gattttgatt ttacatacct    660
ggtaccacca acagtggaat ccaaaacaaa acccttttct gttccaattt taactgttga    720
agaaatgact aattctagat tccctattcc cttggaaaaa ttgtttactg gtccatcttc    780
tactattgtt gttcaacctc aaaatggtag atgtactact gatggtgttt tgttaggtac    840
tactcaattg tctcccgtta acatttgtac tttcagaggt gatgttactc atattgctgg    900
tactcaagaa tatactatga acttagcttc tcaaaattgg aacaattacg atccaactga    960
agaaattcct gctcccttag gtacaccaga ttttgttggt aaaattcaag gtgttttgac   1020
tcaaactact agaagagatg gttctacaag aggtcataaa gctactgttt ctactggttc   1080
tgttaatttc actcctaagt tgggtagaat tcaattttct actgatactt ctaacgattt   1140
tgaaactggt caatctacta gatttactcc cgttggtgtt gttcaagatg gttcaactac   1200
tcatcaaaat gaaccacaac aatgggtttt acctgattat tctggtagag attctcataa   1260
tgttcatttg gctcccgctg ttgctccatc ttttccaggt gaacaattat tgtttttcag   1320
atctactatg cccggttgtt ctggttatcc aaatatgaac ttagattgtt tgttacctca   1380
agaatgggtt caacattttt atcaagaagc tgctcccgct caatctgatg ttgctttgtt   1440
aagatttgtt aatccagata ctggtagagt tttgttcgaa tgtaaattac ataaatctgg   1500
ttatgttact gttgctcata ctggtcaaca tgatttggtt attcctccca atggttactt   1560
tagatctgat tcttgggtta atcaatttta cactttagct ccaatgggta atggtactgg   1620
tagaagaaga gctttgtaat gagtcgac                                      1648
```

<210> SEQ ID NO 17
<211> LENGTH: 544
<212> TYPE: PRT
<213> ORGANISM: Norwalk virus

<400> SEQUENCE: 17

```
Met Met Met Ala Ser Lys Asp Ala Pro Thr Asn Met Asp Gly Thr Ser
1               5                   10                  15

Gly Ala Gly Gln Leu Val Pro Glu Ala Asn Thr Ala Glu Pro Ile Ser
            20                  25                  30

Met Asp Pro Val Ala Gly Ala Ala Thr Ala Val Ala Thr Ala Gly Gln
        35                  40                  45

Ile Asn Met Ile Asp Pro Trp Ile Met Ser Asn Phe Val Gln Ala Pro
    50                  55                  60

Gln Gly Glu Phe Thr Val Ser Pro Asn Asn Thr Pro Gly Asp Val Leu
65                  70                  75                  80
```

-continued

```
Phe Asp Leu Gln Leu Gly Pro Gln Leu Asn Pro Phe Leu Ala His Leu
                85                  90                  95

Ala Gln Met Tyr Asn Gly Trp Val Gly Asn Met Arg Val Lys Val Leu
            100                 105                 110

Leu Ala Gly Asn Ala Phe Thr Ala Gly Lys Ile Ile Ile Ser Cys Ile
        115                 120                 125

Pro Pro Gly Phe Thr Ser Gln Asn Ile Ser Ile Ala Gln Met Thr Met
    130                 135                 140

Phe Pro His Val Ile Ala Asp Val Arg Val Leu Glu Pro Ile Glu Val
145                 150                 155                 160

Pro Leu Glu Asp Val Arg Asn Val Leu Phe His Thr Asn Asp Asn Arg
                165                 170                 175

Pro Thr Met Arg Leu Val Cys Met Leu Tyr Thr Pro Leu Arg Ala Asn
            180                 185                 190

Gly Ser Ser Ser Gly Thr Asp Pro Phe Val Ile Ala Gly Arg Val Leu
        195                 200                 205

Thr Cys Pro Asp Ser Asn Phe Ser Phe Leu Phe Leu Val Pro Pro Asn
    210                 215                 220

Val Glu Gln Lys Thr Arg Pro Phe Ser Val Pro Asn Ile Pro Leu Asn
225                 230                 235                 240

Thr Leu Ser Asn Ser Arg Val Pro Ser Leu Ile Lys Ser Met Thr Ile
                245                 250                 255

Ser Arg Asp Gln Asn Gln Ile Ile Gln Phe Gln Asn Gly Arg Val Thr
            260                 265                 270

Leu Asp Gly Gln Leu Gln Gly Thr Thr Pro Thr Ser Val Ser Gln Leu
        275                 280                 285

Cys Lys Ile Arg Gly Thr Thr Tyr His Ala Thr Gly Gly Asn Gly Ile
    290                 295                 300

Asn Leu Thr Glu Leu Asn Gly Glu Pro Tyr His Ala Phe Glu Ser Pro
305                 310                 315                 320

Ala Pro Ile Gly Phe Pro Asp Leu Gly Gly Cys Asp Trp His Leu Thr
                325                 330                 335

Ala Thr Pro Thr Gln Ala Phe Asn Asp Gly Ala Lys Val Val Arg Leu
            340                 345                 350

Ser Val Thr Gln Gly Ala Ala Phe Ala Pro His Leu Gly Thr Ile His
        355                 360                 365

Tyr Thr Thr Thr Asp Thr Asp Tyr Ser Pro Asn Thr Ser Ile Ile Cys
    370                 375                 380

Thr Leu Asp Trp Leu Ser Gln Thr Thr Gly Gln Asn Asn Val Asp Pro
385                 390                 395                 400

Trp Gln Ile Pro Thr Tyr Gly Ser Thr Leu Thr Glu Ala Ala Gln Leu
                405                 410                 415

Ala Pro Pro Ile Phe Pro Pro Gly Phe Gly Glu Thr Leu Val Phe Phe
            420                 425                 430

Leu Ser Asp Phe Pro Ile Ser Asn Gly Lys Asn Gly Leu Ser Val Pro
        435                 440                 445

Cys Thr Leu Pro Gln Glu Phe Val Thr His Phe Val Asn Glu Gln Ala
    450                 455                 460

Pro Ile Arg Gly Glu Ala Ala Leu Leu His Tyr Val Asp Pro Asp Thr
465                 470                 475                 480

His Arg Asn Leu Gly Glu Phe Lys Leu Tyr Pro Glu Gly Phe Met Thr
                485                 490                 495

Cys Val Pro Asn Thr Ser Gly Gly Gly Pro Gln Thr Leu Pro Ile Asn
```

```
            500                 505                 510

Gly Val Phe Val Phe Val Ser Trp Val Ser Arg Phe Tyr Gln Leu Lys
        515                 520                 525

Pro Val Gly Thr Ala Gly Ala Ala Arg Arg Leu Gly Ile Arg Arg Ser
    530                 535                 540


<210> SEQ ID NO 18
<211> LENGTH: 530
<212> TYPE: PRT
<213> ORGANISM: Human calicivirus

<400> SEQUENCE: 18

Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Gly Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Gly Met Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335
```

```
His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
        355                 360                 365

Tyr Ile Gly Val Leu Ser Trp Val Ser Pro Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Ile Pro Gly Pro Gly Ala Tyr Ser
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Thr Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
        515                 520                 525

Arg Arg
    530


<210> SEQ ID NO 19
<211> LENGTH: 546
<212> TYPE: PRT
<213> ORGANISM: Norwalk-like virus

<400> SEQUENCE: 19

Met Met Met Ala Ser Lys Asp Ala Pro Gln Ser Ala Asp Gly Ala Ser
1               5                   10                  15

Gly Ala Gly Gln Leu Val Pro Glu Val Asn Thr Ala Asp Pro Leu Pro
            20                  25                  30

Met Glu Pro Val Ala Gly Pro Thr Thr Ala Val Ala Thr Ala Gly Gln
        35                  40                  45

Val Asn Met Ile Asp Pro Trp Ile Val Asn Asn Phe Val Gln Ser Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ser His Leu
                85                  90                  95

Ser Gln Met Tyr Asn Gly Trp Val Gly Asn Met Arg Val Arg Ile Leu
            100                 105                 110

Leu Ala Gly Asn Ala Phe Ser Ala Gly Lys Ile Ile Val Cys Cys Val
        115                 120                 125

Pro Pro Gly Phe Thr Ser Ser Ser Leu Thr Ile Ala Gln Ala Thr Leu
    130                 135                 140

Phe Pro His Val Ile Ala Asp Val Arg Thr Leu Glu Pro Ile Glu Met
145                 150                 155                 160

Pro Leu Glu Asp Val Arg Asn Val Leu Tyr His Thr Asn Asp Asn Gln
                165                 170                 175
```

```
Pro Thr Met Arg Leu Val Cys Met Leu Tyr Thr Pro Leu Arg Thr Gly
            180                 185                 190

Gly Gly Ser Gly Asn Ser Asp Ser Phe Val Val Ala Gly Arg Val Leu
        195                 200                 205

Thr Ala Pro Ser Ser Asp Phe Ser Phe Leu Phe Leu Val Pro Pro Thr
    210                 215                 220

Ile Glu Gln Lys Thr Arg Ala Phe Thr Val Pro Asn Ile Pro Leu Gln
225                 230                 235                 240

Thr Leu Ser Asn Ser Arg Phe Pro Ser Leu Ile Gln Gly Met Ile Leu
                245                 250                 255

Ser Pro Asp Ala Ser Gln Val Val Gln Phe Gln Asn Gly Arg Cys Leu
            260                 265                 270

Ile Asp Gly Gln Leu Leu Gly Thr Thr Pro Ala Thr Ser Gly Gln Leu
        275                 280                 285

Phe Arg Val Arg Gly Lys Ile Asn Gln Gly Ala Arg Thr Leu Asn Leu
    290                 295                 300

Thr Glu Val Asp Gly Lys Pro Phe Met Ala Phe Asp Ser Pro Ala Pro
305                 310                 315                 320

Val Gly Phe Pro Asp Phe Gly Lys Cys Asp Trp His Met Arg Ile Ser
                325                 330                 335

Lys Thr Pro Asn Asn Thr Ser Ser Gly Asp Pro Met Arg Ser Val Ser
            340                 345                 350

Val Gln Thr Asn Val Gln Gly Phe Val Pro His Leu Gly Ser Ile Gln
        355                 360                 365

Phe Asp Glu Val Phe Asn His Pro Thr Gly Asp Tyr Ile Gly Thr Ile
    370                 375                 380

Glu Trp Ile Ser Gln Pro Ser Thr Pro Pro Gly Thr Asp Ile Asn Leu
385                 390                 395                 400

Trp Glu Ile Pro Asp Tyr Gly Ser Ser Leu Ser Gln Ala Ala Asn Leu
                405                 410                 415

Ala Pro Pro Val Phe Pro Pro Gly Phe Gly Glu Ala Leu Val Tyr Phe
            420                 425                 430

Val Ser Ala Phe Pro Gly Pro Asn Asn Arg Ser Ala Pro Asn Asp Val
        435                 440                 445

Pro Cys Leu Leu Pro Gln Glu Tyr Ile Thr His Phe Val Ser Glu Gln
    450                 455                 460

Ala Pro Thr Met Gly Asp Ala Ala Leu Leu His Tyr Val Asp Pro Asp
465                 470                 475                 480

Thr Asn Arg Asn Leu Gly Glu Phe Lys Leu Tyr Pro Gly Gly Tyr Leu
                485                 490                 495

Thr Cys Val Pro Asn Gly Val Gly Ala Gly Pro Gln Gln Leu Pro Leu
            500                 505                 510

Asn Gly Val Phe Leu Phe Val Ser Trp Val Ser Arg Phe Tyr Gln Leu
        515                 520                 525

Lys Pro Val Gly Thr Ala Ser Thr Ala Arg Ser Arg Leu Gly Val Arg
    530                 535                 540

Arg Ile
545
```

<210> SEQ ID NO 20
<211> LENGTH: 545
<212> TYPE: PRT
<213> ORGANISM: Unknown
<220> FEATURE:

```
<221> NAME/KEY: source
<223> OTHER INFORMATION: /note="Description of Unknown: Norovirus
      polypeptide"

<400> SEQUENCE: 20

Met Met Met Ala Ser Lys Asp Ala Pro Thr Asn Met Asp Gly Thr Ser
1               5                   10                  15

Gly Ala Gly Gln Leu Val Pro Glu Ala Asn Thr Ala Glu Pro Ile Ser
            20                  25                  30

Met Glu Pro Val Ala Gly Ala Ala Thr Ala Ala Ala Thr Ala Gly Gln
        35                  40                  45

Val Asn Met Ile Asp Pro Trp Ile Met Asn Asn Tyr Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ser His Leu
                85                  90                  95

Ala Gln Met Tyr Asn Gly Trp Val Gly Asn Met Lys Val Lys Val Leu
            100                 105                 110

Leu Ala Gly Asn Ala Phe Thr Ala Gly Lys Ile Ile Ile Ser Cys Ile
        115                 120                 125

Pro Pro Gly Phe Ala Ala Gln Asn Ile Ser Ile Ala Gln Ala Thr Met
    130                 135                 140

Phe Pro His Val Ile Ala Asp Val Arg Val Leu Glu Pro Ile Glu Val
145                 150                 155                 160

Pro Leu Glu Asp Val Arg Asn Val Leu Phe His Asn Asn Asp Asn Ala
                165                 170                 175

Pro Thr Met Arg Leu Val Cys Met Leu Tyr Thr Pro Leu Arg Ala Ser
            180                 185                 190

Gly Ser Ser Ser Gly Thr Asp Pro Phe Val Ile Ala Gly Arg Val Leu
        195                 200                 205

Thr Cys Pro Ser Pro Asp Phe Ser Phe Leu Phe Leu Val Pro Pro Asn
    210                 215                 220

Val Glu Gln Lys Thr Lys Pro Phe Ser Val Pro Asn Leu Pro Leu Asn
225                 230                 235                 240

Thr Leu Ser Asn Ser Arg Val Pro Ser Leu Ile Lys Ser Met Met Val
                245                 250                 255

Ser Arg Asp His Gly Gln Met Val Gln Phe Gln Asn Gly Arg Val Thr
            260                 265                 270

Leu Asp Gly Gln Leu Gln Gly Thr Thr Pro Thr Ser Ala Ser Gln Leu
        275                 280                 285

Cys Lys Ile Arg Gly Ser Val Phe His Ala Asn Gly Gly Asn Gly Tyr
    290                 295                 300

Asn Leu Thr Glu Leu Asp Gly Ser Pro Tyr His Ala Phe Glu Ser Pro
305                 310                 315                 320

Ala Pro Ile Gly Phe Pro Asp Leu Gly Glu Cys Asp Trp His Met Glu
                325                 330                 335

Ala Ser Pro Thr Thr Gln Phe Asn Thr Gly Asp Val Ile Lys Gln Ile
            340                 345                 350

Asn Val Lys Gln Glu Ser Ala Phe Ala Pro His Leu Gly Thr Ile Gln
        355                 360                 365

Ala Asp Gly Leu Ser Asp Val Ser Val Asn Thr Asn Met Ile Ala Lys
    370                 375                 380

Leu Gly Trp Val Ser Pro Val Ser Asp Gly His Arg Gly Asp Val Asp
```

-continued

```
385                 390                 395                 400

Pro Trp Val Ile Pro Arg Tyr Gly Ser Thr Leu Thr Glu Ala Ala Gln
                405                 410                 415

Leu Ala Pro Pro Ile Tyr Pro Pro Gly Phe Gly Glu Ala Ile Val Phe
            420                 425                 430

Phe Met Ser Asp Phe Pro Ile Ala His Gly Thr Asn Gly Leu Ser Val
        435                 440                 445

Pro Cys Thr Ile Pro Gln Glu Phe Val Thr His Phe Val Asn Glu Gln
    450                 455                 460

Ala Pro Thr Arg Gly Glu Ala Ala Leu Leu His Tyr Leu Asp Pro Asp
465                 470                 475                 480

Thr His Arg Asn Leu Gly Glu Phe Lys Leu Tyr Pro Glu Gly Phe Met
                485                 490                 495

Thr Cys Val Pro Asn Ser Ser Gly Thr Gly Pro Gln Thr Leu Pro Ile
            500                 505                 510

Asn Gly Val Phe Val Phe Val Ser Trp Val Ser Arg Phe Tyr Gln Leu
        515                 520                 525

Lys Pro Val Gly Thr Ala Gly Pro Ala Cys Arg Leu Gly Ile Arg Arg
    530                 535                 540

Ser
545


<210> SEQ ID NO 21
<211> LENGTH: 544
<212> TYPE: PRT
<213> ORGANISM: Chiba virus

<400> SEQUENCE: 21

Met Met Met Ala Ser Lys Asp Ala Thr Pro Ser Ala Asp Gly Ala Thr
1               5                   10                  15

Gly Ala Gly Gln Leu Val Pro Glu Val Asn Thr Ala Asp Pro Ile Pro
            20                  25                  30

Ile Asp Pro Val Ala Gly Ser Ser Thr Ala Leu Ala Thr Ala Gly Gln
        35                  40                  45

Val Asn Leu Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Gln Leu Gly Pro His Leu Asn Pro Phe Leu Ser His Leu
                85                  90                  95

Ser Gln Met Tyr Asn Gly Trp Val Gly Asn Met Arg Val Arg Val Val
            100                 105                 110

Leu Ala Gly Asn Ala Phe Thr Ala Gly Lys Val Ile Ile Cys Cys Val
        115                 120                 125

Pro Pro Gly Phe Gln Ser Arg Thr Leu Ser Ile Ala Gln Ala Thr Leu
    130                 135                 140

Phe Pro His Val Ile Ala Asp Val Arg Thr Leu Asp Pro Val Glu Val
145                 150                 155                 160

Pro Leu Glu Asp Val Arg Asn Val Leu Tyr His Asn Asn Asp Thr Gln
                165                 170                 175

Pro Thr Met Arg Leu Leu Cys Met Leu Tyr Thr Pro Leu Arg Thr Gly
            180                 185                 190

Gly Ala Ser Gly Gly Thr Asp Ser Phe Val Val Ala Gly Arg Val Leu
        195                 200                 205
```

```
Thr Cys Pro Gly Pro Asp Phe Asn Phe Leu Phe Leu Val Pro Pro Thr
    210                 215                 220

Val Glu Gln Lys Thr Arg Pro Phe Thr Val Pro Asn Ile Pro Leu Lys
225                 230                 235                 240

Tyr Leu Ser Asn Ser Arg Ile Pro Asn Pro Ile Glu Gly Met Ser Leu
                245                 250                 255

Ser Pro Asp Gln Thr Gln Asn Val Gln Phe Gln Asn Gly Arg Cys Thr
            260                 265                 270

Ile Asp Gly Gln Pro Leu Gly Thr Thr Pro Val Ser Val Ser Gln Leu
        275                 280                 285

Cys Lys Phe Arg Gly Arg Ile Thr Ser Gly Gln Arg Val Leu Asn Leu
    290                 295                 300

Thr Glu Leu Asp Gly Ser Pro Phe Met Ala Phe Ala Ala Pro Ala Pro
305                 310                 315                 320

Ala Gly Phe Pro Asp Leu Gly Ser Cys Asp Trp His Ile Glu Met Ser
                325                 330                 335

Lys Ile Pro Asn Ser Ser Thr Gln Asn Asn Pro Ile Val Thr Asn Ser
            340                 345                 350

Val Lys Pro Asn Ser Gln Gln Phe Val Pro His Leu Ser Ser Ile Thr
        355                 360                 365

Leu Asp Glu Asn Val Ser Ser Gly Gly Asp Tyr Ile Gly Thr Ile Gln
    370                 375                 380

Trp Thr Ser Pro Pro Ser Asp Ser Gly Gly Ala Asn Thr Asn Phe Trp
385                 390                 395                 400

Lys Ile Pro Asp Tyr Gly Ser Ser Leu Ala Glu Ala Ser Gln Leu Ala
                405                 410                 415

Pro Ala Val Tyr Pro Pro Gly Phe Asn Glu Val Ile Val Tyr Phe Met
            420                 425                 430

Ala Ser Ile Pro Gly Pro Asn Gln Ser Gly Ser Pro Asn Leu Val Pro
        435                 440                 445

Cys Leu Leu Pro Gln Glu Tyr Ile Thr His Phe Ile Ser Glu Gln Ala
    450                 455                 460

Pro Ile Gln Gly Glu Ala Ala Leu Leu His Tyr Val Asp Pro Asp Thr
465                 470                 475                 480

Asn Arg Asn Leu Gly Glu Phe Lys Leu Tyr Pro Gly Gly Tyr Leu Thr
                485                 490                 495

Cys Val Pro Asn Ser Ser Ser Thr Gly Pro Gln Gln Leu Pro Leu Asp
            500                 505                 510

Gly Val Phe Val Phe Ala Ser Trp Val Ser Arg Phe Tyr Gln Leu Lys
        515                 520                 525

Pro Val Gly Thr Ala Gly Pro Ala Arg Gly Arg Leu Gly Val Arg Arg
    530                 535                 540


<210> SEQ ID NO 22
<211> LENGTH: 539
<212> TYPE: PRT
<213> ORGANISM: Norwalk-like virus

<400> SEQUENCE: 22

Met Met Met Ala Ser Lys Asp Ala Pro Thr Ser Pro Asp Gly Ala Ser
1               5                   10                  15

Gly Ala Gly Gln Leu Val Pro Glu Ala Asn Thr Ala Glu Gln Ile Ser
            20                  25                  30

Met Asp Pro Val Ala Gly Ala Ser Thr Ala Val Ala Thr Ala Gly Gln
        35                  40                  45
```

-continued

```
Val Asn Met Ile Asp Pro Trp Ile Phe Asn Asn Phe Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ala His Leu
                85                  90                  95

Ser Gln Met Tyr Asn Gly Trp Val Gly Asn Met Arg Val Arg Ile Leu
            100                 105                 110

Leu Ala Gly Asn Ala Phe Thr Ala Gly Lys Ile Ile Ile Cys Cys Val
        115                 120                 125

Pro Pro Gly Phe Asp Ala Arg Ile Leu Thr Ile Ala Gln Ala Thr Leu
    130                 135                 140

Phe Pro His Leu Ile Ala Asp Val Arg Thr Leu Glu Pro Val Glu Leu
145                 150                 155                 160

Pro Leu Glu Asp Val Arg Asn Val Leu Tyr His Asn Ser Ser Gln Pro
                165                 170                 175

Gln Pro Thr Met Arg Leu Val Ala Met Leu Tyr Thr Pro Leu Arg Thr
            180                 185                 190

Gly Gly Gly Ser Gly Gly Thr Asp Ala Phe Val Val Ala Gly Arg Val
        195                 200                 205

Leu Thr Cys Pro Ala Pro Asp Phe Ser Phe Leu Phe Leu Val Pro Pro
    210                 215                 220

Ser Val Glu Gln Lys Thr Arg Val Phe Ser Val Pro Asn Ile Pro Leu
225                 230                 235                 240

Lys Asp Leu Ser Asn Ser Arg Val Pro Val Pro Ile Gln Gly Met Phe
                245                 250                 255

Met Ser Pro Asp Val Asn Gln Ser Val Gln Phe Gln Asn Gly Arg Cys
            260                 265                 270

Gln Ile Asp Gly Gln Leu Gln Gly Thr Thr Pro Val Ser Leu Ser Gln
        275                 280                 285

Leu Cys Lys Ile Arg Gly Lys Thr Ser Ser Asn Ala Arg Val Leu Asn
    290                 295                 300

Leu Ser Glu Val Asp Gly Thr Pro Phe Ile Pro Leu Glu Ser Pro Ala
305                 310                 315                 320

Pro Val Gly Phe Pro Asp Leu Gly Gly Cys Asp Trp His Val Asn Phe
                325                 330                 335

Thr Phe Gln Ala Gln Asn Gln Asp Pro Ser Gln Ser Val Thr Phe Ala
            340                 345                 350

Thr Asn Asp Ala Ser Phe Val Pro Tyr Leu Gly Ser Ile Ser Pro His
        355                 360                 365

Asn Gly Gly Asp Phe His Ala Gly Asp Ile Ile Gly Ser Leu Gly Trp
    370                 375                 380

Ile Ser Ala Pro Ser Asp Asn Thr Gln Leu Asn Val Trp Thr Ile Pro
385                 390                 395                 400

Lys Tyr Gly Ser Ser Leu Gln Met Ser Leu Thr Leu His Leu Leu Cys
                405                 410                 415

Ser Pro Arg Leu Trp Glu Val Ile Leu Tyr Phe Tyr Ser Thr Phe Pro
            420                 425                 430

Gly Ser Gly Gln Pro Ser Gln Leu Gln Val Pro Cys Leu Leu Pro Gln
        435                 440                 445

Glu Phe Ile Thr His Phe Cys Asn Glu Gln Ala Pro Ile Ala Gly Glu
    450                 455                 460
```

```
Ala Ala Leu Leu His Tyr Val Asp Pro Asp Thr Gly Arg Asn Leu Gly
465                 470                 475                 480

Glu Phe Lys Leu Tyr Pro Asp Gly Phe Met Thr Cys Val Pro Asn Ser
                485                 490                 495

Val Ser Ser Gly Pro Gln Thr Leu Pro Ile Asn Gly Val Phe Val Phe
            500                 505                 510

Val Ser Trp Val Ser Arg Phe Tyr Gln Leu Lys Pro Val Gly Thr Ala
        515                 520                 525

Ser Ala Ala Arg Arg Leu Gly Leu Arg Arg Ile
    530                 535


<210> SEQ ID NO 23
<211> LENGTH: 535
<212> TYPE: PRT
<213> ORGANISM: Hawaii calicivirus

<400> SEQUENCE: 23

Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Met Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Glu Leu Asn Pro Phe Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Ile Pro Pro His Phe
        115                 120                 125

Pro Leu Glu Asn Leu Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Pro Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220

Lys Pro Phe Thr Leu Pro Ile Leu Thr Ile Gly Glu Leu Ser Asn Ser
225                 230                 235                 240

Arg Phe Pro Val Pro Ile Asp Glu Leu Tyr Thr Ser Pro Asn Glu Gly
                245                 250                 255

Val Ile Val Gln Pro Gln Asn Gly Arg Ser Thr Leu Asp Gly Glu Leu
            260                 265                 270

Leu Gly Thr Thr Gln Leu Val Pro Ser Asn Ile Cys Ala Leu Arg Gly
        275                 280                 285

Arg Ile Asn Ala Gln Val Pro Asp Asp His His Gln Trp Asn Leu Gln
    290                 295                 300
```

Val Thr Asn Thr Asn Gly Thr Pro Phe Asp Pro Thr Glu Asp Val Pro
305 310 315 320

Ala Pro Leu Gly Thr Pro Asp Phe Leu Ala Asn Ile Tyr Gly Val Thr
325 330 335

Ser Gln Arg Asn Pro Asn Asn Thr Cys Arg Ala His Asp Gly Val Leu
340 345 350

Ala Thr Trp Ser Pro Lys Phe Thr Pro Lys Leu Gly Ser Val Ile Leu
355 360 365

Gly Thr Trp Glu Glu Ser Asp Leu Asp Leu Asn Gln Pro Thr Arg Phe
370 375 380

Thr Pro Val Gly Leu Phe Asn Thr Asp His Phe Asp Gln Trp Ala Leu
385 390 395 400

Pro Ser Tyr Ser Gly Arg Leu Thr Leu Asn Met Asn Leu Ala Pro Ser
405 410 415

Val Ser Pro Leu Phe Pro Gly Glu Gln Leu Leu Phe Phe Arg Ser His
420 425 430

Ile Pro Leu Lys Gly Gly Thr Ser Asp Gly Ala Ile Asp Cys Leu Leu
435 440 445

Pro Gln Glu Trp Ile Gln His Phe Tyr Gln Glu Ser Ala Pro Ser Pro
450 455 460

Thr Asp Val Ala Leu Ile Arg Tyr Thr Asn Pro Asp Thr Gly Arg Val
465 470 475 480

Leu Phe Glu Ala Lys Leu His Arg Gln Gly Phe Ile Thr Val Ala Asn
485 490 495

Ser Gly Ser Arg Pro Ile Val Val Pro Pro Asn Gly Tyr Phe Arg Phe
500 505 510

Asp Ser Trp Val Asn Gln Phe Tyr Ser Leu Ala Pro Met Gly Thr Gly
515 520 525

Asn Gly Arg Arg Arg Val Gln
530 535

<210> SEQ ID NO 24
<211> LENGTH: 535
<212> TYPE: PRT
<213> ORGANISM: Norwalk virus

<400> SEQUENCE: 24

Met Lys Met Ala Ser Asn Asp Ala Ala Pro Ser Asn Asp Gly Ala Ala
1 5 10 15

Gly Leu Val Pro Glu Val Asn Asn Glu Met Met Ala Leu Glu Pro Val
20 25 30

Ala Gly Ala Ser Ile Ala Ala Pro Leu Thr Gly Gln Asn Asn Val Ile
35 40 45

Asp Pro Trp Ile Arg Met Asn Phe Val Gln Ala Pro Asn Gly Glu Phe
50 55 60

Thr Val Ser Pro Arg Asn Ser Pro Gly Glu Ile Leu Leu Asn Leu Glu
65 70 75 80

Leu Gly Pro Glu Leu Asn Pro Phe Leu Ala His Leu Ser Arg Met Tyr
85 90 95

Asn Gly Tyr Ala Gly Gly Val Glu Val Gln Val Leu Leu Ala Gly Asn
100 105 110

Ala Phe Thr Ala Gly Lys Leu Val Phe Ala Ala Ile Pro Pro Arg Phe
115 120 125

Pro Ile Glu Asn Leu Ser Pro Gly Gln Ile Thr Met Phe Pro His Val

-continued

```
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Glu Pro Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220

Lys Pro Phe Thr Leu Pro Ile Leu Thr Ile Gly Glu Leu Ser Asn Ser
225                 230                 235                 240

Arg Phe Pro Ala Pro Ile Asp Glu Leu Tyr Thr Ser Pro Asn Glu Gly
                245                 250                 255

Leu Val Val Gln Pro Gln Asn Gly Arg Ser Thr Leu Asp Gly Glu Leu
            260                 265                 270

Leu Gly Thr Thr Gln Leu Val Pro Ser Asn Ile Cys Ser Leu Arg Gly
        275                 280                 285

Arg Ile Asn Ala His Leu Pro Asp Asn Gln His Arg Trp Asn Met Gln
    290                 295                 300

Val Thr Asn Ala Asn Gly Thr Pro Phe Asp Pro Thr Glu Asp Val Pro
305                 310                 315                 320

Ala Pro Leu Gly Thr Pro Asp Phe Leu Ala Asn Ile Tyr Gly Val Thr
                325                 330                 335

Ser Gln Arg Asn Pro Asp Asn Thr Cys Arg Ala His Asp Gly Ile Leu
            340                 345                 350

Ala Thr Trp Ser Pro Lys Phe Thr Pro Lys Leu Gly Ser Val Val Leu
        355                 360                 365

Gly Thr Trp Glu Asp Arg Asp Phe Asp Ile Asn Gln Pro Thr Arg Phe
    370                 375                 380

Thr Pro Val Gly Leu Tyr Asp Thr Asp His Phe Asn Gln Trp Ala Leu
385                 390                 395                 400

Pro Asn Tyr Ser Gly Ala Leu Thr Leu Asn Met Asn Leu Ala Pro Ser
                405                 410                 415

Val Ala Pro Leu Phe Pro Gly Glu Gln Leu Leu Phe Phe Arg Ser His
            420                 425                 430

Ile Pro Leu Lys Gly Gly Thr Ser Asn Gly Ala Ile Asp Cys Leu Leu
        435                 440                 445

Pro Gln Glu Trp Val Gln His Phe Tyr Gln Glu Ser Ala Pro Ser Ser
    450                 455                 460

Thr Asp Val Ala Leu Ile Arg Tyr Thr Asn Pro Asp Thr Gly Arg Val
465                 470                 475                 480

Leu Phe Glu Ala Lys Leu His Arg Gln Gly Phe Ile Thr Val Ala Asn
                485                 490                 495

Ser Gly Ser Arg Pro Ile Val Val Pro Pro Asn Gly Tyr Phe Arg Phe
            500                 505                 510

Asp Ser Trp Val Asn Gln Phe Tyr Ser Leu Ala Pro Met Gly Thr Gly
        515                 520                 525

Asn Gly Arg Arg Arg Val Gln
    530                 535
```

<210> SEQ ID NO 25

<211> LENGTH: 542
<212> TYPE: PRT
<213> ORGANISM: Norovirus

<400> SEQUENCE: 25

```
Met Lys Met Ala Ser Asn Asp Ala Ala Pro Ser Thr Asp Gly Ala Ala
1               5                   10                  15

Gly Leu Val Pro Glu Ser Asn Asn Glu Val Met Ala Leu Glu Pro Val
            20                  25                  30

Ala Gly Ala Ala Leu Ala Ala Pro Val Thr Gly Gln Thr Asn Ile Ile
        35                  40                  45

Asp Pro Trp Ile Arg Ala Asn Phe Val Gln Ala Pro Asn Gly Glu Phe
    50                  55                  60

Thr Val Ser Pro Arg Asn Ala Pro Gly Glu Val Leu Leu Ser Leu Glu
65                  70                  75                  80

Leu Gly Pro Glu Leu Asn Pro Tyr Leu Ala His Leu Ala Arg Met Tyr
                85                  90                  95

Asn Gly Tyr Ala Gly Gly Met Glu Val Gln Val Met Leu Ala Gly Asn
            100                 105                 110

Ala Phe Thr Ala Gly Lys Leu Val Phe Ala Ala Val Pro Pro His Phe
        115                 120                 125

Pro Val Glu Asn Leu Ser Pro Gln Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Lys Asp Asp Pro Lys Met
                165                 170                 175

Arg Ile Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Thr Tyr Leu Val Pro Pro Thr Val Glu Ser Lys Thr
    210                 215                 220

Lys Pro Phe Thr Leu Pro Ile Leu Thr Leu Gly Glu Leu Ser Asn Ser
225                 230                 235                 240

Arg Phe Pro Val Ser Ile Asp Gln Met Tyr Thr Ser Pro Asn Glu Val
                245                 250                 255

Ile Ser Val Gln Cys Gln Asn Gly Arg Cys Thr Leu Asp Gly Glu Leu
            260                 265                 270

Gln Gly Thr Thr Gln Leu Gln Val Ser Gly Ile Cys Ala Phe Lys Gly
        275                 280                 285

Glu Val Thr Ala His Leu His Asp Asn Asp His Leu Tyr Asn Val Thr
    290                 295                 300

Ile Thr Asn Leu Asn Gly Pro Pro Phe Asp Pro Ser Glu Asp Ile Pro
305                 310                 315                 320

Ala Pro Leu Gly Val Pro Asp Phe Gln Gly Arg Val Phe Gly Val Ile
                325                 330                 335

Ser Gln Arg Asp Lys Gln Asn Ala Ala Gly His Ser Glu Pro Ala Asn
            340                 345                 350

Arg Gly His Asp Ala Val Val Pro Thr Tyr Thr Ala Gln Tyr Thr Pro
        355                 360                 365

Lys Leu Gly Gln Val Gln Ile Gly Thr Trp Gln Thr Asp Asp Leu Gln
    370                 375                 380

Val Asn Gln Pro Val Lys Phe Thr Pro Val Gly Leu Asn Asp Thr Glu
```

385 390 395 400

His Phe Asn Gln Trp Val Val Pro Arg Tyr Ala Gly Ala Leu Asn Leu
405 410 415

Asn Thr Asn Leu Ala Pro Ser Val Ala Pro Val Phe Pro Gly Glu Arg
420 425 430

Leu Leu Phe Phe Arg Ser Tyr Ile Pro Leu Lys Gly Gly Tyr Gly Asn
435 440 445

Pro Ala Ile Asp Cys Leu Leu Pro Gln Glu Trp Val Gln His Phe Tyr
450 455 460

Gln Glu Ala Ala Pro Ser Met Ser Glu Val Ala Leu Val Arg Tyr Ile
465 470 475 480

Asn Pro Asp Thr Gly Arg Ala Leu Phe Glu Ala Lys Leu His Arg Ala
485 490 495

Gly Phe Val Thr Val Ser Ser Asn Thr Ser Ala Pro Val Val Val Pro
500 505 510

Ala Asn Gly Tyr Phe Arg Phe Asp Ser Trp Val Asn Gln Phe Tyr Ser
515 520 525

Leu Ala Pro Met Gly Ala Gly Asn Gly Arg Arg Arg Val Gln
530 535 540

<210> SEQ ID NO 26
<211> LENGTH: 548
<212> TYPE: PRT
<213> ORGANISM: Unknown
<220> FEATURE:
<221> NAME/KEY: source
<223> OTHER INFORMATION: /note="Description of Unknown: Norovirus polypeptide"

<400> SEQUENCE: 26

Met Lys Met Ala Ser Asn Asp Ala Ala Pro Ser Asn Asp Gly Ala Ala
1 5 10 15

Gly Leu Val Pro Glu Ile Asn Asn Glu Ala Met Ala Leu Asp Pro Val
20 25 30

Ala Gly Ala Ala Ile Ala Ala Pro Leu Thr Gly Gln Gln Asn Ile Ile
35 40 45

Asp Pro Trp Ile Met Asn Asn Phe Val Gln Ala Pro Gly Gly Glu Phe
50 55 60

Thr Val Ser Pro Arg Asn Ser Pro Gly Glu Val Leu Leu Asn Leu Glu
65 70 75 80

Leu Gly Pro Glu Ile Asn Pro Tyr Leu Ala His Leu Ala Arg Met Tyr
85 90 95

Asn Gly Tyr Ala Gly Gly Phe Glu Val Gln Val Val Leu Ala Gly Asn
100 105 110

Ala Phe Thr Ala Gly Lys Ile Ile Phe Ala Ala Ile Pro Pro Asn Phe
115 120 125

Pro Ile Asp Asn Leu Ser Ala Ala Gln Ile Thr Met Cys Pro His Val
130 135 140

Ile Val Asp Val Arg Gln Leu Glu Pro Val Asn Leu Pro Met Pro Asp
145 150 155 160

Val Arg Asn Asn Phe Phe His Tyr Asn Gln Gly Ser Asp Ser Arg Leu
165 170 175

Arg Leu Ile Ala Met Leu Tyr Thr Pro Leu Arg Ala Asn Asn Ser Gly
180 185 190

Asp Asp Val Phe Thr Val Ser Cys Arg Val Leu Thr Arg Pro Ser Pro
195 200 205

Asp Phe Ser Phe Asn Phe Leu Val Pro Pro Thr Val Glu Ser Lys Thr
210 215 220

Lys Pro Phe Thr Leu Pro Ile Leu Thr Ile Ser Glu Met Ser Asn Ser
225 230 235 240

Arg Phe Pro Val Pro Ile Glu Ser Leu His Thr Ser Pro Thr Glu Asn
245 250 255

Ile Val Val Gln Cys Gln Asn Gly Arg Val Thr Leu Asp Gly Glu Leu
260 265 270

Met Gly Thr Thr Gln Leu Leu Pro Ser Gln Ile Cys Ala Phe Arg Gly
275 280 285

Val Leu Thr Arg Ser Thr Ser Arg Ala Ser Asp Gln Ala Asp Thr Ala
290 295 300

Thr Pro Arg Leu Phe Asn Tyr Tyr Trp His Val Gln Leu Asp Asn Leu
305 310 315 320

Asn Gly Thr Pro Tyr Asp Pro Ala Glu Asp Ile Pro Gly Pro Leu Gly
325 330 335

Thr Pro Asp Phe Arg Gly Lys Val Phe Gly Val Ala Ser Gln Arg Asn
340 345 350

Leu Asp Ser Thr Thr Arg Ala His Glu Ala Lys Val Asp Thr Thr Ala
355 360 365

Gly Arg Phe Thr Pro Lys Leu Gly Ser Leu Glu Ile Ser Thr Asp Ser
370 375 380

Asp Asp Phe Asp Gln Asn Gln Pro Thr Lys Phe Thr Pro Val Gly Ile
385 390 395 400

Gly Val Asp Asn Glu Ala Glu Phe Gln Gln Trp Ser Leu Pro Asp Tyr
405 410 415

Ser Gly Gln Phe Thr His Asn Met Asn Leu Ala Pro Ala Val Ala Pro
420 425 430

Asn Phe Pro Gly Glu Gln Leu Leu Phe Phe Arg Ser Gln Leu Pro Ser
435 440 445

Ser Gly Gly Arg Ser Asn Gly Val Leu Asp Cys Leu Val Pro Gln Glu
450 455 460

Trp Val Gln His Phe Tyr Gln Glu Ser Ala Pro Ala Gln Thr Gln Val
465 470 475 480

Ala Leu Val Arg Tyr Val Asn Pro Asp Thr Gly Lys Val Leu Phe Glu
485 490 495

Ala Lys Leu His Lys Leu Gly Phe Met Thr Ile Ala Asn Asn Gly Asp
500 505 510

Ser Pro Ile Thr Val Pro Pro Asn Gly Tyr Phe Arg Phe Glu Ser Trp
515 520 525

Val Asn Pro Phe Tyr Thr Leu Ala Pro Met Gly Thr Gly Asn Gly Arg
530 535 540

Arg Arg Ile Gln
545

<210> SEQ ID NO 27
<211> LENGTH: 548
<212> TYPE: PRT
<213> ORGANISM: Norovirus

<400> SEQUENCE: 27

Met Lys Met Ala Ser Asn Asp Ala Ala Pro Ser Asn Asp Gly Ala Ala
1 5 10 15

Gly Leu Val Pro Glu Ile Asn Asn Glu Ala Met Ala Leu Asp Pro Val

-continued

```
            20                  25                  30

Ala Gly Ala Ala Ile Ala Ala Pro Leu Thr Gly Gln Gln Asn Ile Ile
        35                  40                  45

Asp Pro Trp Ile Met Asn Asn Phe Val Gln Ala Pro Gly Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Ile Asn Pro Tyr Leu Ala His Leu Ala Arg Met Tyr
                85                  90                  95

Asn Gly Tyr Ala Gly Gly Phe Glu Val Gln Val Val Leu Ala Gly Asn
            100                 105                 110

Ala Phe Thr Ala Gly Lys Ile Ile Phe Ala Ala Ile Pro Pro Asn Phe
        115                 120                 125

Pro Ile Asp Asn Leu Ser Ala Ala Gln Ile Thr Met Cys Pro His Val
    130                 135                 140

Ile Val Asp Val Arg Gln Leu Glu Pro Val Asn Leu Pro Met Pro Asp
145                 150                 155                 160

Val Arg Asn Asn Phe Phe His Tyr Asn Gln Gly Ser Asp Ser Arg Leu
                165                 170                 175

Arg Leu Ile Ala Met Leu Tyr Thr Pro Leu Arg Ala Asn Asn Ser Gly
            180                 185                 190

Asp Asp Val Phe Thr Val Ser Cys Arg Val Leu Thr Arg Pro Ser Pro
        195                 200                 205

Asp Phe Ser Phe Asn Phe Leu Val Pro Pro Thr Val Glu Ser Lys Thr
    210                 215                 220

Lys Pro Phe Thr Leu Pro Ile Leu Thr Ile Ser Glu Met Ser Asn Ser
225                 230                 235                 240

Arg Phe Pro Val Pro Ile Glu Ser Leu His Thr Ser Pro Thr Glu Asn
                245                 250                 255

Ile Val Val Gln Cys Gln Asn Gly Arg Val Thr Leu Asp Gly Glu Leu
            260                 265                 270

Met Gly Thr Thr Gln Leu Leu Pro Ser Gln Ile Cys Ala Phe Arg Gly
        275                 280                 285

Val Leu Thr Arg Ser Thr Ser Arg Ala Ser Asp Gln Ala Asp Thr Ala
    290                 295                 300

Thr Pro Arg Leu Phe Asn Tyr Tyr Trp His Val Gln Leu Asp Asn Leu
305                 310                 315                 320

Asn Gly Thr Pro Tyr Asp Pro Ala Glu Asp Ile Pro Gly Pro Leu Gly
                325                 330                 335

Thr Pro Asp Phe Arg Gly Lys Val Phe Gly Val Ala Ser Gln Arg Asn
            340                 345                 350

Pro Asp Ser Thr Thr Arg Ala His Glu Ala Lys Val Asp Thr Thr Ala
        355                 360                 365

Gly Arg Phe Thr Pro Lys Leu Gly Ser Leu Glu Ile Ser Thr Glu Ser
    370                 375                 380

Ser Asp Phe Asp Gln Asn Gln Pro Thr Arg Phe Thr Pro Val Gly Ile
385                 390                 395                 400

Gly Val Asp Asn Glu Ala Asp Phe Gln Gln Trp Ser Leu Pro Asp Tyr
                405                 410                 415

Ser Gly Gln Phe Thr His Asn Met Asn Leu Ala Pro Ala Val Ala Pro
            420                 425                 430

Asn Phe Pro Gly Glu Gln Leu Leu Phe Phe Arg Ser Gln Leu Pro Ser
        435                 440                 445
```

```
Ser Gly Gly Arg Ser Asn Gly Val Leu Asp Cys Leu Val Pro Gln Glu
    450                 455                 460

Trp Val Gln His Phe Tyr Gln Glu Ser Ala Pro Ala Gln Thr Gln Val
465                 470                 475                 480

Ala Leu Val Arg Tyr Val Asn Pro Asp Thr Gly Arg Val Leu Phe Glu
                485                 490                 495

Ala Lys Leu His Lys Leu Gly Phe Met Thr Ile Ala Lys Asn Gly Asp
            500                 505                 510

Ser Pro Ile Thr Val Pro Pro Asn Gly Tyr Phe Arg Phe Glu Ser Trp
        515                 520                 525

Val Asn Pro Phe Tyr Thr Leu Ala Pro Met Gly Thr Gly Asn Gly Arg
    530                 535                 540

Arg Arg Ile Gln
545


<210> SEQ ID NO 28
<211> LENGTH: 548
<212> TYPE: PRT
<213> ORGANISM: Norwalk virus

<400> SEQUENCE: 28

Met Lys Met Ala Ser Asn Asp Ala Ala Pro Ser Asn Asp Gly Ala Ala
1               5                   10                  15

Gly Leu Val Pro Glu Ile Asn Asn Glu Ala Met Ala Leu Glu Pro Val
            20                  25                  30

Ala Gly Ala Ala Ile Ala Ala Pro Leu Thr Gly Gln Gln Asn Ile Ile
        35                  40                  45

Asp Pro Trp Ile Met Asn Asn Phe Val Gln Ala Pro Gly Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Ile Asn Pro Tyr Leu Ala His Leu Ala Arg Met Tyr
                85                  90                  95

Asn Gly Tyr Ala Gly Gly Phe Glu Val Gln Val Val Leu Ala Gly Asn
            100                 105                 110

Ala Phe Thr Ala Gly Lys Val Ile Phe Ala Ala Ile Pro Pro Asn Phe
        115                 120                 125

Pro Ile Asp Asn Leu Ser Ala Ala Gln Ile Thr Met Cys Pro His Val
    130                 135                 140

Ile Val Asp Val Arg Gln Leu Glu Pro Ile Asn Leu Pro Met Pro Asp
145                 150                 155                 160

Val Arg Asn Asn Phe Phe His Tyr Asn Gln Gly Ser Asp Ser Arg Leu
                165                 170                 175

Arg Leu Ile Ala Met Leu Tyr Thr Pro Leu Arg Ala Asn Asn Ser Gly
            180                 185                 190

Asp Asp Val Phe Thr Val Ser Cys Arg Val Leu Thr Arg Pro Ser Pro
        195                 200                 205

Asp Phe Ser Phe Asn Phe Leu Val Pro Pro Thr Val Glu Ser Lys Thr
    210                 215                 220

Lys Leu Phe Thr Leu Pro Ile Leu Thr Ile Ser Glu Met Ser Asn Ser
225                 230                 235                 240

Arg Phe Pro Val Pro Ile Asp Ser Leu His Thr Ser Pro Thr Glu Asn
                245                 250                 255

Ile Val Val Gln Cys Gln Asn Gly Arg Val Thr Leu Asp Gly Glu Leu
```

```
            260                 265                 270

Met Gly Thr Thr Gln Leu Leu Pro Ser Gln Ile Cys Ala Phe Arg Gly
        275                 280                 285

Thr Leu Thr Arg Pro Thr Ser Arg Ala Ser Asp Gln Ala Asp Thr Pro
    290                 295                 300

Thr Pro Arg Leu Phe Asn His Arg Trp His Ile Gln Leu Asp Asn Leu
305                 310                 315                 320

Asn Gly Thr Pro Tyr Asp Pro Ala Glu Asp Ile Pro Ala Pro Leu Gly
                325                 330                 335

Thr Pro Asp Phe Arg Gly Lys Val Phe Gly Val Ala Ser Gln Arg Asn
            340                 345                 350

Pro Asp Ser Thr Thr Arg Ala His Glu Ala Lys Val Asp Thr Thr Ser
        355                 360                 365

Gly Arg Phe Thr Pro Lys Leu Gly Ser Leu Glu Ile Thr Thr Glu Ser
    370                 375                 380

Asp Asp Phe Asp Thr Asn Gln Ser Thr Lys Phe Thr Pro Val Gly Ile
385                 390                 395                 400

Gly Val Asp Asn Glu Ala Glu Phe Gln Gln Trp Ser Leu Pro Asn Tyr
                405                 410                 415

Ser Gly Gln Phe Thr His Asn Met Asn Leu Ala Pro Ala Val Ala Pro
            420                 425                 430

Asn Phe Pro Gly Glu Gln Leu Leu Phe Phe Arg Ser Gln Leu Pro Ser
        435                 440                 445

Ser Gly Gly Arg Ser Asn Gly Val Leu Asp Cys Leu Val Pro Gln Glu
    450                 455                 460

Trp Val Gln His Phe Tyr Gln Glu Ser Ala Pro Ala Gln Thr Gln Val
465                 470                 475                 480

Ala Leu Val Lys Tyr Val Asn Pro Asp Thr Gly Arg Val Leu Phe Glu
                485                 490                 495

Ala Lys Leu His Lys Leu Gly Phe Met Thr Ile Ala Lys Asn Gly Asp
            500                 505                 510

Ser Pro Ile Thr Val Pro Pro Asn Gly Tyr Phe Arg Phe Glu Ser Trp
        515                 520                 525

Val Asn Pro Phe Tyr Thr Leu Ala Pro Met Gly Thr Gly Asn Gly Arg
    530                 535                 540

Arg Arg Ile Gln
545


<210> SEQ ID NO 29
<211> LENGTH: 548
<212> TYPE: PRT
<213> ORGANISM: Norwalk virus

<400> SEQUENCE: 29

Met Lys Met Ala Ser Asn Asp Ala Ala Pro Ser Asn Asp Gly Ala Ala
1               5                   10                  15

Gly Leu Val Pro Glu Ile Asn Asn Glu Ala Met Ala Leu Asp Pro Val
            20                  25                  30

Ala Gly Ala Ala Ile Ala Ala Pro Leu Thr Gly Gln Gln Asn Ile Ile
        35                  40                  45

Asp Pro Trp Ile Met Asn Asn Phe Val Gln Ala Pro Gly Gly Glu Phe
    50                  55                  60

Thr Val Ser Pro Arg Asn Ser Pro Gly Glu Val Leu Leu Asn Leu Glu
65                  70                  75                  80
```

-continued

```
Leu Gly Pro Glu Ile Asn Pro Tyr Leu Ala His Leu Ala Arg Met Tyr
                85                  90                  95

Asn Gly Tyr Ala Gly Gly Phe Glu Val Gln Val Val Leu Ala Gly Asn
            100                 105                 110

Ala Phe Thr Ala Gly Lys Val Ile Phe Ala Ala Ile Pro Pro Asn Phe
        115                 120                 125

Pro Ile Asp Asn Leu Ser Ala Ala Gln Ile Thr Met Cys Pro His Val
    130                 135                 140

Ile Val Asp Val Arg Gln Leu Glu Pro Ile Asn Leu Pro Met Pro Asp
145                 150                 155                 160

Val Arg Asn Asn Phe Phe His Tyr Asn Gln Gly Ser Asp Ser Arg Leu
                165                 170                 175

Arg Leu Ile Ala Met Leu Tyr Thr Pro Leu Arg Ala Asn Asn Ser Gly
            180                 185                 190

Asp Asp Val Phe Thr Val Ser Cys Arg Val Leu Thr Arg Pro Ser Pro
        195                 200                 205

Asp Phe Ser Phe Asn Phe Leu Val Pro Pro Thr Val Glu Ser Lys Thr
    210                 215                 220

Lys Pro Phe Thr Leu Pro Ile Leu Thr Ile Ser Glu Met Ser Asn Ser
225                 230                 235                 240

Arg Phe Pro Val Pro Ile Asp Ser Leu His Thr Ser Pro Thr Glu Ser
                245                 250                 255

Val Val Val Gln Cys Gln Asn Gly Arg Val Thr Leu Asp Gly Glu Leu
            260                 265                 270

Met Gly Thr Thr Gln Leu Leu Pro Ser Gln Ile Cys Ala Phe Arg Gly
        275                 280                 285

Thr Leu Thr Arg Pro Thr Asn Arg Ala Ser Asp Gln Ala Asp Thr Ala
    290                 295                 300

Thr Pro Arg Leu Phe Asn His Gln Trp His Ile Gln Leu Asp Asn Leu
305                 310                 315                 320

Asn Gly Thr Pro Tyr Asp Pro Ala Glu Asp Ile Pro Ala Pro Leu Gly
                325                 330                 335

Thr Pro Asp Phe Arg Gly Lys Val Phe Gly Val Ala Ser Gln Arg Asp
            340                 345                 350

Pro Asp Gly Thr Thr Arg Ala His Glu Ala Lys Val Asp Thr Thr Ser
        355                 360                 365

Gly Arg Phe Thr Pro Lys Leu Gly Ser Leu Glu Ile Thr Thr Glu Ser
    370                 375                 380

Asp Asp Phe Asn Gln Asn Lys Pro Thr Arg Phe Thr Pro Val Gly Ile
385                 390                 395                 400

Gly Val Asp Asn Glu Ala Asp Phe Gln Gln Trp Ile Leu Pro Asp Tyr
                405                 410                 415

Ser Gly Gln Phe Thr His Asn Met Asn Leu Ala Pro Ala Val Ala Pro
            420                 425                 430

Asn Phe Pro Gly Glu Gln Leu Leu Phe Phe Arg Ser Gln Leu Pro Ser
        435                 440                 445

Ser Gly Gly Arg Ser Asn Gly Ile Leu Asp Cys Leu Val Pro Gln Glu
    450                 455                 460

Trp Val Gln His Phe Tyr Gln Glu Ser Ala Pro Ala Gln Thr Gln Val
465                 470                 475                 480

Ala Leu Val Arg Tyr Val Asn Pro Asp Thr Gly Arg Val Leu Phe Glu
                485                 490                 495

Ala Lys Leu His Lys Met Gly Phe Met Thr Ile Ala Lys Asn Gly Asp
```

500 505 510

Ser Pro Ile Thr Val Pro Pro Asn Gly Tyr Phe Arg Phe Glu Ser Trp
515 520 525

Val Asn Pro Phe Tyr Thr Leu Ala Pro Met Gly Thr Gly Lys Gly Arg
530 535 540

Arg Arg Ile Gln
545

<210> SEQ ID NO 30
<211> LENGTH: 548
<212> TYPE: PRT
<213> ORGANISM: Unknown
<220> FEATURE:
<221> NAME/KEY: source
<223> OTHER INFORMATION: /note="Description of Unknown: Norovirus polypeptide"

<400> SEQUENCE: 30

Met Lys Met Ala Ser Asn Asp Ala Ala Pro Ser Asn Asp Gly Ala Ala
1 5 10 15

Gly Leu Val Pro Glu Ile Asn Asn Glu Ala Met Ala Leu Asp Pro Val
20 25 30

Ala Gly Ala Ala Ile Ala Ala Pro Leu Thr Gly Gln Gln Asn Ile Ile
35 40 45

Asp Pro Trp Ile Met Asn Asn Phe Val Gln Ala Pro Gly Gly Glu Phe
50 55 60

Thr Val Ser Pro Arg Asn Ser Pro Gly Glu Val Leu Leu Asn Leu Glu
65 70 75 80

Leu Gly Pro Glu Ile Asn Pro Tyr Leu Ala His Leu Ala Arg Met Tyr
85 90 95

Asn Gly Tyr Ala Gly Gly Phe Glu Val Gln Val Val Leu Ala Gly Asn
100 105 110

Ala Phe Thr Ala Gly Lys Val Ile Phe Ala Ala Ile Pro Pro Asn Phe
115 120 125

Pro Ile Asp Asn Leu Ser Ala Ala Gln Ile Thr Met Cys Pro His Val
130 135 140

Ile Val Asp Val Arg Gln Leu Glu Pro Ile Asn Leu Pro Met Pro Asp
145 150 155 160

Val Arg Asn Asn Phe Phe His Tyr Asn Gln Gly Ser Asp Ser Arg Leu
165 170 175

Arg Leu Ile Ala Met Leu Tyr Thr Pro Leu Arg Ala Asn Asn Ser Gly
180 185 190

Asp Asp Val Phe Thr Val Ser Cys Arg Val Leu Thr Arg Pro Ser Pro
195 200 205

Asp Phe Ser Phe Asn Phe Leu Val Pro Pro Thr Val Glu Ser Lys Thr
210 215 220

Lys Pro Phe Thr Leu Pro Ile Leu Thr Ile Ser Glu Met Ser Asn Ser
225 230 235 240

Arg Phe Pro Val Pro Ile Asp Ser Leu His Thr Ser Pro Thr Glu Asn
245 250 255

Ile Val Val Gln Cys Gln Asn Gly Arg Val Thr Leu Asp Gly Glu Leu
260 265 270

Met Gly Thr Thr Gln Leu Leu Pro Ser Gln Ile Cys Thr Phe Arg Gly
275 280 285

Thr Leu Thr Arg Ser Thr Ser Arg Ala Ser Asp Gln Ala Asp Thr Ala
290 295 300

Thr Pro Arg Leu Phe Asn Tyr Tyr Trp His Ile Gln Leu Asp Asn Leu
305 310 315 320

Asn Gly Thr Pro Tyr Asp Pro Ala Glu Asp Ile Pro Ala Pro Leu Gly
325 330 335

Thr Pro Asp Phe Arg Gly Lys Val Phe Gly Val Ala Ser Gln Arg Asn
340 345 350

Pro Asp Ser Thr Thr Arg Ala His Glu Ala Lys Val Asp Thr Thr Ser
355 360 365

Gly Arg Phe Ile Pro Lys Leu Gly Ser Leu Glu Ile Ser Thr Glu Ser
370 375 380

Asp Asp Phe Asp Gln Asn Gln Pro Thr Arg Phe Thr Pro Val Gly Ile
385 390 395 400

Gly Val Asp Asn Glu Ala Gly Phe Gln Gln Trp Ser Leu Pro Asp Tyr
405 410 415

Ser Gly Gln Phe Thr His Asn Met Asn Leu Ala Pro Ala Val Ala Pro
420 425 430

Asn Phe Pro Gly Glu Gln Leu Leu Phe Phe Arg Ser Gln Leu Pro Ser
435 440 445

Ser Gly Gly Arg Ser Asn Gly Ile Leu Asp Cys Leu Val Pro Gln Glu
450 455 460

Trp Val Gln His Phe Tyr Gln Glu Ser Ala Pro Ala Gln Thr Gln Val
465 470 475 480

Ala Leu Val Arg Tyr Val Asn Pro Asp Thr Gly Arg Val Leu Phe Glu
485 490 495

Ala Lys Leu His Lys Leu Gly Phe Met Thr Ile Ser Lys Asn Gly Asp
500 505 510

Ser Pro Ile Thr Val Pro Pro Asn Gly Tyr Phe Arg Phe Glu Ser Trp
515 520 525

Val Asn Pro Phe Tyr Thr Leu Ala Pro Met Gly Thr Gly Asn Gly Arg
530 535 540

Arg Arg Ile Gln
545

<210> SEQ ID NO 31
<211> LENGTH: 539
<212> TYPE: PRT
<213> ORGANISM: Norwalk-like virus

<400> SEQUENCE: 31

Met Lys Met Ala Ser Asn Asp Ala Asn Pro Ser Asp Gly Ser Thr Ala
1 5 10 15

Asn Leu Val Pro Glu Val Asn Asn Glu Val Met Ala Leu Glu Pro Val
20 25 30

Val Gly Ala Ala Ile Ala Ala Pro Val Ala Gly Gln Gln Asn Val Ile
35 40 45

Asp Pro Trp Ile Arg Asn Asn Phe Val Gln Ala Pro Gly Gly Glu Phe
50 55 60

Thr Val Ser Pro Arg Asn Ala Pro Gly Glu Ile Leu Trp Ser Ala Pro
65 70 75 80

Leu Gly Pro Asp Leu Asn Pro Tyr Leu Ser His Leu Ala Arg Met Tyr
85 90 95

Asn Gly Tyr Ala Gly Gly Phe Glu Val Gln Val Ile Leu Ala Gly Asn
100 105 110

Ala Phe Thr Ala Gly Lys Ile Ile Phe Ala Ala Val Pro Pro Asn Phe

-continued

```
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Ser Asn Ser
225                 230                 235                 240

Arg Phe Pro Ile Pro Leu Glu Lys Leu Tyr Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Ala Val Asn Ile Cys Thr Phe Arg Gly
        275                 280                 285

Asp Val Thr His Ile Ala Gly Ser His Asp Tyr Thr Met Asn Leu Ala
    290                 295                 300

Ser Gln Asn Trp Ser Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Arg Glu Asp Gly Ser Thr Arg Ala His Lys Ala Thr Val Ser
            340                 345                 350

Thr Gly Ser Val His Phe Thr Pro Lys Leu Gly Ser Val Gln Tyr Thr
        355                 360                 365

Thr Asp Thr Asn Asn Asp Phe Gln Thr Gly Gln Asn Thr Lys Phe Thr
    370                 375                 380

Pro Val Gly Val Ile Gln Asp Gly Asn Asn His Gln Asn Glu Pro Gln
385                 390                 395                 400

Gln Trp Val Leu Pro Asn Tyr Ser Gly Arg Thr Gly His Asn Val His
                405                 410                 415

Leu Ala Pro Ala Val Ala Pro Thr Phe Pro Gly Glu Gln Leu Leu Phe
            420                 425                 430

Phe Arg Ser Thr Met Pro Gly Cys Ser Gly Tyr Pro Asn Met Asn Leu
        435                 440                 445

Asp Cys Leu Leu Pro Gln Glu Trp Val Gln His Phe Cys Gln Glu Ala
    450                 455                 460

Ala Pro Ala Gln Ser Asp Val Ala Leu Leu Arg Phe Val Asn Pro Asp
465                 470                 475                 480

Thr Gly Arg Val Leu Phe Glu Cys Lys Leu His Lys Ser Gly Tyr Val
                485                 490                 495

Thr Val Ala His Thr Gly Pro His Asp Leu Val Ile Pro Pro Asn Gly
            500                 505                 510

Tyr Phe Arg Phe Asp Ser Trp Val Asn Gln Phe Tyr Thr Leu Ala Pro
        515                 520                 525

Met Gly Asn Gly Ala Gly Arg Arg Arg Ala Leu
    530                 535
```

<210> SEQ ID NO 32
<211> LENGTH: 540
<212> TYPE: PRT
<213> ORGANISM: Unknown
<220> FEATURE:
<221> NAME/KEY: source
<223> OTHER INFORMATION: /note="Description of Unknown: Norovirus polypeptide"

<400> SEQUENCE: 32

```
Met Lys Met Ala Ser Asn Asp Ala Thr Pro Ser Asn Asp Gly Ala Ala
1               5                   10                  15

Gly Leu Val Pro Glu Ser Asn Asn Glu Ala Met Ala Leu Glu Pro Val
            20                  25                  30

Val Gly Ala Ser Leu Ala Ala Pro Val Thr Gly Gln Thr Asn Ile Ile
        35                  40                  45

Asp Pro Trp Ile Arg Thr Asn Phe Val Gln Ala Pro Asn Gly Glu Phe
    50                  55                  60

Thr Val Ser Pro Arg Asn Ser Pro Gly Glu Ile Leu Val Asn Leu Glu
65                  70                  75                  80

Leu Gly Pro Glu Leu Asn Pro Tyr Leu Ala His Leu Ala Arg Met Tyr
                85                  90                  95

Asn Gly Tyr Ala Gly Gly Met Glu Val Gln Val Met Leu Ala Gly Asn
            100                 105                 110

Ala Phe Thr Ala Gly Lys Ile Ile Phe Ala Ala Val Pro Pro Tyr Phe
        115                 120                 125

Pro Val Glu Asn Leu Ser Pro Ser Gln Ile Thr Met Phe Pro His Val
    130                 135                 140

Ile Ile Asp Val Arg Thr Leu Glu Pro Val Leu Leu Pro Met Pro Asp
145                 150                 155                 160

Val Arg Ser Thr Leu Phe His Phe Asn Gln Lys Asp Glu Pro Lys Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Ile Leu Thr Arg Pro Ser Pro
        195                 200                 205

Glu Phe Asp Phe Thr Tyr Leu Val Pro Pro Thr Val Glu Ser Lys Thr
    210                 215                 220

Lys Pro Phe Thr Leu Pro Val Leu Thr Leu Gly Glu Leu Ser Asn Ser
225                 230                 235                 240

Arg Phe Pro Leu Ser Ile Asp Glu Met Val Thr Ser Pro Asn Glu Ser
                245                 250                 255

Ile Val Val Gln Pro Gln Asn Gly Arg Val Thr Leu Asp Gly Glu Leu
            260                 265                 270

Leu Gly Thr Thr Gln Leu Gln Ala Cys Asn Ile Cys Ser Ile Arg Gly
        275                 280                 285

Lys Val Thr Gly Gln Val Pro Ser Glu Gln His Met Trp Asn Leu Glu
    290                 295                 300

Ile Thr Asn Leu Asn Gly Thr Gln Phe Asp Pro Thr Asp Asp Val Pro
305                 310                 315                 320

Ala Pro Leu Gly Val Pro Asp Phe Ala Gly Glu Val Phe Gly Val Leu
                325                 330                 335

Ser Gln Arg Asn Arg Gly Glu Ser Asn Pro Ala Asn Arg Ala His Asp
            340                 345                 350
```

```
Ala Val Val Ala Thr Tyr Ser Asp Lys Tyr Thr Pro Lys Leu Gly Leu
        355                 360                 365

Val Gln Ile Gly Thr Trp Asn Thr Asn Asp Val Glu Asn Gln Pro Thr
    370                 375                 380

Lys Phe Thr Pro Ile Gly Leu Asn Glu Val Ala Asn Gly His Arg Phe
385                 390                 395                 400

Glu Gln Trp Thr Leu Pro Arg Tyr Ser Gly Ala Leu Thr Leu Asn Met
                405                 410                 415

Asn Leu Ala Pro Ala Val Ala Pro Leu Phe Pro Gly Glu Arg Leu Leu
            420                 425                 430

Phe Phe Arg Ser Tyr Val Pro Leu Lys Gly Gly Phe Gly Asn Pro Ala
        435                 440                 445

Ile Asp Cys Ser Val Pro Gln Glu Trp Val Gln His Phe Tyr Gln Glu
    450                 455                 460

Ser Ala Pro Ser Leu Gly Asp Val Ala Leu Val Arg Tyr Val Asn Pro
465                 470                 475                 480

Asp Thr Gly Arg Val Leu Phe Glu Ala Lys Leu His Lys Gly Gly Phe
                485                 490                 495

Leu Thr Val Ser Ser Thr Ser Thr Gly Pro Val Val Val Pro Ala Asn
            500                 505                 510

Gly Tyr Phe Lys Phe Asp Ser Trp Val Asn Gln Phe Tyr Ser Leu Ala
        515                 520                 525

Pro Met Gly Thr Gly Asn Gly Arg Arg Arg Val Gln
    530                 535                 540


<210> SEQ ID NO 33
<211> LENGTH: 550
<212> TYPE: PRT
<213> ORGANISM: Norwalk-like virus

<400> SEQUENCE: 33

Met Lys Met Ala Ser Asn Asp Ala Ala Pro Ser Asn Asp Gly Ala Ala
1               5                   10                  15

Asn Leu Val Pro Glu Ala Asn Asp Glu Val Met Ala Leu Glu Pro Val
            20                  25                  30

Val Gly Ala Ser Ile Ala Ala Pro Val Val Gly Gln Gln Asn Ile Ile
        35                  40                  45

Asp Pro Trp Ile Arg Glu Asn Phe Val Gln Ala Pro Gln Gly Glu Phe
    50                  55                  60

Thr Val Ser Pro Arg Asn Ser Pro Gly Glu Met Leu Leu Asn Leu Glu
65                  70                  75                  80

Leu Gly Pro Glu Leu Asn Pro Tyr Leu Ser His Leu Ser Arg Met Tyr
                85                  90                  95

Asn Gly Tyr Ala Gly Gly Met Gln Val Gln Val Val Leu Ala Gly Asn
            100                 105                 110

Ala Phe Thr Ala Gly Lys Ile Ile Phe Ala Ala Val Pro Pro His Phe
        115                 120                 125

Pro Val Glu Asn Ile Ser Ala Ala Gln Ile Thr Met Cys Pro His Val
    130                 135                 140

Ile Val Asp Val Arg Gln Leu Glu Pro Val Leu Leu Pro Leu Pro Asp
145                 150                 155                 160

Ile Arg Asn Arg Phe Phe His Tyr Asn Gln Glu Asn Thr Pro Arg Met
                165                 170                 175

Arg Leu Val Ala Met Leu Tyr Thr Pro Leu Arg Ala Asn Ser Gly Glu
            180                 185                 190
```

```
Asp Val Phe Thr Val Ser Cys Arg Val Leu Thr Arg Pro Ala Pro Asp
        195                 200                 205

Phe Glu Phe Thr Phe Leu Val Pro Pro Thr Val Glu Ser Lys Thr Lys
    210                 215                 220

Pro Phe Thr Leu Pro Ile Leu Thr Leu Gly Glu Leu Ser Asn Ser Arg
225                 230                 235                 240

Phe Pro Ala Ala Ile Asp Met Leu Tyr Thr Asp Pro Asn Glu Ser Ile
                245                 250                 255

Val Val Gln Pro Gln Asn Gly Arg Cys Thr Leu Asp Gly Thr Leu Gln
            260                 265                 270

Gly Thr Thr Gln Leu Val Pro Thr Gln Ile Cys Ala Phe Arg Gly Thr
        275                 280                 285

Leu Ile Ser Gln Thr Ala Arg Ala Ala Asp Ser Thr Asp Ser Pro Gln
    290                 295                 300

Arg Ala Arg Asn His Pro Leu His Val Gln Val Lys Asn Leu Asp Gly
305                 310                 315                 320

Thr Gln Tyr Asp Pro Thr Asp Asp Ile Pro Ala Val Leu Gly Ala Ile
                325                 330                 335

Asp Phe Lys Gly Thr Val Phe Gly Val Ala Ser Gln Arg Asp Val Ser
            340                 345                 350

Gly Gln Gln Glu Gln Gly His Tyr Ala Thr Arg Ala His Glu Ala His
        355                 360                 365

Ile Asp Thr Thr Asp Pro Lys Tyr Ala Pro Lys Leu Gly Thr Ile Leu
    370                 375                 380

Ile Lys Ser Gly Ser Asp Asp Phe Asn Thr Asn Gln Pro Ile Arg Phe
385                 390                 395                 400

Thr Pro Val Gly Met Gly Asp Asn Asn Trp Arg Gln Trp Glu Leu Pro
                405                 410                 415

Asp Tyr Ser Gly Arg Leu Thr Leu Asn Met Asn Leu Ala Pro Ala Val
            420                 425                 430

Ser Pro Ser Phe Pro Gly Glu Arg Ile Leu Phe Phe Arg Ser Ile Val
        435                 440                 445

Pro Ser Ala Gly Gly Tyr Gly Ser Gly Tyr Ile Asp Cys Leu Ile Pro
    450                 455                 460

Gln Glu Trp Val Gln His Phe Tyr Gln Glu Ala Ala Pro Ser Gln Ser
465                 470                 475                 480

Ala Val Ala Leu Val Arg Tyr Val Asn Pro Asp Thr Gly Arg Asn Ile
                485                 490                 495

Phe Glu Ala Lys Leu His Arg Glu Gly Phe Leu Thr Val Ala Asn Cys
            500                 505                 510

Gly Asn Asn Pro Ile Val Val Pro Pro Asn Gly Tyr Phe Arg Phe Glu
        515                 520                 525

Ala Trp Gly Asn Gln Phe Tyr Thr Leu Ala Pro Met Gly Ser Gly Gln
    530                 535                 540

Gly Arg Arg Arg Ala Gln
545                 550


<210> SEQ ID NO 34
<211> LENGTH: 549
<212> TYPE: PRT
<213> ORGANISM: Norwalk virus

<400> SEQUENCE: 34

Met Lys Met Ala Ser Asn Asp Ala Ala Pro Ser Asn Asp Gly Ala Ala
```

-continued

```
1               5                   10                  15

Asn Leu Val Pro Glu Ala Asn Asn Glu Val Met Ala Leu Glu Pro Val
            20                  25                  30

Val Gly Ala Ser Ile Ala Ala Pro Val Val Gly Gln Gln Asn Ile Ile
        35                  40                  45

Asp Pro Trp Ile Arg Glu Asn Phe Val Gln Ala Pro Gln Gly Glu Phe
    50                  55                  60

Thr Val Ser Pro Arg Asn Ser Pro Gly Glu Met Leu Leu Asn Leu Glu
65                  70                  75                  80

Leu Gly Pro Glu Leu Asn Pro Tyr Leu Ser His Leu Ser Arg Met Tyr
                85                  90                  95

Asn Gly Tyr Ala Gly Gly Met Gln Val Gln Val Val Leu Ala Gly Asn
            100                 105                 110

Ala Phe Thr Ala Gly Lys Ile Ile Phe Ala Ala Val Pro Pro His Phe
        115                 120                 125

Pro Val Asp Asn Ile Ser Ala Ala Gln Ile Thr Met Cys Pro His Val
    130                 135                 140

Ile Val Asp Val Arg Gln Leu Glu Pro Val Leu Leu Pro Leu Pro Asp
145                 150                 155                 160

Ile Arg Asn Arg Phe Phe His Tyr Asn Gln Glu Asn Thr Pro Arg Met
                165                 170                 175

Arg Leu Val Ala Met Leu Tyr Thr Pro Leu Arg Ala Asn Ser Gly Glu
            180                 185                 190

Asp Val Phe Thr Val Ser Cys Arg Val Leu Thr Arg Pro Ala Pro Asp
        195                 200                 205

Phe Glu Phe Thr Phe Leu Val Pro Pro Thr Val Glu Ser Lys Thr Lys
    210                 215                 220

Pro Phe Thr Leu Pro Ile Leu Thr Leu Gly Glu Leu Ser Asn Ser Arg
225                 230                 235                 240

Phe Pro Ala Ala Ile Asp Met Leu Tyr Ala Asp Pro Asn Glu Ser Ile
                245                 250                 255

Val Val Gln Pro Gln Asn Gly Arg Cys Thr Leu Asp Gly Thr Leu Gln
            260                 265                 270

Gly Thr Thr Gln Leu Val Pro Thr Gln Ile Cys Ala Phe Arg Gly Thr
        275                 280                 285

Leu Ile Ser Gln Thr Ala Arg Ala Thr Asp Ser Thr Asp Ser Pro Gln
    290                 295                 300

Arg Ala Arg Asp His Pro Leu His Val Gln Val Lys Asn Leu Asp Gly
305                 310                 315                 320

Thr Gln Tyr Asp Pro Thr Asp Asp Ile Pro Ala Val Leu Gly Ala Ile
                325                 330                 335

Asp Phe Lys Gly Thr Val Phe Gly Val Ala Ser Gln Arg Asp Val Ser
            340                 345                 350

Gly Pro Gln Glu Gln Gly His Tyr Ala Thr Arg Ala His Glu Ala His
        355                 360                 365

Ile Asp Thr Thr Asp Pro Lys Tyr Ala Pro Lys Leu Gly Thr Ile Leu
    370                 375                 380

Ile Lys Ser Glu Ser Asn Asp Phe Ile Thr Asn Gln Pro Ile Arg Phe
385                 390                 395                 400

Thr Pro Val Gly Met Gly Asp Asn Asn Trp Arg Gln Trp Glu Leu Pro
                405                 410                 415

Asp Tyr Ser Gly Arg Leu Thr Leu Asn Met Asn Leu Ala Pro Ala Val
            420                 425                 430
```

Ser Pro Ser Phe Pro Gly Glu Arg Ile Leu Phe Phe Arg Ser Ile Val
435 440 445

Pro Ser Ala Gly Gly Tyr Gly Ser Gly Tyr Ile Asp Cys Leu Ile Pro
450 455 460

Gln Glu Trp Gly Gln His Phe Tyr Gln Glu Ala Ala Pro Ser Gln Ser
465 470 475 480

Ala Val Ala Leu Val Arg Tyr Val Asn Pro Asp Thr Gly Arg Asn Ile
485 490 495

Phe Glu Ala Lys Leu His Arg Glu Gly Phe Leu Thr Val Ala Asn Ser
500 505 510

Gly Asn Asn Pro Ile Val Val Pro Pro Asn Gly Tyr Phe Arg Phe Glu
515 520 525

Ala Trp Val Asn Gln Phe Tyr Thr Leu Ala Pro Met Gly Ser Gly Gln
530 535 540

Gly Arg Arg Arg Ala
545

<210> SEQ ID NO 35
<211> LENGTH: 541
<212> TYPE: PRT
<213> ORGANISM: Unknown
<220> FEATURE:
<221> NAME/KEY: source
<223> OTHER INFORMATION: /note="Description of Unknown: Norovirus polypeptide"

<400> SEQUENCE: 35

Met Lys Met Ala Ser Asn Asp Ala Ala Pro Ser Ser Asp Gly Ala Ala
1 5 10 15

Gly Leu Val Pro Glu Ile Asn Asn Glu Val Met Pro Leu Glu Pro Val
20 25 30

Ala Gly Ala Ser Leu Ala Thr Pro Val Val Gly Gln Gln Asn Ile Ile
35 40 45

Asp Pro Trp Ile Arg Asn Asn Phe Val Gln Ala Pro Ala Gly Glu Phe
50 55 60

Thr Val Ser Pro Arg Asn Ser Pro Gly Glu Ile Leu Leu Asp Leu Glu
65 70 75 80

Leu Gly Pro Asp Leu Asn Pro Tyr Leu Ala His Leu Ala Arg Met Tyr
85 90 95

Asn Gly His Ala Gly Gly Met Glu Val Gln Ile Val Leu Ala Gly Asn
100 105 110

Ala Phe Thr Ala Gly Lys Ile Ile Phe Ala Ala Ile Pro Pro Gly Phe
115 120 125

Pro Tyr Glu Asn Leu Ser Pro Ser Gln Ile Thr Met Cys Pro His Val
130 135 140

Ile Ile Asp Val Arg Gln Leu Glu Pro Phe Leu Leu Pro Met Pro Asp
145 150 155 160

Ile Trp Asn Asn Phe Phe His Tyr Asn Gln Gly Asn Asp Pro Lys Leu
165 170 175

Arg Leu Val Ala Met Leu Tyr Thr Pro Leu Arg Ala Asn Asn Ser Gly
180 185 190

Asp Asp Val Phe Thr Val Ser Cys Arg Val Leu Thr Lys Pro Ser Pro
195 200 205

Asp Phe Glu Phe Thr Phe Leu Val Pro Pro Thr Val Glu Ser Lys Thr
210 215 220

```
Lys Gln Phe Ala Leu Pro Ile Leu Lys Ile Ser Glu Met Thr Asn Ser
225                 230                 235                 240

Arg Phe Pro Val Pro Val Asp Val Met Tyr Thr Ala Arg Asn Glu Asn
                245                 250                 255

Gln Val Val Gln Pro Gln Asn Gly Arg Val Thr Leu Asp Gly Glu Leu
            260                 265                 270

Leu Gly Thr Thr Pro Leu Leu Ala Val Asn Ile Cys Lys Phe Lys Gly
        275                 280                 285

Glu Val Ile Ala Lys Asn Gly Asp Val Arg Ser Tyr Arg Met Asp Met
    290                 295                 300

Glu Ile Thr Asn Thr Asp Gly Thr Pro Ile Asp Pro Thr Glu Asp Thr
305                 310                 315                 320

Pro Gly Pro Ile Gly Ser Pro Asp Phe Gln Gly Ile Leu Phe Gly Val
                325                 330                 335

Ala Ser Gln Arg Asn Lys Asn Glu Gln Asn Pro Ala Thr Arg Ala His
            340                 345                 350

Glu Ala Ile Ile Asn Thr Gly Gly Asp His Leu Cys Pro Gln Ile Ser
        355                 360                 365

Ser Ser Glu Ile Tyr Leu Thr Ser Pro Asn Ile Leu Arg Cys Thr Asn
    370                 375                 380

Pro Gln Pro Leu Pro Gln Ser Gly Leu Arg Gly Thr Ile Leu Ile Arg
385                 390                 395                 400

Ser Asp Asn Gly His Cys His Asp Met Val Gly Thr Ser Pro Thr Thr
                405                 410                 415

Pro Thr Trp Pro Gln Gln Trp Arg Arg Cys Ser Arg Gly Ser Asn Cys
            420                 425                 430

Cys Ser Ser Gly His Arg Tyr Pro Val Pro Val Val Met Asn Arg Val
        435                 440                 445

Thr Trp Ile Val Leu Ser His Lys Ser Gly Phe Ser Thr Ser Thr Arg
    450                 455                 460

Lys Leu Pro Gln Leu Asn Leu Arg Trp Pro Leu Ile Arg Phe Ile Asn
465                 470                 475                 480

Pro Asp Thr Gly Arg Val Leu Phe Glu Ala Arg Leu His Lys Gln Gly
                485                 490                 495

Phe Ile Thr Val Ala His Thr Gly Asp Asn Pro Ile Val Met Pro Pro
            500                 505                 510

Asn Gly Tyr Phe Arg Phe Glu Ala Trp Val Asn Gln Phe Tyr Ser Leu
        515                 520                 525

Ala Pro Val Gly Thr Gly Lys Gly Arg Arg Arg Val Gln
    530                 535                 540


<210> SEQ ID NO 36
<211> LENGTH: 537
<212> TYPE: PRT
<213> ORGANISM: Norwalk-like virus

<400> SEQUENCE: 36

Met Lys Met Ala Ser Asn Asp Ala Ala Pro Ser Asn Asp Gly Ala Ala
1               5                   10                  15

Gly Leu Val Pro Glu Ile Asn His Glu Val Met Ala Ile Glu Pro Val
            20                  25                  30

Ala Gly Ala Ser Leu Ala Ala Pro Val Val Gly Gln Leu Asn Ile Ile
        35                  40                  45

Asp Pro Trp Ile Arg Asn Asn Phe Val Gln Ala Pro Ala Gly Glu Phe
    50                  55                  60
```

-continued

```
Thr Val Ser Pro Arg Asn Ala Pro Gly Glu Phe Leu Leu Asp Leu Glu
65                  70                  75                  80

Leu Gly Pro Glu Leu Asn Pro Tyr Leu Ala His Leu Ala Arg Met Tyr
                85                  90                  95

Asn Gly His Ala Gly Gly Met Glu Val Gln Ile Val Leu Ala Gly Asn
            100                 105                 110

Ala Phe Thr Ala Gly Lys Ile Leu Phe Ala Val Ile Pro Pro Gly Phe
        115                 120                 125

Pro Tyr Glu Asn Leu Ser Pro Ala Gln Leu Thr Met Cys Pro His Val
    130                 135                 140

Val Val Asp Val Arg Gln Leu Glu Pro Ile Leu Leu Pro Met Pro Asp
145                 150                 155                 160

Ile Arg Asn Thr Phe Phe His Tyr Asn Gln Ser Asn Gly Pro Lys Leu
                165                 170                 175

Arg Leu Val Ala Met Leu Tyr Thr Pro Leu Arg Ala Asn Asn Ala Gly
            180                 185                 190

Glu Asp Val Phe Thr Val Ser Cys Arg Val Leu Thr Arg Pro Ser Pro
        195                 200                 205

Asp Phe Glu Phe Asn Phe Leu Val Pro Pro Ser Val Glu Ser Lys Thr
    210                 215                 220

Lys Ala Phe Thr Leu Pro Ile Leu Lys Ile Ser Glu Met Thr Asn Ser
225                 230                 235                 240

Arg Phe Pro Ile Pro Val Asp Gln Met Tyr Thr Ser Arg Asn Glu Asn
                245                 250                 255

Ile Val Val Gln Pro Gln Asn Gly Arg Val Thr Leu Asp Gly Glu Leu
            260                 265                 270

Gln Gly Thr Thr Thr Leu Gln Pro Val Ser Ile Cys Gly Phe Arg Gly
        275                 280                 285

Thr Leu Gln Thr Arg Leu Ala Asp Gln Pro Asn Tyr Thr Tyr Gln Val
    290                 295                 300

His Leu Glu Asn Leu Asp Gly Ser Pro Val Asp Pro Thr Asp Glu Val
305                 310                 315                 320

Pro Ala Pro Leu Gly Thr Pro Asp Phe Gln Ala Gln Leu Phe Gly Val
                325                 330                 335

Ile Ser Gln Arg Ser Ser Asp Asn Ala Thr Arg Ala His Glu Ala Arg
            340                 345                 350

Val Asn Thr Asn Asp Pro Thr Phe Ala Pro Gln Ile Ala Gln Val Arg
        355                 360                 365

Phe Lys Ser Pro Ser Asn Asp Phe Phe Asp Asn Glu Pro Ile Lys Phe
    370                 375                 380

Thr Pro Val Gly Ile Ser Val Asp Ser Gln Asn Ser Tyr Asn Gln Trp
385                 390                 395                 400

Leu Leu Pro Arg Tyr Gly Gly His Leu Thr Asn Asn Thr His Leu Ala
                405                 410                 415

Pro Ser Val Ser Pro Met Phe Pro Gly Glu Gln Ile Leu Phe Phe Arg
            420                 425                 430

Ser Phe Met Pro Gly Ala Ser Gly His Thr Asp Gly Ala Ile Asp Cys
        435                 440                 445

Leu Leu Pro Gln Glu Trp Val Ala His Phe Tyr Gln Glu Ala Ala Thr
    450                 455                 460

Ala Gln Thr Asp Val Ala Leu Ile Arg Phe Val Asn Pro Asp Thr Gly
465                 470                 475                 480
```

```
Arg Val Leu Phe Glu Gly Lys Leu His Lys Gln Gly Phe Ile Thr Ile
                485                 490                 495

Ser Asn Ser Gly Asp His Pro Ile Val Met Pro Ala Asn Gly Tyr Phe
            500                 505                 510

Arg Phe Glu Ala Trp Val Asn Gln Phe Tyr Ser Leu Ala Pro Val Gly
        515                 520                 525

Thr Gly Ser Gly Arg Arg Arg Ile Gln
    530                 535


<210> SEQ ID NO 37
<211> LENGTH: 548
<212> TYPE: PRT
<213> ORGANISM: Norwalk virus

<400> SEQUENCE: 37

Met Lys Met Ala Ser Asn Asp Ala Ala Pro Ser Asn Asp Gly Ala Ala
1               5                   10                  15

Gly Leu Val Pro Glu Ser Asn Asn Glu Val Met Ala Leu Glu Pro Val
            20                  25                  30

Ala Gly Ala Ser Leu Ala Ala Pro Val Thr Gly Gln Thr Asn Ile Ile
        35                  40                  45

Asp Pro Trp Ile Arg Met Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Gly Met Glu Val Gln Ile Met Leu Ala Gly Asn
            100                 105                 110

Ala Phe Thr Ala Gly Lys Leu Ile Phe Ala Ala Val Pro Pro His Phe
        115                 120                 125

Pro Ile Glu Asn Leu Ser Pro Pro Gln Ile Thr Met Phe Pro His Val
    130                 135                 140

Ile Ile Asp Val Arg Thr Leu Glu Pro Val Leu Leu Pro Met Pro Asp
145                 150                 155                 160

Ile Arg Asn Ser Phe Phe His Phe Ile Gln Arg Asp Glu Pro Lys Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Asp Phe Thr Tyr Leu Val Pro Pro Thr Val Glu Ser Lys Ser
    210                 215                 220

Lys Pro Phe Thr Leu Pro Ile Leu Thr Leu Gly Glu Leu Thr Asn Ser
225                 230                 235                 240

Arg Phe Pro Leu Pro Ile Asp Val Leu Tyr Thr Asn Pro Asn Glu Ser
                245                 250                 255

Ala Ile Val Gln Cys Gln Asn Gly Arg Cys Thr Leu Asp Gly Glu Leu
            260                 265                 270

Gln Gly Thr Thr Gln Leu Leu Pro Thr Gly Ile Cys Ala Phe Arg Gly
        275                 280                 285

Lys Val Thr Gln Gln Val Gln Asp Glu His Arg Gly Thr His Trp Asn
    290                 295                 300

Met Thr Val Thr Asn Leu Asn Gly Thr Pro Phe Asp Pro Thr Glu Asp
305                 310                 315                 320
```

Val Pro Ala Pro Leu Gly Thr Pro Asp Phe Ser Gly Gln Ile Tyr Gly
325 330 335

Val Ile Ser Gln Arg Asn Thr Asn Thr Val Pro Gly Glu Gly Asn Leu
340 345 350

Pro Ala Asn Arg Ala His Glu Ala Val Ile Ala Thr Tyr Ser Pro Lys
355 360 365

Phe Thr Pro Lys Leu Gly Asn Ile Gln Phe Ser Thr Trp Glu Thr Gln
370 375 380

Asp Val Ser Ser Gly Gln Pro Thr Lys Phe Thr Pro Val Gly Leu Ala
385 390 395 400

Ser Val Asp Ala Asn Ser His Phe Asp Gln Trp Thr Leu Pro Ser Tyr
405 410 415

Ser Gly Ala Leu Thr Leu Asn Met Asn Leu Ala Pro Ser Val Ala Pro
420 425 430

Val Phe Pro Gly Glu Cys Leu Leu Phe Phe Arg Ser Phe Ile Pro Leu
435 440 445

Lys Gly Gly Tyr Gly Asn Pro Ala Ile Asp Cys Leu Met Pro Gln Glu
450 455 460

Trp Val Gln His Leu Tyr Gln Glu Ser Ala Pro Ser Leu Ser Asp Val
465 470 475 480

Ala Leu Val Arg Tyr Val Asn Pro Glu Thr Gly Arg Thr Leu Phe Glu
485 490 495

Ala Lys Leu His Arg Asn Gly Phe Leu Thr Val Ala Arg Asn Ser Ala
500 505 510

Gly Pro Val Val Ala Pro Thr Asn Gly Tyr Phe Arg Phe Asp Ser Trp
515 520 525

Val Asn Gln Phe Tyr Thr Leu Ala Pro Met Gly Asn Gly Ser Gly Arg
530 535 540

Arg Arg Met Gln
545

<210> SEQ ID NO 38
<211> LENGTH: 535
<212> TYPE: PRT
<213> ORGANISM: Chitta virus

<400> SEQUENCE: 38

Met Lys Met Ala Ser Asn Asp Ala Ala Pro Ser Asn Asp Gly Ala Ala
1 5 10 15

Gly Leu Val Pro Glu Ala Asn Asn Glu Thr Met Ala Leu Glu Pro Val
20 25 30

Ala Gly Ala Ser Ile Ala Ala Pro Leu Thr Gly Gln Asn Asn Ile Ile
35 40 45

Asp Pro Trp Ile Arg Leu Asn Phe Val Gln Ala Pro Asn Gly Glu Phe
50 55 60

Thr Val Ser Pro Arg Asn Ser Pro Gly Glu Val Leu Leu Asn Leu Glu
65 70 75 80

Leu Gly Pro Glu Leu Asn Pro Tyr Leu Ala His Leu Ser Arg Met Tyr
85 90 95

Asn Gly Tyr Ala Gly Gly Val Glu Val Gln Val Leu Leu Ala Gly Asn
100 105 110

Ala Phe Thr Ala Gly Lys Leu Val Phe Ala Ala Val Pro Pro His Phe
115 120 125

Pro Leu Glu Asn Ile Ser Pro Gly Gln Ile Thr Met Phe Pro His Val

```
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Leu Glu Ser Lys Thr
    210                 215                 220

Lys Pro Phe Thr Leu Pro Ile Leu Thr Ile Gly Glu Leu Thr Asn Ser
225                 230                 235                 240

Arg Phe Pro Val Pro Ile Asp Glu Leu Tyr Thr Ser Pro Asn Glu Ser
                245                 250                 255

Leu Val Val Gln Pro Gln Asn Gly Arg Cys Ala Leu Asp Gly Glu Leu
            260                 265                 270

Gln Gly Thr Thr Gln Leu Leu Pro Thr Ala Ile Cys Ser Phe Arg Gly
        275                 280                 285

Arg Ile Asn Gln Lys Val Ser Gly Glu Asn His Val Trp Asn Met Gln
    290                 295                 300

Val Thr Asn Ile Asn Gly Thr Pro Phe Asp Pro Thr Gly Asp Val Pro
305                 310                 315                 320

Ala Pro Leu Gly Thr Pro Asp Phe Ser Gly Lys Leu Phe Gly Val Leu
                325                 330                 335

Ser Gln Arg Asp His Asp Asn Ala Cys Arg Ser His Asp Ala Val Ile
            340                 345                 350

Ala Thr Asn Ser Ala Lys Phe Thr Pro Lys Leu Gly Ala Ile Gln Ile
        355                 360                 365

Gly Thr Trp Glu Glu Asp Asp Val His Ile Asn Gln Pro Thr Lys Phe
    370                 375                 380

Thr Pro Val Gly Leu Phe Glu Asn Glu Gly Phe Asn Gln Trp Thr Leu
385                 390                 395                 400

Pro Asn Tyr Ser Gly Ala Leu Thr Leu Asn Met Gly Leu Ala Pro Pro
                405                 410                 415

Val Ala Pro Thr Phe Pro Gly Glu Gln Ile Leu Phe Phe Arg Ser His
            420                 425                 430

Ile Pro Leu Lys Gly Gly Val Ala Asp Pro Val Ile Asp Cys Leu Leu
        435                 440                 445

Pro Gln Glu Trp Ile Gln His Leu Tyr Gln Glu Ser Ala Pro Ser Gln
    450                 455                 460

Ser Asp Val Ala Leu Ile Arg Phe Thr Asn Pro Asp Thr Gly Arg Val
465                 470                 475                 480

Leu Phe Glu Ala Lys Leu His Arg Ser Gly Tyr Ile Thr Val Ala Asn
                485                 490                 495

Thr Gly Ser Arg Pro Ile Val Val Pro Ala Asn Gly Tyr Phe Arg Phe
            500                 505                 510

Asp Thr Trp Val Asn Gln Phe Tyr Ser Leu Ala Pro Met Gly Thr Gly
        515                 520                 525

Asn Gly Arg Arg Arg Val Gln
    530                 535
```

<210> SEQ ID NO 39

<211> LENGTH: 542
<212> TYPE: PRT
<213> ORGANISM: Norwalk-like virus

<400> SEQUENCE: 39

Met Lys Met Ala Ser Asn Asp Ala Ala Pro Ser Asn Asp Gly Ala Ala
1               5                   10                  15

Ser Leu Val Pro Glu Gly Ile Asn Glu Thr Met Pro Leu Glu Pro Val
            20                  25                  30

Ala Gly Ala Ser Ile Ala Ala Pro Val Ala Gly Gln Thr Asn Ile Ile
        35                  40                  45

Asp Pro Trp Ile Arg Thr Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Asp Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Ile Leu Phe Ala Ala Ile Pro Pro Asn Phe
        115                 120                 125

Leu Val Asp Met Ile Ser Pro Ala Gln Ile Thr Met Leu Pro His Leu
    130                 135                 140

Ile Val Asp Val Arg Thr Leu Glu Pro Ile Met Thr Pro Leu Pro Asp
145                 150                 155                 160

Val Arg Asn Val Phe Tyr His Phe Asn Asn Gln Pro Gln Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Glu Phe Ile Tyr Leu Val Pro Pro Ser Val Glu Ser Lys Thr
    210                 215                 220

Lys Pro Phe Thr Leu Pro Ile Leu Thr Ile Ser Glu Leu Thr Asn Ser
225                 230                 235                 240

Arg Phe Pro Ile Pro Ile Glu Gln Leu Tyr Thr Ala Pro Asn Glu Thr
                245                 250                 255

Asn Val Val Gln Cys Gln Asn Gly Arg Cys Thr Leu Asp Gly Glu Leu
            260                 265                 270

Gln Gly Thr Thr Gln Leu Leu Ser Ser Ala Val Cys Phe Leu Gln Gly
        275                 280                 285

Arg Thr Val Ala Asp Asn Gly Asp Asn Trp Asp Gln Asn Leu Leu Gln
    290                 295                 300

Leu Thr Tyr Pro Asn Gly Ala Ser Tyr Asp Pro Thr Asp Glu Val Pro
305                 310                 315                 320

Ala Pro Leu Gly Thr Gln Asp Phe Ser Gly Met Leu Tyr Gly Val Leu
                325                 330                 335

Thr Gln Asp Asn Val Asn Val Ser Thr Gly Glu Ala Lys Asn Ala Lys
            340                 345                 350

Gly Ile Tyr Ile Ser Thr Thr Ser Gly Lys Phe Thr Pro Lys Ile Gly
        355                 360                 365

Ser Ile Gly Leu His Ser Ile Thr Glu His Val His Pro Asn Gln Gln
    370                 375                 380

Ser Arg Phe Thr Pro Val Gly Val Ala Val Asp Glu Asn Thr Pro Phe

-continued

```
385                 390                 395                 400

Gln Gln Trp Val Leu Pro His Tyr Ala Gly Ser Leu Ala Leu Asn Thr
                405                 410                 415

Asn Leu Ala Pro Ala Val Ala Pro Thr Phe Pro Gly Glu Gln Leu Leu
            420                 425                 430

Phe Phe Arg Ser Arg Val Pro Cys Val Gln Gly Leu Gln Gly Gln Asp
        435                 440                 445

Ala Phe Ile Asp Cys Leu Leu Pro Gln Glu Trp Val Asn His Phe Tyr
    450                 455                 460

Gln Glu Ala Ala Pro Ser Gln Ala Asp Val Ala Leu Ile Arg Tyr Val
465                 470                 475                 480

Asn Pro Asp Thr Gly Arg Thr Leu Phe Glu Ala Lys Leu His Arg Ser
                485                 490                 495

Gly Phe Ile Thr Val Ser His Thr Gly Ala Tyr Pro Leu Val Val Pro
            500                 505                 510

Pro Asn Gly His Phe Arg Phe Asp Ser Trp Val Asn Gln Phe Tyr Ser
        515                 520                 525

Leu Ala Pro Met Gly Thr Gly Asn Gly Arg Arg Arg Ile Gln
    530                 535                 540


<210> SEQ ID NO 40
<211> LENGTH: 535
<212> TYPE: PRT
<213> ORGANISM: Norwalk-like virus

<400> SEQUENCE: 40

Met Lys Met Ala Ser Ser Asp Ala Ala Pro Ser Asn Asp Gly Ala Ala
1               5                   10                  15

Gly Leu Val Pro Glu Ala Asn Asn Glu Thr Met Ala Leu Glu Pro Val
            20                  25                  30

Ala Gly Ala Ser Ile Ala Ala Pro Leu Thr Gly Gln Asn Asn Ile Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
        115                 120                 125

Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220
```

-continued

```
Lys Pro Phe Thr Leu Pro Ile Leu Thr Ile Gly Glu Leu Thr Asn Ser
225                 230                 235                 240

Arg Phe Pro Val Pro Ile Asp Glu Leu Tyr Thr Ser Pro Asn Glu Ser
                245                 250                 255

Leu Val Val Gln Pro Gln Asn Gly Arg Cys Ala Leu Asp Gly Glu Leu
            260                 265                 270

Gln Gly Thr Thr Gln Leu Leu Pro Thr Ala Ile Cys Ser Phe Arg Gly
        275                 280                 285

Arg Ile Asn Gln Lys Val Ser Gly Glu Asn His Val Trp Asn Met Gln
    290                 295                 300

Val Thr Asn Ile Asn Gly Thr Pro Phe Asp Pro Thr Glu Asp Val Pro
305                 310                 315                 320

Ala Pro Leu Gly Thr Pro Asp Phe Ser Gly Lys Leu Phe Gly Val Leu
                325                 330                 335

Ser Gln Arg Asp His Asp Asn Ala Cys Arg Ser His Asp Ala Val Ile
            340                 345                 350

Ala Thr Asn Ser Ala Lys Phe Thr Pro Lys Leu Gly Ala Ile Gln Ile
        355                 360                 365

Gly Thr Trp Glu Glu Asp Asp Val His Ile Asn Gln Pro Thr Lys Phe
    370                 375                 380

Thr Pro Val Gly Leu Phe Glu Asp Gly Gly Phe Asn Gln Trp Thr Leu
385                 390                 395                 400

Pro Asn Tyr Ser Gly Ala Leu Thr Leu Asn Met Gly Leu Ala Pro Pro
                405                 410                 415

Val Ala Pro Thr Phe Pro Gly Glu Gln Ile Leu Phe Phe Arg Ser His
            420                 425                 430

Ile Pro Leu Lys Gly Gly Val Ala Asp Pro Val Ile Asp Cys Leu Leu
        435                 440                 445

Pro Gln Glu Trp Ile Gln His Leu Tyr Gln Glu Ser Ala Pro Ser Gln
    450                 455                 460

Ser Asp Val Ala Leu Ile Arg Phe Thr Asn Pro Asp Thr Gly Arg Val
465                 470                 475                 480

Leu Phe Glu Ala Lys Leu His Arg Ser Gly Tyr Ile Thr Val Ala Asn
                485                 490                 495

Thr Gly Ser Arg Pro Ile Val Val Pro Ala Asn Gly Tyr Phe Arg Phe
            500                 505                 510

Asp Ser Trp Val Asn Gln Phe Tyr Ser Leu Ala Pro Met Gly Thr Gly
        515                 520                 525

Asn Gly Arg Arg Arg Val Gln
    530                 535
```

<210> SEQ ID NO 41
<211> LENGTH: 556
<212> TYPE: PRT
<213> ORGANISM: Norwalk virus

<400> SEQUENCE: 41

```
Met Lys Met Ala Ser Asn Asp Ala Ala Pro Ser Thr Asp Gly Ala Gly
1               5                   10                  15

Asn Leu Val Pro Glu Ser Gln Gln Glu Val Leu Pro Leu Ala Pro Val
            20                  25                  30

Ala Gly Ala Ala Leu Ala Ala Pro Val Val Gly Gln Thr Asn Ile Ile
        35                  40                  45

Asp Pro Trp Ile Lys Glu Asn Phe Val Gln Ala Pro Gln Gly Glu Phe
    50                  55                  60
```

```
Thr Val Ser Pro Lys Asn Ser Pro Gly Glu Ile Leu Val Asn Leu Glu
65                  70                  75                  80

Leu Gly Pro Lys Leu Asn Pro Tyr Leu Asp His Leu Ser Arg Met Tyr
                85                  90                  95

Asn Ser Tyr Ala Gly Gly Ile Asp Val Met Val Val Leu Ala Gly Asn
            100                 105                 110

Ala Phe Thr Ala Gly Lys Val Leu Ile Ala Ala Ile Pro Pro Asn Phe
        115                 120                 125

Pro Val Glu Gly Val Ser Ala Ser Gln Ala Thr Gln Phe Pro His Val
    130                 135                 140

Val Ile Asp Val Arg Thr Leu Asp Pro Val Arg Leu Pro Leu Pro Asp
145                 150                 155                 160

Val Arg Ser Thr Phe Phe His Tyr Thr Asn Asp Thr Glu Pro Lys Met
                165                 170                 175

Arg Leu Val Ile Trp Leu Tyr Thr Pro Leu Arg Thr Asn Gly Ser Gly
            180                 185                 190

Asp Asp Ser Phe Thr Val Ser Gly Arg Ile Leu Thr Arg Pro Ser Gln
        195                 200                 205

Asp Phe Glu Phe Ala Phe Leu Ile Pro Pro Thr Val Glu Thr Lys Thr
    210                 215                 220

Thr Pro Phe Ser Val Pro Gly Phe Ser Val Gln Glu Met Ser Asn Ser
225                 230                 235                 240

Arg Trp Pro Ala Ala Ile Ser Ala Met Val Val Arg Gly Asn Glu Pro
                245                 250                 255

Gln Val Val Gln Phe Gln Asn Gly Arg Ala His Leu Asp Gly Met Leu
            260                 265                 270

Leu Gly Thr Thr Pro Val Ser Pro Asn Tyr Ile Ala Ser Tyr Arg Gly
        275                 280                 285

Ile Ser Thr Gly Asn Ser Arg Ser Ala Ser Ser Glu Ala Asp Glu Arg
    290                 295                 300

Ala Val Gly Ser Phe Asp Val Trp Val Arg Leu Gln Glu Pro Asp Gly
305                 310                 315                 320

Gln Pro Tyr Asp Ile Phe Gly Lys Gln Pro Ala Pro Ile Gly Thr Pro
                325                 330                 335

Asp Phe Lys Ala Val Ile Val Gly Phe Ala Ala Arg Pro Leu Thr Ser
            340                 345                 350

Gly Ser Tyr Ala Asn Glu Ala Tyr Val Asn Thr Thr Ala Ser Asp Tyr
        355                 360                 365

Ala Pro Ala Thr Gly Asn Met Arg Phe Thr Val Arg Asn Gly Gly Thr
    370                 375                 380

Gly His Ile Ser Ala Asn Lys Tyr Trp Glu Phe Lys Ser Phe Gly Val
385                 390                 395                 400

Glu Gly Glu Gly His Thr Asn Ile Gln Tyr Gln Glu Tyr Glu Leu Pro
                405                 410                 415

Asp Tyr Ser Gly Gln Val Ala Ser Asn His Asn Leu Ala Pro Pro Val
            420                 425                 430

Ala Pro Arg Met Pro Gly Glu Ser Leu Leu Leu Phe Gln Ser Ser Met
        435                 440                 445

Pro Val Trp Asp Asp Gly His Gly Glu Ser Thr Pro Lys Lys Ile His
    450                 455                 460

Cys Leu Leu Pro Gln Glu Phe Ile Gly His Phe Phe Asp Lys Gln Ala
465                 470                 475                 480
```

-continued

```
Pro Ser Leu Gly Asp Ala Ala Leu Leu Arg Tyr Val Asn Gln Glu Thr
                485                 490                 495

Asn Arg Val Leu Phe Glu Cys Lys Leu Tyr Arg Asp Gly Tyr Ile Thr
            500                 505                 510

Val Ala Ala Ser Ser Gly Leu Leu Asp Phe Pro Leu Asp Gly Phe Phe
        515                 520                 525

Arg Phe Asp Ser Trp Val Ser Ser Phe Tyr Ile Leu Ser Pro Val Gly
    530                 535                 540

Ser Gly Gln Gly Arg Arg Gly Arg Val Arg Phe Gln
545                 550                 555
```

NOROVIRUS DERIVED IMMUNOGENIC COMPOSITIONS AND METHODS

This application is a continuation of U.S. patent application Ser. No. 13/808,157, which is the U.S. National Phase of International Application No. PCT/US2011/042979, filed Jul. 5, 2011 and published in English, which claims the benefit of U.S. Provisional Application No. 61/361,581, filed Jul. 6, 2010, the complete contents of which are hereby incorporated herein by reference for all purposes.

REFERENCE TO SEQUENCE LISTING SUBMITTED ELECTRONICALLY

This application contains a Sequence Listing which has been submitted electronically in ASCII format and which is incorporated by reference in its entirety. Said ASCII file is named 54021_Sequence_Listing.txt, is 139,000 bytes in size and was created on Jul. 5, 2011.

Noroviruses (formerly known as Norwalk-like viruses, NVLs, or Norwalk viruses) are the primary etiological agents of acute viral gastroenteritis in adults and children. noroviruses are highly infectious and spread by ingestion of contaminated food, such as oysters and water. Noroviruses also spread rapidly by person-to-person transmission through the fecal-oral route in semiclosed communities, such as hospitals, schools, nursing homes, and cruise ships. These characteristics make noroviruses a major public health concern. For example, in the United States alone, noroviruses cause greater than 95% of viral gastroenteritis outbreaks and an estimated 23 million cases of gastroenteritis per year (Fankhauser et al. (2002) J. Infect. Dis. 186:1-7; MMWR Morb. Mortal Weekly Rep. (2000) 49:207-211).

The symptoms of norovirus infection include diarrhea and vomiting as well as fever, headaches, chills and stomachaches. The cause of such symptoms may be related to the binding of noroviruses to carbohydrate receptors of intestinal epithelial cells, which results in an imbalance in ion transfer (Marionneau et al. (2002) Gastroenterology 122: 1967-1977; Hutson et al. (2003) J. Virol. 77:405-415). Extremely contagious, noroviruses can cause disease by infection with as few as 10 virions. Although otherwise healthy, people infected with noroviruses may recover within 2-4 days, they may still shed virus for up to 2 weeks after the onset of symptoms. Approximately 30-40% of infected people may remain symptom-free but spread infection by shedding of virus to others who may be more susceptible to infection (Hutson et al. (2004) Trends Microbiol. 12(6):279-287).

Noroviruses are members of the Caliciviridae family of small, nonenveloped, icosahedral viruses, 27-40 nm in diameter, containing a single-strand of positive-sense RNA. Phylogenic studies show that the genus Norovirus is made up of at least 40 diverse virus strains categorized into 5 genogroups, GI-GV, on the basis of sequence similarity. Among these 5 genogroups, GI and GII are the most important genogroups for human infection. Each genogroup is further divided into genotypes. Currently, GI includes 8 distinct genotypes and GII has at least 17 different genotypes. At the genomic level, strains in a genogroup have 51-56% nucleotide sequence identity, and strains in a genotype have 69-70% nucleotide sequence similarity (Donaldson et al., Nat. Rev. Microbiol. 2010 Feb. 2. [e-pub ahead of print]).

Norovirus RNA includes three open reading frames (ORFs), which encode the structural and non-structural proteins of the virus. The major structural protein of noroviruses is viral protein 1 (VP1). It is exclusively encoded by ORF2 of the norovirus RNA and forms the norovirus capsid structure. The norovirus capsid is made up of 180 copies of VP1 monomers. When VP1 is expressed recombinantly, it can self-assemble into an icosahedral capsid structure that lacks a viral genome and is known as virus-like particle (VLP).

X-ray crystallography studies have revealed that each capsid protein, VP1, is made up of two distinct domains, the shell (S) domain and the protruding (P) domain. These two domains are tethered together by a short flexible linker or hinge. The S-domains of the VP1 monomers collectively form the core of the norovirus VLP, and the P-domains extend radially on the surface of VLP and include the bulk of the known antigenic epitopes of norovirus. The P domain (aa 226-530, Norwalk strain numbering) is divided into two subdomains, P1 and P2. The P2 domain is located at the outermost surface of the virion (or VLP) radially and is considered to be hypervariable in sequence. (See, e.g., Chen et al. (2004) *J. Virol.* 78:6469-6479). The P2 domain is the least conserved region of VP1 among norovirus strains and is thought to play an important role in receptor binding and immune reactivity. (Kitamoto et al. (2002) J. Clin. Microbiol. 40:2459-2465; Prasad et al. (1999) Science 286:287-290; Tan et al. (2003) J. Virol. 77:12562-12571; White et al. (1996) J. Virol. 70:6589-6597; Vance et al. (2005) J. General Virol. 86:2799-2806). Structural studies have shown diversity in the shape and size of the P2 subdomains of different noroviruses, consistent with the observed sequence variability of the P2 subdomains. Chen et al. (2004) J. Virology 78(12):6469-6479.

The expression and self-assembly of Norwalk virus VLPs was first demonstrated using the baculovirus-infected insect cell expression system (Jiang et al. (1992) J. Virol. 66:6527-6532) and then using a Venezuelan equine encephalitis vector-infected mammalian cell expression system (Baric et al. (2002) J. Virol. 76:3025-3030). When expressed at high levels in eukaryotic expression systems, the VP1 monomers in Norwalk virus, and certain other noroviruses, self-assemble into VLPs that structurally mimic native norovirus virions. VLPs preserve the authentic conformation of the viral capsid protein but lack norovirus genetic material. When injected into animals, norovirus VLPs can elicit an appropriate host immune response.

Despite what is known about the antigenic properties of norovirus, the development of an effective vaccine against norovirus has been slow and challenging. There are several reasons why it has been a challenge to develop a norovirus vaccine that is effective against a broad range of norovirus strains, including field isolates from different genogroups and genotypes. One reason has been the complex antigenic diversity that exists among different norovirus strains. Genotypic variations can result in new ligand-binding characteristics and antigenic properties (Donaldson et al., Nat. Rev. Microbiol. 2010 Feb. 2. [e-pub ahead of print]). A second reason is the sequential replacement of the dominant circulating norovirus strains (Siebenga et al. (2007) J. Virol 81:9932-9941). A third reason is the lack of a cell culture model for human noroviruses, preventing the development of a neutralization assay. A fourth reason is the lack of an animal model for human noroviruses, limiting preclinical testing of vaccine efficacy and impeding research to understand norovirus pathogensis and immunity (Donaldson et al. (2010) Nature Rev. Microbiol. 8:231-241).

To present immunodominant norovirus epitopes as vaccines, previously, VLPs containing either one type of VP1 protein from only one norovirus strain (also known as monovalent VLPs) or a mixture of non-chimeric VP1 proteins from two or more norovirus strains (also known as multivalent VLPs) have been prepared. See, e.g., WO2009039229. Monovalent VLPs may be less effective against a broad range of norovirus strains than multivalent VLPs. Current multivalent VLPs may be constrained in the range of VP1's from different strains that can be co-assembled due to their differences in VP1-VP1 interaction surfaces between strains. Because of these problems, neither of the above-mentioned vaccine systems are suitable for rapid customization against the new noroviruses that emerge due to viral evolution.

Noroviruses undergo progressive changes in antigenic type, with new antigenic variants replacing older antigenic variants. Therefore, it is likely that there will be a need to periodically change the strain composition of a norovirus vaccine, as is done today for seasonal influenza vaccines. The assembly of VLPs from VP1 of different norovirus strains occurs with different levels of efficiency, and the resulting VLPs have different levels of yield and stability. This variability between strains would impede the speed, reliability, and facility of needed strain changes in a norovirus vaccine composition.

Therefore, there remains a need for an improved norovirus vaccine development approach that allows for rapid changes in the strain composition of efficiently prepared, stable, and properly presented norovirus immunogenic materials from any desired norovirus strain, including new field and/or clinical isolates.

SUMMARY OF THE INVENTION

The present invention, in part, provides immunogenic compositions comprising norovirus antigens and materials and methods that can be used for rapid development of such compositions. The norovirus antigens of the invention comprise chimeric norovirus VP1 proteins in which all or a portion of the P-domain is replaced with all or a portion of a P-domain from a different norovirus strain.

In one aspect the invention relates to a chimeric norovirus viral protein 1 (VP1), which contains the S-domain of VP1 from a first norovirus strain and at least a portion of the P-domain of VP1 from a second norovirus strain, and optionally, a linker peptide that operably links the S-domain and the P-domain. When present, the linker peptide can be any suitable linker, such as the linker peptide of the VP1 from the first norovirus strain, from the second norovirus strain, or from a third norovirus strain. The chimeric VP1 can have a structure according to Formula (I):

$$A\text{-}S\text{-}L\text{-}P\text{-}B \quad (I).$$

In Formula (I), A and B are independently absent or any desired amino acid sequence; S is the S-domain of VP1 from a first norovirus strain; L is absent or a linker peptide; and P is a norovirus VP1 P-domain; wherein at least a portion of the P-domain is from a second norovirus strain.

In some embodiments, P is the P-domain from a second norovirus strain. In other embodiments, P comprises a P1-subdomain, or portion thereof, from the first norovirus strain and a P2-subdomain from a second norovirus strain.

The chimeric VP1 protein can contain portions, e.g., S-domain, P-domain, from any desired norovirus strain, such as the norovirus strains listed in Table 1. In some embodiments, the S-domain is from the Snow Mountain strain. In these embodiments, the P-domain or a portion thereof (e.g., P2 subdomain) can be from any other norovirus strain, such as those listed in Table 1. In particular embodiments, the S-domain is from the Snow Mountain strain and the P-domain or a portion thereof (e.g., P2 subdomain) is from a different norovirus strain from genogroup GII, a norovirus strain from genogroup GI or a norovirus strain from genogroup GIV. In more particular embodiments, the S-domain is from the Snow Mountain strain and the P-domain or a portion thereof (e.g., P2 subdomain) is from Norwalk virus, GII.4.2006a, or New Orleans.

In another aspect, the invention relates to a norovirus virus like particle (VLP) comprising a chimeric VP1 protein as described herein. The VLP can be monovalent or multivalent. The multivalent VLP can comprise two or more different chimeric VP1 protein as described herein. The multivalent VLP can comprise a chimeric VP1 protein as described herein and a naturally occurring norovirus VP1 protein.

The invention also relates to recombinant nucleic acids that encode a chimeric norovirusVP1 protein as described herein. The recombinant nucleic acid can be, for example, RNA or DNA, and if desired, can comprise a vector. In some embodiments, the recombinant nucleic acid is self-replicating, such as a self-replicating RNA.

In another aspect, the invention relates to immunogenic compositions comprising a chimeric norovirus VP1 protein as described herein, a VLP as described herein or combinations thereof. The invention also relates to an immunogenic composition comprising a recombinant nucleic acid that encodes encode a chimeric norovirusVP1 protein as described herein.

In another aspect, the invention relates to a recombinant host cell comprising a recombinant nucleic acid that encodes encode a chimeric norovirusVP1 protein as described herein. The host cell can be, for example, insect cells, mammalian cells, avian cells, bacteria, yeast cells, *Tetrahymena* cells and combinations thereof.

The invention also relates to a method of producing a chimeric norovirus VP1 protein and/or VLP, comprising culturing a recombinant host cell as described herein under conditions whereby the recombinant nucleic acid is expressed and chimericVP1 protein is produced. In some embodiments, the recombinant host cell is maintained under conditions suitable for formation of VLPs. In some embodiments, the method further comprises isolating the chimeric norovirus VP1 protein and/or VLPs from the culture media and/or the recombinant host cells.

BRIEF DESCRIPTION OF THE DRAWINGS

FIG. 3 is an amino acid alignment of VP1 proteins from three different norovirus strains, Norwalk (norw) genotype G1.1 (SEQ ID NO:11), Snow Mountain (snow) genotype GII.2 (SEQ ID NO:12), and 2006a (g2.4) GII.4 (SEQ ID NO:13). As shown, the shell domain (S-domain) is residues 1-221, the linker peptide is residues 222-230, and the protruding domain (P-domain) is residues 231-530.

FIG. 4A depicts the nucleotide sequence (SEQ ID NO:14) of ORF2 in norovirus strain Snow Mountain, which encodes the VP1 protein in that strain. FIG. 4B show the translated amino acid sequence (SEQ ID NO:12) of VP1 protein encoded by ORF2 of Snow Mountain.

FIG. 5 depicts a nucleic acid (SEQ ID NO:15) encoding a chimeric VP1 protein whose S-domain is derived from the Snow Mountain strain, and P-domain is derived from the Norwalk strain.

FIG. 6 depicts a nucleic acid (SEQ ID NO:16) encoding a chimeric VP1 protein whose S-domain is derived from the Snow Mountain strain, and P-domain is derived from the GII.4 2006a strain.

FIGS. 8A-8E show a multiple amino acid alignment of VP1 sequences of several norovirus strains. See, Hansman et al. (2006) J. General Virology 87:909-919. The following regions are indicated in these figures: N-terminal region (line); S-domain (filled box), $P_{1-1}$-subdomain (open box); P2-subdomain (XXX); $P_{1-2}$-subdomain (open box) and C-terminal region (line). Asterisks indicate conserved amino acids. The sequences depicted are from the following norovirus strains: #8 (SEQ ID NO:17) (AB058547, a GI/11 strain); SeV (SEQ ID NO:18) (AB031013, a GI/1 strain); 258 (SEQ ID NO:19) (AB078335, a GI/2 strain); 645 (SEQ ID NO:20) (BD011871, a GI/3 strain); CV (SEQ ID NO:21) (AB042808, a GI/4 strain); WUG1 (SEQ ID NO:22) (AB081723, a GI/8 strain); HV (SEQ ID NO:23) (U07611, a GII/1 strain); 485 (SEQ ID NO:24) (DQ093065, a GII/1 strain); Ina (SEQ ID NO:25) (AB195225, a GII/2 strain); 809 (SEQ ID NO:26) (BD011876, a GII/3 strain); Sh5 (SEQ ID NO:27) (AB195226, a GII/3 strain); 18-3 (SEQ ID NO:28) (DQ093062, a GII/3 strain); 336 (SEQ ID NO:29) (DQ093063, a GII/3 strain); 1152 (SEQ ID NO:30) (DQ0930); 104 (SEQ ID NO:31) (AB078336, a GII/4 strain); 754 (SEQ ID NO:32) (BD011877, a GII/5 strain); 7 k (SEQ ID NO:33) (AB078337, GII/6 strain); 445 (SEQ ID NO:34) (DQ093064, a GII/6 strain); 10-25 (SEQ ID NO:35) (9BD011881, a GII/7 strain); U25 (SEQ ID NO:36) (AB039780, a GII/8 strain); 026 (SEQ ID NO:37) (AF504671, a GII/10 strain); CHV (SEQ ID NO:38) (AB032758, a GII/12 strain); 47 (SEQ ID NO:39) (AB078334, a GII/14 strain); Hiro (SEQ ID NO:40) (AB044366, a GII/12 strain); Alph23 (SEQ ID NO:41) (DQ093067, a GII/17 strain).

FIG. 9 is a table showing amino acid residues identified by Chakavarty et al. (2005) J. Virology, 79(1):554-568, from S and P domains, that distinguish different known and suggested antigenic norovirus strains and classes.

DETAILED DESCRIPTION OF THE INVENTION

Figure 1:
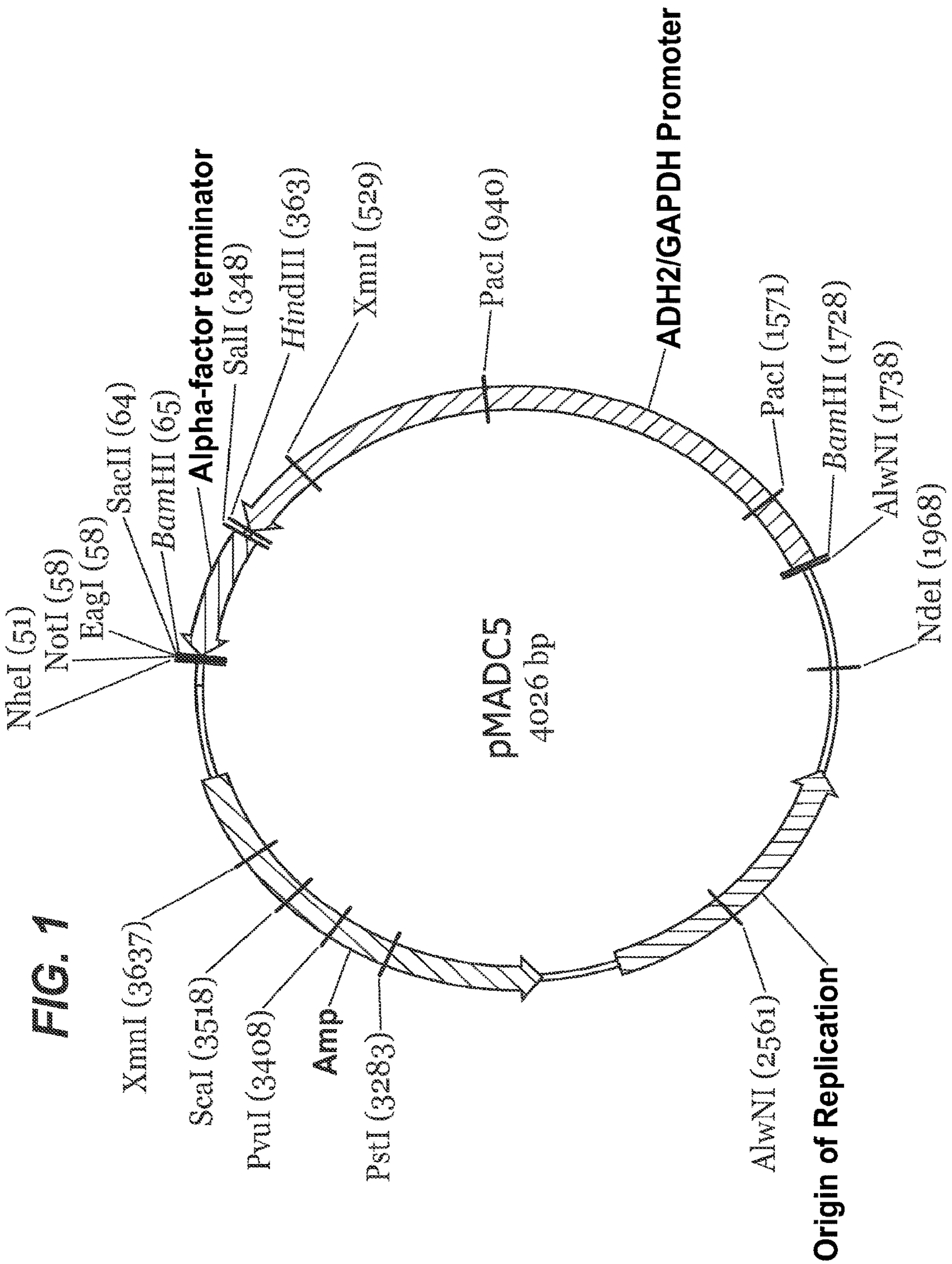
FIG. 1 depicts the diagram for vector pMADC5 suitable for subcloning and amplification of the chimeric VP1 oligonucleotides of the invention.

The present invention provides compositions and methods for production and use of chimeric norovirus VP1 proteins. The invention further provides immunogenic compositions that include norovirus VLPs comprising said chimeric VP1 proteins in which the S-domain is derived from a first norovirus strain and all or part of the P-domain is derived from a second norovirus strain.

Other aspects of the present invention include nucleic acids and polypeptides, and methods for preparing and purifying such nucleic acids and polypeptides. These aspects of the invention together with the VLPs of the invention and their use in immunogenic compositions and methods of using such compositions in the treatment or prevention of norovirus are described in more detail below.

I. DEFINITIONS

All scientific and technical terms used in this application have meanings commonly used in the art unless otherwise specified. As used in this application, the following words or phrases have the meanings specified.

As used herein, "a", "an" and "the" include singular and plural references unless the content clearly dictates otherwise. Thus, for example, reference to "a polynucleotide" includes a mixture of two or more such polynucleotides, and the like.

The term "about" in relation to a numerical value x means, for example, x+10%.

As used herein, the terms "norovirus" and "Norwalk-like virus" refer to members of the genus norovirus of the family Caliciviridae of positive-sense, single-stranded RNA, non-enveloped viruses (Green et al., Human Caliciviruses, in Fields Virology Vol. 1, pp. 841-874 (Knipe and Howley, editors-in-chief, 4th ed., Lippincott Williams & Wilkins 2001)). The term norovirus includes strains in all genogroups of the virus. Currently, norovirus strains are divided into five genogroups (GI-GV), which are subdivided into at least 20 genetic clusters or genotypes. In particular, the term norovirus includes, but is not limited to, the species Norwalk virus (NV), Lordsdale virus (LV), Mexico virus (MV), Hawaii virus (HV), Snow Mountain virus (SMV), Desert Shield virus (DSV), and Southhampton virus (SV). A large number of norovirus isolates have been partially or completely sequenced. See, e.g., the GenBank database (ncbi.nlm.nih.gov), the Taxonomy Database at National Center for Biotechnology Information (ncbi.nlm.nih.gov) or the PathoSystems Resource Integration Center Database on Caliciviridae (patric.vbi.vt.edu). The term norovirus also includes isolates not characterized at the time of filing.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

"Substantially purified" generally refers to isolation of a substance (compound, polynucleotide, protein, polypeptide, polypeptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By “isolated” is meant, when referring to a polypeptide, that the indicated molecule is separate and discrete from the whole organism with which the molecule is found in nature or is present in the substantial absence of other biological macro-molecules of the same type. The term “isolated” with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

“Recombinant” as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term “recombinant” as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term “transformation” refers to the insertion of an exogenous polynucleotide into a host cell, irrespective of the method used for the insertion. For example, direct uptake, transfection, transduction or f-mating are included. The exogenous polynucleotide may be maintained as a non-integrated vector, for example, a plasmid, or alternatively, may be integrated into the host genome.

“Recombinant host cells”, “host cells,” “cells”, “cell lines,” “cell cultures”, and other such terms denoting micro-organisms or higher eukaryotic cell lines cultured as unicellular entities refer to cells which can be, or have been, used as recipients for recombinant vector or other transferred DNA, and include the original progeny of the original cell which has been transfected.

A “coding sequence” or a sequence which “encodes” a selected polypeptide, is a nucleic acid molecule which is transcribed (in the case of DNA) and translated (in the case of mRNA) into a polypeptide in vivo when placed under the control of appropriate regulatory sequences (or “control elements”). The boundaries of the coding sequence can be determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA or RNA, and even synthetic DNA sequences. A transcription termination sequence may be located 3' to the coding sequence.

Typical “control elements,” include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

The term “nucleic acid” includes DNA and RNA, and also their analogues, such as those containing modified backbones (e.g. phosphorothioates, etc.), and also peptide nucleic acids (PNA), etc. The invention includes nucleic acids comprising sequences complementary to those described above (e.g. for antisense or probing purposes).

The term “self-replicating” refers to a nucleic acid molecule that encodes a polymerase, contains nucleotide sequence elements that enable that polymerase to replicate the nucleic acid molecule and, preferably, also encodes a desired polypeptide, such as a chimeric norovirus VP1. Preferably, the self-replication nucleic acid is a self-replicating RNA molecule. For example, a self-replicating RNA molecule can be based on an alphavirus genome, and encode nonstructural proteins that can direct replication of the RNA molecule, contains a replication recognition sequence sufficient to allow replication of the RNA molecule, and also encode a desired target polypeptide, such as such as a chimeric norovirus VP1. Optionally, one or more structural viral genes (e.g., capsid and/or envelope glycoproteins) are deleted or omitted from the self-replicating RNA molecule. Suitable alphaviruses that can be used to produce self-replicating RNA molecules include Sindbis virus, Semliki forest virus, Eastern Equine Encephalitis virus, Venezuelan equine encephalitis virus and the like. (See, e.g., EP 1 751 289 B1; Ying et al. (1999) Nat. Med. 5(7):823-827; Racanelli et al. (2004) Immunity, 20(1):47-58, regarding self-replicating RNA molecules.)

“Operably linked” refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered “operably linked” to the coding sequence.

“Encoded by” refers to a nucleic acid sequence which codes for a polypeptide sequence, wherein the polypeptide sequence or a portion thereof contains an amino acid sequence of at least 3 amino acids.

“Expression cassette” or “expression construct” refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a “mammalian” origin of replication (e.g., a SV40 or adenovirus origin of replication).

“Purified polynucleotide” refers to a polynucleotide of interest or fragment thereof which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

A “vector” is capable of transferring nucleic acid sequences to target cells (e.g., viral vectors, non-viral vectors, particulate carriers, and liposomes). Typically, “vector construct,” “expression vector,” and “gene transfer vector,” mean any nucleic acid construct capable of directing the expression of a nucleic acid of interest and which can transfer nucleic acid sequences to target cells. Thus, the term includes cloning and expression vehicles, as well as viral vectors.

As used herein, the term “epitope” generally refers to the site on an antigen which is recognized by a T-cell receptor and/or an antibody. It may be a short peptide derived from or as part of a protein antigen. The three-dimensional structure of the epitope may or may not be important for its function. However the term is also intended to include peptides with glycopeptides and carbohydrate epitopes. Several different epitopes may be carried by a single antigenic molecule. The term “epitope” also includes modified sequences of amino acids or carbohydrates which stimulate responses which recognize the whole organism. It is advantageous if the selected epitope is an epitope of an infectious agent, which causes the infectious disease.

For a description of various norovirus capsid epitopes, see, e.g., Hardy et al., U.S. Patent Application Publication No. 2005/0152911; incorporated herein by reference in its entirety. In particular, Hardy et al. have identified epitopes of the Norwalk virus capsid protein at residues 133-137 and of the Snow Mountain virus capsid protein at residues 319-327, comprising the following sequences: WTRGSHNL, (SEQ ID NO:1), WTRGGHGL, (SEQ ID NO:2), WTRGQHQL (SEQ ID NO:3), or WLPAPIDKL (SEQ ID NO:4). Immunogenic polypeptides comprising such capsid epitopes and nucleic acids encoding them may be used in the practice of the invention.

As used herein, the term “T cell epitope” refers generally to those features of a peptide structure which are capable of inducing a T cell response and a “B cell epitope” refers generally to those features of a peptide structure which are capable of inducing a B cell response.

An “immunological response” to an antigen or composition is the development in a subject of a humoral and/or a cellular immune response to an antigen present in the composition of interest. For purposes of the present invention, a “humoral immune response” refers to an immune response mediated by antibody molecules, while a “cellular immune response” is one mediated by T-lymphocytes and/or other white blood cells. One important aspect of cellular immunity involves an antigen-specific response by cytolytic T-cells (“CTL”s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A “cellular immune response” also refers to the production of cytokines, chemokines and other such molecules produced by activated T-cells and/or other white blood cells, including those derived from CD4+ and CD8+ T-cells.

An immunogenic composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al. (1993) J. Immunol. 151:4189-4199; Doe et al. (1994) Eur. J. Immunol. 24:2369-2376. Recent methods of measuring cell-mediated immune response include measurement of intracellular cytokines or cytokine secretion by T-cell populations, or by measurement of epitope specific T-cells (e.g., by the tetramer technique) (reviewed by McMichael, A. J. and O'Callaghan, C. A. (1998) J. Exp. Med. 187(9)1367-1371; Mcheyzer-Williams, M. G. et al. (1996), Immunol. Rev. 150:5-21; Lalvani, A. et al. (1997) J. Exp. Med. 186:859-865).

Thus, an immunological response as used herein may be one that stimulates the production of antibodies (e.g., neutralizing antibodies that block bacterial toxins and pathogens such as viruses entering cells and replicating by binding to toxins and pathogens, typically protecting cells from infection and destruction). The antigen of interest may also elicit production of CTLs. Hence, an immunological response may include one or more of the following effects: the production of antibodies by B-cells; and/or the activation of suppressor T-cells and/or memory/effector T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays. The innate immune system of mammals also recognizes and responds to molecular features of pathogenic organisms via activation of Toll-like receptors and similar receptor molecules on immune cells. Upon activation of the innate immune system, various non-adaptive immune response cells. are activated to, e.g., produce various cytokines, lymphokines and chemokines. Cells activated by an innate immune response include immature and mature Dendritic cells of the monocyte and plasmacytoid lineage (MDC, PDC), as well as gamma, delta, alpha and beta T cells and B cells and the like. Thus, the present invention also contemplates an immune response wherein the immune response involves both an innate and adaptive response.

An “immunogenic composition” is a composition that comprises an antigenic molecule where administration of the composition to a subject results in the development in the subject of a humoral and/or a cellular immune response to the antigenic molecule of interest.

The terms “immunogenic” protein or polypeptide refer to an amino acid sequence which elicits an immunological response as described above. An “immunogenic” protein or polypeptide, as used herein, includes the full-length natural or recombinant sequence of the protein in question, including the precursor and mature forms, analogs thereof, or immunogenic fragments thereof.

A norovirus polynucleotide, oligonucleotide, nucleic acid, protein, polypeptide, or peptide, as defined above, is a molecule derived from a norovirus, respectively, including, without limitation, any of the various isolates of norovirus. The molecule need not be physically derived from the particular isolate in question, but may be synthetically or recombinantly produced.

In particular, the genomes of norovirus strains contain three open reading frames: ORF1, which is transcribed into a polyprotein; ORF2, which is transcribed into the major capsid protein VP1; and ORF3, which is transcribed into the minor structural protein VP2. In norovirus strain Norwalk, the boundaries of the polypeptide domains within the VP1 protein are as follows: the shell (S) domain formed by amino acid residues 1-221, a flexible hinge region at amino acid residues 222-230, and the protruding (P) domain formed by amino residues 231-530. The P-domain is further divided into two subdomains, P1 and the hypervariable P2, which extends farthest out from the capsid shell and contains the putative receptor-binding sites (Choi, et al. (2008) Proc. Natl. Aacd. Sci. USA 105:9175-9180, Prasad et al. (1999) Science 286:287-290). Although, the foregoing numbering is relative to the polyprotein amino acid sequence of Norwalk strain (SEQ ID NO:11), it is to be understood that the corresponding amino acid positions in sequences obtained from other genotypes and isolates of norovirus are also intended to be encompassed by the present invention. For example, see FIG. 3. Any one of the polypeptides encoding the full-length VP1 or VP2, as well as variants thereof, immunogenic fragments thereof, and nucleic acids encoding such polypeptides, variants or immunogenic fragments can be used in the practice of the invention.

Nucleic acid and protein sequences for a number of norovirus isolates are known. Representative norovirus VP1 and VP2 sequences are presented in FIGS. 4A-4B and 5A-5B. Additional representative sequences, including sequences of ORF1, ORF2, ORF3, and their encoded polypeptides from norovirus isolates are listed in the National Center for Biotechnology Information (NCBI) database. See, for example, GenBank entries: norovirus genogroup 1 strain Hu/NoV/West Chester/2001/USA, GenBank Accession No. AY502016; norovirus genogroup 2 strain Hu/NoV/Braddock Heights/1999/USA, GenBank Accession No. AY502015; norovirus genogroup 2 strain Hu/NoV/Fayette/1999/USA, GenBank Accession No. AY502014; norovirus genogroup 2 strain Hu/NoV/Fairfield/1999/USA, GenBank Accession No. AY502013; norovirus genogroup 2 strain Hu/NoV/Sandusky/1999/USA, GenBank Accession No. AY502012; norovirus genogroup 2 strain Hu/NoV/Canton/1999/USA, GenBank Accession No. AY502011; norovirus genogroup 2 strain Hu/NoV/Tiffin/1999/USA, GenBank Accession No. AY502010; norovirus genogroup 2 strain Hu/NoV/CS-E1/2002/USA, GenBank Accession No. AY50200; norovirus genogroup 1 strain Hu/NoV/Wisconsin/2001/USA, GenBank Accession No. AY502008; norovirus genogroup 1 strain Hu/NoV/CS-841/2001/USA, GenBank Accession No. AY502007; norovirus genogroup 2 strain Hu/NoV/Hiram/2000/USA, GenBank Accession No. AY502006; norovirus genogroup 2 strain Hu/NoV/Tontogany/1999/USA, GenBank Accession No. AY502005; Norwalk virus, complete genome, GenBank Accession No. NC-001959; norovirus Hu/GI/Otofuke/1979/JP genomic RNA, complete genome, GenBank Accession No. AB187514; norovirus Hu/Hokkaido/133/2003/JP, GenBank Accession No. AB212306; norovirus Sydney 2212, GenBank Accession No. AY588132; Norwalk virus strain SN2000JA, GenBank Accession No. AB190457; Lordsdale virus complete genome, GenBank Accession No. X86557; Norwalk-like virus genomic RNA, Gifu'96, GenBank Accession No. AB045603; Norwalk virus strain Vietnam 026, complete genome, GenBank Accession No. AF504671; norovirus Hu/GII.4/2004/N/L, GenBank Accession No. AY883096; norovirus Hu/GII/Hokushin/03/JP, GenBank Accession No. AB195227; norovirus Hu/GII/Kamo/03/JP, GenBank Accession No. AB195228; norovirus Hu/GII/Sinsiro/97/JP, GenBank Accession No. AB195226; norovirus Hu/GII/Ina/02/JP, GenBank Accession No. AB195225; norovirus Hu/NLV/GII/Neustrelitz260/2000/DE, GenBank Accession No. AY772730; norovirus Hu/NLV/Dresden174/pUS-NorII/1997/GE, GenBank Accession No. AY741811; norovirus Hu/NLV/Oxford/B2S16/2002/UK, GenBank Accession No. AY587989; norovirus Hu/NLV/Oxford/B4S7/2002/UK, GenBank Accession No. AY587987; norovirus Hu/NLV/Witney/B7S2/2003/UK, GenBank Accession No. AY588030; norovirus Hu/NLV/Banbury/B9S23/2003/UK, GenBank Accession No. AY588029; norovirus Hu/NLV/ChippingNorton/2003/UK, GenBank Accession No. AY588028; norovirus Hu/NLV/Didcot/B9S2/2003/UK, GenBank Accession No. AY588027; norovirus Hu/NLV/Oxford/B8S5/2002/UK, GenBank Accession No. AY588026; norovirus Hu/NLV/Oxford/B6S4/2003/UK, GenBank Accession No. AY588025; norovirus Hu/NLV/Oxford/B6S5/2003/UK, GenBank Accession No. AY588024; norovirus Hu/NLV/Oxford/B5S23/2003/UK, GenBank Accession No. AY588023; norovirus Hu/NLV/Oxford/B6S2/2003/UK, GenBank Accession No. AY588022; norovirus Hu/NLV/Oxford/B6S6/2003/UK, GenBank Accession No. AY588021; Norwalk-like virus isolate Bo/Thirsk10/00/UK, GenBank Accession No. AY126468; Norwalk-like virus isolate Bo/Penrith55/00/UK, GenBank Accession No. AY126476; Norwalk-like virus isolate Bo/Aberystwyth24/00/UK, GenBank Accession No. AY126475; Norwalk-like virus isolate Bo/Dumfries/94/UK, GenBank Accession No. AY126474; norovirus NLV/IF2036/2003/Iraq, GenBank Accession No. AY675555; norovirus NLV/IF1998/2003/Iraq, GenBank Accession No. AY675554; norovirus NLV/BUDS/2002/USA, GenBank Accession No. AY660568; norovirus NLV/Paris Island/2003/USA, GenBank Accession No. AY652979; Snow Mountain virus, complete genome, GenBank Accession No. AY134748; Norwalk-like virus NLV/Fort Lauderdale/560/1998/US, GenBank Accession No. AF414426; Hu/norovirus/hiroshima/1999/JP(9912-02F), GenBank Accession No. AB044366; Norwalk-like virus strain 11MSU-MW, GenBank Accession No. AY274820; Norwalk-like virus strain B-1SVD, GenBank Accession No. AY274819; norovirus genogroup 2 strain Hu/NoV/Farmington Hills/2002/USA, GenBank Accession No. AY502023; norovirus genogroup 2 strain Hu/NoV/CS-G4/2002/USA, GenBank Accession No. AY502022; norovirus genogroup 2 strain Hu/NoV/CS-G2/2002/USA, GenBank Accession No. AY502021; norovirus genogroup 2 strain Hu/NoV/CS-G12002/USA, GenBank Accession No. AY502020; norovirus genogroup 2 strain Hu/NoV/Anchorage/2002/USA, GenBank Accession No. AY502019; norovirus genogroup 2 strain Hu/NoV/CS-D1/2002/CAN, GenBank Accession No. AY502018; norovirus genogroup 2 strain Hu/NoV/Germanton/2002/USA, GenBank Accession No. AY502017; Human calicivirus NLV/GII/Langen1061/2002/DE, complete genome, GenBank Accession No. AY485642; Murine norovirus 1 polyprotein, GenBank Accession No. AY228235; Norwalk virus, GenBank Accession No. AB067536; Human calicivirus NLV/Mex7076/1999, GenBank Accession No. AF542090; Human calicivirus NLV/Oberhausen 455/01/DE, GenBank Accession No. AF539440; Human calicivirus NLV/Herzberg 385/01/DE, GenBank Accession No. AF539439; Human calicivirus NLV/Boxer/2001/US, GenBank Accession No. AF538679; Norwalk-like virus genomic RNA, complete genome, GenBank Accession No. AB081723; Norwalk-like virus genomic RNA, complete genome, isolate:Saitama U201, GenBank Accession No. AB039782;

Norwalk-like virus genomic RNA, complete genome, isolate:Saitama U18, GenBank Accession No. AB039781; Norwalk-like virus genomic RNA, complete genome, isolate: Saitama U25, GenBank Accession No. AB039780; Norwalk virus strain:U25GII, GenBank Accession No. AB067543; Norwalk virus strain:U201 GII, GenBank Accession No. AB067542; Norwalk-like viruses strain 416/97003156/1996/LA, GenBank Accession No. AF080559; Norwalk-like viruses strain 408/97003012/1996/FL, GenBank Accession No. AF080558; Norwalk-like virus NLV/Burwash Landing/331/1995/US, GenBank Accession No. AF414425; Norwalk-like virus NLV/Miami Beach/326/1995/US, GenBank Accession No. AF414424; Norwalk-like virus NLV/White River/290/1994/US, GenBank Accession No. AF414423; Norwalk-like virus NLV/New Orleans/306/1994/US, GenBank Accession No. AF414422; Norwalk-like virus NLV/Port Canaveral/301/1994/US, GenBank Accession No. AF414421; Norwalk-like virus NLV/Honolulu/314/1994/US, GenBank Accession No. AF414420; Norwalk-like virus NLV/Richmond/283/1994/US, GenBank Accession No. AF414419; Norwalk-like virus NLV/Westover/302/1994/US, GenBank Accession No. AF414418; Norwalk-like virus NLV/UK3-17/12700/1992/GB, GenBank Accession No. AF414417; Norwalk-like virus NLV/Miami/81/1986/US, GenBank Accession No. AF414416; Snow Mountain strain, GenBank Accession No. U70059; Desert Shield virus DSV395, GenBank Accession No. U04469; Norwalk virus, complete genome, GenBank Accession No. AF093797; Hawaii calicivirus, GenBank Accession No. U07611; Southampton virus, GenBank Accession No. L07418; Norwalk virus (SRSV-KY-89/89/J), GenBank Accession No. L23828; Norwalk virus (SRSV-SMA/76/US), GenBank Accession No. L23831; Camberwell virus, GenBank Accession No. U46500; Human calicivirus strain Melksham, GenBank Accession No. X81879; Human calicivirus strain MX, GenBank Accession No. U22498; Minireovirus TV24, GenBank Accession No. U02030; and Norwalk-like virus NLV/Gwynedd/273/1994/US, GenBank Accession No. AF414409; all of which sequences (as entered by the date of filing of this application) are herein incorporated by reference. Additional norovirus sequences are disclosed in the following patent publications: WO 05/030806, WO 00/79280, JP2002020399, US2003129588, U.S. Pat. No. 6,572,862, WO 94/05700, and WO 05/032457, all of which are herein incorporated by reference in their entireties. See also Green et al. (2000) J. Infect. Dis. 181(Suppl. 2):S322-S330; Wang et al. (1994) J. Virol. 68:5982-5990; Chen et al. (2004) J. Virol. 78: 6469-6479; Chakravarty et al. (2005) J. Virol. 79: 554-568; and Fankhauser et al. (1998) J. Infect. Dis. 178:1571-1578; for sequence comparisons and a discussion of genetic diversity and phylogenetic analysis of noroviruses.

As used herein, the terms "major capsid protein" or "major capsid polypeptide" or "VP1" in reference to a norovirus refer to a polypeptide comprising a sequence homologous or identical to the ORF2-encoded polypeptide of a norovirus, and includes sequences displaying at least about 70-100% or about 80-100% amino acid sequence identity thereto, including any percent identity within this range, such as 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% amino acid sequence identity thereto.

As used herein, the terms "minor structural protein" or "minor structural polypeptide" or "VP2" or "small basic protein" in reference to a norovirus refer to a polypeptide comprising a sequence homologous or identical to the ORF3-encoded polypeptide of a norovirus, and includes sequences displaying at least about 70-100% or about 80-100% amino acid sequence identity thereto, including any percent identity within this range, such as 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% amino acid sequence identity thereto.

As used herein, the term "virus-like particle" or "VLP" refers to a nonreplicating, noninfectious viral shell, that contains a viral capsid but lacks all or part of the viral genome, in particular, the replicative and infectious components of the viral genome. VLPs are generally composed of one or more viral proteins, such as, but not limited to those proteins referred to as capsid, coat, shell, surface, structural proteins (e.g., VP1, VP2). norovirus VLPs can form spontaneously upon recombinant expression of VP1 in an appropriate expression system. Methods for producing particular VLPs are known in the art and discussed more fully below. The presence of VLPs following recombinant expression of viral proteins can be detected using conventional techniques known in the art, such as by electron microscopy, biophysical characterization, and the like. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions. Negative stained electron microscopy can be performed on norovirus or norovirus VLP samples after coating with an electron-dense negative contrast agent, such as uranyl acetate, uranuyl formate, or phosphotungstic acid.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components. In particular, norovirus may be obtained from biological samples such as vomit or diarrhea from individuals infected with the viruses.

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

"Homology" refers to the percent identity between two polynucleotide or two polypeptide moieties. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353-358, National biomedical Research Foundation, Washington, D.C., which adapts the local homology algorithm of Smith and Waterman (1981) Advances in Appl. Math. 2:482-489 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art.

Amino acid substitutions, when present in the chimeric VP1 proteins, are preferably conservative in nature, i.e., substitutions in which a first amino acid is replaced with a second amino acid that have similar properties based on their side chains. Specifically, amino acids are generally divided into four families and substitutions with families are considered to be conservative substitutions. The four families are: (1) acidic amino acids—aspartate and glutamate; (2) basic amino acids—lysine, arginine, histidine; (3) non-polar amino acids—alanine, valine, leucine, isoleucine, proline, phenylalanine, methionine, tryptophan; and (4) uncharged polar amino acids—glycine, asparagine, glutamine, cysteine, serine, threonine, tyrosine. Phenylalanine, tryptophan, and tyrosine are sometimes classified as aromatic amino acids.

By "therapeutically effective amount" in the context of the immunogenic compositions is meant an amount of an immunogen (e.g., chimeric VP1 protein, VLP, or nucleic acid encoding an antigen) which will induce an immunological response, either for antibody production or for treatment or prevention of norovirus infection or disease. Such a response will generally result in the development in the subject of an antibody-mediated and/or a secretory or cellular immune response to the composition. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or γδT cell populations.

For purposes of the present invention, an "effective amount" of an adjuvant will be that amount which enhances an immunological response to a coadministered antigen or nucleic acid encoding an antigen.

As used herein, "treatment" refers to any of (i) the prevention of infection or reinfection or disease, (ii) the reduction or elimination of symptoms, and (iii) the substantial or complete elimination of the pathogen in question. Treatment may be effected prophylactically (prior to infection) or therapeutically (following infection).

II. MODES OF CARRYING OUT THE INVENTION

The invention described herein is not limited to particularly exemplified molecules or process parameters as such may vary. The terminology used herein is for the purpose of describing particular aspects, features and embodiments of the invention only, and is not intended to be limiting. In addition, the practice of the present invention will employ conventional methods of virology, microbiology, molecular biology, recombinant DNA techniques and immunology all of which are within the ordinary skill of the art. Such techniques are explained fully in the literature. See, e.g., Sambrook, et al., Molecular Cloning: A Laboratory Manual (3rd Edition, 2000); DNA Cloning: A Practical Approach, vol. I & II (D. Glover, ed.); Oligonucleotide Synthesis (N. Gait, ed., 1984); A Practical Guide to Molecular Cloning (1984); and Fundamental Virology, 4th Edition, 2001 (B. N. Fields and D. M. Knipe, eds.); Handbook of Experimental Immunology, Vols. I-IV (D. M. Weir and C. C. Blackwell eds., Blackwell Scientific Publications); A. L. Lehninger, Biochemistry (Worth Publishers, Inc., current addition); Methods In Enzymology (S. Colowick and N. Kaplan eds., Academic Press, Inc.). Although a number of methods and materials similar or equivalent to those described herein can be used in the practice of the present invention, the preferred materials and methods are described herein. In addition, all publications, patents and patent applications cited herein, whether supra or infra, are hereby incorporated by reference in their entireties.

The present invention is, in part, based on the discovery that all or a portion of the P-domain of the VP1 protein of a first norovirus strain can be replaced with all or the corresponding portion of the P-domain of a second norovirus strain, and that when expressed, such chimeric VP1 proteins can self-assemble into VLPs. It has also been discovered that VLPs that contain any desired VP1 P-domain, even P-domains from VP1 proteins of norovirus strains that are not expressed well in recombinant host cells and therefore do not readily form VLPs. This is accomplished by preparing a chimeric VP1 protein that contains the S-domain of a VP1 from a norovirus strain that is well expressed and, therefore, can readily form VLPs, and all or a portion of the P-domain of a VP1 protein of any other desired norovirus strain. Accordingly, the present invention provides chimeric norovirus VP1 proteins, and norovirus VLPs, that contain all or a portion of any desired P-domain. Now, chimeric norovirus VP1 proteins, and norovirus VLPs, that contain all or a portion of any P-domain, including P-domains from emerging norovirus strains can be produced relatively easily and rapidly.

Therefore, the present invention provides compositions and methods for rapid generation of immunogenic compositions that can be used to induce an immune response in a subject, that preferably can protect the subject from norovirus infection and/or norovirus disease. The invention provides immunogenic compositions comprising chimeric norovirus VP1 protein in the form of monomers or in the form of VLPs. The chimeric norovirus VP1 proteins contain the VP1 S-domain from a first norovirus strain and all or a portion of the VP1 P-domain from a second norovirus strain.

The norovirus VLPs of the present invention can be monovalent, and be composed of a single type of chimeric VP1 protein. Such monovalent VLPs contain multiple copies of a single VP1 P-domain from a single norovirus strain. If desired, the norovirus VLP of the present invention can be multivalent, and be composed of two or more different chimeric VP1 proteins. Preferably, the two or more different chimeric VP1 proteins contain the VP1 S-domain from the same norovirus strain, but VP1 P-domains from different norovirus strains.

In addition, the immunogenic compositions of the present invention can further comprise one or more adjuvants or nucleic acids encoding adjuvants, wherein immunogenic polypeptides and/or VLPs are mixed or co-expressed with adjuvants. Immunogenic compositions may also comprise additional antigens other than norovirus antigens, such as antigens that can be used in immunization against pathogens that cause diarrheal diseases.

Also provided are immunogenic compositions that comprise a nucleic acid molecule that encodes a chimeric norovirus VP1, such as an RNA molecule or a self-replicating RNA molecule. Such compositions can be administered to a subject and the encoded chimeric norovirus VP1 can be produced in the subject, preferably in the form of a VLP.

In order to further understand other aspects of the present invention, including nucleic acids, polypeptides and/or VLPs and methods for their preparation, purification and use in the treatment or prevention of norovirus infection, more detailed discussions are provided below.

A. Polypeptides and VLPs

The chimeric norovirus VP1 protein contains the S-domain of VP1 of a first norovirus strain and a P-domain that contains at least a portion of the P-domain of VP1 of a second norovirus strain. The S-domain and the P-domain of the chimeric norovirus VP1 protein are generally joined through a linker peptide, as they are in naturally occurring VP1 proteins. The linker peptide can allow the chimeric VP1 protein to fold properly, so that it self-assembles to form VLPs. The linker peptide can be any suitable amino acid sequence, such as the linker peptide from the VP1 protein of the first norovirus strain, the second norovirus strain or a third norovirus strain. The first, second, and third norovirus strains can be any desired norovirus strains, such as any of the strains listed in Table 1. For example, the first norovirus strain can be the Snow Mountain strain, and the second norovirus strain can be any other strain, such as the Norwalk strain or the 2006a strain.

Figure 8B:
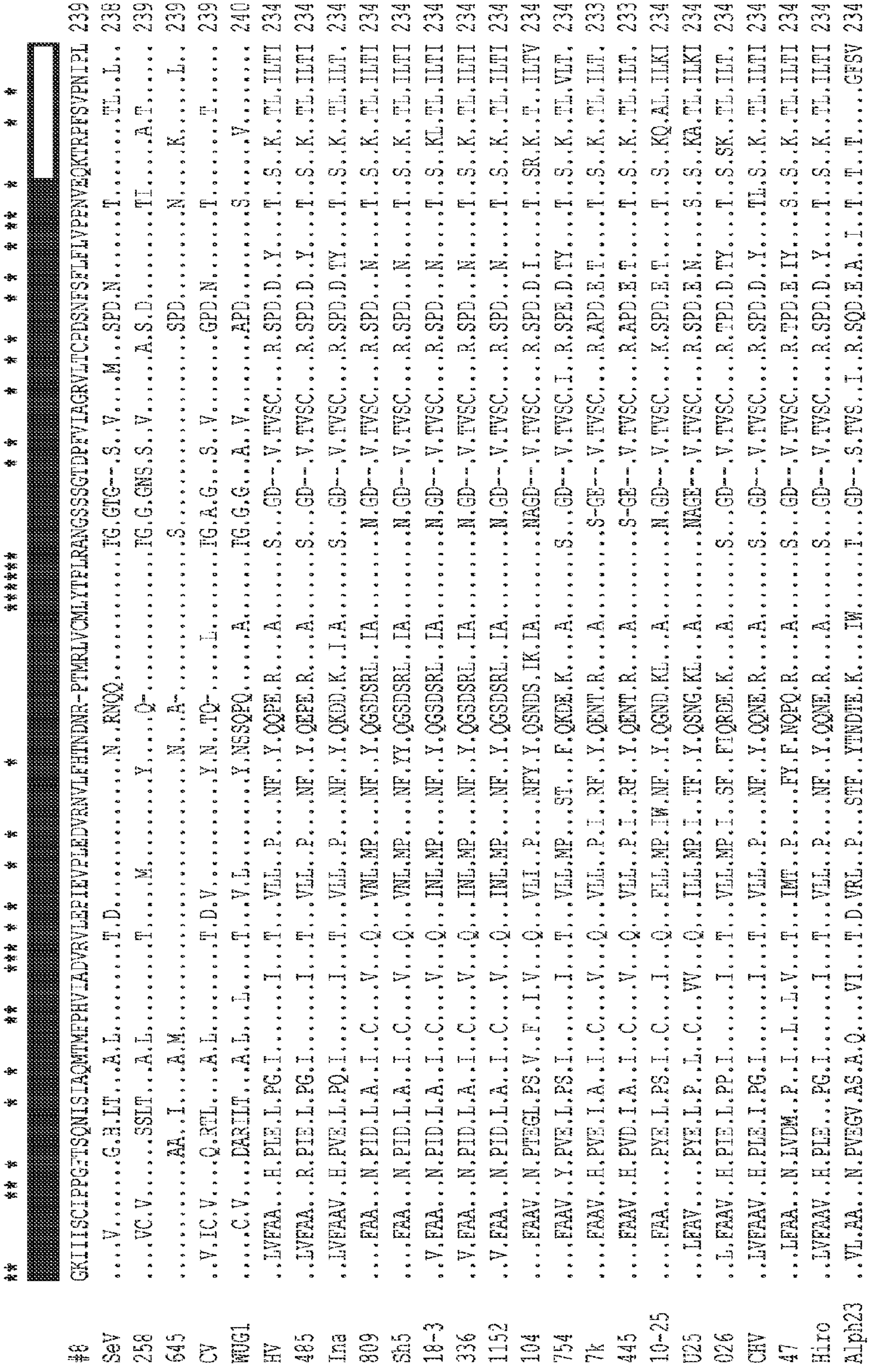
Figure 8C:
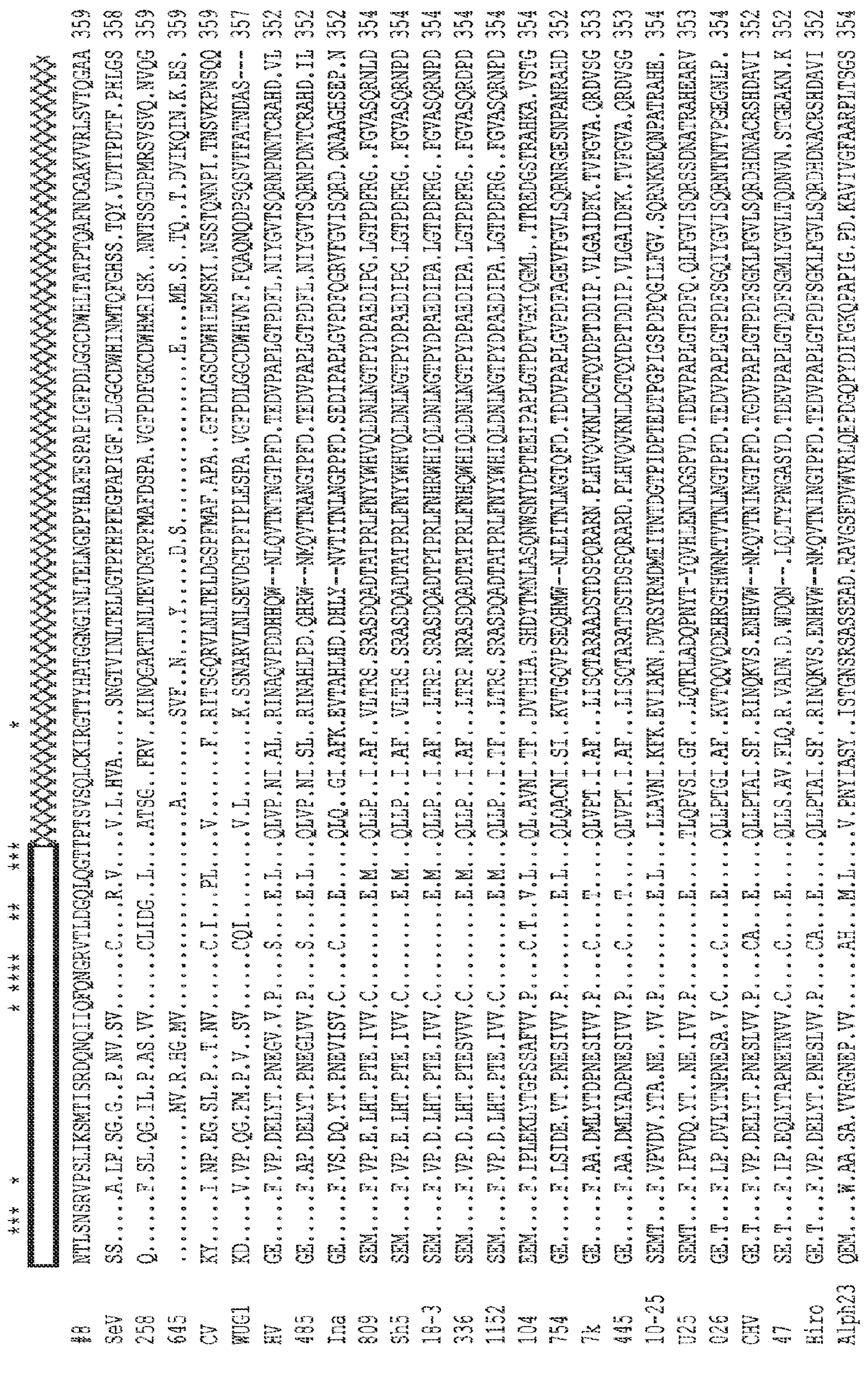
Figure 10A:
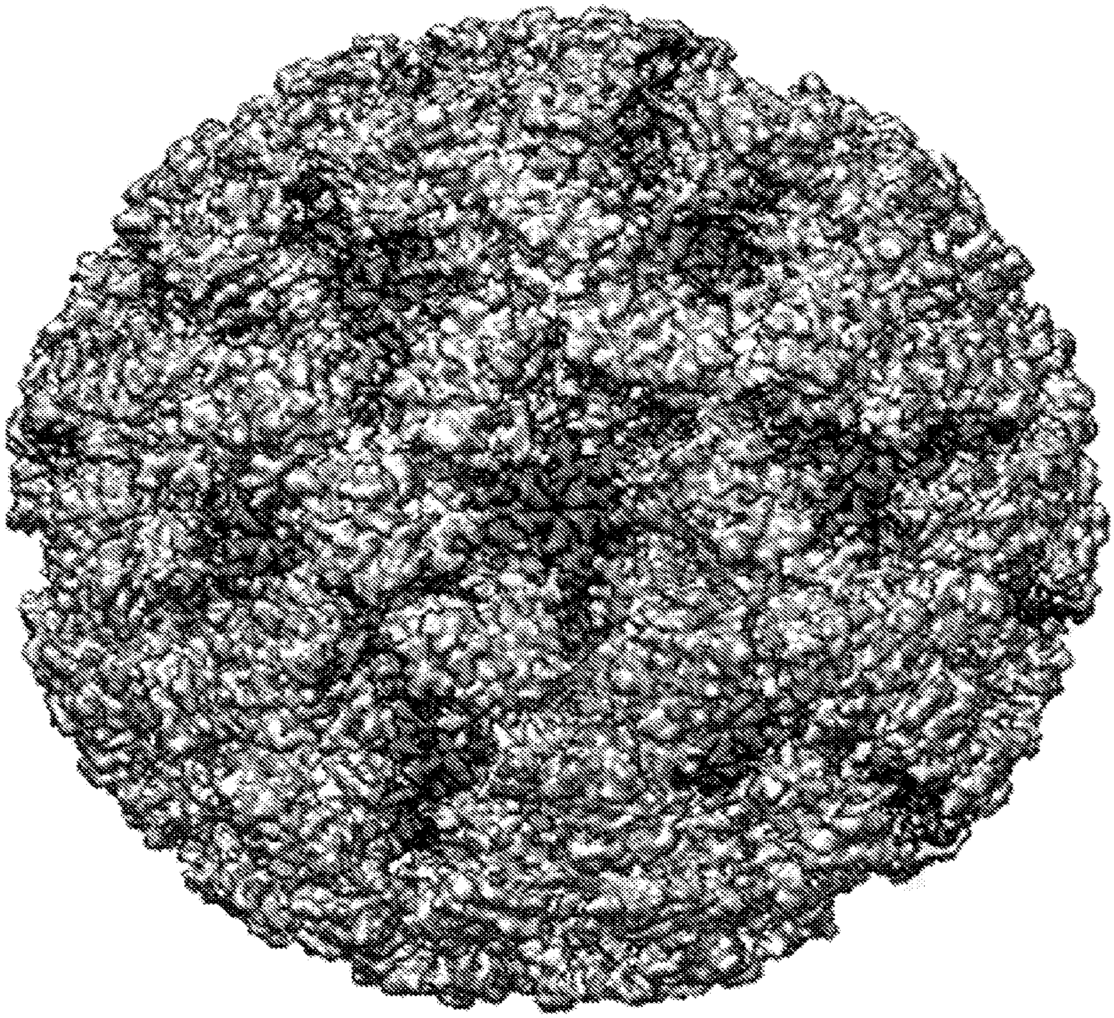
FIG. 10A is an X-ray structure of Norwalk virus-like particles with the S-domain (internal) in dark gray and the P-domain (external) in light grey.
Figure 10B:
FIG. 10B is a view of a single monomer colored as in FIG. 10A.
Figure 11A:
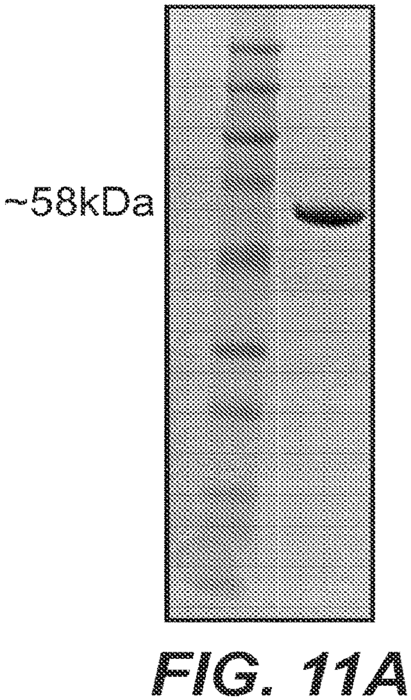
FIG. 11A is an image depicting a purified protein of Snow Mountain VLPs.
Figure 11B:
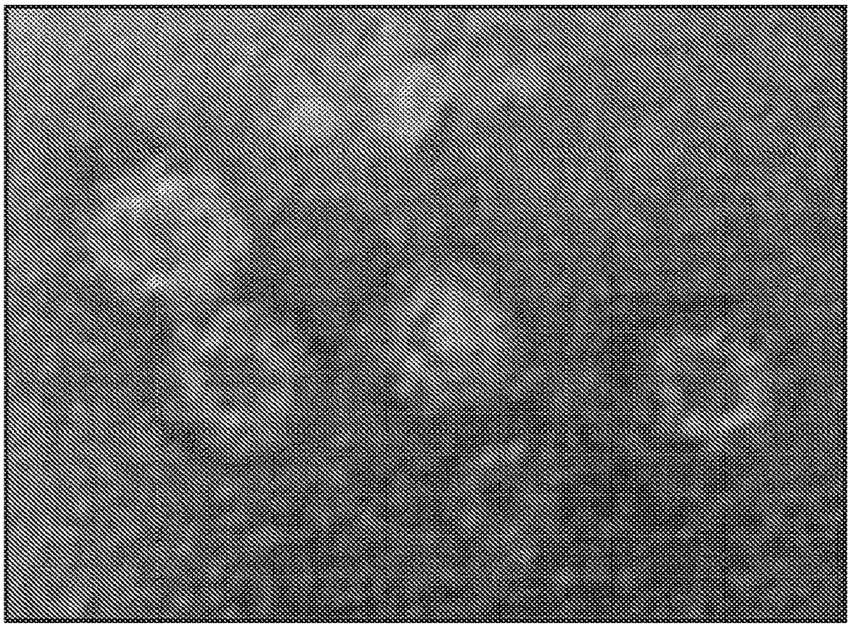
FIG. 11B is an electron micrograph of Snow Mountain VLPs.
Figure 12A:
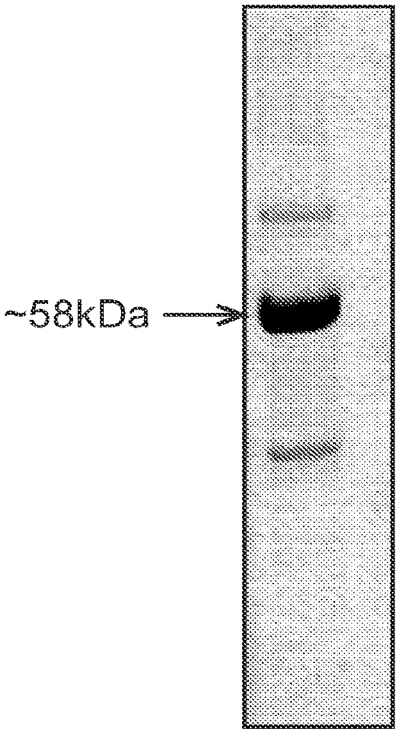
FIG. 12A is an image depicting a purified protein of Snow Mountain/Norwalk VLP chimera.
Figure 12B:
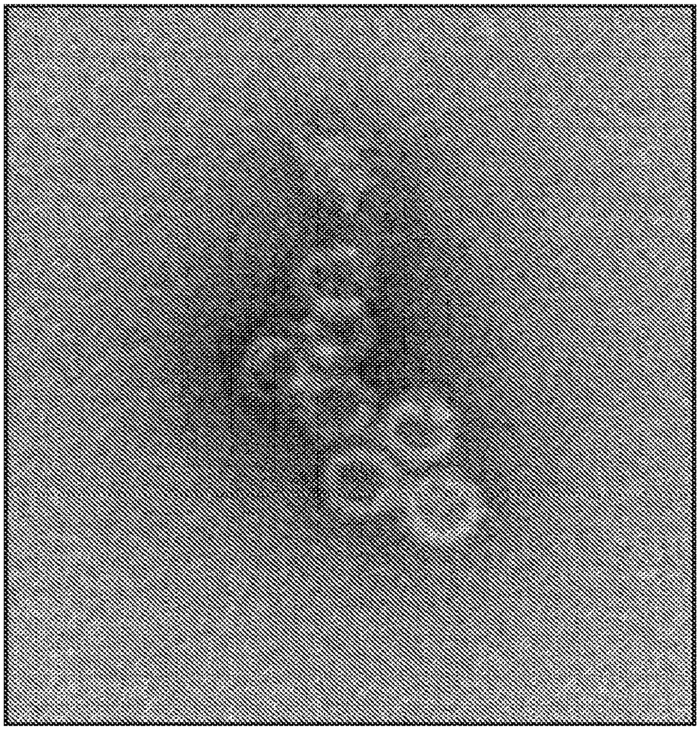
FIG. 12B is an electron micrograph of Snow Mountain/Norwalk chimeric VLPs.

If desired, the amino acid sequence of the S domain, linker and/or P domain of a chimeric VP1 may differ from the corresponding naturally occurring amino acid sequence by one or more amino acid replacement, addition or deletion (e.g., mutation, substitution, insertion, deletion, truncation and the like). Such sequence changes should not prevent the chimeric VP1 proteins from folding properly and self-assembling into VLPs. Generally, it is acceptable for amino acid sequences to vary (including by addition or deletion of one or more amino acids) from naturally occurring sequences in areas that are not highly conserved. For example, as shown in FIGS. 8A-8B alignment of the amino acid sequences of several norovirus VP1 proteins reveals that the S domain is highly conserved whereas the P domain, and the P2 subdomain in particular, is more variable. Accordingly, amino acid sequence variation can be introduced, if desired, into the amino-terminal region, carboxy-terminal region, and P domain. Some amino acid sequence variations can also be introduced into the S domain and/or P1 subdomain, preferably at nonconserved positions, which are not marked with an asterisk in FIG. 8A.

The VP1 proteins of some norovirus strains are difficult to produce in high yields by recombinant expression in host cells, such as yeast. However, when the chimeric norovirus VP1 protein contains an S-domain from a strain that is a high expressor (such as the Snow Mountain strain where expression can be >40 mg per liter of yeast cells) in a desired host cell, such as yeast cells, the chimeric protein can be produced in high yield in that host cell even if the P-domain is from a strain that is not well expressed. For example, the secreted soluble expression of Norwalk P-domain can be increased greater than 5-fold by generating a chimeric construct as described with a Snow Mountain S-domain. Accordingly, the chimeric VP1 proteins of the invention can be used to make VLPs that contain the VP1 P-domain from strains that are not well expressed in host cells, and therefore do not readily form VLPs. Thus, it is generally preferred that the S-domain is from the VP1 protein of a strain that is well expressed in a desired host cell, such as yeast cells. Preferably, the high expressor norovirus strain is a strain whose VP1 protein can be produced recombinantly in a host cell, preferably yeast, in a quantity of at least about 5 mg/liter of cells, at least about 10 mg/liter of cells, at least about 15 mg/liter of cells, at least about 20 mg/liter of cells, at least about 25 mg/liter of cells, at least about 30 mg/liter of cells, at least about 35 mg/liter of cells, or at least about 40 mg/liter of cells.

The chimeric norovirus VP1 protein can have a structure according to Formula I:

$$A\text{-}S\text{-}L\text{-}P\text{-}B \qquad (I)$$

wherein,

A and B are independently absent or any desired amino acid sequence;

S is the S-domain of VP1 of a first norovirus strain;

L is a linker peptide or absent; and

P is a norovirus VP1 P-domain, wherein at least a portion of P is from the P-domain of a second norovirus strain.

The linker peptide (L) can be any amino acid sequence that allows the chimeric VP1 protein to fold properly and to self-assemble to form a VLP. Suitable linker peptides include the linker peptide from the VP1 protein of the first norovirus strain, the second norovirus strain or a third norovirus strain. Alternatively, the linker peptide (L) can be a short amino acid sequence that permits the chimeric protein to fold properly and self-assemble into VLPs, e.g., 20 or fewer amino acids (i.e., 20, 19, 18, 17, 16, 15, 14, 13, 12, 11, 10, 9, 8, 7, 6, 5, 4, 3, 2, 1 amino acids), preferably about 9 amino acids. Examples of suitable linker peptides (L) include poly-glycine linkers ($Gly_n$ where n=2, 3, 4, 5, 6, 7, 8, 9, 10 or more (SEQ ID NO:5)), and (GGGS)n wherein n=1, 2, 3 or 4 (SEQ ID NO:6), and highly charged linkers, such as (SRSK)n wherein n=1, 2, 3 or 4 (SEQ ID NO:7). Preferably, L is the linker peptide from the VP1 protein of the first norovirus strain, the second norovirus strain or a third norovirus strain.

A and B, when present, are independently any desired amino acid sequence, such as, a sequence of about 1-500 amino acids, about 1-250 amino acids, about 1-100 amino acids, about 1-50 amino acids, about 1-40 amino acids, about 1-30 amino acids, about 1-20 amino acids, about 1-10 amino acids, or about 1-5 amino acids. For example, A and B can be one or more amino acids that are added to the chimeric protein to facilitate or as a result of cloning, or to facilitate protein purification such as an epitope tag or a histidine tag ($His_n$ where n=3, 4, 5, 6, 7, 8, 9, 10 (SEQ ID NO:8)). An epitope tag could consist of a strong T cell epitope or a modified epitope designed to improve the immunogenicity of the protein. These additional residues could comprise a modified TLR agonist as part of an immunomodulator strategy. If desired, A and/or B can comprise immunogenic fragments including, for example, the heat shock proteins or fragments, such as those disclosed in U.S. Publication No. 20060264609, or viral and bacterial antigens, such as those disclosed in U.S. Pat. No. 7,527,801. Alternately, A and/or B can comprise a full length protein, for example a recombinant protein that is to be displayed on a norovirus VP1 fusion protein, or that is to be used to display norovirus VP1 or portion thereof. In some embodiments, A and B are both absent.

As described herein, the P-domain of VP1 comprises a $P^1$ subdomain and a $P^2$ subdomain. Thus, in the formulas disclosed herein, P can be depicted as $P^1$-$P^2$, wherein $P^1$ is the $P^1$ subdomain and $P^2$ is the $P^2$ subdomain.

In the primary structure of the P-domain, the $P^2$ subdomain amino acids are inserted into the sequence of the $P^1$ subdomain amino acids, and the primary structure has the formula $P^1$-1-$P^2$-$P^1$-2, where $P^1$-1 is the amino-terminal portion of the sequence of the $P^1$ subdomain, $P^1$-2 is the remainder of the sequence of the $P^1$ subdomain, and $P^2$ is the sequence of the $P^2$ subdomain.

In some exemplary embodiments, the chimeric norovirus VP1 protein can be of Formula I, wherein S is from a first norovirus strain, and P is from a second norovirus strain. In such embodiments, L can be any suitable linker, such as the natural linker from the first norovirus strain or the second norovirus strain, or be absent.

As described herein, the chimeric norovirus VP1 protein can contain a P-domain in which a portion of the P-domain is from the same strain as the S domain, and a portion of the P-domain is from a different strain. The portion from the different stain can be the $P^1$ domain or a portion thereof, the $P^2$ domain or a portion thereof and any combination of portions of the $P^1$ domain and the $P^2$ domain. Preferably, the portion from the different strain is the $P^2$ domain or a portion thereof. For example, in some embodiments, the chimeric norovirus VP1 protein can have a structure according to Formula II or Formula III.

A-S-L-$P^1$-$P^2$-B (II)

A-S-$P^1$-$P^2$-B (III)

In Formulas II and III, the variables A, S, L and B are as described in Formula I, $P^1$ is the $P^1$ domain of VP1 and $P^2$ is the $P^2$ domain of VP1, and at least one of $P^1$ and $P^2$ is from a norovirus stain different from the strain that provides S. In some embodiments, S and $P^1$ are from a first norovirus stain and $P^2$ is from a second norovirus strain. In other embodiments, S and $P^2$ are from a first norovirus strain and $P^1$ is from a second norovirus strain. In such embodiments, the linker L, if present, can be any suitable linker, such as the linker from the first norovirus strain or the second norovirus strain. In some embodiments, the chimeric norovirus VP1 protein is of Formula II wherein S, L and $P^1$ are from a first norovirus strain and $P^2$ is from a second norovirus strain. This description of exemplary embodiments encompassed by Formulas II and III is illustrative of chimeric norovirus VP1 proteins that contain a P-domain in which a portion of the P domain is from the same strain as the S domain, and a portion of the P domain is from a different strain.

In some embodiments, the chimeric norovirus VP1 protein has a structure according to any one of Formulas IV and XVII: $S_{NV}$-L-$P_{SMV}$ (IV), $S_{SMV}$-L-$P_{NV}$ (V), $S_{NV}$-L-$P_{DSV}$ (VI), $S_{SMV}$-L-$P_{DSV}$ (VII), $S_{NV}$-L-$P_{GI}$ (VIII), $S_{NV}$-L-$P_{GII}$ (IX), $S_{NV}$-L-$P_{GIII}$ (X), $S_{NV}$-L-$P_{GIV}$ (XI), $S_{NV}$-L-$P_{GV}$ (XII), $S_{SMV}$-L-$P_{GI}$ (XIII), $S_{NV}$-L-$P_{GII}$ (XIV), $S_{SMV}$-L-$P_{GIII}$ (XV), $S_{SMV}$-L-$P_{GIV}$ (XVI), $S_{SMV}$-L-$P_{GV}$ (XVII), where P represents the P-domain, including the $P^1$ and $P^2$ subdomains, where the subscript indicates that the S-domain or the P-domain is from the following strains: NV, Norwalk strain; SMV, Snow Mountain strain; DSV, Desert Storm strain; and GI, GII, GIII, GIV and GV are any norovirus from genogroups GI, GII, GIII, GIV and GV, respectively.

In particular embodiments, the chimeric norovirus VP1 protein comprises an S-domain from the VP1 of Snow Mountain strain, the linker peptide from the VP1 of Snow Mountain strain, and a P-domain that contains at least a portion of the P-domain of the VP1 of another norovirus strain. In more particular embodiments, the P-domain or portion thereof is from the VP1 of the Norwalk strain, 2006a strain, or the New Orleans strain.

In some embodiments, the chimeric norovirus VP1 protein has a primary structure according to Formula XVIII:

A-$S_{First}$-L-P1-$1_{(First)}$-$P2_{(Second)}$-P1-$2_{(First)}$-B (XVIII),

In formula XVIII, the subscripts First and Second indicate that the domain is from a first strain or a second strain, respectively. In certain examples, the chimeric norovirus VP1 protein has a primary structure according to any one of Formulas XIX-XLVI: A-$S_{NV}$-L-$P^1$-$1_{(NV)}$-$P^2_{(SMV)}$-$P_1$-$2_{(NV)}$-B (XIX), A-$S_{SMV}$-L-$P^1$-$1_{(SMV)}$-$P2_{(NV)}$-P1-$2_{(SMV)}$-B (XX), A-$S_{NV}$-L-$P^1$-$1_{(NV)}$-$P2_{(DSV)}$-P1-$2_{(NV)}$-B (XXI), A-$S_{SMV}$-L-$P^1$-$1_{(SMV)}$-$P2_{(DSV)}$-P1-$2_{(SMV)}$-B (XXII), A-$S_{NV}$-L-$P^1$-$1_{(NV)}$-$P2_{(GI)}$-P1-$2_{(NV)}$-B (XXIII), A-$S_{NV}$-L-$P^1$-$1_{(NV)}$-$P2_{(GII)}$-P1-$2_{(NV)}$-B (XXIV), A-$S_{NV}$-L-$P^1$-$1_{(NV)}$-$P2_{(GIII)}$-P1-$2_{(NV)}$-B (XXV), A-$S_{NV}$-L-$P^1$-$1_{(NV)}$-$P2_{(GIV)}$-P1-$2_{(NV)}$-B (XXVI), A-$S_{NV}$-L-$P^1$-$1_{(NV)}$-$P2_{(GV)}$-P1-$2_{(NV)}$-B (XXVII), A-$S_{SMV}$-L-$P^1$-$1_{(SMV)}$-$P2_{(GI)}$-P1-$2_{(SMV)}$-B (XXVIII), A-$S_{SMV}$-L-$P^1$-$1_{(SMV)}$-$P2_{(GII)}$-P1-$2_{(SMV)}$-B (XXIX), A-$S_{SMV}$-L-$P^1$-$1_{(SMV)}$-$P2_{(GIII)}$-P1-$2_{(SMV)}$-B (XXX), A-$S_{SMV}$-L-$P^1$-$1_{(SMV)}$-$P2_{(GIV)}$-P1-$2_{(SMV)}$-B (XXXI), A-$S_{SMV}$-L-$P^1$-$1_{(SMV)}$-$P2_{(GV)}$-P1-$2_{(SMV)}$-B (XXXII), A-$S_{NV}$-L-$P^1$-$1_{(NV)}$-

$P2_{(SMV)}$-B (XXXIII), A-$S_{SMV}$-L-$P^1$-$1_{(SMV)}$-$P2_{(NV)}$-B (XXXIV), A-$S_{NV}$-L-$P^1$-$1_{(NV)}$-$P2_{(DSV)}$-B (XXXV), A-$S_{SMV}$-L-$P^1$-$1_{(SMV)}$-$P2_{(DSV)}$-B (XXXVI), A-$S_{NV}$-L-$P^1$-$1_{(NV)}$-$P2_{(GI)}$-B (XXXVII), A-$S_{NV}$-L-$P^1$-$1_{(NV)}$-$P2_{(GII)}$-B (XXXVIII), A-$S_{NV}$-L-$P^1$-$1_{(NV)}$-$P2_{(GIII)}$-B (XXXIX), A-$S_{NV}$-L-$P^1$-$1_{(NV)}$-$P2_{(GIV)}$-B (XL), A-$S_{NV}$-L-$P^1$-$1_{(NV)}$-$P2_{(GV)}$-B (XLI), A-$S_{SMV}$-L-$P^1$-$1_{(SMV)}$-$P2_{(GI)}$-B (XLII), A-$S_{SMV}$-L-$P^1$-$1_{(SMV)}$-$P2_{(GII)}$-B (XLIII), A-$S_{SMV}$-L-$P^1$-$1_{(SMV)}$-$P^2{}_{(GIII)}$-B (XLIV), A-$S_{SMV}$-L-$P^1$-$1_{(SMV)}$-$P2_{(GIV)}$-B (XLV), A-$S_{SMV}$-L-$P^1$-$1_{(SMV)}$-$P2_{(GV)}$-B (XLVI), wherein the subscript indicates that the S-domain or the P-subdomain is from the following strains: NV, Norwalk strain; SMV, Snow Mountain strain; DSV, Desert Storm strain; and GI, GII, GIII, GIV and GV are any norovirus from genogroups GI, GII, GIII, GIV and GV, respectively.

By following the teachings of this invention, a vast number of different chimeric VP1 proteins can be produced by recombinant means using standard procedures. The amino acid sequences of VP1 proteins, and the nucleotide sequences encoding them, from the different strains of norovirus can be obtained from the GenBank database (ncbi.nlm.nih.gov), the Taxonomy Database at National Center for Biotechnology Information (ncbi.nlm.nih.gov) or the PathoSystems Resource Integration Center Database on Caliciviridae (patric.vbi.vt.edu).

When the chimeric VP1 proteins of the invention are produced by expression in a host cell, such as yeast cells, they can self-assemble into VLPs. This is particularly the case for chimeric VP1 proteins that contain an S-domain of VP1 of a norovirus strain that is well expressed in the host cell, such as the S-domain of the Snow Mountain strain. Thus, the present invention further provides VLPs that contain a chimeric VP1. The VLPs can be monovalent or bivalent or multivalent. Monovalent VLPs contain a chimeric VP1 protein and only one P-domain. In some embodiments, the monovalent VLP can contain a chimeric VP1 and a naturally occurring VP1 that each contain the same P-domain. Preferred monovalent VLPs are composed of multiple copies (e.g., 180 copies) of a single chimeric VP1 protein. Accordingly, in certain embodiments, the monovalent VLPs of the invention include 180 copies of a single chimeric VP1 of any one of Formulas I-XLVI, for example.

Bivalent and multivalent VLPs contain a chimeric VP1 protein and at least 2 different P-domains. For example, in some embodiments, a bivalent VLP can contain a chimeric VP1 that contains a first P-domain and a naturally occurring VP1 that contains a second P-domain. In such embodiments, it is preferred that the S-domain in the chimeric VP1 and in naturally occurring VP1 is the same. In other embodiments, the bivalent or multivalent VLP contains two or more different chimeric VP1 proteins that contain P-domains from different strains. Preferably the two or more chimeric VP1 proteins contain the same S-domain.

In certain other embodiments, the bivalent or multivalent VLPs of the invention include two or more chimeric VP1 proteins selected from the group consisting of chimeric VP1 proteins according to Formulas I-XLVI, for example.

If desired, the amino acid sequence of one or both of the S- and P-domains (including P-subdomains) of a chimeric VP1 can be altered (by insertion, deletion, mutation, substitution) to include one or more amino acid insertion(s), deletion(s), mutation(s) or substitution(s) that render the amino acid sequence of the domain or subdomain different from the corresponding naturally occurring amino acid sequence, for example by up to about 20%, up to about 1%, up to about 2%, up to about 3%, up to about 4%, up to about 5%, up to about 10%, up to about 15%, or up to about 20% over the length of the amino acid sequence of the domain or subdomain.

As shown in FIGS. 8A-8E, alignment of naturally occurring VP1 amino acid sequences demonstrates that the N-terminal region (aa 1-49), S-domain (aa 50-225) and $P_{1-1}$ subdomain (aa 226-278) amino acid sequences are more conserved (asterisks indicate conserved amino acids) than the amino acid sequence of the P2 subdomain (aa 279-405), P1-2 domain (aa 406-520) and C-terminal region (Hansman et al. (2006) J. General Virology 87: 909-919). Because conserved amino acid residues are often important for proper folding or function, it is preferred that any amino acid sequence alterations that are present are not introduced at conserved positions. For example, conserved amino acids in the S-domain may be important for proper folding and formation of VLPs. Therefore, in the chimeric VP1 proteins of the present invention, conserved amino acid residues are preferably not deleted or replaced.

Thus, in some embodiments, the S-domain of the chimeric VP1 protein of the invention can have at least about 70-100% or about 80-100% amino acid sequence identity to a naturally occurring S-domain, including any percent identity within this range, such as at least about 70, at least about 71, at least about 72, at least about 73, at least about 74, at least about 75, at least about 76, at least about 77, at least about 78, at least about 79, at least about 80, at least about 81, at least about 82, at least about 83, at least about 84, at least about 85, at least about 86, at least about 87, at least about 88, at least about 89, at least about 90, at least about 91, at least about 92, at least about 93, at least about 94, at least about 95, at least about 96, at least about 97, at least about 98, at least about 99, or 100% amino acid sequence identity. Alternatively or in addition, the P1-1-subdomain of the chimeric VP1 protein of the invention can have at least about 70-100% or about 80-100% amino acid sequence identity relative to a naturally occurring P1-1-subdomain, including any percent identity within this range, such as at least about 70, at least about 71, at least about 72, at least about 73, at least about 74, at least about 75, at least about 76, at least about 77, at least about 78, at least about 79, at least about 80, at least about 81, at least about 82, at least about 83, at least about 84, at least about 85, at least about 86, at least about 87, at least about 88, at least about 89, at least about 90, at least about 91, at least about 92, at least about 93, at least about 94, at least about 95, at least about 96, at least about 97, at least about 98, at least about 99, or 100% amino acid sequence identity. Alternatively or in addition, the P2-subdomain of the chimeric VP1 protein of the invention can have at least about 70-100% or about 80-100% amino acid sequence identity to a naturally occurring $P_2$-subdomain, including any percent identity within this range, such as at least about 70, at least about 71, at least about 72, at least about 73, at least about 74, at least about 75, at least about 76, at least about 77, at least about 78, at least about 79, at least about 80, at least about 81, at least about 82, at least about 83, at least about 84, at least about 85, at least about 86, at least about 87, at least about 88, at least about 89, at least about 90, at least about 91, at least about 92, at least about 93, at least about 94, at least about 95, at least about 96, at least about 97, at least about 98, at least about 99, or 100% amino acid sequence identity. Alternatively or in addition, the P1-2-subdomain of the chimeric VP1 protein of the invention can have at least about 70-100% or about 80-100% amino acid sequence identity to a naturally occurring P1-2-subdomain, including any percent identity within this range, such as at least about 70, at least about 71, at least about 72, at least about 73, at least about 74, at least about 75, at least about 76, at least about 77, at least about 78, at least about 79, at least about 80, at least about 81, at least about 82, at least about 83, at least about 84, at least about 85, at least about 86, at least about 87, at least about 88, at least about 89, at least about 90, at least about 91, at least about 92, at least about 93, at least about 94, at least about 95, at least about 96, at least about 97, at least about 98, at least about 99, or 100% amino acid sequence identity.

The S-domains of the VP1 proteins of the invention are full-length or near full-length relative to a naturally occurring S-domain. Truncation at either N- or C-terminals or both and internal deletions, are acceptable provided that the ability to form VLPs under conditions that favor VLP formation is preserved. Accordingly, the S-domain may comprise the full-length sequence, fragments, truncated and partial sequences, as well as analogs and precursor forms of the reference or native S-domain. In some embodiments, the S-domain of the VP1 proteins of the invention is truncated at its N-terminal end by 5, 10, 15, 20, 25, 30, 35, 40, 45 or 50 amino acid residues. Alternatively or in addition, the S-domain of the VP1 proteins of the invention can be truncated at its C-terminal end by 5, 10, 15, 20, 25, 30, 35, 40, 45 or 50 amino acid residues. Alternatively or in addition, the S-domain of the VP1 proteins of the invention can contain an internal deletion of 5, 10, 15, 20, 25, 30, 35, 40, 45 or 50 amino acid residues in length.

The P1-1-subdomains of the VP1 proteins of the invention are full-length or near full-length relative to a naturally occurring P1-1-subdomain, with sequence truncation at either N- or C-terminals or both and/or with internal deletions. Accordingly, the P1-1-subdomain may comprise the full-length sequence, fragments, truncated and partial sequences, as well as analogs and precursor forms of the naturally occurring P1-1-domain. In some embodiments, the P1-1-subdomain of the VP1 proteins of the invention is truncated at its N-terminal end by 1, 2, 3, 4, 5, 6, 7, 8, 9 or 10 amino acid residues. Alternatively, or in addition, the P1-1-subdomain of the VP1 proteins of the invention can be truncated at its C-terminal end by 1, 2, 3, 4, 5, 6, 7, 8, 9 or 10 amino acid residues. Alternatively or in addition, the P1-1-subdomain of the VP1 proteins of the invention can contain an internal deletion of 1, 2, 3, 4, 5, 6, 7, 8, 9 or 10 amino acid residues in length.

The P2-subdomains of the VP1 proteins of the invention are full-length or near full-length relative to the naturally occurring P2-subdomain, with sequence truncation at either N- or C-terminals or both and/or with internal deletions. Accordingly, the P2-subdomain may comprise the full-length sequence, fragments, truncated and partial sequences, as well as analogs and precursor forms of the naturally occurring P2-domain. In some embodiments, the P2-subdomain of the VP1 proteins of the invention is truncated at its N-terminal end by 1 to about 26 amino acids, such as 1, 2, 3, 4, 5, 6, 7, 8, 9, 10, 12, 16, 20, 24 or 26 amino acid residues. Alternatively, or in addition, the P2-subdomain of the VP1 proteins of the invention can be truncated at its C-terminal end by 1 to about 26 amino acids, such as 1, 2, 3, 4, 5, 6, 7, 8, 9, 10, 12, 16, 20, 24 or 26 amino acid residues. Alternatively, or in addition, the P2-subdomain of the VP1 proteins of the invention can contain an internal deletion of 1 to about 26 amino acids, such as 1, 2, 3, 4, 5, 6, 7, 8, 9, 10, 12, 16, 20, 24 or 26 amino acid residues.

The P1-2-subdomains of the VP1 proteins of the invention are full-length or near full-length relative to the native or reference P1-2-subdomain, with sequence truncation at either N- or C-terminals or both and/or with internal deletions. Accordingly, the P1-2-subdomain may comprise the full-length sequence, fragments, truncated and partial sequences, as well as analogs and precursor forms of the naturally occurring P1-2-domain. In some embodiments, the P1-2-subdomain of the VP1 proteins of the invention is truncated at its N-terminal end by 1 to about 26 amino acids, such as 1, 2, 3, 4, 5, 6, 7, 8, 9, 10, 12, 16, 20, 24 or 26 amino acid residues. Alternatively, or in addition, the P1-2-subdomain of the VP1 proteins of the invention can be truncated at its C-terminal end by 1 to about 26 amino acids, such as 1, 2, 3, 4, 5, 6, 7, 8, 9, 10, 12, 16, 20, 24 or 26 amino acid residues. Alternatively or in addition, the P1-2-subdomain of the VP1 proteins of the invention can contain an internal deletion of 1 to about 26 amino acids, such as 1, 2, 3, 4, 5, 6, 7, 8, 9, 10, 12, 16, 20, 24 or 26 amino acid residues.

In some embodiments, the P-domains (including P1-1, P2 and P1-2 subdomains) of the chimeric VP1 proteins of the invention can include amino acid sequence insertions or replacements that are portions of other polypeptides, such as polypeptides that are displayed on the chimeric VP1. For example, the P-domain can be fused to another polypeptide or portion of another polypeptide. For example, in Formula 1 B can be an amino acid sequence of another polypeptide that is displayed on the chimeric VP1. In such situations, the other polypeptide can be displayed on the surface of a VLP that contains the chimeric VP1 protein.

The chimeric VP1 proteins of the invention can be produced by expression in suitable recombinant host cells, such as yeast cells, using any suitable methods, including those described herein.

B. Nucleic Acids

The invention further provides recombinant nucleic acids that encode the chimeric norovirus VP1 proteins described herein. These nucleic acids contain a first nucleotide sequence that encodes the S-domain of VP1 of a first norovirus strain, a second nucleotide sequence that encodes a P-domain that contains at least a portion of the P-domain of a second norovirus strain, and optionally, third, forth and fifth nucleotide sequences that encode a linker peptide, and amino acid sequences A and B, respectively. The nucleic acid sequences are operably linked so that the nucleic acid can be transcribed and/or translated to produce a chimeric VP1 protein that self assembles into a VLP. Any suitable nucleic acid sequences that encode the S-domain and the P-domain of VP1 from desired norovirus strains can be used. For example, nucleic acids that have the same nucleotide sequences as the corresponding sequences in ORF2 in the genome of the desired norovirus strain, or codon optimized variants thereof that are optimized for recombinant expression in a desired host cell, such as yeast cells, can be used.

A representative norovirus ORF2 sequence from the Snow Mountain strain is known and is presented in FIG. 4A. The nucleotide sequences of ORF2 of many other norovirus strains are known in the art, such as the ORF2 sequences of Norwalk virus, GenBank Accession No. M87661, Hawaii virus; GenBank Accession No. U07611, and sequences disclosed in the following patent publications: WO 05/030806, WO 00/79280, JP2002020399, US2003129588, U.S. Pat. No. 6,572,862, WO 94/05700, and WO 05/032457. See also Green et al. (2000) J. Infect. Dis. 181(Suppl. 2):S322-330; Wang et al. (1994) J. Virol. 68:5982-5990; Chen et al. (2004) J. Virol. 78: 6469-6479; Chakravarty et al. (2005) J. Virol. 79: 554-568; and Fankhauser et al. (1998) J. Infect. Dis. 178:1571-1578; for sequence comparisons of different norovirus strains. Further information about nucleotide sequences of noroviruses can be obtained from the GenBank database (ncbi.nlm.nih.gov), the Taxonomy Database at National Center for Biotechnology Information (ncbi.nlm.nih.gov) or the PathoSystems Resource Integration Center Database on Caliciviridae (patric.vbi.vt.edu).

In some aspects, the recombinant nucleic acids encode a chimeric VP1 protein described herein, such as a chimeric VP1 protein according to Formula I. For example, the recombinant nucleic acid can include a coding sequence according to Formula LIV

A'-S'-L'-P'-B' (XLVII)

wherein,

A' and B' are independently absent or a nucleotide sequence encoding any desired amino acid sequence;

S' is a nucleotide sequence encoding the S-domain of VP1 of a first norovirus strain;

L' is absent or a nucleotide sequence encoding a linker peptide and;

P' is a nucleotide sequence encoding a norovirus VP1 P-domain, wherein at least a portion of P is from the P-domain of a second norovirus strain.

The linker peptide encoded by L', and the amino acid sequences encoded by A', S', P' and B' are as described herein for L, A, S, P, and B, respectively.

In particular embodiments, the recombinant nucleic acid contains a coding sequence that encodes a chimeric VP1 protein according to any one of Formulas I-XLVI.

Figure 7:
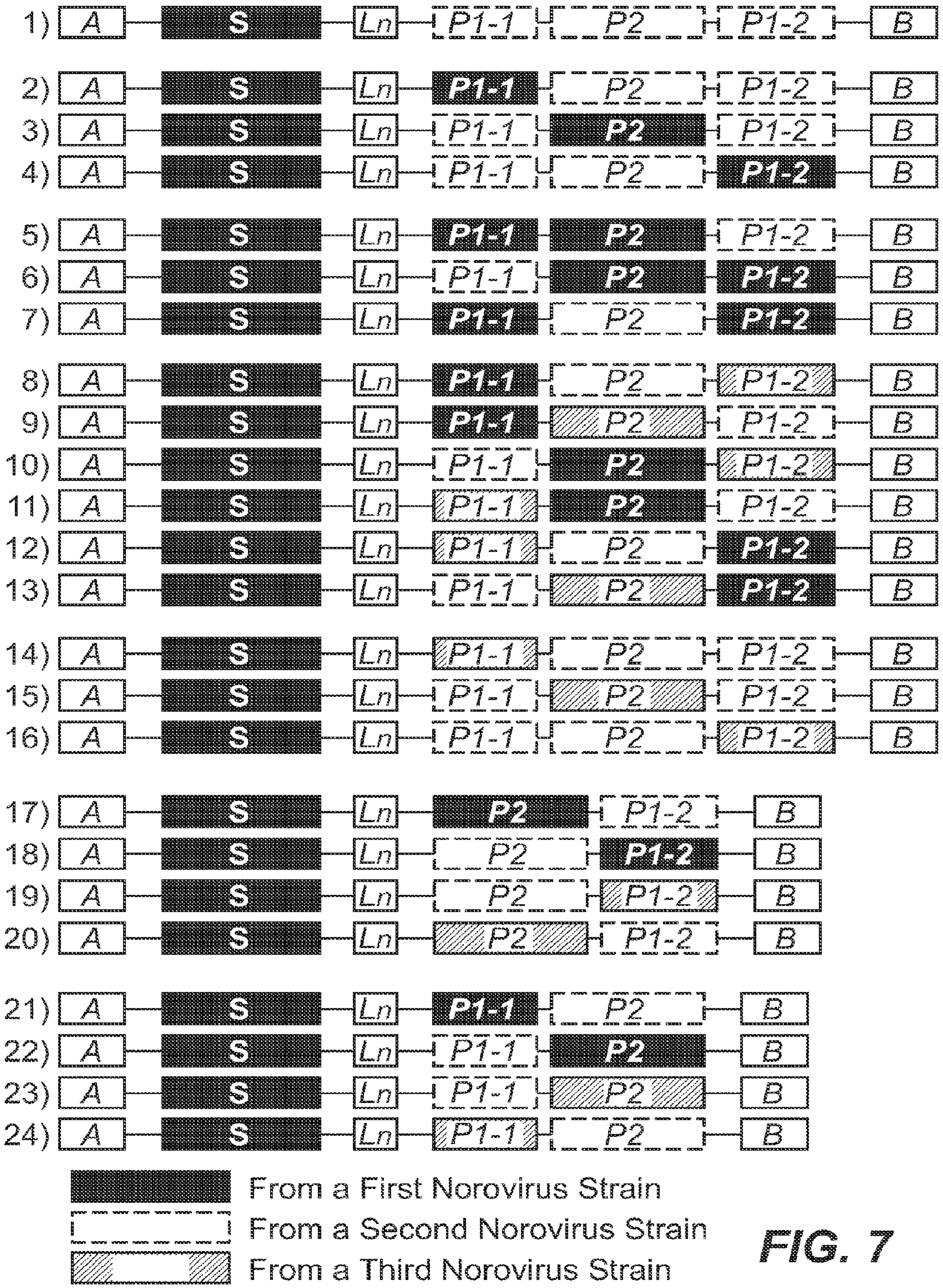
FIG. 7 shows 24 schematic representations of the primary structure of exemplary chimeric VP1 proteins of the invention. The variables A, S, L, P1-1, P2, P1-2, and B are as described herein.

In other particular embodiments, the recombinant nucleic acid contains a coding sequence that encodes a chimeric VP1 protein have any of the primary structures shown in FIG. 7.

Representative recombinant nucleic acids that encode chimeric VP1 proteins that contain the S-sequence from Snow Mountain strain and the P-sequence from Norwalk stain; or the S-sequence from Snow Mountain strain and the P-sequence from GII.4 2006a.OPTI.P strain are shown in FIGS. 5 and 6 respectively. In the case of the Snow Mountain sequence, the S-domain encompasses residues 1-216 and the linker includes residues 217 to 226. For Norwalk the P-sequence encompassed residues 231-530. For the 2006a sequence, the P-sequence encompassed residues 227-541. Additional representative norovirus sequences are Norwalk virus, GenBank Accession No. M87661, Snow Mountain virus, GenBank Accession No. U70059; Snow Mountain virus, GenBank Accession No. AY134748, Hawaii virus; GenBank Accession No. U07611, and sequences disclosed in the following patent publications: WO 05/030806, WO 00/79280, JP2002020399, US2003129588, U.S. Pat. No. 6,572,862, WO 94/05700, and WO 05/032457. See also Green et al. (2000) J. Infect. Dis. 181(Suppl. 2):S322-330; Wang et al. (1994) J. Virol. 68:5982-5990; Chen et al. (2004) J. Virol. 78:6469-6479; Chakravarty et al. (2005) J. Virol. 79:554-568; and Fankhauser et al. (1998) J. Infect. Dis. 178:1571-1578; for sequence comparisons of different norovirus strains.

A nucleic acid encoding a chimeric VP1 protein can be RNA or DNA, can be constructed using any suitable method (e.g. by chemical synthesis, using recombinant DNA technology) and can take various forms (e.g. single stranded, double stranded, vectors, etc.). Many suitable methods for producing recombinant constructs are well-known and conventional in the art. For example, the recombinant nucleic acids can be produced from two or more oligonucleotides comprising sequences encoding portions of the chimeric VP1 protein or by ligating oligonucleotides to form a coding sequence for the full length chimeric VP1 protein using standard molecular biology techniques. See, e.g., U.S. Pat. No. 6,632,601 and U.S. Pat. No. 6,630,298. Preferably, nucleic acids are prepared in substantially pure form (i.e. substantially free from other host cell or non host cell nucleic acids).

Polynucleotides that encode VP1 proteins of interest can be isolated from a genomic library derived from viral RNA, present in, for example, stool or vomit samples from an infected individual. Alternatively, norovirus nucleic acids can be isolated from infected humans or other mammals or from stool or vomit samples collected from infected individuals as described in e.g., Estes et al. U.S. Pat. No. 6,942,865; Guntapong et al. (2004) Jpn J. Infect. Dis. 57:276-278; Harrington et al. (2004) J. Virol. 78:3035-3045; Fankhauser et al. (1998) J. Infect. Dis. 178:1571-1578; and Dolin et al. (1971) J. Infect. Dis. 123:307-312. Porcine viruses can be grown in LLC-PK cells in the presence of intestinal fluid containing bile acids (Chang et al. (2004) Proc. Natl. Acad. Sci. U.S.A. 101:8733-8738). An amplification method such as PCR can be used to amplify polynucleotides from either norovirus genomic RNA or cDNA encoding therefore. Alternatively, polynucleotides can be chemically synthesized. The nucleotide sequence can be designed with the appropriate codons for the particular amino acid sequence desired. Preferably, synthetic constructs will contain codons optimized for expression in the intended host cell in which the chimeric VP1 protein will be produced. The complete sequence of the polynucleotide of interest can be assembled from overlapping oligonucleotides prepared by standard methods and assembled into a complete coding sequence. See, e.g., Edge (1981) Nature 292:756; Nambair et al. (1984) Science 223:1299; Jay et al. (1984) J. Biol. Chem. 259:6311; Stemmer et al. (1995) Gene 164:49-53. The polynucleotides can be RNA or single- or double-stranded DNA. Preferably, the polynucleotides are isolated free of other components, such as proteins and lipids.

Alternatively, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. See, e.g., Sambrook, supra. In particular, one method of obtaining nucleotide sequences encoding the desired sequences is by annealing complementary sets of overlapping synthetic oligonucleotides, followed by ligation with an appropriate DNA ligase and amplification of the ligated nucleotide sequence via PCR. See, e.g., Jayaraman et al. (1991) Proc. Natl. Acad. Sci. USA 88:4084-4088. Additionally, oligonucleotide directed synthesis (Jones et al. (1986) Nature 54:75-82), oligonucleotide directed mutagenesis of pre-existing nucleotide regions (Riechmann et al. (1988) Nature 332:323-327 and Verhoeyen et al. (1988) Science 239:1534-1536), and enzymatic filling-in of gapped oligonucleotides using T4 DNA polymerase (Queen et al. (1989) Proc. Natl. Acad. Sci. USA 86:10029-10033) can be used.

Recombinant constructs encoding chimeric VP1 proteins can be prepared in suitable vectors, such as expression vectors, using conventional methods. The recombinant construct, such as an expression vector, includes a nucleic acid sequence which encodes a chimeric norovirus VP1 protein. The recombinant construct can be in the form of DNA, RNA, and can be either single or double stranded. For example, the construct can be in the form of a plasmid. A number of suitable vectors for expression of recombinant proteins in a desired host cell are well-known and conventional in the art. Suitable vectors can contain a number of components, including, but not limited to one or more of the following: an origin of replication; a selectable marker gene; one or more expression control elements, such as a transcriptional control element (e.g., a promoter, an enhancer, a terminator), and/or one or more translation signals; and a signal sequence or leader sequence for targeting to the secretory pathway in a selected host cell (e.g., of mammalian origin or from a heterologous mammalian or non-mammalian species). For example, for expression in insect cells a suitable baculovirus expression vector, such as pFastBac (Invitrogen), is used to produce recombinant baculovirus particles. The baculovirus particles are amplified and used to infect insect cells to express recombinant protein. For expression in mammalian cells, a vector that will drive expression of the construct in the desired mammalian host cell (e.g., Chinese hamster ovary cells) is used. Similarly, for expression in yeast, a vector that will drive expression in the desired yeast host cell (e.g., *Saccharomyces cerevisiae, Candida albicans, Candida maltosa, Hansenual polymorpha, Kluyveromyces fragilis, Kluyveromyces lactis, Pichia guillerimondii, Pichia pastoris, Schizosaccharomyces pombe* and *Yarrowia lipolytica*) is used.

Viral vectors can be used for the production of VLPs of the invention in eukaryotic cells, such as those derived from the pox family of viruses, including vaccinia virus and avian poxvirus. Additionally, a vaccinia based infection/transfection system, as described in Tomei et al. (1993) J. Virol. 67:4017-4026 and Selby et al. (1993) J. Gen. Virol. 74:1103-1113, will also find use with the present invention. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. Alternately, T7 can be added as a purified protein or enzyme as in the "Progenitor" system (Studier and Moffatt (1986) J. Mol. Biol. 189:113-130). The method provides for high level, transient, cytoplasmic production of large quantities of RNA and its translation product(s).

The recombinant nucleic acids can be in the form of, or components of, a vectored expression system, such as a self-replicating nucleic acid molecule (e.g., RNA), an alphavirus particle, an alphavirus replicon, and the like.

If desired, the vector can include a detectable marker. For example, the detectable marker can be a polypeptide that confers resistance to one or more antibiotics. Additional information about the vectors of the invention is provided below in section C.

C. Production of Viral-Like Particles (VLPs) & Host Cells for Same

The invention further provides recombinant host cells that contain a nucleic acid that encodes a chimeric norovirus VP1 protein, and methods for producing a chimeric norovirus VP1 protein and VLPs that contain the chimeric VP1 protein. The chimeric VP1 proteins can be produced using any suitable method. Generally, they are produced by expression of recombinant constructs that encode the chimeric VP1 protein in suitable recombinant host cells, such as insect cells (e.g., *Aedes aegypti, Autographa californica, Bombyx mori, Drosophila melanogaster, Spodoptera frugiperda*, and *Trichoplusia ni*), mammalian cells (e.g., human, non-human primate, horse, cow, sheep, dog, cat, and rodent (e.g., hamster), avian cells (e.g., chicken, duck, and geese, bacteria (e.g., *E. coli, Bacillus subtilis*, and *Streptococcus* spp.), yeast cells (e.g., *Saccharomyces cerevisiae, Candida albicans, Candida maltosa, Hansenual polymorpha, Kluyveromyces fragilis, Kluyveromyces lactis, Pichia guillerimondii, Pichia pastoris, Schizosaccharomyces pombe* and *Yarrowia lipolytica*), *Tetrahymena* cells (e.g., *Tetrahymena thermophila*) or combinations thereof. Many suitable insect cells and mammalian cells are well-known in the art. Suitable insect cells include, for example, Sf9 cells, Sf21 cells, Tn5 cells, Schneider S2 cells, and High Five cells (a clonal isolate derived from the parental *Trichoplusia ni* BTI-TN-5B1-4 cell line (Invitrogen)). Suitable mammalian cells include, for example, Chinese hamster ovary (CHO) cells, human embryonic kidney cells (HEK293 cells, typically transformed by sheared adenovirus type 5 DNA), NIH-3T3 cells, 293-T cells, Vero cells, HeLa cells, PERC.6 cells (ECACC deposit number 96022940), Hep G2 cells, MRC-5 (ATCC CCL-171), WI-38 (ATCC CCL-75), fetal rhesus lung cells (ATCC CL-160), Madin-Darby bovine kidney ("MDBK") cells, Madin-Darby canine kidney ("MDCK") cells (e.g., MDCK (NBL2), ATCC CCL34; or MDCK 33016, DSM ACC 2219), baby hamster kidney (BHK) cells, such as BHK21-F, HKCC cells, and the like. Suitable avian cells include, for example, chicken embryonic stem cells (e.g., EBx® cells), chicken embryonic fibroblasts, chicken embryonic germ cells, duck cells (e.g., AGE1.CR and AGE1.CR.pIX cell lines (ProBioGen) which are described, for example, in *Vaccine* 27:4975-4982 (2009) and WO2005/042728), EB66 cells, and the like.

Suitable insect cell expression systems, such as baculovirus systems, are known to those of skill in the art and described in, e.g., Summers and Smith, *Texas Agricultural Experiment Station Bulletin* No. 1555 (1987). Materials and methods for baculovirus/insect cell expression systems are commercially available in kit form from, inter alia, Invitrogen, San Diego Calif. Avian cell expression systems are also known to those of skill in the art and described in, e.g., U.S. Pat. Nos. 5,340,740; 5,656,479; 5,830,510; 6,114,168; and 6,500,668; European Patent No. EP 0787180B; European Patent Publication No. EP1500699; WO 03/043415; and WO 03/076601. Similarly, yeast, bacterial and mammalian cell expression systems are also known in the art and described in, e.g., *Yeast Genetic Engineering* (Barr et al., eds., 1989) Butterworths, London.

In some aspects, the method for producing a chimeric norovirus VP1 protein comprises culturing a host cell transformed with a recombinant nucleic acid that encodes a chimeric VP1 protein under conditions suitable for expression of the nucleic acid, whereby a chimeric norovirus VP1 protein is produced. Chimeric VP1 proteins can self-assemble to form VLPs, and preferably the host cell is maintained under conditions suitable for VLP formation. Conditions suitable for the formation of VLPs are well known and easily determined by a person of ordinary skill in the art. See, e.g., U.S. Pat. No. 7,527,801, which describes the production of viral particles in yeast cells (*Saccharornyces cerevisiae*) and insect cells (SF9), and Taube, S. et al. (2005) Archives of Virology 150:1425-1431, which describes the production of VLPs in HEK293T cells. If desired, the method can further include the step of isolating or purifying the chimeric norovirus VP1 protein, VLPs containing the chimeric VP1 protein, or a combination thereof from the culture media or cells. In some preferred embodiments, the host cell used to produce the chimeric VP1 protein and/or VLPs containing the chimeric VP1 protein is a yeast cell, insect cell, or a combination thereof.

The invention also provides methods for the production of multivalent VLPs. Multivalent VLPs can be prepared by maintaining a host cell that contains recombinant nucleic acids encoding two different chimeric VLPs. For example, this can be accomplished using a bicistronic expression vector, such as pCDC.7 for expression in yeast. Alternatively, two or more monovalent VLPs can be prepared, and optionally purified, and then mixed to produce a formulation of VLPs that is multivalent.

The norovirus chimeric VP1 proteins, and VLPs, can also be produced by expression of a recombinant nucleic acid molecule that encodes a norovirus chimeric VP1 proteins, e.g., in the form of or as a component of a vectored expression system, by the cells of a mammal following administration of the recombinant nucleic acid to the mammal.

D. Isolation and Purification of VLPs

The present invention further provides a method of isolating or purifying norovirus VLPs from culture media, host cells or a combination thereof. Preferably, the VLPs are isolated or purified directly from the host cell culture media, i.e., conditioned culture media. However, if desired, the host cells can be recovered, for example by centrifugation, a host cell homogenate or lysate can be formed using any suitable methods, and VLPs can be isolated. Suitable chemical, physical or mechanical means, which lyse the cells yet keep the VLPs substantially intact are known in the art and are described in, e.g., Protein Purification Applications: A Practical Approach, (E. L. V. Harris and S. Angal, Eds., 1990).

VLPs can be isolated from culture media or host cells, e.g., a cell lysate or homogenate, using any suitable method. Suitable methods that maintain the integrity of VLPs, such as, density gradient centrifugation, e.g., sucrose gradients, PEG-precipitation, pelleting, and the like (see, e.g., Kirnbauer et al. (1993) J. Virol. 67:6929-6936), as well as standard purification techniques including, e.g., ion exchange and gel filtration chromatography can be used. Centrifugation, on a sucrose cushion or sucrose gradient is convenient method for isolating VLPs from VP1 monomers or oligomers and from other cellular components. These methods can be used singly, consecutively and integrated into a larger purification scheme. For example, VLPs that are purified on a sucrose cushion or gradient can then be further purified if desired, for example, using ion exchange chromatography, size exclusion chromatography or any other suitable method. In a particular example, norovirus virus-like particles (VLPs) can be purified from the media of yeast cells expressing the norovirus VP1 protein. A low speed spin (15,000×g) can be performed on the media to remove extra cells or cellular debris. Following this step a high speed spin (100,000×g) through a 40% sucrose cushion can be performed to separate the virus-like particles from free protein and other material. The pellet containing the VLPs can be resuspended in buffer (50 mM Tris pH 7.5, 100 mM NaCl) and loaded onto an ion exchange column. The VLPs can be eluted from the column using a salt gradient. Finally, the eluted fractions containing the VLPs can be concentrated and buffer exchanged into a lower salt buffer (20 mM Tris pH 7.5, 100 mM NaCl) and stored at 4° Celsius until needed.

E. Immunogenic Compositions

As described earlier, the invention also provides immunogenic compositions comprising one or more chimeric VP1 proteins, preferably in the form of a VLP. Two or more different chimeric VP1 proteins, monovalent VLPs, or multivalent VLPs may be mixed together to produce a multivalent immunogenic composition that contains two or more different VP1 P-domains.

The immunogenic compositions may comprise a mixture of chimeric VP1 proteins, VLPs and nucleic acids, which in turn may be delivered using the same or different vehicles. Antigens may be administered individually or in combination, in e.g., prophylactic (i.e., to prevent infection) or therapeutic (to treat infection) immunogenic compositions. The immunogenic composition may be given more than once (e.g., a “prime” administration followed by one or more “boosts”) to achieve the desired effects. The same composition can be administered in one or more priming and one or more boosting steps. Alternatively, different compositions can be used for priming and boosting.

The immunogenic composition may further comprise one or more other antigens, from a norovirus or from another pathogen, if desired. For example, a combination immunogenic composition can contain a norovirus VLP that comprises a chimeric VP1 protein and one or more antigens from another pathogen, such as a bacterial, viral or fungal pathogen. For example, the immunogenic composition of the invention can comprise a norovirus VLP that comprises a chimeric VP1 protein as described herein, and one or more rotavirus antigens such as a live attenuated rotavirus (e.g., ROTARIX (rotavirus vaccine, live, oral; GlaxoSmithKline)), one or more live reassortant rotaviruses (e.g., ROTATEQ (rotavirus vaccine, live, oral, pentavalent; Merck), ROTASHIELD (rotavirus vaccine, live, oral, tetravalent; Wyeth-Lederle)), non-human rotaviruses (e.g., lamb (Lanzhou), bovine, rhesus), reassortant rotaviruses (e.g., human-bovine, human-lamb, human-rhesus), inactivated rotavirus (e.g., heat inactivated), rotavirus subunits (e.g., VP2, VP4, VP6, VP7, or any combination thereof), rotavirus subunit VLP or vaccines.

In another aspect, the immunogenic composition comprises a recombinant nucleic acid molecule that encodes a norovirus chimeric VP1 protein. If desired, such immunogenic compositions can contain a suitable nucleic acid delivery system, such as liposomes, lipoplexes, emulsions (nanoemulsions, microemulsions), particles (nanoparticles, microparticles), a vector, such as a viral particle, a replicon, and the like.

The immunogenic compositions generally include one or more “pharmaceutically acceptable excipients or vehicles” such as water, saline, glycerol, ethanol, and the like singly or in combination Immunogenic compositions will typically, in addition to the components mentioned above, comprise one or more “pharmaceutically acceptable carriers.” These include any carrier which does not itself induce the production of antibodies harmful to the individual receiving the composition. Suitable carriers typically are large, slowly metabolized macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. Additionally, an auxiliary substance, such as a wetting or emulsifying agent, pH buffering substance, and the like, may be present. A thorough discussion of pharmaceutically acceptable components is available in Gennaro (2000) Remington: The Science and Practice of Pharmacy. 20th ed., ISBN: 0683306472.

Pharmaceutically acceptable salts can also be used in immunogenic compositions of the invention, for example, mineral salts such as hydrochlorides, hydrobromides, phosphates, or sulfates, as well as salts of organic acids such as acetates, proprionates, malonates, or benzoates.

If desired, antigens can be adsorbed to, entrapped within or otherwise associated with liposomes and particulate carriers such as poly(D,L-lactide co-glycolide) (PLG)

microparticles or nanoparticles. Antigens can be conjugated to a carrier protein in order to enhance immunogenicity. See Ramsay et al. (2001) Lancet 357(9251):195-196; Lindberg (1999) Vaccine 17 Suppl 2:S28-36; Buttery & Moxon (2000) J R Coll Physicians Lond 34:163-168; Ahmad & Chapnick (1999) Infect Dis Clin North Am 13:113-133, vii; Goldblatt (1998) J. Med. Microbiol. 47:563-567; European patent 0 477 508; U.S. Pat. No. 5,306,492; WO98/42721; Conjugate Vaccines (eds. Cruse et al.) ISBN 3805549326, particularly vol. 10:48-114; Hermanson (1996) Bioconjugate Techniques ISBN: 0123423368 or 012342335X.

Immunogenic compositions of the present invention may be administered in conjunction with other immunoregulatory agents. For example, an immunogenic composition of the invention can include an adjuvant. Preferred adjuvants include, but are not limited to, one or more of the following types of adjuvants described below. Immunogenic compositions of the present invention may also be pre-mixed with an adjuvant before administration.

Alum

In one embodiment, the adjuvant for use in the present invention is alum (aluminum potassium sulfate ($AlK(SO_4)_2$)), or an alum derivative, such as that formed in-situ by mixing an antigen in phosphate buffer with alum, followed by titration and precipitation with a base such as ammonium hydroxide or sodium hydroxide.

Retinoic Acid

In one embodiment, the adjuvant for use in the present invention is retinoic acid, the oxidized form of Vitamin A, with only partial vitamin A function.

MF59C.1

In one embodiment, the adjuvant for use in the present invention is MF59C.1, an oil-in-water emulsion (squalene) in citrate buffer. MF59C.1 has been shown to be an effective adjuvant and enhance the production of high titers of neutralizing antibodies against parvovirus B19 (Ballou et al. (2003) JID, 187:675-678).

Mineral Containing Compositions

Mineral containing compositions suitable for use as adjuvants in the invention include mineral salts, such as aluminum salts and calcium salts. Suitable mineral salts include hydroxides (e.g. oxyhydroxides), phosphates (e.g. hydroxyphosphates, orthophosphates), sulfates, etc. (e.g. see chapters 8 & 9 of Vaccine Design . . . (1995) eds. Powell & Newman. ISBN: 030644867X. Plenum.), or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt (WO00/23105).

The adjuvants known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide $Al(OH)_3$, by infrared (IR) spectroscopy, in particular by the presence of an adsorption band at 1070 $cm^{-1}$ and a strong shoulder at 3090-3100 $cm^{-1}$ [chapter 9 of *Vaccine Design* . . . (1995) eds. Powell & Newman. ISBN: 030644867X. Plenum.] The degree of crystallinity of an aluminum hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminum hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg $Al^{+++}$ at pH 7.4 have been reported for aluminium hydroxide adjuvants.

The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Hydroxyphosphates generally have a $PO_4/Al$ molar ratio between 0.3 and 1.2. Hydroxyphosphates can be distinguished from strict $AlPO_4$ by the presence of hydroxyl groups. For example, an IR spectrum band at 3164 $cm^{-1}$ (e.g. when heated to 200° C.) indicates the presence of structural hydroxyls [ch. 9 of *Vaccine Design* . . . (1995) eds. Powell & Newman. ISBN: 030644867X. Plenum.].

The $PO_4/Al^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4/Al$ molar ratio between 0.84 and 0.92, included at 0.6 mg $Al^{3+}$/ml. The aluminium phosphate will generally be particulate (e.g. plate-like morphology as seen in transmission electron micrographs). Typical diameters of the particles are in the range 0.5-20 μm (e.g. about 5-10 μm) after any antigen adsorption. Adsorptive capacities of between 0.7-1.5 mg protein per mg $Al^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

In one embodiment, an adjuvant component includes a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc.

The concentration of $Al^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of <0.85 mg/dose is preferred.

Oil-Emulsions

Oil emulsion compositions suitable for use as adjuvants in the invention include squalene-water emulsions, such as MF59 [Chapter 10 of *Vaccine Design* . . . (1995) eds. Powell & Newman. ISBN: 030644867X. Plenum.] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

Various suitable oil-in-water emulsions are known, and they typically include at least one oil and at least one surfactant, with the oil(s) and surfactant(s) being biodegradable (metabolisable) and biocompatible. The oil droplets in the emulsion are generally less than 5 μm in diameter, and advantageously the emulsion comprises oil droplets with a sub-micron diameter, with these small sizes being achieved with a microfluidiser to provide stable emulsions. Droplets with a size less than 220 nm are preferred as they can be subjected to filter sterilization.

The invention can be used with oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoid known as squalene, 2,6,10,15,19,23-hexamethyl-2,6,10,14,18,22-tetracosahexaene. Other preferred oils are the tocopherols (see below). Oil in water emulsions comprising sqlauene are particularly preferred. Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Preferred surfactants for including in the emulsion are Tween 80 (polyoxyethylene sorbitan monooleate), Span 85 (sorbitan trioleate), lecithin and Triton X-100. As mentioned above, detergents such as Tween 80 may contribute to the thermal stability seen in the examples below.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Specific oil-in-water emulsion adjuvants useful with the invention include, but are not limited to:

- A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59'. The MF59 emulsion advantageously includes citrate ions e.g. 10 mM sodium citrate buffer.
- An emulsion comprising squalene, an α-tocopherol, and polysorbate 80. These emulsions may have from 2 to 10% squalene, from 2 to 10% tocopherol and from 0.3 to 3% Tween 80, and the weight ratio of squalene:tocopherol is preferably ≤1 (e.g. 0.90) as this provides a more stable emulsion. Squalene and Tween 80 may be present volume ratio of about 5:2, or at a weight ratio of about 11:5. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.
- An emulsion of squalene, a tocopherol, and a Triton detergent (e.g. Triton X-100). The emulsion may also include a 3d-MPL (see below). The emulsion may contain a phosphate buffer.
- An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.
- An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant (0.05-1% Thr-MDP, 5% squalane, 2.5% Pluronic L121 and 0.2% polysorbate 80). It can also be used without the Thr-MDP, as in the "AF" adjuvant (5% squalane, 1.25% Pluronic L121 and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm. The emulsion may also include one or more of: alditol; a cryoprotective agent (e.g. a sugar, such as dodecylmaltoside and/or sucrose); and/or an alkylpolyglycoside. Such emulsions may be lyophilized.

An emulsion having from 0.5-50% of an oil, 0.1-10% of a phospholipid, and 0.05-5% of a non-ionic surfactant. Preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, produced by addition of aliphatic amine to desacylsaponin via the carboxyl group of glucuronic acid), dimethyidioctadecylammonium bromide and/or N,N-dioctadecyl-N,N-bis (2-hydroxyethyl)propanediamine.

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) (see WO2006/113373).

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) (see WO2006/113373).

An emulsion in which a saponin (e.g. QuilA or QS21) and a sterol (e.g. a cholesterol) are associated as helical micelles.

Antigens (VLPs) and adjuvants in a composition will typically be in admixture at the time of delivery to a patient. The emulsions may be mixed with antigen (VLP) during manufacture, or extemporaneously, at the time of delivery. Thus the adjuvant and antigen (VLP) may be kept separately in a packaged or distributed vaccine, ready for final formulation at the time of use. The antigen (VLP) will generally be in an aqueous form, such that the vaccine is finally prepared by mixing two liquids. The volume ratio of the two liquids for mixing can vary (e.g. between 5:1 and 1:5) but is generally about 1:1.

Saponin Formulations (see chapter 22 of *Vaccine Design* . . . (1995) eds. Powell & Newman. ISBN: 030644867X. Plenum.).

Saponin formulations may also be used as adjuvants in the invention. Saponins are a heterogeneous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol.

Combinations of saponins and cholesterols can be used to form unique particles called immunostimulating complexes (ISCOMs) (chapter 23 of *Vaccine Design* . . . (1995) eds. Powell & Newman. ISBN: 030644867X. Plenum.). ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in WO96/33739. Optionally, the ISCOMS may be devoid of additional detergent.

Virosomes and Virus Like Particles (VLPs)

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qß-phage (such as coat proteins), GA-phage, fr-phage, AP205 phage, and Ty (such as retrotransposon Ty protein p1).

Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in EP-A-0689454. Such "small particles" of 3dMPL are small enough to be sterile filtered through a 0.22 μm membrane (EP-A-0689454). Other non-toxic LPS derivatives include monophosphoryl lipid A mimics, such as aminoalkyl glucosaminide phosphate derivatives e.g. RC-529.

Lipid A derivatives include derivatives of lipid A from *Escherichia coli* such as OM-174. OM-174 is described for example in Meraldi et al. (2003) *Vaccine* 21:2485-2491 and Pajak et al. (2003) *Vaccine* 21:836-842.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References Kandimalla et al. (2003) *Nucleic Acids Research* 31:2393-2400; WO02/26757, and WO99/62923 disclose possible analog substitutions e.g. replacement of guanosine with 2'-deoxy-7-deazaguanosine. The adjuvant effect of CpG oligonucleotides is further discussed in Krieg (2003) Nature Medicine 9:831-835; McCluskie et al. (2002) FEMS Immunology and Medical Microbiology 32:179-185; WO98/40100; U.S. Pat. No. 6,207,646; U.S. Pat. No. 6,239,116; and U.S. Pat. No. 6,429,199.

The CpG sequence may be directed to TLR9, such as the motif GTCGTT or TTCGTT (Kandimalla et al. (2003) *Biochemical Society Transactions* 31 (part 3):654-658). The CpG sequence may be specific for inducing a Th1 immune response, such as a CpG-A ODN, or it may be more specific for inducing a B cell response, such a CpG-B ODN. CpG-A and CpG-B ODNs are discussed in Blackwell et al. (2003) J Immunol 170:4061-4068; Krieg (2002) Trends Immunol 23:64-65 and WO01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla et al. (2003) *Biochemical Society Transactions* 31 (part 3):654-658 & Kandimalla et al. (2003) BBRC 306:948-953; Bhagat et al. (2003) BBRC 300:853-861 and WO03/035836.

A particularly useful adjuvant based around immunostimulatory oligonucleotides is known as TC-31™ (Schellack et al. (2006) *Vaccine* 24:5461-5472). Thus an adjuvant used with the invention may comprise a mixture of (i) an oligonucleotide (e.g. between 15-40 nucleotides) including at least one (and preferably multiple) CpI motifs (i.e. a cytosine linked to an inosine to form a dinucleotide), and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising 26-mer sequence 5'-$(IC)_{13}$-3' (SEQ ID NO:9). The polycationic polymer may be a peptide comprising 11-mer amino acid sequence KLKLLLLLKLK (SEQ ID NO:10).

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in WO95/17211 and as parenteral adjuvants in WO98/42375. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in Beignon et al. (2002) Infect Immun 70:3012-3019; Pizza et al. (2001) Vaccine 19:2534-2541; Pizza et al. (2000) Int J Med Microbiol 290:455-461; Scharton-Kersten et al. (2000) Infect Immun 68:5306-5313; Ryan et al. (1999) Infect Immun 67:6270-6280; Partidos et al. (1999) Immunol Lett 67:209-216; Peppoloni et al. (2003) Expert Rev Vaccines 2:285-293; Pine et al. (2002) J Control Release 85:263-270 and Tebbey et al. (2000) Vaccine 18:2723-34. A useful CT mutant is or CT-E29H. Numerical reference for amino acid substitutions is preferably based on the alignments of the A and B subunits of ADP-ribosylating toxins set forth in Domenighini et al. (1995) *Mol Microbiol* 15:1165-1167, specifically incorporated herein by reference in its entirety.

Human Immunomodulators

Human immunomodulators suitable for use as adjuvants in the invention include cytokines, such as interleukins (e.g. IL-1, IL-2, IL-4, IL-5, IL-6, IL-7, IL-12, etc.) (WO99/40936 and WO99/44636), interferons (e.g. interferon-γ), macrophage colony stimulating factor, and tumor necrosis factor. A preferred immunomodulator is IL-12.

Bioadhesives and Mucoadhesives

Bioadhesives and mucoadhesives may also be used as adjuvants in the invention. Suitable bioadhesives include esterified hyaluronic acid microspheres (Singh et al. (2001) *J. Cont. Release* 70:267-276) or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention (WO99/27960).

Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

Liposomes (Chapters 13 & 14 of *Vaccine Design . . .* (1995) eds. Powell & Newman. ISBN: 030644867X. Plenum.).

Examples of liposome formulations suitable for use as adjuvants are described in U.S. Pat. No. 6,090,406, U.S. Pat. No. 5,916,588 and EP A 0626169.

Polyoxyethylene Ether and Polyoxyethylene Ester Formulations

Adjuvants suitable for use in the invention include polyoxyethylene ethers and polyoxyethylene esters (WO99/52549). Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152). Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

Polyphosphazene (PCPP)

PCPP formulations are described, for example, in Andrianov et al. (1998) *Biomaterials* 19:109-115 and Payne et al. (1998) *Adv Drug Delivery Review* 31:185-196.

Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

Imidazoquinolone Compounds

Examples of imidazoquinolone compounds suitable for use as adjuvants in the invention include Imiquamod and its homologues (e.g. "Resiquimod 3M"), described further in Stanley (2002) *Clin Exp Dermatol* 27:571-577 and Jones (2003) *Curr Opin Investig Drugs* 4:214-218.

Benzonaphthyridines

Examples of benzonaphthyridine compounds suitable for use as adjuvants in the invention are described in WO 2009/111337.

Lipopeptides

Lipopeptides (i.e., compounds comprising one or more fatty acid residues and two or more amino acid residues) are known to have immunostimulating character. Lipopeptides based on glycerylcysteine are particularly suitable for use as adjuvants in the invention. Specific examples of such peptides include compounds of the following formula:

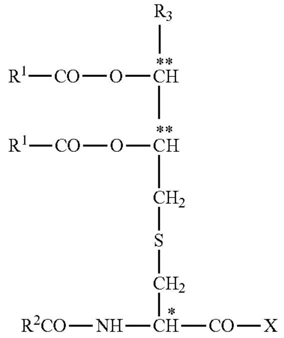

* = R
** = R or S in which each of $R^1$ and $R^2$ represents a saturated or unsaturated, aliphatic or mixed aliphatic-cycloaliphatic hydrocarbon radical having from 8 to 30, preferably 11 to 21, carbon atoms that is optionally also substituted by oxygen functions, $R^3$ represents hydrogen or the radical $R_1$—CO—O—$CH_2$— in which $R^1$ has the same meaning as above, and X represents an amino acid bonded by a peptide linkage and having a free, esterified or amidated carboxy group, or an amino acid sequence of from 2 to 10 amino acids of which the terminal carboxy group is in free, esterified or amidated form. In certain embodiments, the amino acid sequence comprises a D-amino acid, for example, D-glutamic acid (D-Glu) or D-gamma-carboxy-glutamic acid (D-Gla).

Bacterial lipopeptides generally recognize TLR2, without requiring TLR6 to participate. (TLRs operate cooperatively to provide specific recognition of various triggers, and TLR2 plus TLR6 together recognize peptidoglycans, while TLR2 recognizes lipopeptides without TLR6.) These are sometimes classified as natural lipopeptides and synthetic lipopeptides. Synthetic lipopeptides tend to behave similarly, and are primarily recognized by TLR2.

Lipopeptides suitable for use as adjuvants in the invention include compounds with the following formula:

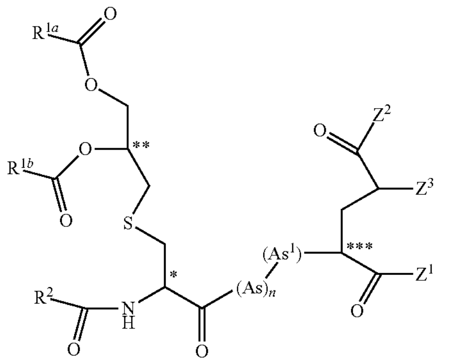

where the chiral center labeled * and the one labeled *** are both in the R configuration;

the chiral center labeled ** is either in the R or S configuration;

each $R^{1a}$ and $R^{1b}$ is independently an aliphatic or cycloaliphatic-aliphatic hydrocarbon group having 7-21 carbon atoms, optionally substituted by oxygen functions, or one of $R^{1a}$ and $R^{1b}$, but not both, is H;

$R^2$ is an aliphatic or cycloaliphatic hydrocarbon group having 1-21 carbon atoms and optionally substituted by oxygen functions;

n is 0 or 1;

As represents either —O-Kw-CO— or —NH-Kw-CO—, where Kw is an aliphatic hydrocarbon group having 1-12 carbon atoms;

$As^1$ is a D- or L-alpha-amino acid;

$Z^1$ and $Z^2$ each independently represent —OH or the N-terminal radical of a D- or L-alpha amino acid of an amino-(lower alkane)-sulfonic acid or of a peptide having up to 6 amino acids selected from the D- and L-alpha aminocarboxylic acids and amino-lower alkyl-sulfonic acids; and $Z^3$ is H or —CO—$Z^4$, where $Z^4$ is —OH or the N-terminal radical of a D- or L-alpha amino acid of an amino-(lower alkane)-sulfonic acid or of a peptide having up to 6 amino acids selected from the D and L-alpha aminocarboxylic acids and amino-lower alkyl-sulfonic acids; or an ester or amide formed from the carboxylic acid of such compounds. Suitable amides include —$NH_2$ and NH (lower alkyl), and suitable esters include C1-C4 alkyl esters. (lower alkyl or lower alkane, as used herein, refers to $C_1$-$C_6$ straight chain or branched alkyls).

Such compounds are described in more detail in U.S. Pat. No. 4,666,886. An example of a lipopeptide compound suitable for use as an adjuvant in the invention is a lipopeptide with the following formula:

Another example of a lipopeptide species is called LP40, and is an agonist of TLR2. Akdis et al. (2003) *Eur. J. Immunology,* 33: 2717-2726.

These are related to a known class of lipopeptides from *E. coli,* referred to as murein lipoproteins. Certain partial degradation products of those proteins called murein lipopeptides are described in Hantke et al. (1973) *Eur. J. Biochem.,* 34: 284-296. These comprise a peptide linked to N-acetyl muramic acid and are thus related to Muramyl peptides, which are described in Baschang, et al., *Tetrahedron* (1989) 45(20): 6331-6360.

The invention may also comprise combinations of aspects of one or more of the adjuvants identified above. For example, the following adjuvant compositions may be used in the invention: (1) a saponin and an oil-in-water emulsion (WO99/11241); (2) a saponin (e.g. QS21)+a non-toxic LPS derivative (e.g. 3dMPL) (WO94/00153); (3) a saponin (e.g. QS21)+a non-toxic LPS derivative (e.g. 3dMPL)+a cholesterol; (4) a saponin (e.g. QS21)+3dMPL+IL-12 (optionally+a sterol) (WO98/57659); (5) combinations of 3dMPL with, for example, QS21 and/or oil-in-water emulsions (European patent applications 0835318, 0735898 and 0761231); (6) SAF, containing 10% squalane, 0.4% Tween 80™, 5% pluronic-block polymer L121, and thr-MDP, either microfluidized into a submicron emulsion or vortexed to generate a larger particle size emulsion; (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3 dMPL).

Other substances that act as immunostimulating agents are disclosed in chapter 7 of *Vaccine Design* . . . (1995) eds. Powell & Newman. ISBN: 030644867X. Plenum. The use of an aluminium hydroxide and/or aluminium phosphate adjuvant is useful, particularly in children, and antigens are generally adsorbed to these salts. Squalene-in-water emulsions are also preferred, particularly in the elderly. Useful adjuvant combinations include combinations of Th1 and Th2 adjuvants such as CpG and alum or resiquimod and alum. A combination of aluminium phosphate and 3dMPL may be used.

In some embodiments, the invention is an immunogenic composition that contains a parvovirus VLP that contains VP1 and VP2, as described herein, and an adjuvant, such as MF59. The VLP and the adjuvant (e.g, MF59) can be premixed and provided as a single composition, or can be provided as separate components that are to be mixed prior to administration.

E. Administration

Compositions of the invention (e.g., compositions that contain norovirus chimeric VP1 proteins, VLPs, and nucleic acids that encode norovirus chimeric VP1 proteins) will generally be administered directly to a patient. Direct delivery may be accomplished by parenteral injection (e.g. subcutaneously, intraperitoneally, intravenously, intramuscularly, or to the interstitial space of a tissue), or mucosally, such as by rectal, oral (e.g. tablet, spray), vaginal, topical, transdermal (See e.g. WO99/27961) or transcutaneous (See e.g. WO02/074244 and WO02/064162), intranasal (See e.g. WO03/028760), ocular, aural, pulmonary or other mucosal administration. Transdermal delivery can be achieved, for example, using microneedles. Immunogenic compositions can also be administered topically by direct transfer to the surface of the skin. Topical administration can be accomplished without utilizing any devices, or by contacting naked skin with the immunogenic composition utilizing a bandage or a bandage-like device (see, e.g., U.S. Pat. No. 6,348,450).

Preferably the mode of administration is parenteral, mucosal or a combination of mucosal and parenteral immunizations. Even more preferably, the mode of administration is parenteral, mucosal or a combination of mucosal and parenteral immunizations in a total of 1-2 vaccinations 1-3 weeks apart. Preferably the route of administration includes but is not limited to oral delivery, intra-muscular delivery and a combination of oral and intramuscular delivery.

It has already been demonstrated that mucosal and systemic immune responses to antigens from mucosal pathogens, such as *Helicobacter pylori* antigens can be enhanced through mucosal priming followed by systemic boosting immunizations (see Vajdy et al. (2003) Immunology 110: 86-94). In some embodiments, the method for treating or preventing an infection by a norovirus, comprises mucosally administering to a subject in need thereof a first immunogenic composition comprising one or more norovirus antigens followed by parenterally administering a therapeutically effective amount of a second immunogenic composition comprising one or more norovirus antigens.

The immunogenic composition may be used to elicit systemic and/or mucosal immunity, preferably to elicit an enhanced systemic and/or mucosal immunity.

Preferably the immune response is characterized by the induction of a serum IgG and/or intestinal IgA immune response.

As noted above, prime-boost methods are preferably employed where one or more gene delivery vectors and/or polypeptide antigens are delivered in a "priming" step and, subsequently, one or more second gene delivery vectors and/or polypeptide antigens are delivered in a "boosting" step. In certain embodiments, priming and boosting with one or more gene delivery vectors or polypeptide antigens described herein is followed by additional boosting with one or more polypeptide-containing compositions (e.g., polypeptides comprising norovirus antigens).

In any method involving co-administration, the various compositions can be delivered in any order. Thus, in embodiments including delivery of multiple different compositions or molecules, the nucleic acids need not be all delivered before the polypeptides. For example, the priming step may include delivery of one or more polypeptides and the boosting comprises delivery of one or more nucleic acids and/or one or more polypeptides. Multiple polypeptide administrations can be followed by multiple nucleic acid administrations or polypeptide and nucleic acid administrations can be performed in any order. Thus, one or more of the gene delivery vectors described herein and one or more of the polypeptides described herein can be co-administered in any order and via any administration route. Therefore, any combination of polynucleotides and polypeptides described herein can be used to elicit an immune reaction.

(i). Dosage Regime

Dosage treatment can be according to a single dose schedule or a multiple dose schedule. Multiple doses may be used in a primary immunization schedule and/or in a booster immunization schedule. In a multiple dose schedule, the various doses may be given by the same or different routes, e.g. a parenteral prime and mucosal boost, a mucosal prime and parenteral boost, etc.

Preferably the dosage regime enhances the avidity of the antibody response leading to antibodies with a neutralizing characteristic.

In some cases there is a correlation between serum antibody levels and protection from disease caused by norovirus. For example, in multiple challenge studies, serum antibody levels were associated with protection after repeated (2-3) oral challenges with high doses of Norwalk virus (Johnson et al. (1990) J. Infect. Dis. 161:18-21). In another study, 18 of 23 infants without pre-existing antibodies developed gastroenteritis caused by human Caliciviruses, whereas 15 of 18 with pre-existing antibody levels did not become ill (Ryder et al. (1985) J. Infect. Dis. 151:99-105). In yet another study, 47% of persons with a baseline Norwalk antibody titre of less than 1:100 developed Norwalk infection compared to 13% of persons with a baseline antibody titre of greater than 1:100 ($p<0.001$) (Ryder et al. (1985) J. Infect. Dis. 151:99-105). Because some individuals do not produce the receptor for certain norovirus strains and are, therefore, inherently resistant to those norovirus strains, anomalous results can be seen in which the presence of antibody correlates with susceptibility to certain strains rather than with protection. See, Parrino et al. (1997) N. Engl. J. Med. 297:86-89.

Chimeric norovirus VP1 proteins and VLPs as described above can be administered to a mammal, such as a mouse, baboon, chimpanzee, or human, to activate norovirus-specific T cells in vivo. Administration can be by any means known in the art, including parenteral, intranasal, intramuscular or subcutaneous injection, including injection using a biological ballistic gun, as discussed above.

A composition of the invention comprising a chimeric norovirus VP1 protein or VLP is administered in a manner compatible with the particular composition used and in an amount which is effective to induce an immune response (e.g., a T cell response and/or a humoral response), preferably a protective immune response.

Norovirus-specific T cell responses can be measured by, inter alia, a 51Cr release assay, a lymphoproliferation assay, or by intracellular staining for IFN-γ. The proteins can be administered either to a mammal which is not infected with a norovirus or can be administered to a norovirus-infected mammal. The particular dosages of the fusion proteins in a composition will depend on many factors including, but not limited to, the species, age, and general condition of the mammal to which the composition is administered, and the mode of administration of the composition. An effective amount of the composition of the invention can be readily determined using only routine experimentation. In vitro and in vivo models can be employed to identify appropriate doses. Generally, 0.5, 0.75, 1.0, 1.5, 2.0, 2.5, 5 or 10 mg of a norovirus polypeptide or VLP will be administered to a large mammal, such as a baboon, chimpanzee, or human. If desired, co-stimulatory molecules or adjuvants can also be provided before, after, or together with the compositions.

Immune responses of the mammal generated by the delivery of a composition of the invention, including activation of norovirus-specific T cells, can be enhanced by varying the dosage, route of administration, or boosting regimens. Compositions of the invention may be given in a single dose schedule, or preferably in a multiple dose schedule in which a primary course of vaccination includes 1-10 separate doses, followed by other doses given at subsequent time intervals required to maintain and/or reinforce an immune response, for example, at 1-4 months for a second dose, and if needed, a subsequent dose or doses after several months.

F. Tests to Determine the Efficacy of an Immune Response

One way of checking efficacy of therapeutic treatment involves monitoring infection after administration of the compositions of the invention. Another way of checking efficacy of prophylactic treatment involves monitoring immune responses both systemically (such as monitoring the level of IgG1 and IgG2a production) and mucosally (such as monitoring the level of IgA production) against the antigens in the compositions of the invention after administration of the composition. Typically, serum specific antibody responses are determined post-immunization but pre-challenge whereas mucosal specific antibody responses are determined post-immunization and post-challenge.

Another way of assessing the immunogenicity of the component proteins of the immunogenic compositions of the present invention is to express the proteins recombinantly and to screen patient sera or mucosal secretions by immunoblot. A positive reaction between the protein and the patient serum indicates that the patient has previously mounted an immune response to the protein in question—that is, the protein is an immunogen. This method may also be used to identify immunodominant proteins and/or epitopes.

In vivo efficacy models include a human challenge model, which is supported by the NIH and the Center for Disease Control (CDC) (see for example, Lindesmith et al. (2003) Nat. Med. 9: 548-553 and Lindesmith et al. (2005) J. Virol. 79: 2900-2909).

The immune response may be one or both of a TH1 immune response and a TH2 response. The immune response may be an improved or an enhanced or an altered immune response. The immune response may be one or both of a systemic and a mucosal immune response. Preferably the immune response is an enhanced systemic and/or mucosal response.

An enhanced systemic and/or mucosal immunity is reflected in an enhanced TH1 and/or TH2 immune response. Preferably, the enhanced immune response includes an increase in the production of IgG1 and/or IgG2a and/or IgA. Preferably the mucosal immune response is a TH2 immune response. Preferably, the mucosal immune response includes an increase in the production of IgA.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH1 immune response may include one or more of an increase in CTLs, an increase in one or more of the cytokines associated with a TH1 immune response (such as IL-2, IFNγ, and TNFβ), an increase in activated macrophages, an increase in NK activity, or an increase in the production of IgG2a. Preferably, the enhanced TH1 immune response will include an increase in IgG2a production.

Immunogenic compositions of the invention, in particular, immunogenic composition comprising one or more antigens of the present invention may be used either alone or in combination with other antigens optionally with an immunoregulatory agent capable of eliciting a Th1 and/or Th2 response.

The invention also comprises an immunogenic composition comprising one or more immunoregulatory agents, such as a mineral salt, such as an aluminium salt and an oligonucleotide containing a CpG motif. Most preferably, the immunogenic composition includes both an aluminium salt and an oligonucleotide containing a CpG motif. Alternatively, the immunogenic composition includes an ADP ribosylating toxin, such as a detoxified ADP ribosylating toxin and an oligonucleotide containing a CpG motif. Preferably, the one or more immunoregulatory agents include an adjuvant. The adjuvant may be selected from one or more of the group consisting of a TH1 adjuvant and TH2 adjuvant, further discussed above.

The immunogenic compositions of the invention will preferably elicit both a cell mediated immune response as well as a humoral immune response in order to effectively address an infection. This immune response will preferably induce long lasting (e.g., neutralizing) antibodies and a cell mediated immunity that can quickly respond upon exposure to one or more infectious antigens.

G. Use of the Immunogenic Compositions as Medicaments

The invention also provides a composition of the invention for use as a medicament, in particular for making or for use as a vaccine. The medicament is preferably able to raise an immune response in a mammal (i.e. it is an immunogenic composition) and is more preferably a vaccine. The invention also provides the use of the compositions of the invention in the manufacture of a medicament for raising an immune response in a mammal. The medicament is preferably a vaccine. Preferably the vaccine is used to prevent and/or treat an intestinal infection such as gastroenteritis, preferably acute gastroenteritis. The gastroenteritis may result from an imbalance in ion and/or water transfer resulting in both watery diarrhea and/or intestinal peristalisis and/or motility. The gastroenteritis may also result in vomiting.

The invention provides methods for inducing or increasing an immune response using the compositions described above. The immune response is preferably protective and can include antibodies and/or cell-mediated immunity (including systemic and mucosal immunity). Immune responses include booster responses.

The invention also provides a method for raising an immune response in a mammal comprising the step of administering an effective amount of a composition of the invention. The immune response is preferably protective and preferably involves antibodies and/or cell-mediated immunity. Preferably, the immune response includes one or both of a TH1 immune response and a TH2 immune response. The method may raise a booster response.

The mammal is preferably a human. Where the immunogenic composition, preferably a vaccine, is for prophylactic use, the human is preferably a child (e.g. an infant or toddler, pre-schooler, such as a child one year or less, from one to three, or four, or five, or six, or seven, or eight, or nine, or ten years onwards), a teenager, an elderly person (e.g., about 60 years old or older) or a person in a high risk group, such as military personnel, travelers, healthcare workers, child care (day care) providers, and food handlers. The immunogenic composition or vaccine can also be administered to such individuals for therapeutic use. A vaccine intended for children may also be administered to adults (e.g. to assess safety, dosage, immunogenicity, etc.).

Other target groups for the immunogenic compositions (e.g., vaccines) of the present invention include: transplant and immunocompromised individuals; adults and children in, e.g., USA, Canada and Europe including but not limited to the following: food handlers; healthcare workers such as but not limited to hospital and nursing home personnel; day care providers; travelers, including cruise ship travelers; military personnel; and pediatric and/or elderly populations as discussed above.

(i). Norovirus Specific T Cells

Norovirus-specific T cells, which are activated by the chimeric VP1 proteins or VLPs expressed in vivo or in vitro, preferably recognize an epitope of the P-domain of the VP1. Norovirus-specific T cells can be CD8+ or CD4+.

Norovirus-specific CD8+ T cells can be cytotoxic T lymphocytes (CTL) which can kill norovirus-infected cells that display any of these epitopes complexed with an MHC class I molecule. Norovirus-specific CD8+ T cells can be detected by, for example, 51Cr release assays. 51Cr release assays measure the ability of norovirus-specific CD8+ T cells to lyse target cells displaying one or more of these epitopes. Norovirus-specific CD8+ T cells which express antiviral agents, such as IFN-γ, are also contemplated herein and can also be detected by immunological methods, preferably by intracellular staining for IFN-γ or like cytokine after in vitro stimulation with one or more of the norovirus polypeptides, such as those described herein.

Norovirus-specific CD4+ T cells can be detected by a lymphoproliferation assay. Lymphoproliferation assays measure the ability of norovirus-specific CD4+ T cells to proliferate in response to, e.g., a VP1.

(ii) Methods of Activating Norovirus-Specific T Cells

The chimeric norovirus VP1 proteins and VLPs can be used to activate norovirus-specific T cells either in vitro or in vivo. Activation of norovirus-specific T cells can be used, inter alia, to provide model systems to optimize CTL responses to norovirus and to provide prophylactic or therapeutic treatment against norovirus infection. For in vitro activation, proteins are preferably supplied to T cells via a plasmid or a viral vector, such as an adenovirus vector, as described above.

Polyclonal populations of T cells can be derived from the blood, and preferably from peripheral lymphoid organs, such as lymph nodes, spleen, or thymus, of mammals that have been infected with a norovirus. Preferred mammals include mice, chimpanzees, baboons, and humans. Infection with norovirus serves to expand the number of activated norovirus-specific T cells in the mammal. The norovirus-specific T cells derived from the mammal can then be restimulated in vitro by adding, a norovirus immunogenic polypeptide, and/or fusion protein according to the present invention. The norovirus-specific T cells can then be tested for, inter alia, proliferation, the production of IFN-γ, and the ability to lyse target cells displaying, for example, VP1 polypeptide epitopes in vitro.

H. Kits

The invention also provides kits comprising one or more containers of immunogenic compositions of the invention. Compositions can be in liquid form or can be lyophilized, as can individual antigens. Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle).

The kit can further comprise a second container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery device. The kit may further include a third component comprising an adjuvant.

The kit can also comprise a package insert containing written instructions for methods of inducing immunity or for treating infections. The package insert can be an unapproved draft package insert or can be a package insert approved by the Food and Drug Administration (FDA) or other regulatory body.

The invention also provides a delivery device pre-filled with the immunogenic compositions of the invention.

III. EXPERIMENTAL

Below are examples of specific embodiments for carrying out the present invention. The examples are offered for illustrative purposes only, and are not intended to limit the scope of the present invention in any way.

Example 1

Expression Constructs for Snow Mountain/Norwalk Chimeric VP1 Proteins

Constructs for production of chimeric norovirus VP1 proteins, and VLPs containing the chimeric proteins, *Saccharomyces cerevisiae* strain AD3 were created by cloning sequences encoding chimeric VP1 proteins into the yeast expression vector pBS24.1. The pBS24.1 vector is described in detail in commonly owned U.S. Pat. No. 382,805, filed Jul. 19, 1989, which application is hereby incorporated by reference in its entirety herein. The pBS24.1 vector contains the 2-micron sequence for autonomous replication in yeast and the yeast genes leu2d and URA3 as selectable markers. The β-lactamase gene and the ColE1 origin of replication, required for plasmid replication in bacteria, are also present in this expression vector. Regulation of expression was put under the control of a hybrid ADH2/GAPDH promoter (described in U.S. Pat. No. 6,183,985) and an alpha-factor terminator.

Figure 2:
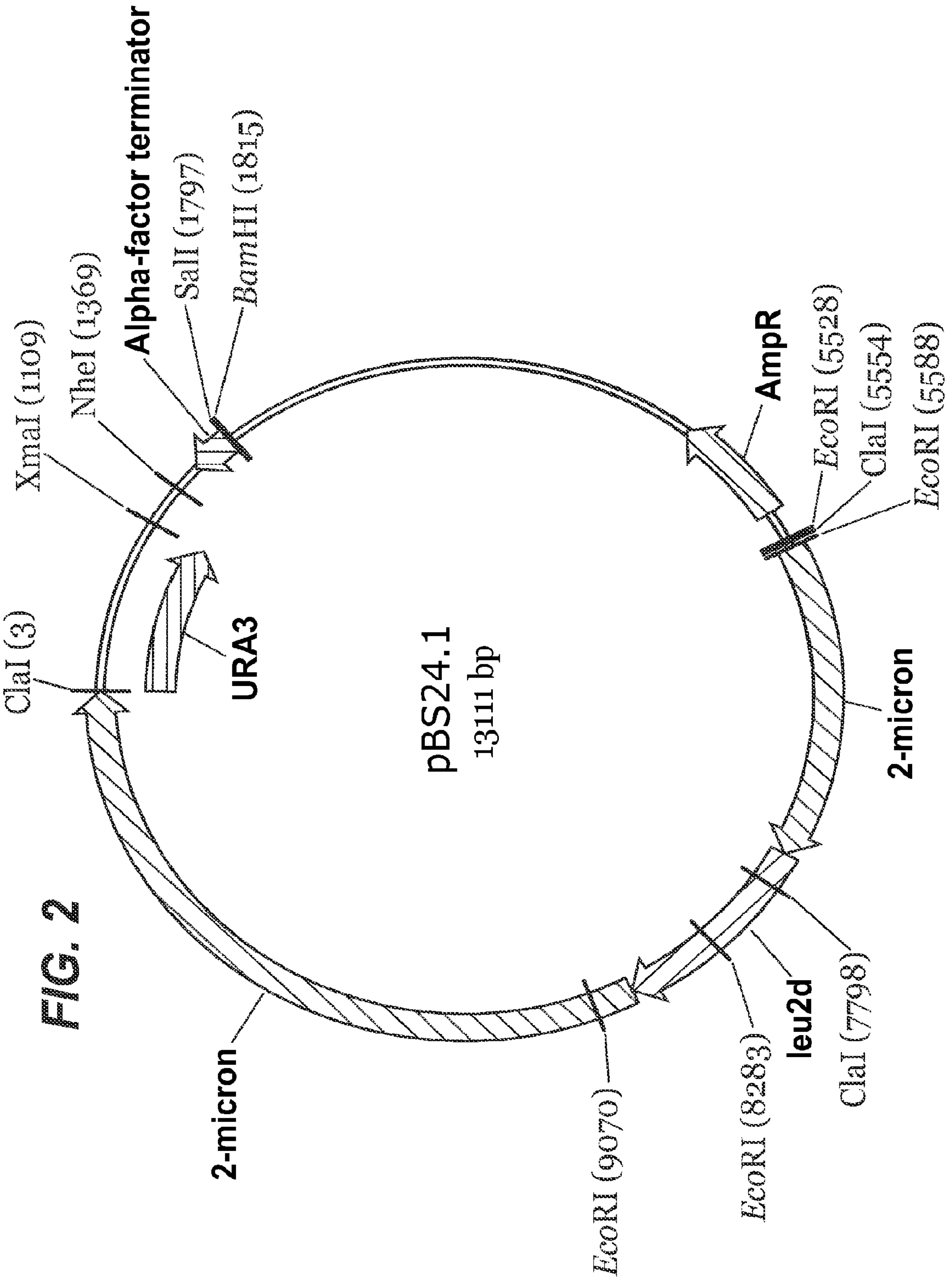
FIG. 2 depicts the diagram of a vector pBS24.1 suitable for expression of chimeric VP1 proteins and VLPs in *S. cerevisiae.*

The constructs were created and utilized for expression of Snow Mountain (SMVO/Norwalk VP1 proteins included the polynucleotide sequence shown in FIG. 6 (SEQ ID NO:16). To do that, a fragment corresponding to the S-domain of the a previously generated Snow Mountain gene, excised by restriction enzymes HindIII and Acc651, was ligated to a fragment corresponding to the P-domain of Norwalk gene that was generated using restriction enzymes Alw211 and Sal1. This new chimeric DNA was ligated into a pMADC5 subcloning vector (FIG. 1) at the HindIII-SalI site and amplified. The amplified fragment (shown in FIG. 5) was then cloned into the expression vector pBS24.1 (FIG. 2), at the BamHI+SalI site, for expression of the SMV/Norwalk chimeric VP1 protein in *S. cervisiae* strain AD3.

Example 2

Expression Constructs for Snow Mountain/GII.4.2006a Chimeras

In this example, expression vector pBS24.1 was used in production of Snow Mountain/GII.4.2006a VLPs (SMV/GII.4.2006a/chimeras) in *Saccharomyces cerevisiae* strain AD3. The coding sequence that was utilized for the expression of chimeric SMV/GII.4.2006a VP1 proteins is shown in FIG. 7. The coding sequence was generated using synthetic oligonucleotides, based on the cDNA sequences of VP1 S- and P-domains of Snow Mountain and GII.4.2006a viruses.

In this example, a fragment corresponding to the S-domain of a previously generated Snow Mountain gene, excised by restriction enzymes HindIII and Acc651, was ligated to a fragment corresponding to the P-domain of the GII.4.2006a gene that was generated using restriction enzymes XbaI-SalI. This new chimeric DNA was ligated into a pMADC5 subcloning vector (FIG. 1) at the HindIII-SalI site and amplified. The amplified fragment (shown in FIG. 6) was then cloned into the expression vector pBS24.1 (FIG. 2), at the BamHI+SalI site, for expression of the SMV/Norwalk chimeric VP1 protein in *S. cervisiae* strain AD3.

Example 3

Expression of Chimeric VLPs in Yeast

*S. cerevisiae* strain AD3 (MATa, leu2, ura3-52, prb1-1122, pep4-3, prc1-407, gal2, [cir0], ::pDM15(pGAP/ADR1 ::G418R), ::Yip5ΔleuAD) was transformed with the expression plasmids described above. Before the transformation, the yeast cells were streaked on YEPD (yeast extract bactopeptone 2% glucose) plates and a single colony was selected for preparation of competent cells for transformation.

Yeast transformation was performed using the Invitrogen S.c. EasyComp™ Transformation Kit. After transformation, several Ura-transformants were streaked onto Ura-8% glucose plates in order to obtain single colonies. The single colonies were subsequently patched onto Leu-8% glucose plates to increase the plasmid copy number. Leu-starter cultures were grown for 24 hours at 30° C. and then diluted 1:20 in YEPD (yeast extract bactopeptone 2% glucose) or Veggie (Novagen Veggie Peptone and Veggie Yeast Extract) media. Cells were grown for 48-72 hours at 30° C. to allow depletion of the glucose in the media and then harvested. Induction occurred upon depletion of glucose from the media. This system provided a high cell mass before the foreign genes were induced.

Example 4

Purification of Chimeric VLPs

Norovirus virus-like particles (VLPs) were purified from the media of yeast cells expressing the norovirus chimeric VP1 protein. A low speed spin (15,000×g) was performed on the media to remove extra cells or cellular debris. Following this step, the supernatant was subjected to a four hour high speed spin (100,000×g) through a 40% sucrose cushion to separate the virus-like particles from free protein and other material. The pellet containing the VLPs was resuspended in buffer (50 mM Tris pH 7.5, 100 mM NaCl) and loaded onto a Capto™ Q column and eluted with high salt. The VLPs were eluted from the column during a gradient of increasing salt. Finally, the eluted fraction containing the VLPs were concentrated and buffer exchanged into a lower salt buffer (20 mM Tris pH 7.5, 100 mM NaCl) and stored at 4° C. until use.

TABLE 1

| *Norovirus* Strains | |
|---|---|
| *Norovirus* genus | |
| Norwalk virus | Chitta virus |
| Camberwell virus | Hawaii calicivirus |
| Chiba virus | Maryland calicivirus 1 |
| *Norovirus* genogroup 1 | |
| Desert Shield virus | *Norovirus* Hu/GI/KE/230207-1/2007/SGP |
| *Norovirus* genogroup G1 unidentified subgroup | *Norovirus* Hu/GI/KE/230207-2/2007/SGP |
| | *Norovirus* Hu/GI/KE/230207-3/2007/SGP |
| Human calicivirus HU/NLV/Birmingham/93/UK | *Norovirus* Hu/GI/KE/240407-1/2007/SGP |
| | *Norovirus* Hu/GI/KE/240407-2/2007/SGP |

TABLE 1-continued

| *Norovirus* Strains | |
|---|---|
| Human calicivirus | *Norovirus* Hu/GI/KE/270607-1/2007/SGP |
| HU/NLV/Koblenz/433/2000/DE | *Norovirus* Hu/GI/KE/270607-2/2007/SGP |
| Human calicivirus HU/NLV/Musgrove/89/UK | *Norovirus* Hu/GI/KE/270607-3/2007/SGP |
| Human calicivirus HU/NLV/Rbh/93/UK | *Norovirus* Hu/GI/KE/290507-1/2007/SGP |
| Human calicivirus | *Norovirus* Hu/GI/KE/290507-2/2007/SGP |
| HU/NLV/Sindlesham/95/UK | *Norovirus* Hu/GI/KE/290507-3/2007/SGP |
| Human calicivirus HU/NLV/Thistlehall/90/UK | *Norovirus* Hu/GI/KS/200307-1/2007/SGP |
| Human calicivirus HU/NLV/Valetta/95/Malta | *Norovirus* Hu/GI/KS/200307-2/2007/SGP |
| Human calicivirus HU/NLV/Whiterose/96/UK | *Norovirus* Hu/GI/KS/200307-3/2007/SGP |
| Human calicivirus | *Norovirus* Hu/GI/KS/230107-1/2007/SGP |
| HU/NLV/Winchester/94/UK | *Norovirus* Hu/GI/KS/230107-2/2007/SGP |
| Human calicivirus HU/NLV/Wortley/90/UK | *Norovirus* Hu/GI/KS/230107-3/2007/SGP |
| Human calicivirus NLV/Stav/95/Nor | *Norovirus* Hu/GI/KS/230207-1/2007/SGP |
| Human calicivirus | *Norovirus* Hu/GI/KS/230207-2/2007/SGP |
| NLV/Wyoming/US/genogroup 1 | *Norovirus* Hu/GI/KS/240407-1/2007/SGP |
| *Norovirus* clam/GI/Shijimi1/JPN | *Norovirus* Hu/GI/KS/240407-2/2007/SGP |
| *Norovirus* clam/GI/Shijimi11/JPN | *Norovirus* Hu/GI/KS/270607-1/2007/SGP |
| *Norovirus* clam/GI/Shijimi12a/JPN | *Norovirus* Hu/GI/KS/270607-2/2007/SGP |
| *Norovirus* clam/GI/Shijimi12b/JPN | *Norovirus* Hu/GI/KS/270607-3/2007/SGP |
| *Norovirus* clam/GI/Shijimi12c/JPN | *Norovirus* Hu/GI/KS/290507-1/2007/SGP |
| *Norovirus* clam/GI/Shijimi12d/JPN | *Norovirus* Hu/GI/KS/290507-2/2007/SGP |
| *Norovirus* clam/GI/Shijimi13/JPN | *Norovirus* Hu/GI/Marina48/2001/Botswana |
| *Norovirus* clam/GI/Shijimi16a/JPN | *Norovirus* Hu/GI/Marina60/2003/Botswana |
| *Norovirus* clam/GI/Shijimi16b/JPN | *Norovirus* Hu/GI/N9/2003/Irl |
| *Norovirus* clam/GI/Shijimi16c/JPN | *Norovirus* Hu/GI/NoV360/2004/CAN |
| *Norovirus* clam/GI/Shijimi16d/JPN | *Norovirus* Hu/GI/NoV69/2004/CAN |
| *Norovirus* clam/GI/Shijimi17/JPN | *Norovirus* Hu/GI/NoV730/2004/CAN |
| *Norovirus* clam/GI/Shijimi18/JPN | *Norovirus* Hu/GI/NoV748/2004/CAN |
| *Norovirus* clam/GI/Shijimi19a/JPN | *Norovirus* Hu/GI/Nsk-D81/2009/RUS |
| *Norovirus* clam/GI/Shijimi19b/JPN | *Norovirus* Hu/GI/Orstad/749/2004/NOR |
| *Norovirus* clam/GI/Shijimi2/JPN | *Norovirus* Hu/GI/Osaka1115/2006/JPN |
| *Norovirus* clam/GI/Shijimi20a/JPN | *Norovirus* Hu/GI/Osaka896/2006/JPN |
| *Norovirus* clam/GI/Shijimi20b/JPN | *Norovirus* Hu/GI/Oslo/1504/2002/NOR |
| *Norovirus* clam/GI/Shijimi21/JPN | *Norovirus* Hu/GI/Oslo/776/2004/NOR |
| *Norovirus* clam/GI/Shijimi22/JPN | *Norovirus* Hu/GI/R1D-011106/2006/SGP |
| *Norovirus* clam/GI/Shijimi23/JPN | *Norovirus* Hu/GI/R1D-111206/2006/SGP |
| *Norovirus* clam/GI/Shijimi25a/JPN | *Norovirus* Hu/GI/R1D-201106/2006/SGP |
| *Norovirus* clam/GI/Shijimi25b/JPN | *Norovirus* Hu/GI/R1U-031006/2006/SGP |
| *Norovirus* clam/GI/Shijimi26/JPN | *Norovirus* Hu/GI/R1U-111206/2006/SGP |
| *Norovirus* clam/GI/Shijimi28/JPN | *Norovirus* Hu/GI/R2D-011106/2006/SGP |
| *Norovirus* clam/GI/Shijimi29/JPN | *Norovirus* Hu/GI/R2D-111206/2006/SGP |
| *Norovirus* clam/GI/Shijimi30/JPN | *Norovirus* Hu/GI/R2D-150806/2006/SGP |
| *Norovirus* clam/GI/Shijimi31/JPN | *Norovirus* Hu/GI/R2D-220606/2006/SGP |
| *Norovirus* clam/GI/Shijimi4/JPN | *Norovirus* Hu/GI/R2D-240706/2006/SGP |
| *Norovirus* clam/GI/Shijimi5/JPN | *Norovirus* Hu/GI/R2U-031006/2006/SGP |
| *Norovirus* clam/GI/Shijimi6/JPN | *Norovirus* Hu/GI/R2U-111206-1/2006/SGP |
| *Norovirus* clam/GI/Shijimi7/JPN | *Norovirus* Hu/GI/R2U-111206-2/2006/SGP |
| *Norovirus* clam/GI/Shijimi8/JPN | *Norovirus* Hu/GI/R2U-150806/2006/SGP |
| *Norovirus* clam/GI/Shijimi9/JPN | *Norovirus* Hu/GI/R2U-201106/2006/SGP |
| *Norovirus* Cor/Gunma/Apr-3/GI/2004/JP | *Norovirus* Hu/GI/R2U-220606-1/2006/SGP |
| *Norovirus* Cor/Gunma/Apr-4/GI/2004/JP | *Norovirus* Hu/GI/R2U-220606-2/2006/SGP |
| *Norovirus* Cor/Gunma/Dec-1/GI/2004/JP | *Norovirus* Hu/GI/R3D-251006/2006/SGP |
| *Norovirus* Cor/Gunma/Dec-2/GI/2004/JP | *Norovirus* Hu/GI/R3U-251006-1/2006/SGP |
| *Norovirus* Cor/Gunma/Dec-3/GI/2004/JP | *Norovirus* Hu/GI/R3U-251006-2/2006/SGP |
| *Norovirus* Cor/Gunma/Dec-4/GI/2004/JP | *Norovirus* Hu/GI/R3U-251006-3/2006/SGP |
| *Norovirus* Cor/Gunma/Dec-5/GI/2004/JP | *Norovirus* Hu/GI/R3U-251006-4/2006/SGP |
| *Norovirus* Cor/Gunma/Feb-2/GI/2004/JP | *Norovirus* Hu/GI/R3U-251006-5/2006/SGP |
| *Norovirus* Cor/Gunma/Feb-3/GI/2004/JP | *Norovirus* Hu/GI/Shenzhen193-06/2006/CHN |
| *Norovirus* Cor/Gunma/Feb-5/GI/2004/JP | *Norovirus* Hu/GI/Shenzhen197-06/2006/CHN |
| *Norovirus* Cor/Gunma/Jan-1/GI/2004/JP | *Norovirus* Hu/GI/Shenzhen198-06/2006/CHN |
| *Norovirus* Cor/Gunma/Jan-2/GI/2004/JP | *Norovirus* Hu/GI/Shenzhen199-06/2006/CHN |
| *Norovirus* Cor/Gunma/Jun-2/GI/2004/JP | *Norovirus* Hu/GI/Shenzhen200-06/2006/CHN |
| *Norovirus* Cor/Gunma/Mar-1/GI/2004/JP | *Norovirus* Hu/GI/Shenzhen202-06/2006/CHN |
| *Norovirus* Cor/Gunma/May-1/GI/2004/JP | *Norovirus* Hu/GI/Shenzhen84-06/2006/CHN |
| *Norovirus* Cor/Gunma/May-3/GI/2004/JP | *Norovirus* Hu/GI/SI-2002/2006/SVN |
| *Norovirus* Cor/Gunma/May-4/GI/2004/JP | *Norovirus* Hu/GI/Skovde/IV8406/2002/SE |
| *Norovirus* Cor/Gunma/Nov-1/GI/2004/JP | *Norovirus* Hu/GI/SL4450/2005/Arg |
| *Norovirus* Cor/Gunma/Nov-2/GI/2004/JP | *Norovirus* Hu/GI/Stavanger/754/2004/NOR |
| *Norovirus* Cor/Gunma/Oct-2/GI/2004/JP | *Norovirus* Hu/GI/Stockholm/IV1353/2002/SE |
| *Norovirus* env/GGI/956/2007/ITA | *Norovirus* Hu/GI/Trondheim/4448/2000/NOR |
| *Norovirus* GI/103/2005/RJ/BRA | *Norovirus* Hu/GI/UE/200307-1/2007/SGP |
| *Norovirus* GI/104/2005/RJ/BRA | *Norovirus* Hu/GI/UE/200307-2/2007/SGP |
| *Norovirus* GI/110/2005/RJ/BRA | *Norovirus* Hu/GI/UE/230107-1/2007/SGP |
| *Norovirus* GI/56/2005/RJ/BRA | *Norovirus* Hu/GI/UE/230107-2/2007/SGP |
| *Norovirus* GI/57/2005/RJ/BRA | *Norovirus* Hu/GI/UE/230107-3/2007/SGP |
| *Norovirus* GI/Lopburi105/2006/THA | *Norovirus* Hu/GI/UE/230107-4/2007/SGP |
| *Norovirus* groundwater/GI/HE-a-1/2007/KOR | *Norovirus* Hu/GI/UE/230207-1/2007/SGP |
| *Norovirus* groundwater/GI/HE-b-1/2007/KOR | *Norovirus* Hu/GI/UE/230207-2/2007/SGP |

TABLE 1-continued

| *Norovirus* Strains |
| --- |
| *Norovirus* groundwater/GI/HE-c-1/2007/KOR |
| *Norovirus* groundwater/GI/SS-c-1/2007/KOR |
| *Norovirus* groundwater/GI/SS-f-1/2007/KOR |
| *Norovirus* Han River/GI/Dukpoong/Aug01/2005/KOR |
| *Norovirus* Han River/GI/Dukpoong/Feb01/2006/KOR |
| *Norovirus* Han River/GI/Dukpoong/Feb02/2006/KOR |
| *Norovirus* Han River/GI/Dukpoong/Jul01/2005/KOR |
| *Norovirus* Han River/GI/Dukpoong/Jul02/2005/KOR |
| *Norovirus* Han River/GI/Dukpoong/May01/2006/KOR |
| *Norovirus* Han River/GI/Jamsil/Oct01/2005/KOR |
| *Norovirus* Han River/GI/Jamsil/Oct02/2005/KOR |
| *Norovirus* Han River/GI/Kyoungan/Feb01/2006/KOR |
| *Norovirus* Han River/GI/Kyoungan/Feb02/2006/KOR |
| *Norovirus* Han River/GI/Kyoungan/Jan01/2006/KOR |
| *Norovirus* Han River/GI/Kyoungan/Jul01/2005/KOR |
| *Norovirus* Han River/GI/Kyoungan/Jul02/2005/KOR |
| *Norovirus* Han River/GI/Kyoungan/May01/2006/KOR |
| *Norovirus* Han River/GI/Sungnae/Jan01/2006/KOR |
| *Norovirus* Han River/GI/Sungnae/Jul01/2005/KOR |
| *Norovirus* Han River/GI/Sungnae/Jul02/2005/KOR |
| *Norovirus* Han River/GI/Sungnae/May01/2006/KOR |
| *Norovirus* Han River/GI/Sungnae/May02/2006/KOR |
| *Norovirus* Han River/GI/Sungnae/May03/2006/KOR |
| *Norovirus* Han River/GI/Sungnae/May04/2006/KOR |
| *Norovirus* Han River/GI/Wangsuk/Aug01/2005/KOR |
| *Norovirus* Han River/GI/Wangsuk/Feb01/2006/KOR |
| *Norovirus* Han River/GI/Wangsuk/Feb02/2006/KOR |
| *Norovirus* Han River/GI/Wangsuk/Jan01/2006/KOR |
| *Norovirus* Han River/GI/Wangsuk/Jul01/2005/KOR |
| *Norovirus* Han River/GI/Wangsuk/Jul02/2005/KOR |
| *Norovirus* Han River/GI/Wangsuk/May01/2006/KOR |
| *Norovirus* Hu/G1/2232/2006/BRA |
| *Norovirus* Hu/G1/2525/2006/BRA |
| *Norovirus* Hu/G1/Fin-Kauh/1999/Finland |
| *Norovirus* Hu/G1/Fin-Keur/1998/Finland |
| *Norovirus* Hu/G1/Fin-Kola/1999/Finland |
| *Norovirus* Hu/G1/Fin-Nurm/2000/Finland |
| *Norovirus* Hu/G1/Fin-Part/1999/Finland |
| *Norovirus* Hu/G1/Fin-Porv/1999/Finland |
| *Norovirus* Hu/G1/Fin-Sod/2003/Finland |
| *Norovirus* Hu/G1/Hamburg CN/2005 |
| *Norovirus* Hu/GGI/New Delhi/120/02/IND |
| *Norovirus* Hu/GGI/New Delhi/64/02/IND |
| *Norovirus* Hu/GGI/NL20010045/2001/NL |
| *Norovirus* Hu/GI/1/JPN |
| *Norovirus* Hu/GI/10B/2004/South Korea |
| *Norovirus* Hu/GI/11B/2004/South Korea |
| *Norovirus* Hu/GI/12/JPN |
| *Norovirus* Hu/GI/1278/2006/Ghana |
| *Norovirus* Hu/GI/12B/2004/South Korea |
| *Norovirus* Hu/GI/UE/230207-3/2007/SGP |
| *Norovirus* Hu/GI/UE/240407-1/2007/SGP |
| *Norovirus* Hu/GI/UE/240407-2/2007/SGP |
| *Norovirus* Hu/GI/UE/270607-1/2007/SGP |
| *Norovirus* Hu/GI/UE/270607-2/2007/SGP |
| *Norovirus* Hu/GI/UE/270607-3/2007/SGP |
| *Norovirus* Hu/GI/UE/290507-1/2007/SGP |
| *Norovirus* Hu/GI/UE/290507-2/2007/SGP |
| *Norovirus* Hu/GI/UE/290507-3/2007/SGP |
| *Norovirus* Hu/GI/Uppsala/IV11029/2002/SE |
| *Norovirus* Hu/GI/US/200307-1/2007/SGP |
| *Norovirus* Hu/GI/US/200307-2/2007/SGP |
| *Norovirus* Hu/GI/US/230107-1/2007/SGP |
| *Norovirus* Hu/GI/US/230107-2/2007/SGP |
| *Norovirus* Hu/GI/US/230107-3/2007/SGP |
| *Norovirus* Hu/GI/US/230207-1/2007/SGP |
| *Norovirus* Hu/GI/US/230207-2/2007/SGP |
| *Norovirus* Hu/GI/US/230207-3/2007/SGP |
| *Norovirus* Hu/GI/US/240407-1/2007/SGP |
| *Norovirus* Hu/GI/US/240407-2/2007/SGP |
| *Norovirus* Hu/GI/US/240407-3/2007/SGP |
| *Norovirus* Hu/GI/US/270607-1/2007/SGP |
| *Norovirus* Hu/GI/US/270607-2/2007/SGP |
| *Norovirus* Hu/GI/US/270607-3/2007/SGP |
| *Norovirus* Hu/GI/US/290507-1/2007/SGP |
| *Norovirus* Hu/GI/US/290507-2/2007/SGP |
| *Norovirus* Hu/GI/US/290507-3/2007/SGP |
| *Norovirus* Hu/GI/Water-1B/2004/South Korea |
| *Norovirus* Hu/GI/Water-2B/2004/South Korea |
| *Norovirus* Hu/GI/Water-A/2004/South Korea |
| *Norovirus* Hu/GI4/51059/Jilin/06/CHN |
| *Norovirus* Hu/GI4/51296/Anhui/06/CHN |
| *Norovirus* Hu/Gunma/3/GI/JP |
| *Norovirus* Hu/Gunma/4/GI/JP |
| *Norovirus* Hu/Gunma/5/GI/JP |
| *Norovirus* Hu/Mashhad4/GGI/Iran |
| *Norovirus* Hu/NFL-1107V6/GI/07-2004/CAN |
| *Norovirus* Hu/NV/I/Hualien/LWT/2003/TW |
| *Norovirus* Hu/Pune/PC01-GI/2005/India |
| *Norovirus* oyster/cultured/GI/05/JP |
| *Norovirus* oyster/cultured/GI/MAT/Apr05a/05/JP |
| *Norovirus* oyster/cultured/GI/MAT/Dec05/05/JP |
| *Norovirus* oyster/cultured/GI/MAT/May05a/05/JP |
| *Norovirus* oyster/cultured/GI/MAT05a/05/JP |
| *Norovirus* oyster/cultured/GI/MAT05b/05/JP |
| *Norovirus* oyster/cultured/GI/MAT05e/05/JP |
| *Norovirus* oyster/cultured/GI/ONG05b/05/JP |
| *Norovirus* oyster/GI/BFDA-GI-01/2009/TAW |
| *Norovirus* oyster/GI/BFDA-GI-02/2009/TAW |
| *Norovirus* oyster/GI/BFDA-GI-04/2009/TAW |
| *Norovirus* oyster/GI/BFDA-GI-05/2009/TAW |
| *Norovirus* oyster/GI/BFDA-GI-06/2009/TAW |
| *Norovirus* oyster/GI/BFDA-GI-07/2009/TAW |
| *Norovirus* oyster/GI/BFDA-GI-08/2009/TAW |
| *Norovirus* oyster/GI/BFDA-GI-09/2008/TAW |
| *Norovirus* oyster/GI/BFDA-GI-10/2008/TAW |
| *Norovirus* oyster/GI/BFDA-GI-11/2008/TAW |
| *Norovirus* oyster/GI/BFDA-GI-12/2008/TAW |
| *Norovirus* oyster/GI/FP19A/2004/CAN |
| *Norovirus* oyster/GI/FP19D/2004/CAN |
| *Norovirus* oyster/GI/FP19F/2004/CAN |
| *Norovirus* oyster/GI/FP19J/2004/CAN |
| *Norovirus* oyster/GI/FP50A/2004/CAN |
| *Norovirus* oyster/GI/FP50C/2004/CAN |
| *Norovirus* oyster/GI/FP50J/2004/CAN |
| *Norovirus* oyster/GI/FP55A/2004/CAN |
| *Norovirus* oyster/GI/FP55B/2004/CAN |
| *Norovirus* oyster/GI/FP58A/2004/CAN |
| *Norovirus* oyster/GI/FP58D/2004/CAN |
| *Norovirus* oyster/GI/FP58G/2004/CAN |
| *Norovirus* oyster/GI/FP58J/2004/CAN |
| *Norovirus* oyster/GI/FP67J/2004/CAN |
| *Norovirus* oyster/GI/FP68F/2004/CAN |
| *Norovirus* oyster/GI/FP69B/2004/CAN |
| *Norovirus* oyster/GI/FP72A/2004/CAN |
| *Norovirus* oyster/GI/FP72F/2004/CAN |
| *Norovirus* oyster/GI/Hiroshimacity/29/02/JP |
| *Norovirus* oyster/GI/Hiroshimacity/36/03/JP |

TABLE 1-continued

| *Norovirus* Strains | |
|---|---|
| *Norovirus* Hu/GI/1313/2006/Ghana | *Norovirus* oyster/GI/Yamaguchi/32B/03/JP |
| *Norovirus* Hu/GI/1370/2006/Ghana | *Norovirus* oyster/GI/Yamaguchi/33C/03/JP |
| *Norovirus* Hu/GI/13B/2004/South Korea | *Norovirus* oyster/GI/Yamaguchi/39B/03/JP |
| *Norovirus* Hu/GI/14B/2004/South Korea | *Norovirus* oyster/GI/Yamaguchi/43A/03/JP |
| *Norovirus* Hu/GI/1507/2006/Ghana | *Norovirus* oyster/GI/Yamaguchi/43C/03/JP |
| *Norovirus* Hu/GI/15B/2004/South Korea | *Norovirus* oyster/GI/Yamaguchi/45C/03/JP |
| *Norovirus* Hu/GI/16B/2004/South Korea | *Norovirus* oyster/GI/Yamaguchi/57A/03/JP |
| *Norovirus* Hu/GI/17/JPN | *Norovirus* oyster/GI/Yamaguchi/57B/03/JP |
| *Norovirus* Hu/GI/17B/2004/South Korea | *Norovirus* oyster/GI/Yamaguchi/H16-105B/04/JP |
| *Norovirus* Hu/GI/18B/2004/South Korea | *Norovirus* oyster/GI/Yamaguchi/H16-109B/04/JP |
| *Norovirus* Hu/GI/19B/2004/South Korea | *Norovirus* oyster/GI/Yamaguchi/H16-117B/04/JP |
| *Norovirus* Hu/GI/1A/2004/South Korea | *Norovirus* oyster/GI/Yamaguchi/H16-21C/03/JP |
| *Norovirus* Hu/GI/1B/2004/South Korea | *Norovirus* oyster/GI/Yamaguchi/H16-32B/03/JP |
| *Norovirus* Hu/GI/2002/2222/Moscow/RUS | *Norovirus* oyster/GI/Yamaguchi/H16-51A/04/JP |
| *Norovirus* Hu/GI/2003/3168/Moscow/RUS | *Norovirus* oyster/GI/Yamaguchi/H16-57C/04/JP |
| *Norovirus* Hu/GI/2005/5831/Moscow/RUS | *Norovirus* oyster/GI/Yamaguchi/H17-105B/05/JP |
| *Norovirus* Hu/GI/2005/6833/Chelyabinsk/RUS | *Norovirus* oyster/GI/Yamaguchi/H17-110D/05/JP |
| *Norovirus* Hu/GI/2005/6835/Chelyabinsk/RUS | *Norovirus* oyster/GI/Yamaguchi/H17-117A/05/JP |
| *Norovirus* Hu/GI/2005/6836/Chelyabinsk/RUS | *Norovirus* oyster/GI/Yamaguchi/H17-123A/05/JP |
| *Norovirus* Hu/GI/2005/7656/Nizhny Novgorod/RUS | *Norovirus* oyster/GI/Yamaguchi/H17-21B/04/JP |
| | *Norovirus* oyster/GI/Yamaguchi/H17-25B/04/JP |
| *Norovirus* Hu/GI/2005/7987/Chelyabinsk/RUS | *Norovirus* oyster/GI/Yamaguchi/H17-80A/05/JP |
| *Norovirus* Hu/GI/2005/8064/Chelyabinsk/RUS | *Norovirus* oyster/GI/Yamaguchi/H17-81A/05/JP |
| *Norovirus* Hu/GI/2005/8086/Chelyabinsk/RUS | *Norovirus* oyster/GI/Yamaguchi/H17-81B/05/JP |
| *Norovirus* Hu/GI/2005/8088/Chelyabinsk/RUS | *Norovirus* oyster/GI/Yamaguchi/H17-97C/05/JP |
| *Norovirus* Hu/GI/2005/8388/Chelyabinsk/RUS | *Norovirus* oyster/wild/GI/SHG/ST1/Mar05a/05/JP |
| *Norovirus* Hu/GI/2005/8763/Tyumen/RUS | *Norovirus* oyster/wild/GI/SHG/ST1/Mar05f/05/JP |
| *Norovirus* Hu/GI/2006/10882/Chelyabinsk/RUS | *Norovirus* oyster/wild/GI/SHG/ST2/Mar05a/05/JP |
| | *Norovirus* oyster/wild/GI/SHG/ST2/Mar05b/05/JP |
| *Norovirus* Hu/GI/2006/11227/Nizhny Novgorod/RUS | *Norovirus* oyster/wild/GI/SHG/ST2/Mar05e/05/JP |
| | *Norovirus* oyster/wild/GI/SHG/ST2/Mar05f/05/JP |
| *Norovirus* Hu/GI/2006/9564/Chelyabinsk/RUS | *Norovirus* oyster/wild/GI/SHG/ST3/Apr05a/05/JP |
| *Norovirus* Hu/GI/2006/9636/Chelyabinsk/RUS | *Norovirus* oyster/wild/GI/SHG/ST3/Apr05c/05/JP |
| *Norovirus* Hu/GI/20B/2004/South Korea | *Norovirus* oyster/wild/GI/SHG/ST3/Apr05d/05/JP |
| *Norovirus* Hu/GI/21B/2004/South Korea | *Norovirus* oyster/wild/GI/SHG/ST3/Dec05c/05/JP |
| *Norovirus* Hu/GI/22B/2004/South Korea | *Norovirus* oyster/wild/GI/SHG/ST3/Feb06/06/JP |
| *Norovirus* Hu/GI/23B/2004/South Korea | *Norovirus* oyster/wild/GI/SHG/ST3/Jan06a/06/JP |
| *Norovirus* Hu/GI/24B/2004/South Korea | *Norovirus* oyster/wild/GI/SHG/ST3/Jan06c/06/JP |
| *Norovirus* Hu/GI/25B/2004/South Korea | *Norovirus* oyster/wild/GI/SHG/ST3/Mar05/05/JP |
| *Norovirus* Hu/GI/28/JPN | *Norovirus* oyster/wild/GI/SHG/ST3/Mar06a/06/JP |
| *Norovirus* Hu/GI/2A/2004/South Korea | *Norovirus* oyster/wild/GI/SHG/ST3/Mar06c/06/JP |
| *Norovirus* Hu/GI/2B/2004/South Korea | *Norovirus* sewage/GI/Toyama/Apr-1/2006/JP |
| *Norovirus* Hu/GI/3A/2004/South Korea | *Norovirus* sewage/GI/Toyama/Apr-2/2006/JP |
| *Norovirus* Hu/GI/3B/2004/South Korea | *Norovirus* sewage/GI/Toyama/Apr/2007/JP |
| *Norovirus* Hu/GI/4B/2004/South Korea | *Norovirus* sewage/GI/Toyama/Aug-1/2007/JP |
| *Norovirus* Hu/GI/5B/2004/South Korea | *Norovirus* sewage/GI/Toyama/Aug-2/2007/JP |
| *Norovirus* Hu/GI/6/8014/2005/BRA | *Norovirus* sewage/GI/Toyama/Aug/2006/JP |
| *Norovirus* Hu/GI/6B/2004/South Korea | *Norovirus* sewage/GI/Toyama/Dec/2007/JP |
| *Norovirus* Hu/GI/7/JPN | *Norovirus* sewage/GI/Toyama/Feb/2007/JP |
| *Norovirus* Hu/GI/7B/2004/South Korea | *Norovirus* sewage/GI/Toyama/Feb/2008/JP |
| *Norovirus* Hu/GI/8/JPN | *Norovirus* sewage/GI/Toyama/Jan-1/2008/JP |
| *Norovirus* Hu/GI/8014/2004/BRA | *Norovirus* sewage/GI/Toyama/Jan-P2/2008/JP |
| *Norovirus* Hu/GI/8B/2004/South Korea | *Norovirus* sewage/GI/Toyama/Jan/2007/JP |
| *Norovirus* Hu/GI/9B/2004/South Korea | *Norovirus* sewage/GI/Toyama/Jul/2006/JP |
| *Norovirus* Hu/GI/Babbacombe/1996/GBR | *Norovirus* sewage/GI/Toyama/Jul/2007/JP |
| *Norovirus* Hu/GI/BCCDC03028/2003/CAN | *Norovirus* sewage/GI/Toyama/Jun/2006/JP |
| *Norovirus* Hu/GI/BCCDC04003/2004/CAN | *Norovirus* sewage/GI/Toyama/Jun/2007/JP |
| *Norovirus* Hu/GI/BCCDC04008/2004/CAN | *Norovirus* sewage/GI/Toyama/Mar-1/2007/JP |
| *Norovirus* Hu/GI/BE/200307/2007/SGP | *Norovirus* sewage/GI/Toyama/Mar-2/2007/JP |
| *Norovirus* Hu/GI/BE/230107-1/2007/SGP | *Norovirus* sewage/GI/Toyama/Mar-P2/2007/JP |
| *Norovirus* Hu/GI/BE/230107-2/2007/SGP | *Norovirus* sewage/GI/Toyama/Mar/2008/JP |
| *Norovirus* Hu/GI/BE/230107-3/2007/SGP | *Norovirus* sewage/GI/Toyama/May-2/2006/JP |
| *Norovirus* Hu/GI/BE/230207-1/2007/SGP | *Norovirus* sewage/GI/Toyama/May-P1/2006/JP |
| *Norovirus* Hu/GI/BE/230207-2/2007/SGP | *Norovirus* sewage/GI/Toyama/May/2006/JP |
| *Norovirus* Hu/GI/BE/240407-1/2007/SGP | *Norovirus* sewage/GI/Toyama/May/2007/JP |
| *Norovirus* Hu/GI/BE/240407-2/2007/SGP | *Norovirus* sewage/GI/Toyama/NoV-1/2006/JP |
| *Norovirus* Hu/GI/BE/240407-3/2007/SGP | *Norovirus* sewage/GI/Toyama/NoV-P2/2006/JP |
| *Norovirus* Hu/GI/BE/270607-1/2007/SGP | *Norovirus* sewage/GI/Toyama/NoV/2007/JP |
| *Norovirus* Hu/GI/BE/270607-2/2007/SGP | *Norovirus* sewage/GI/Toyama/Sep-1/2006/JP |
| *Norovirus* Hu/GI/BE/290507-1/2007/SGP | *Norovirus* sewage/GI/Toyama/Sep-2/2006/JP |
| *Norovirus* Hu/GI/BE/290507-2/2007/SGP | *Norovirus* sewage/GI/Toyama/Sep-P1/2006/JP |
| *Norovirus* Hu/GI/BE/290507-3/2007/SGP | *Norovirus* sewage/GI/Toyama/Sep/2007/JP |
| *Norovirus* Hu/GI/Beijing/50/2007 | *Norovirus* sewage/GI/Toyama/SW0609-7/2006/JP |
| *Norovirus* Hu/GI/Beijing/60/2007 | *Norovirus* sewage/GI/Toyama/SW0701-2/2006/JP |
| *Norovirus* Hu/GI/BHL37/2000/Botswana | *Norovirus* sewage/GI/Toyama/SW0702-7/2007/JP |
| *Norovirus* Hu/GI/BS/200307-1/2007/SGP | *Norovirus* sewage/GI/Toyama/SW0703-18/2007/JP |
| *Norovirus* Hu/GI/BS/200307-2/2007/SGP | *Norovirus* sewage/GI/Toyama/SW0705-9/2007/JP |
| *Norovirus* Hu/GI/BS/230107-1/2007/SGP | *Norovirus* sewage/GI/Toyama/SW0708-1/2007/JP |

TABLE 1-continued

| *Norovirus* Strains |
|---|
| *Norovirus* Hu/GI/BS/230107-2/2007/SGP |
| *Norovirus* Hu/GI/BS/230107-3/2007/SGP |
| *Norovirus* Hu/GI/BS/230107-4/2007/SGP |
| *Norovirus* Hu/GI/BS/230107-5/2007/SGP |
| *Norovirus* Hu/GI/BS/230207-1/2007/SGP |
| *Norovirus* Hu/GI/BS/230207-2/2007/SGP |
| *Norovirus* Hu/GI/BS/240407-1/2007/SGP |
| *Norovirus* Hu/GI/BS/240407-2/2007/SGP |
| *Norovirus* Hu/GI/BS/240407-3/2007/SGP |
| *Norovirus* Hu/GI/BS/270607-1/2007/SGP |
| *Norovirus* Hu/GI/BS/270607-2/2007/SGP |
| *Norovirus* Hu/GI/BS/270607-3/2007/SGP |
| *Norovirus* Hu/GI/BS/290507-1/2007/SGP |
| *Norovirus* Hu/GI/BS/290507-2/2007/SGP |
| *Norovirus* Hu/GI/C1-011106-1/2006/SGP |
| *Norovirus* Hu/GI/C1-011106-2/2006/SGP |
| *Norovirus* Hu/GI/C1-111206/2006/SGP |
| *Norovirus* Hu/GI/C1-150806/2006/SGP |
| *Norovirus* Hu/GI/C1-201106/2006/SGP |
| *Norovirus* Hu/GI/C1-220606/2006/SGP |
| *Norovirus* Hu/GI/C1-240706-1/2006/SGP |
| *Norovirus* Hu/GI/C1-240706-2/2006/SGP |
| *Norovirus* Hu/GI/C1-271206/2006/SGP |
| *Norovirus* Hu/GI/C2-230507/2007/SGP |
| *Norovirus* Hu/GI/C7-157/2005/KOR |
| *Norovirus* Hu/GI/C7-167/2005/KOR |
| *Norovirus* Hu/GI/Cardrona/2006/NZL |
| *Norovirus* Hu/GI/E-110407-1/2007/SGP |
| *Norovirus* Hu/GI/E-110407-2/2007/SGP |
| *Norovirus* Hu/GI/E-140307/2007/SGP |
| *Norovirus* Hu/GI/Eiken/5587/2002/NOR |
| *Norovirus* Hu/GI/FH-A/2004/South Korea |
| *Norovirus* Hu/GI/FH-B/2004/South Korea |
| *Norovirus* Hu/GI/Furutangen/4200/2002/NOR |
| *Norovirus* Hu/GI/GpN/2004/Irl |
| *Norovirus* Hu/GI/Guadalajara/TD1 |
| *Norovirus* Hu/GI/Guadalajara/TD12 |
| *Norovirus* Hu/GI/Guadalajara/TD7 |
| *Norovirus* Hu/GI/Guadalajara/TD8 |
| *Norovirus* Hu/GI/Guangxi/NN07230/2007/CHN |
| *Norovirus* Hu/GI/GuRIV/Caracas/2007/VEN |
| *Norovirus* Hu/GI/GuRV/Caracas/2007/VEN |
| *Norovirus* Hu/GI/GuRVII/Caracas/2008/VEN |
| *Norovirus* Hu/GI/Hemsedal/114/2001/NOR |
| *Norovirus* Hu/GI/Hiroshima/40-20/04/JP |
| *Norovirus* Hu/GI/Hiroshima/61-1/05/JP |
| *Norovirus* Hu/GI/HK/CU050101/2005/CHN |
| *Norovirus* Hu/GI/HK/CU050113/2005/CHN |
| *Norovirus* Hu/GI/HK/CU050210/2005/CHN |
| *Norovirus* Hu/GI/HK/CU050335/2005/CHN |
| *Norovirus* Hu/GI/HK/CU050431/2005/CHN |
| *Norovirus* Hu/GI/HK/CU050432/2005/CHN |
| *Norovirus* Hu/GI/HK/CU050448/2005/CHN |
| *Norovirus* water/GI/Gyeonggi/A12/2002/KOR |
| *Norovirus* water/GI/Gyeonggi/A14/2003/KOR |
| *Norovirus* water/GI/Gyeonggi/A15/2003/KOR |
| *Norovirus* water/GI/Gyeonggi/A2-1/2002/KOR |
| *Norovirus* water/GI/Gyeonggi/A2-2/2002/KOR |
| *Norovirus* water/GI/Gyeonggi/A7/2002/KOR |
| *Norovirus* water/GI/Gyeonggi/A8/2002/KOR |
| *Norovirus* water/GI/Gyeonggi/H10/2002/KOR |
| *Norovirus* water/GI/Gyeonggi/H12/2002/KOR |
| *Norovirus* water/GI/Gyeonggi/H13/2003/KOR |
| *Norovirus* water/GI/Gyeonggi/H14/2003/KOR |
| *Norovirus* water/GI/Gyeonggi/H15/2003/KOR |
| *Norovirus* water/GI/Gyeonggi/H2/2002/KOR |
| *Norovirus* water/GI/Gyeonggi/H3/2002/KOR |
| *Norovirus* water/GI/Gyeonggi/H6/2002/KOR |
| *Norovirus* water/GI/Gyeonggi/H7/2002/KOR |
| *Norovirus* water/GI/Gyeonggi/H8/2002/KOR |
| *Norovirus* water/GI/Gyeonggi/H9/2002/KOR |
| *Norovirus* water/GI/Gyeonggi/I14/2003/KOR |
| *Norovirus* water/GI/Gyeonggi/I15/2003/KOR |
| *Norovirus* water/GI/Gyeonggi/I2/2002/KOR |
| *Norovirus* water/GI/Gyeonggi/I8/2002/KOR |
| *Norovirus* water/GI/Gyeonggi/S1/2002/KOR |
| *Norovirus* water/GI/Gyeonggi/S10/2002/KOR |
| *Norovirus* water/GI/Gyeonggi/S11/2002/KOR |
| *Norovirus* water/GI/Gyeonggi/S12/2002/KOR |
| *Norovirus* water/GI/Gyeonggi/S14/2003/KOR |
| *Norovirus* water/GI/Gyeonggi/S15/2003/KOR |
| *Norovirus* water/GI/Gyeonggi/S3/2002/KOR |
| *Norovirus* water/GI/Gyeonggi/S4/2002/KOR |
| *Norovirus* water/GI/Gyeonggi/S7-1/2002/KOR |
| *Norovirus* water/GI/Gyeonggi/S7-2/2002/KOR |
| *Norovirus* water/GI/Gyeonggi/S8/2002/KOR |
| *Norovirus* water/GI/Gyeonggi/S9/2002/KOR |
| *Norovirus* Hu/GI/ICB1159/1996/Brazil |
| *Norovirus* Hu/GI/ICB1230/1996/Brazil |
| *Norovirus* Hu/GI/ICB1242C2/1996/Brazil |
| *Norovirus* Hu/GI/ICB1346C2/1996/Brazil |
| *Norovirus* Hu/GI/ICB1436C2/1996/Brazil |
| *Norovirus* Hu/GI/ICB1918/1996/Brazil |
| *Norovirus* Hu/GI/ICB1969C2/1997/Brazil |
| *Norovirus* Hu/GI/ICB2484/1998/Brazil |
| *Norovirus* Hu/GI/Jeju-43/2007/KOR |
| *Norovirus* Hu/GI/Jeju-50/2007/KOR |
| *Norovirus* Hu/GI/KD125/2005/Iraq |
| *Norovirus* Hu/GI/KD25/2005/Iraq |
| *Norovirus* Hu/GI/KD88/2005/Iraq |
| *Norovirus* Hu/GI/KE/200307-1/2007/SGP |
| *Norovirus* Hu/GI/KE/200307-2/2007/SGP |
| *Norovirus* Hu/GI/KE/230107-1/2007/SGP |
| *Norovirus* Hu/GI/KE/230107-2/2007/SGP |
| *Norovirus* Hu/GI/KE/230107-3/2007/SGP |
| *Norovirus* genogroup GI.1 |
| *Norovirus* Env/GGI.1/679/2006/IT |
| *Norovirus* Hu/GI-1/414003-3/2004/UK |
| *Norovirus* Hu/GI.1/2003/4529/Moscow/RUS |
| *Norovirus* Hu/GI.1/2003/4580/Moscow/RUS |
| *Norovirus* Hu/GI.1/2003/4602/Moscow/RUS |
| *Norovirus* Hu/GI.1/2003/4661/Moscow/RUS |
| *Norovirus* Hu/GI.1/2005/6067/Bishkek/RUS |
| *Norovirus* Hu/GI.1/2005/7685/Nizhny Novgorod/RUS |
| *Norovirus* Hu/GI.1/2005/8156/Moscow/RUS |
| *Norovirus* Hu/GI.1/2005/8227/St. Petersburg/RUS |
| *Norovirus* Hu/GI.1/2006/10246/Odessa/RUS |
| *Norovirus* Hu/GI.1/2006/10305/Odessa/RUS |
| *Norovirus* Hu/GI.1/2007/11580/Moscow/RUS |
| *Norovirus* Hu/GI.1/2007/2384/Moscow/RUS |
| *Norovirus* Hu/GI.1/Beijing/45/2007 |
| *Norovirus* Hu/GI.1/Cuernavaca/7183/2007/MEX |
| *Norovirus* Hu/GI.1/Dhaka234/2000/BGD |
| *Norovirus* Hu/GI.1/Mussels/M10nov2004/Foto/Sweden |
| *Norovirus* Hu/GI.1/Mussels/M8nov2004/Foto/Sweden |
| *Norovirus* Hu/GI.1/P2.Delsjo2004/Gothenburg/Sweden |
| *Norovirus* Hu/GI.1/P3.Delsjo2004/Gothenburg/Sweden |
| *Norovirus* Hu/GI.1/P4.Delsjo2004/Gothenburg/Sweden |
| *Norovirus* Hu/GI.1/P5.Delsjo2004/Gothenburg/Sweden |
| *Norovirus* Hu/GI.1/P6.Delsjo2004/Gothenburg/Sweden |
| *Norovirus* Hu/GI.1/P7-587/2007/Stromstad/Sweden |
| *Norovirus* Hu/GI.1/P7.Delsjo2004/Gothenburg/Sweden |
| *Norovirus* Hu/GI.1/P715.Delsjo2004/Gothenburg/Sweden |
| *Norovirus* Hu/GI.1/P725.Delsjo2004/Gothenburg/Sweden |
| *Norovirus* Hu/GI.1/P726.Delsjo2004/Gothenburg/Sweden |
| *Norovirus* |

TABLE 1-continued

| *Norovirus* Strains | |
|---|---|
| *Norovirus* Hu/GI.1/Mussels/M127nov2004/Foto/Sweden | Hu/GI.1/P738.Delsjo2004/Gothenburg/Sweden |
| *Norovirus* Hu/GI.1/Mussels/M28nov2004/Foto/Sweden | *Norovirus* Hu/GI.1/P774.Delsjo2004/Gothenburg/Sweden |
| | *Norovirus* Hu/GI.1/P8.Delsjo2004/Gothenburg/Sweden |
| | *Norovirus* Hu/GI.1/P9.Delsjo2004/Gothenburg/Sweden |
| | *Norovirus* Hu/GI.1/PI.Delsjo2004/Gothenburg/Sweden |
| | *Norovirus* oyster/GI.1/1A/Stromstad/Sweden |
| | *Norovirus* oyster/GI.1/1B/Stromstad/Sweden |
| | *Norovirus* oyster/GI.1/2/Stromstad/Sweden |
| *Norovirus* genogroup GI.2 | |
| *Norovirus* Env/GGI.2/671/2006/IT | *Norovirus* Hu/GGI.2/patient M/2006/NLD |
| *Norovirus* Env/GGI.2/677/2006/IT | *Norovirus* Hu/GGI.2/Southampton32609/2007/US |
| *Norovirus* Env/GGI.2/680/2006/IT | *Norovirus* Hu/GI-2/414003-1/2004/UK |
| *Norovirus* Env/GGI.2/704/2006/IT | *Norovirus* Hu/GI.2/13375/2007/RJ/BRA |
| *Norovirus* Hu/GG1-2/Berlin/90068.04-8-BA4/2004/DE | *Norovirus* Hu/GI.2/13397/2007/RJ/BRA |
| *Norovirus* Hu/GG1-2/Berlin/90405.04-1-BA1/2004/DE | *Norovirus* Hu/GI.2/Leuven/2003/BEL |
| *Norovirus* Hu/GG1-2/Berlin/90961.04-2-BA1/2004/DE | *Norovirus* Hu/GI.2/Mussels/M39nov2004/Foto/Sweden |
| *Norovirus* Hu/GG1-2/Berlin/91192.05-7-BA3/2004/DE | *Norovirus* septic system/GGI.2/Southampton31845/2007/US |
| *Norovirus* Hu/GG1-2/Berlin/91568.04-6-BA3/2004/DE | *Norovirus* well water/GGI.2/Southampton31818/2007/US |
| *Norovirus* genogroup GI.3 | |
| *Norovirus* Hu/GI-3/512057-1/2005/UK | *Norovirus* Hu/GI.3/P14.ASpen2004/Lerum/Sweden |
| *Norovirus* Hu/GI.3/13440/2007/RJ/BRA | *Norovirus* Hu/GI.3/P15.ASpen2004/Lerum/Sweden |
| *Norovirus* Hu/GI.3/13484/2007/RJ/BRA | *Norovirus* Hu/GI.3/P16.ASpen2004/Lerum/Sweden |
| *Norovirus* Hu/GI.3/Guadalajara/50074v1/2007/MEX | *Norovirus* Hu/GI.3/P17.ASpen2004/Lerum/Sweden |
| *Norovirus* Hu/GI.3/JKPG_881/SWE/2007 | *Norovirus* Hu/GI.3/P18.ASpen2004/Lerum/Sweden |
| *Norovirus* Hu/GI.3/JKPG_882/SWE/2007 | *Norovirus* Hu/GI.3/P2.ASpen2004/Lerum/Sweden |
| *Norovirus* Hu/GI.3/JKPG_883/SWE/2007 | *Norovirus* Hu/GI.3/P3.ASpen2004/Lerum/Sweden |
| *Norovirus* Hu/GI.3/P1.ASpen2004/Lerum/Sweden | *Norovirus* Hu/GI.3/P4.ASpen2004/Lerum/Sweden |
| *Norovirus* Hu/GI.3/P10.ASpen2004/Lerum/Sweden | *Norovirus* Hu/GI.3/P5.ASpen2004/Lerum/Sweden |
| *Norovirus* Hu/GI.3/P11.ASpen2004/Lerum/Sweden | *Norovirus* Hu/GI.3/P7.ASpen2004/Lerum/Sweden |
| *Norovirus* | *Norovirus* Hu/GI.3/P8.ASpen2004/Lerum/Sweden |
| | *Norovirus* Hu/GI.3/P9.ASpen2004/Lerum/Sweden |
| | Hu/GI.3/P12.ASpen2004/Lerum/Sweden |
| | *Norovirus* Hu/GI.3/P13.ASpen2004/Lerum/Sweden |
| *Norovirus* genogroup GI.4 | |
| *Norovirus* Env/GGI.4/678/2006/IT | *Norovirus* Hu/GI-4/E-1/2005/UK |
| *Norovirus* Hu/GG1-4/Berlin/91568.04-6-BA3/2004/DE | *Norovirus* Hu/GI-4/Inba/061217/2006/JP |
| *Norovirus* Hu/GG1-4/Berlin/92617.04-3-BA2/2004/DE | *Norovirus* Hu/GI.4/1643/2008/US |
| *Norovirus* Hu/GG1-4/Berlin/92672.04-4-BA2/2004/DE | *Norovirus* Hu/GI.4/pa-nov/2009/FIN |
| *Norovirus* Hu/GG1-4/Berlin/92674.04-5-BA2/2004/DE | *Norovirus* oyster A clone 1/GGI.2/2006/NLD |
| *Norovirus* Hu/GI-4/612057-1/2006/UK | *Norovirus* raspberries/GI.4/be-nov/2009/FIN |
| | *Norovirus* sewage/GI.4/Toyama/SW0702-1/2007/JP |
| | *Norovirus* Hu/GI-4/612058-1/2006/UK |
| | *Norovirus* Hu/GI-4/714124-1/2007/UK |
| *Norovirus* genogroup GI.5 | |
| *Norovirus* env/GGI.5/1120/2007/ITA | *Norovirus* env/GGI.5/1160/2007/ITA |
| *Norovirus* env/GGI.5/1130/2007/ITA | *Norovirus* Hu/GI-5/Newquay-1/2008/UK |
| *Norovirus* env/GGI.5/1132/2007/ITA | *Norovirus* Hu/GI.5/Cuernavaca/7253/2007/MEX |
| *Norovirus* env/GGI.5/1136/2007/ITA | |
| *Norovirus* genogroup GI.6 | |
| *Norovirus* Hu/GI-6/Q-1/2007/US | |
| *Norovirus* genogroup GI.7 | |
| *Norovirus* Hu/GI.7/4349a/2008/ZAF | *Norovirus* sewage/GI.7/Toyama/SW0703-10/2007/JP |
| *Norovirus* sewage/GI.7/Toyama/SW0702-11/2007/JP | |
| *Norovirus* genogroup GI.8 | |
| *Norovirus* Hu/GI-8/C6-48/South Korea | *Norovirus* Hu/GI.8/Cuernavaca/7162/2007/MEX |
| *Norovirus* Hu/GI-8/C6-49/South Korea | *Norovirus* Hu/GI.8/Cuernavaca/7172/2007/MEX |
| *Norovirus* Hu/GI-8/C6-52/South Korea | *Norovirus* Hu/GI.8/Guadalajara/50061/2007/MEX |
| *Norovirus* Hu/GI-8/C6-53/South Korea | *Norovirus* Hu/GI.8/Guadalajara/50074v2/2008/MEX |
| *Norovirus* Hu/GI-8/C7-157/South Korea | |

TABLE 1-continued

| *Norovirus* Strains | |
|---|---|
| *Norovirus* Hu/GI-8/C7-163/South Korea | *Norovirus* Hu/GI.8/Guadalajara/50081/2007/MEX |
| *Norovirus* Hu/GI-8/Kimitsu/060754/2006/JP | *Norovirus* Hu/GI.8/HME-394/2005/TWN |
| *Norovirus* Hu/GI.8/2008890321/2008/US | *Norovirus* Hu/GI.8/HME-401/2005/TWN |
| *Norovirus* Hu/GI.8/Cuernavaca/50416/2007/MEX | *Norovirus* Hu/GI.8/HME-406/2005/TWN |
| | *Norovirus* Hu/GI.8/HME-407/2005/TWN |
| *Norovirus* Hu/GI.8/Cuernavaca/7125/2007/MEX | *Norovirus* Hu/GI.8/HME-419/2005/TWN |
| | *Norovirus* Hu/GI.8/HME-462/2005/TWN |
| *Norovirus* Hu/GI.8/Cuernavaca/7145/2007/MEX | *Norovirus* Hu/GI.8/HME-468/2005/TWN |
| | *Norovirus* Hu/GI.8/Cuernavaca/7158/2007/MEX |
| Southampton virus | |
| *Norovirus* genogroup 2 | |
| Lordsdale virus | *Norovirus* Hu/GII/Farsund/2681/2002/NOR |
| *Norovirus* genogroup GII unidentified subgroup | *Norovirus* Hu/GII/FH-A/2004/South Korea |
| Human calcivirus NV/GII/Bollnas/IV6650/2003/SE | *Norovirus* Hu/GII/flag1/nursing home/Flagstaff/USA/2004 |
| Human calcivirus NV/GII/Falkoping/IV6744/2002/SE | *Norovirus* Hu/GII/GI.3/P6.ASpen2004/Lerum/Sweden |
| Human calcivirus NV/GII/Karlstad/IV12375/2002/SE | *Norovirus* Hu/GII/Goulburn Valley G5175 A/1983/AUS |
| Human calcivirus NV/GII/Lidkoping/IV6546/2003/SE | *Norovirus* Hu/GII/Goulburn Valley G5175 B/1983/AUS |
| Human calcivirus NV/GII/Mariestad/IV12677/2002/SE | *Norovirus* Hu/GII/Goulburn Valley G5175 C/1983/AUS |
| Human calcivirus NV/GII/Motala/IV3248/2002/SE | *Norovirus* Hu/GII/GpB/2004/Irl |
| Human calcivirus NV/GII/Norrtalje/IV12537/2002/SE | *Norovirus* Hu/GII/GpC/2004/Irl |
| Human calcivirus NV/GII/Norrtalje/IV1382/2003/SE | *Norovirus* Hu/GII/GpD/2004/Irl |
| Human calcivirus NV/GII/Norrtalje/IV1760/2002/SE | *Norovirus* Hu/GII/GpE/2003/4/Irl |
| Human calcivirus NV/GII/Norrtalje/IV2839/2002/SE | *Norovirus* Hu/GII/GpF/2004/Irl |
| Human calcivirus NV/GII/Skovde/IV12503/2002/SE | *Norovirus* Hu/GII/GpG/2004/Irl |
| Human calcivirus NV/GII/Skovde/IV6547/2003/SE | *Norovirus* Hu/GII/GpH/2003/4/Irl |
| Human calcivirus NV/GII/Stockholm/IV1018/2001/SE | *Norovirus* Hu/GII/GPH56/1999/Botswana |
| Human calcivirus NV/GII/Stockholm/IV1124/2003/SE | *Norovirus* Hu/GII/GpI/2004/Irl |
| Human calcivirus NV/GII/Stockholm/IV11320/2002/SE | *Norovirus* Hu/GII/GpJ/2004/Irl |
| Human calcivirus NV/GII/Stockholm/IV1138/2003/SE | *Norovirus* Hu/GII/GpK/2004/Irl |
| Human calcivirus NV/GII/Stockholm/IV1142/2003/SE | *Norovirus* Hu/GII/GpL/2004/Irl |
| Human calcivirus NV/GII/Stockholm/IV1163/2003/SE | *Norovirus* Hu/GII/GpM/2004/Irl |
| Human calcivirus NV/GII/Stockholm/IV1167/2003/SE | *Norovirus* Hu/GII/Guadalajara/TDII1 |
| Human calcivirus NV/GII/Stockholm/IV11835/2002/SE | *Norovirus* Hu/GII/GuRII/Caracas/2007/VEN |
| Human calcivirus NV/GII/Stockholm/IV12197/2002/SE | *Norovirus* Hu/GII/GuRX/Caracas/2008/VEN |
| Human calcivirus NV/GII/Stockholm/IV1229/2003/SE | *Norovirus* Hu/GII/GuRXI/Caracas/2008/VEN |
| Human calcivirus NV/GII/Stockholm/IV1259/2001/SE | *Norovirus* Hu/GII/GuRXII/Caracas/2008/VEN |
| Human calcivirus NV/GII/Stockholm/IV12699/2002/SE | *Norovirus* Hu/GII/GuRXIII/Caracas/2008/VEN |
| Human calcivirus NV/GII/Stockholm/IV1273/2003/SE | *Norovirus* Hu/GII/GuRXIV/Caracas/2008/VEN |
| Human calcivirus NV/GII/Stockholm/IV13229/2002/SE | *Norovirus* Hu/GII/GuRXV/Caracas/2008/VEN |
| Human calcivirus NV/GII/Stockholm/IV1342/2003/SE | *Norovirus* Hu/GII/GuRXVI/Caracas/2008/VEN |
| Human calcivirus NV/GII/Stockholm/IV1464/2001/SE | *Norovirus* Hu/GII/GuRXVII/Caracas/2008/VEN |
| Human calcivirus NV/GII/Stockholm/IV1472/2002/SE | *Norovirus* Hu/GII/GuRXVIII/Caracas/2008/VEN |
| Human calcivirus NV/GII/Stockholm/IV1513/2002/SE | *Norovirus* Hu/GII/GZ-1/2008/CHN |
| Human calcivirus NV/GII/Stockholm/IV1526/2001/SE | *Norovirus* Hu/GII/GZ-2/2008/CHN |
| Human calcivirus | *Norovirus* Hu/GII/GZ-3/2008/CHN |
| | *Norovirus* Hu/GII/Hamburg/1614/2006/Ger |
| | *Norovirus* Hu/GII/Hamburg/21407/2006/Ger |
| | *Norovirus* Hu/GII/Hamburg/2241/2006/Ger |
| | *Norovirus* Hu/GII/Hiroshima/2005/JP |
| | *Norovirus* Hu/GII/Hiroshima/33-2/03/JP |
| | *Norovirus* Hu/GII/Hiroshima/39-6/03/JP |
| | *Norovirus* Hu/GII/Hiroshima/54-3/04/JP |
| | *Norovirus* Hu/GII/Hiroshima/571-1/05/JP |
| | *Norovirus* Hu/GII/HK/CU041206/2004/CHN |
| | *Norovirus* Hu/GII/HK/CU041213/2004/CHN |
| | *Norovirus* Hu/GII/HK/CU041220/2004/CHN |
| | *Norovirus* Hu/GII/HK/CU041222/2004/CHN |
| | *Norovirus* Hu/GII/HK/CU041225/2004/CHN |
| | *Norovirus* Hu/GII/HK/CU041245/2004/CHN |
| | *Norovirus* Hu/GII/HK/CU041247/2004/CHN |
| | *Norovirus* Hu/GII/HK/CU050106/2005/CHN |
| | *Norovirus* Hu/GII/HK/CU050111/2005/CHN |
| | *Norovirus* Hu/GII/HK/CU050113/2005/CHN |
| | *Norovirus* Hu/GII/HK/CU050118/2005/CHN |
| | *Norovirus* Hu/GII/HK/CU050119/2005/CHN |
| | *Norovirus* Hu/GII/HK/CU050128/2005/CHN |
| | *Norovirus* Hu/GII/HK/CU050130/2005/CHN |
| | *Norovirus* Hu/GII/HK/CU050135/2005/CHN |
| | *Norovirus* Hu/GII/HK/CU050136/2005/CHN |
| | *Norovirus* Hu/GII/HK/CU050140/2005/CHN |
| | *Norovirus* Hu/GII/HK/CU050141/2005/CHN |
| | *Norovirus* Hu/GII/HK/CU050149/2005/CHN |

TABLE 1-continued

| *Norovirus* Strains | |
|---|---|
| NV/GII/Stockholm/IV1678/2002/SE | *Norovirus* Hu/GII/HK/CU050152/2005/CHN |
| Human calcivirus | *Norovirus* Hu/GII/HK/CU050211/2005/CHN |
| NV/GII/Stockholm/IV1759/2002/SE | *Norovirus* Hu/GII/HK/CU050214/2005/CHN |
| Human calcivirus | *Norovirus* Hu/GII/HK/CU050217/2005/CHN |
| NV/GII/Stockholm/IV1772/2001/SE | *Norovirus* Hu/GII/HK/CU050227/2005/CHN |
| Human calcivirus | *Norovirus* Hu/GII/HK/CU050240/2005/CHN |
| NV/GII/Stockholm/IV1813/2002/SE | *Norovirus* Hu/GII/HK/CU050403/2005/CHN |
| Human calcivirus | *Norovirus* Hu/GII/HK/CU050431/2005/CHN |
| NV/GII/Stockholm/IV2045/2001/SE | *Norovirus* Hu/GII/HK/CU050476/2005/CHN |
| Human calcivirus | *Norovirus* Hu/GII/HK/CU050852/2005/CHN |
| NV/GII/Stockholm/IV2168/2001/SE | *Norovirus* Hu/GII/HK/CU051013/2005/CHN |
| Human calcivirus | *Norovirus* Hu/GII/HK/CU051039/2005/CHN |
| NV/GII/Stockholm/IV2180/2001/SE | *Norovirus* Hu/GII/HK/CU051120/2005/CHN |
| Human calcivirus | *Norovirus* Hu/GII/HK/CU051139/2005/CHN |
| NV/GII/Stockholm/IV2182/2001/SE | *Norovirus* Hu/GII/HK/CU051146/2005/CHN |
| Human calcivirus | *Norovirus* Hu/GII/HK/CU051149/2005/CHN |
| NV/GII/Stockholm/IV2546/2001/SE | *Norovirus* Hu/GII/HK/CU051155/2005/CHN |
| Human calcivirus | *Norovirus* Hu/GII/Hokkaido/2004/JP |
| NV/GII/Stockholm/IV2682/2001/SE | *Norovirus* Hu/GII/Hokushin/03/JP |
| Human calcivirus | *Norovirus* Hu/GII/HS66/2001/US |
| NV/GII/Stockholm/IV2763/2002/SE | *Norovirus* Hu/GII/I1/JPN |
| Human calcivirus | *Norovirus* Hu/GII/I13/JPN |
| NV/GII/Stockholm/IV2765/2002/SE | *Norovirus* Hu/GII/I14/JPN |
| Human calcivirus | *Norovirus* Hu/GII/I7/JPN |
| NV/GII/Stockholm/IV2859/2001/SE | *Norovirus* Hu/GII/IAl-C104/2004/BRA |
| Human calcivirus | *Norovirus* Hu/GII/IAL-C112/2004/BRA |
| NV/GII/Stockholm/IV2863/2001/SE | *Norovirus* Hu/GII/IAl-C152/2005/BRA |
| Human calcivirus | *Norovirus* Hu/GII/IAL-C16/1995/BRA |
| NV/GII/Stockholm/IV2873/2002/SE | *Norovirus* Hu/GII/IAl-C174/2005/BRA |
| Human calcivirus | *Norovirus* Hu/GII/IAl-C176/2005/BRA |
| NV/GII/Stockholm/IV2877/2002/SE | *Norovirus* Hu/GII/IAl-C178/2005/BRA |
| Human calcivirus | *Norovirus* Hu/GII/IAl-C19/1995/BRA |
| NV/GII/Stockholm/IV2919/2001/SE | *Norovirus* Hu/GII/IAl-C21/1995/BRA |
| Human calcivirus | *Norovirus* Hu/GII/IAl-C22/1995/BRA |
| NV/GII/Stockholm/IV2925/2001/SE | *Norovirus* Hu/GII/IAl-C65/1995/BRA |
| Human calcivirus | *Norovirus* Hu/GII/IAl-C70/1995/BRA |
| NV/GII/Stockholm/IV3307/2001/SE | *Norovirus* Hu/GII/ICB1200/1996/Brazil |
| Human calcivirus | *Norovirus* Hu/GII/ICB1207/1996/Brazil |
| NV/GII/Stockholm/IV3355/2002/SE | *Norovirus* Hu/GII/ICB1208/1996/Brazil |
| Human calcivirus | *Norovirus* Hu/GII/ICB1235/1996/Brazil |
| NV/GII/Stockholm/IV3400/2002/SE | *Norovirus* Hu/GII/ICB1241/1996/Brazil |
| Human calcivirus | *Norovirus* Hu/GII/ICB1242C1/1996/Brazil |
| NV/GII/Stockholm/IV3480/2002/SE | *Norovirus* Hu/GII/ICB1244/1996/Brazil |
| Human calcivirus | *Norovirus* Hu/GII/ICB1248/1996/Brazil |
| NV/GII/Stockholm/IV3514/2002/SE | *Norovirus* Hu/GII/ICB1257/1996/Brazil |
| Human calcivirus | *Norovirus* Hu/GII/ICB1258/1996/Brazil |
| NV/GII/Stockholm/IV3602/2001/SE | *Norovirus* Hu/GII/ICB1261/1996/Brazil |
| Human calcivirus | *Norovirus* Hu/GII/ICB1262/1996/Brazil |
| NV/GII/Stockholm/IV3626/2001/SE | *Norovirus* Hu/GII/ICB1263/1996/Brazil |
| Human calcivirus | *Norovirus* Hu/GII/ICB1346C1/1996/Brazil |
| NV/GII/Stockholm/IV3728/2001/SE | *Norovirus* Hu/GII/ICB1429/1996/Brazil |
| Human calcivirus | *Norovirus* Hu/GII/ICB1430/1996/Brazil |
| NV/GII/Stockholm/IV3837/2001/SE | *Norovirus* Hu/GII/ICB1431/1996/Brazil |
| Human calcivirus | *Norovirus* Hu/GII/ICB1432/1996/Brazil |
| NV/GII/Stockholm/IV3882/2001/SE | *Norovirus* Hu/GII/ICB1434/1996/Brazil |
| Human calcivirus | *Norovirus* Hu/GII/ICB1435/1996/Brazil |
| NV/GII/Stockholm/IV3911/2001/SE | *Norovirus* Hu/GII/ICB1436C1/1996/Brazil |
| Human calcivirus | *Norovirus* Hu/GII/ICB1441/1996/Brazil |
| NV/GII/Stockholm/IV4348/2001/SE | *Norovirus* Hu/GII/ICB1443/1996/Brazil |
| Human calcivirus | *Norovirus* Hu/GII/ICB1444/1996/Brazil |
| NV/GII/Stockholm/IV4724/2001/SE | *Norovirus* Hu/GII/ICB1445/1996/Brazil |
| Human calcivirus | *Norovirus* Hu/GII/ICB1450/1996/Brazil |
| NV/GII/Stockholm/IV478/2001/SE | *Norovirus* Hu/GII/ICB1454/1996/Brazil |
| Human calcivirus | *Norovirus* Hu/GII/ICB1456/1996/Brazil |
| NV/GII/Stockholm/IV4884/2001/SE | *Norovirus* Hu/GII/ICB1467/1996/Brazil |
| Human calcivirus | *Norovirus* Hu/GII/ICB1521/1996/Brazil |
| NV/GII/Stockholm/IV4902/2001/SE | *Norovirus* Hu/GII/ICB1529/1996/Brazil |
| Human calcivirus | *Norovirus* Hu/GII/ICB1530/1996/Brazil |
| NV/GII/Stockholm/IV5350/2001/SE | *Norovirus* Hu/GII/ICB1912/1996/Brazil |
| Human calcivirus | *Norovirus* Hu/GII/ICB1913/1996/Brazil |
| NV/GII/Stockholm/IV5366/2001/SE | *Norovirus* Hu/GII/ICB1915/1996/Brazil |
| Human calcivirus | *Norovirus* Hu/GII/ICB1925/1997/Brazil |
| NV/GII/Stockholm/IV6189/2002/SE | *Norovirus* Hu/GII/ICB1928/1997/Brazil |
| Human calcivirus | *Norovirus* Hu/GII/ICB1929/1997/Brazil |
| NV/GII/Stockholm/IV620/2001/SE | *Norovirus* Hu/GII/ICB1932/1997/Brazil |
| Human calcivirus | *Norovirus* Hu/GII/ICB1963/1997/Brazil |
| NV/GII/Stockholm/IV6211/2002/SE | *Norovirus* Hu/GII/ICB1969C1/1997/Brazil |
| Human calcivirus | *Norovirus* Hu/GII/ICB1977/1997/Brazil |

TABLE 1-continued

| *Norovirus* Strains | |
|---|---|
| NV/GII/Stockholm/IV6253/2003/SE | *Norovirus* Hu/GII/ICB1983/1997/Brazil |
| Human calcivirus | *Norovirus* Hu/GII/ICB1987C1/1997/Brazil |
| NV/GII/Stockholm/IV6271/2002/SE | *Norovirus* Hu/GII/ICB1987C2/1997/Brazil |
| Human calcivirus | *Norovirus* Hu/GII/ICB1988/1997/Brazil |
| NV/GII/Stockholm/IV6285/2002/SE | *Norovirus* Hu/GII/ICB2109/1997/Brazil |
| Human calcivirus | *Norovirus* Hu/GII/ICB2160/1997/Brazil |
| NV/GII/Stockholm/IV6312/2003/SE | *Norovirus* Hu/GII/ICB2162/1998/Brazil |
| Human calcivirus | *Norovirus* Hu/GII/ICB2230/1998/Brazil |
| NV/GII/Stockholm/IV6515/2002/SE | *Norovirus* Hu/GII/ICB2482/1998/Brazil |
| Human calcivirus | *Norovirus* Hu/GII/ICB2617/1999/Brazil |
| NV/GII/Stockholm/IV6819/2003/SE | *Norovirus* Hu/GII/ICB2620/1999/Brazil |
| Human calcivirus | *Norovirus* Hu/GII/ICB2670/1999/Brazil |
| NV/GII/Stockholm/IV6970/2003/SE | *Norovirus* Hu/GII/ICB2784/1999/Brazil |
| Human calcivirus | *Norovirus* Hu/GII/ICB2785/1999/Brazil |
| NV/GII/Stockholm/IV6984/2003/SE | *Norovirus* Hu/GII/ICB2787/1999/Brazil |
| Human calcivirus | *Norovirus* Hu/GII/ICB2791/1999/Brazil |
| NV/GII/Stockholm/IV6989/2002/SE | *Norovirus* Hu/GII/ICB2891/1999/Brazil |
| Human calcivirus | *Norovirus* Hu/GII/Ichimiya/04/JP |
| NV/GII/Stockholm/IV6998/2003/SE | *Norovirus* Hu/GII/Ina/02/JP |
| Human calcivirus | *Norovirus* Hu/GII/J1/JPN |
| NV/GII/Stockholm/IV7137/2002/SE | *Norovirus* Hu/GII/J2/JPN |
| Human calcivirus | *Norovirus* Hu/GII/K1/JPN |
| NV/GII/Stockholm/IV76/2002/SE | *Norovirus* Hu/GII/K2/JPN |
| Human calcivirus | *Norovirus* Hu/GII/K3/JPN |
| NV/GII/Sundsvall/IV6891/2002/SE | *Norovirus* Hu/GII/Kamo/03/JP |
| Human calcivirus | *Norovirus* Hu/GII/KD106/2005/Iraq |
| NV/GII/Uppsala/IV1348/2003/SE | *Norovirus* Hu/GII/KD142/2005/Iraq |
| Human calcivirus | *Norovirus* Hu/GII/KD180/2005/Iraq |
| NV/GII/Uppsala/IV6477/2003/SE | *Norovirus* Hu/GII/KD203/2005/Iraq |
| Human calicivirus HU/NLV/Bham132/95/UK | *Norovirus* Hu/GII/KD22/2005/Iraq |
| Human calicivirus HU/NLV/Borna 185/00/DE | *Norovirus* Hu/GII/KD244/2005/Iraq |
| Human calicivirus Hu/NLV/GII/MD101- | *Norovirus* Hu/GII/KD77/2005/Iraq |
| 2/1987/US | *Norovirus* Hu/GII/KE/200307-1/2007/SGP |
| Human calicivirus Hu/NLV/GII/MD134- | *Norovirus* Hu/GII/KE/200307-2/2007/SGP |
| 10/1987/US | *Norovirus* Hu/GII/KE/230107/2007/SGP |
| Human calicivirus Hu/NLV/GII/MD134- | *Norovirus* Hu/GII/KE/230207-1/2007/SGP |
| 7/1987/US | *Norovirus* Hu/GII/KE/230207-2/2007/SGP |
| Human calicivirus Hu/NLV/GII/MD145- | *Norovirus* Hu/GII/KE/240407-1/2007/SGP |
| 12/1987/US | *Norovirus* Hu/GII/KE/240407-2/2007/SGP |
| Human calicivirus Hu/NLV/Hillingdon/90/UK | *Norovirus* Hu/GII/KE/270607-1/2007/SGP |
| Human calicivirus Hu/NLV/Leeds/90/UK | *Norovirus* Hu/GII/KE/270607-2/2007/SGP |
| Human calicivirus Hu/NLV/Parkroyal/95/UK | *Norovirus* Hu/GII/KE/270607-3/2007/SGP |
| Human calicivirus Hu/NLV/Seacroft/90/UK | *Norovirus* Hu/GII/KE/290507-1/2007/SGP |
| Human calicivirus Hu/NLV/Symgreen/95/UK | *Norovirus* Hu/GII/KE/290507-2/2007/SGP |
| Human calicivirus NLV/Aichi/124-89/JP | *Norovirus* Hu/GII/KE/290507-3/2007/SGP |
| Human calicivirus NLV/Aichi/12A-94/JP | *Norovirus* Hu/GII/KE/290507-4/2007/SGP |
| Human calicivirus NLV/Aichi/12B-94/JP | *Norovirus* Hu/GII/Kongsvinger/1793/2005/NOR |
| Human calicivirus NLV/Aichi/12C-94/JP | *Norovirus* Hu/GII/Kristiansand/1299/2001/NOR |
| Human calicivirus NLV/Aichi/12D-94/JP | *Norovirus* Hu/GII/KS/200307-1/2007/SGP |
| Human calicivirus NLV/Aichi/12E-94/JP | *Norovirus* Hu/GII/KS/200307-2/2007/SGP |
| Human calicivirus NLV/Aichi/13A-95/JP | *Norovirus* Hu/GII/KS/200307-3/2007/SGP |
| Human calicivirus NLV/Aichi/15A-96/JP | *Norovirus* Hu/GII/KS/230107/2007/SGP |
| Human calicivirus NLV/Aichi/16A-96/JP | *Norovirus* Hu/GII/KS/230207-1/2007/SGP |
| Human calicivirus NLV/Aichi/4A-88/JP | *Norovirus* Hu/GII/KS/230207-2/2007/SGP |
| Human calicivirus NLV/Aichi/8A-90/JP | *Norovirus* Hu/GII/KS/240407/2007/SGP |
| Human calicivirus NLV/Beeskow/124/00/DE | *Norovirus* Hu/GII/KS/270607-1/2007/SGP |
| Human calicivirus NLV/Berlin/491/00/DE | *Norovirus* Hu/GII/KS/270607-2/2007/SGP |
| Human calicivirus NLV/Berlin/495/00/DE | *Norovirus* Hu/GII/KS/270607-3/2007/SGP |
| Human calicivirus | *Norovirus* Hu/GII/KS/290507-1/2007/SGP |
| NLV/Chesterfield/434/1997/US | *Norovirus* Hu/GII/KS/290507-2/2007/SGP |
| Human calicivirus NLV/DIJON171/96 | *Norovirus* Hu/GII/KS/290507-3/2007/SGP |
| Human calicivirus NLV/Erfurt/007/00/DE | *Norovirus* Hu/GII/KS/290507-4/2007/SGP |
| Human calicivirus NLV/Erfurt/546/00/DE | *Norovirus* Hu/GII/KSDA52/2006/Botswana |
| Human calicivirus | *Norovirus* Hu/GII/KSDA63/2006/Botswana |
| NLV/Frankfurt(Oder)/170/99/DE | *Norovirus* Hu/GII/KSDA74/2006/Botswana |
| Human calicivirus NLV/Idaho | *Norovirus* Hu/GII/L1a/JPN |
| Falls/378/1996/US | *Norovirus* Hu/GII/L1b/JPN |
| Human calicivirus | *Norovirus* Hu/GII/L3/JPN |
| NLV/Koenigswusterhausen/130/00/DE | *Norovirus* Hu/GII/L4/JPN |
| Human calicivirus | *Norovirus* Hu/GII/Leverkusen267/2005/DE |
| NLV/Ludwigslust/218/99/DE | *Norovirus* Hu/GII/Luckenwalde591/2002/DE |
| Human calicivirus | *Norovirus* Hu/GII/Maizuru/7714/2007/JPN |
| NLV/Ludwigslust/221/99/DE | *Norovirus* Hu/GII/Maizuru/7718/2007/JPN |
| Human calicivirus | *Norovirus* Hu/GII/Maizuru/7719/2007/JPN |
| NLV/Oberschleissheim/112/99/DE | *Norovirus* Hu/GII/Maizuru/7723/2007/JPN |
| Human calicivirus NLV/Pirna/110/00/DE | *Norovirus* Hu/GII/Maizuru/7724/2007/JPN |
| Human calicivirus | *Norovirus* Hu/GII/Maizuru/7725/2007/JPN |
| NLV/Wyoming/US/genogroup 2 | *Norovirus* Hu/GII/Maizuru/7727/2007/JPN |

TABLE 1-continued

| *Norovirus* Strains | |
|---|---|
| Human calicivirus NV/Berlin029/02/DE | *Norovirus* Hu/GII/Maizuru/7731/2007/JPN |
| Human calicivirus NV/Berlin040/02/DE | *Norovirus* Hu/GII/Maizuru/7732/2007/JPN |
| Human calicivirus NV/Berlin131/01/DE | *Norovirus* Hu/GII/Maizuru/7734/2007/JPN |
| Human calicivirus NV/Berlin159/01/DE | *Norovirus* Hu/GII/Maizuru/7744/2007/JPN |
| Human calicivirus NV/Berlin245/01/DE | *Norovirus* Hu/GII/Maizuru/7748/2007/JPN |
| Human calicivirus NV/Berlin264/01/DE | *Norovirus* Hu/GII/Maizuru/7749/2007/JPN |
| Human calicivirus NV/Berlin376/01/DE | *Norovirus* Hu/GII/Maizuru/7752/2007/JPN |
| Human calicivirus NV/Berlin428/01/DE | *Norovirus* Hu/GII/Maizuru/7755/2007/JPN |
| Human calicivirus NV/Berlin642/01/DE | *Norovirus* Hu/GII/Maizuru/7759/2007/JPN |
| Human calicivirus NV/Berlin750/01/DE | *Norovirus* Hu/GII/Maizuru/7760/2007/JPN |
| Human calicivirus | *Norovirus* Hu/GII/Maizuru/7761/2007/JPN |
| NV/GII/Avesta/1817/2002/SE | *Norovirus* Hu/GII/Maizuru/7764/2007/JPN |
| Human calicivirus NV/GII/Bollnas/1999/SE | *Norovirus* Hu/GII/Maizuru/7768/2007/JPN |
| Human calicivirus | *Norovirus* Hu/GII/Maizuru/7770/2007/JPN |
| NV/GII/Boras/0016/1998/SE | *Norovirus* Hu/GII/Marina58/2003/Botswana |
| Human calicivirus | *Norovirus* Hu/GII/Melbourne/1998-06/AU |
| NV/GII/Boras/0082/2003/SE | *Norovirus* Hu/GII/Melbourne/1998-07/AU |
| Human calicivirus | *Norovirus* Hu/GII/Melbourne/1998-21/AU |
| NV/GII/Boras/2076/2000/SE | *Norovirus* Hu/GII/Melbourne/1999-13/AU |
| Human calicivirus | *Norovirus* Hu/GII/Melbourne/1999-14/AU |
| NV/GII/Falun/0019/1998/SE | *Norovirus* Hu/GII/Melbourne/1999-15/AU |
| Human calicivirus | *Norovirus* Hu/GII/Melbourne/1999-18/AU |
| NV/GII/Falun/0036/2002/SE | *Norovirus* Hu/GII/Melbourne/2000-02/AU |
| Human calicivirus NV/GII/Goteborg/1998/SE | *Norovirus* Hu/GII/Melbourne/2000-08/AU |
| Human calicivirus | *Norovirus* Hu/GII/Melbourne/2000-10/AU |
| NV/GII/Hudiksvall/0330/2000/SE | *Norovirus* Hu/GII/Melbourne/2000-12/AU |
| Human calicivirus | *Norovirus* Hu/GII/Melbourne/2000-13/AU |
| NV/GII/Jonkoping/0026/2002/SE | *Norovirus* Hu/GII/Melbourne/2001-01/AU |
| Human calicivirus | *Norovirus* Hu/GII/Melbourne/2001-13/AU |
| NV/GII/Kalmar/0220/1998/SE | *Norovirus* Hu/GII/Melbourne/2001-25/AU |
| Human calicivirus | *Norovirus* Hu/GII/Melbourne/2002-33/AU |
| NV/GII/Kristianstad/0553/2000/SE | *Norovirus* Hu/GII/Miyagi/03093/03/JP |
| Human calicivirus | *Norovirus* Hu/GII/Miyagi/03219/03/JP |
| NV/GII/Kristinehamn/0938/2001/SE | *Norovirus* Hu/GII/Miyagi/03375/03/JP |
| Human calicivirus | *Norovirus* Hu/GII/Moscow/10514/2006/RUS |
| NV/GII/Landskrona/0228/1998/SE | *Norovirus* Hu/GII/Moscow/10516/2006/RUS |
| Human calicivirus | *Norovirus* Hu/GII/Moscow/10525/2006/RUS |
| NV/GII/Linkoping/0227/1997/SE | *Norovirus* Hu/GII/Moscow/10526/2006/RUS |
| Human calicivirus | *Norovirus* Hu/GII/Moscow/10539/2006/RUS |
| NV/GII/Linkoping/0538/2000/SE | *Norovirus* Hu/GII/Moscow/10540/2006/RUS |
| Human calicivirus | *Norovirus* Hu/GII/Moscow/10541/2006/RUS |
| NV/GII/Linkoping/1020/1998/SE | *Norovirus* Hu/GII/Moscow/10555/2006/RUS |
| Human calicivirus | *Norovirus* Hu/GII/Moscow/10557/2006/RUS |
| NV/GII/Linkoping/1999/0440/SE | *Norovirus* Hu/GII/Moscow/10579/2006/RUS |
| Human calicivirus | *Norovirus* Hu/GII/Moscow/10581/2006/RUS |
| NV/GII/Ljusdal/1251/1997/SE | *Norovirus* Hu/GII/Moscow/10586/2006/RUS |
| Human calicivirus | *Norovirus* Hu/GII/Moscow/10588/2006/RUS |
| NV/GII/Ludvika/1001/2002/SE | *Norovirus* Hu/GII/Moscow/10598/2006/RUS |
| Human calicivirus | *Norovirus* Hu/GII/Moscow/10652/2006/RUS |
| NV/GII/Malmo/0144/2000/SE | *Norovirus* Hu/GII/Moscow/10654/2006/RUS |
| Human calicivirus | *Norovirus* Hu/GII/Moscow/10664/2006/RUS |
| NV/GII/Malmo/1229/1999/SE | *Norovirus* Hu/GII/Moscow/6395/2005/RUS |
| Human calicivirus | *Norovirus* Hu/GII/Moscow/7844/2005/RUS |
| NV/GII/Malmo/4708/2002/SE | *Norovirus* Hu/GII/Moscow/7971/2005/RUS |
| Human calicivirus | *Norovirus* Hu/GII/Moscow/8558/2005/RUS |
| NV/GII/Malmo/5092/2002/SE | *Norovirus* Hu/GII/Moscow/9062/2006/RUS |
| Human calicivirus | *Norovirus* Hu/GII/Moscow/9088/2006/RUS |
| NV/GII/Molndal/1651/1997/SE | *Norovirus* Hu/GII/Moscow/9156/2006/RUS |
| Human calicivirus | *Norovirus* |
| NV/GII/Mora/1692/1997/SE | Hu/GII/Mussels/M10mar2004/Foto/Sweden |
| Human calicivirus NV/GII/Mora/1999/SE | *Norovirus* |
| Human calicivirus | Hu/GII/Mussels/M2mar2004/Foto/Sweden |
| NV/GII/Norrkoping/0081/2002/SE | *Norovirus* |
| Human calicivirus | Hu/GII/Mussels/M5mar2004/Foto/Sweden |
| NV/GII/Norrkoping/0575/2001/SE | *Norovirus* |
| Human calicivirus | Hu/GII/Mussels/M7mar2004/Foto/Sweden |
| NV/GII/Ostersund/0983/1998/SE | *Norovirus* |
| Human calicivirus | Hu/GII/Mussels/M8Amar2004/Foto/Sweden |
| NV/GII/Ostersund/142501/1999/SE | *Norovirus* |
| Human calicivirus | Hu/GII/Mussels/M8Bmar2004/Foto/Sweden |
| NV/GII/Sandviken/1062/1997/SE | *Norovirus* |
| Human calicivirus | Hu/GII/Mussels/M9mar2004/Foto/Sweden |
| NV/GII/Solleftea/0898/2002/SE | *Norovirus* Hu/GII/N147/2004/Irl |
| Human calicivirus | *Norovirus* Hu/GII/N162/2004/Irl |
| NV/GII/Stockholm/0551/2001/SE | *Norovirus* Hu/GII/N176/2004/Irl |
| Human calicivirus | *Norovirus* Hu/GII/N189/2004/Irl |
| NV/GII/Stockholm/0686/2001/SE | *Norovirus* Hu/GII/N26/2003/Irl |
| Human calicivirus | *Norovirus* Hu/GII/N314/2004/Irl |

TABLE 1-continued

| *Norovirus* Strains |
| --- |
| NV/GII/Stockholm/0736/2003/SE |
| Human calicivirus NV/GII/Stockholm/0849/1997/SE |
| Human Calicivirus NV/GII/Stockholm/2032/1999/SE |
| Human calicivirus NV/GII/Stockholm/82601/1999/SE |
| Human calicivirus NV/GII/Trollhattan/0847/2002/SE |
| Human calicivirus NV/GII/Uddevalla/0032/2002/SE |
| Human calicivirus NV/GII/Uppsala/0979/2002/SE |
| Human calicivirus NV/GII/Vara/1582/1997/SE |
| Human calicivirus NV/GII/Vaxjo/0157/1998/SE |
| Human calicivirus NV/GII/Vaxjo/0394/2000/SE |
| Human calicivirus strain Mc100 |
| Human calicivirus strain Mc124 |
| Human calicivirus strain Mc17 |
| Human calicivirus strain Mc24 |
| Human calicivirus strain Mc37 |
| Human calicivirus strain Mc52 |
| Human calicivirus strain Mc99 |
| Human calicivirus strain Melksham |
| Human calicivirus strain St1 |
| *Norovirus* ark clam/GII/YanTai/ZY319/China/2008 |
| *Norovirus* bo/GII/CE-M-06-0532/2006/CAN |
| *Norovirus* clam/GII/Shijimi1/JPN |
| *Norovirus* clam/GII/Shijimi10a/JPN |
| *Norovirus* clam/GII/Shijimi10b/JPN |
| *Norovirus* clam/GII/Shijimi10c/JPN |
| *Norovirus* clam/GII/Shijimi13/JPN |
| *Norovirus* clam/GII/Shijimi14/JPN |
| *Norovirus* clam/GII/Shijimi15/JPN |
| *Norovirus* clam/GII/Shijimi16a/JPN |
| *Norovirus* clam/GII/Shijimi16b/JPN |
| *Norovirus* clam/GII/Shijimi16c/JPN |
| *Norovirus* clam/GII/Shijimi17a/JPN |
| *Norovirus* clam/GII/Shijimi17b/JPN |
| *Norovirus* clam/GII/Shijimi18/JPN |
| *Norovirus* clam/GII/Shijimi19/JPN |
| *Norovirus* clam/GII/Shijimi2/JPN |
| *Norovirus* clam/GII/Shijimi22/JPN |
| *Norovirus* clam/GII/Shijimi24/JPN |
| *Norovirus* clam/GII/Shijimi25/JPN |
| *Norovirus* clam/GII/Shijimi26/JPN |
| *Norovirus* clam/GII/Shijimi27/JPN |
| *Norovirus* clam/GII/Shijimi28a/JPN |
| *Norovirus* clam/GII/Shijimi28b/JPN |
| *Norovirus* clam/GII/Shijimi28c/JPN |
| *Norovirus* clam/GII/Shijimi28d/JPN |
| *Norovirus* clam/GII/Shijimi29/JPN |
| *Norovirus* clam/GII/Shijimi3/JPN |
| *Norovirus* clam/GII/Shijimi30/JPN |
| *Norovirus* clam/GII/Shijimi4a/JPN |
| *Norovirus* clam/GII/Shijimi4b/JPN |
| *Norovirus* clam/GII/Shijimi6/JPN |
| *Norovirus* clam/GII/Shijimi7a/JPN |
| *Norovirus* clam/GII/Shijimi7b/JPN |
| *Norovirus* clam/GII/Shijimi8a/JPN |
| *Norovirus* clam/GII/Shijimi8b/JPN |
| *Norovirus* clam/GII/Shijimi8c/JPN |
| *Norovirus* clam/GII/Shijimi8d/JPN |
| *Norovirus* clam/GII/Shijimi8e/JPN |
| *Norovirus* clam/GII/Shijimi9a/JPN |
| *Norovirus* clam/GII/Shijimi9b/JPN |
| *Norovirus* clam/GII/WeiHai/SD279/China/2008 |
| *Norovirus* Cor/Gunma/Apr-1/GII/2004/JP |
| *Norovirus* Cor/Gunma/Apr-2/GII/2004/JP |
| *Norovirus* Cor/Gunma/Aug-1/GII/2004/JP |
| *Norovirus* Cor/Gunma/Aug-2/GII/2004/JP |
| *Norovirus* Cor/Gunma/Dec-1/GII/2004/JP |
| *Norovirus* Cor/Gunma/Dec-2/GII/2004/JP |
| *Norovirus* Cor/Gunma/Dec-3/GII/2004/JP |
| *Norovirus* Hu/GII/N36/2003/Irl |
| *Norovirus* Hu/GII/N390/2004/Irl |
| *Norovirus* Hu/GII/N430/2004/Irl |
| *Norovirus* Hu/GII/N438/2004/Irl |
| *Norovirus* Hu/GII/N477/2004/Irl |
| *Norovirus* Hu/GII/N79/2004/Irl |
| *Norovirus* Hu/GII/N97/2004/Irl |
| *Norovirus* Hu/GII/Nagano/2004/H/JP |
| *Norovirus* Hu/GII/Nagano/2004/JP |
| *Norovirus* Hu/GII/Nagasaki/2004/H/Hokkaido/JP |
| *Norovirus* Hu/GII/New Delhi/183/IND |
| *Norovirus* Hu/GII/New Delhi/209/IND |
| *Norovirus* Hu/GII/New Delhi/228/IND |
| *Norovirus* Hu/GII/NFL26-2VR7/03-2005/CAN |
| *Norovirus* Hu/GII/Nijmegen-Lourdes/81021-26069/2008/NLD |
| *Norovirus* Hu/GII/Nizhny Novgorod/7691/2005/RUS |
| *Norovirus* Hu/GII/Nizhny Novgorod/7692/2005/RUS |
| *Norovirus* Hu/GII/Nizhny Novgorod/8252/2005/RUS |
| *Norovirus* Hu/GII/Nizhny Novgorod/8261//2005RUS |
| *Norovirus* Hu/GII/NoV296/2004/CAN |
| *Norovirus* Hu/GII/NoV355/2004/CAN |
| *Norovirus* Hu/GII/NoV64/2004/CAN |
| *Norovirus* Hu/GII/NoV750/2004/CAN |
| *Norovirus* Hu/GII/NoV752/2004/CAN |
| *Norovirus* Hu/GII/NoV784/2004/CAN |
| *Norovirus* Hu/GII/NoV79/2004/CAN |
| *Norovirus* Hu/GII/NoV793/2004/CAN |
| *Norovirus* Hu/GII/NoV804/2004/CAN |
| *Norovirus* Hu/GII/NoV809/2004/CAN |
| *Norovirus* Hu/GII/NSC042/PA/1993/BRA |
| *Norovirus* Hu/GII/NSC053/PA/1993/BRA |
| *Norovirus* Hu/GII/NSC076/PA/1993/BRA |
| *Norovirus* Hu/GII/NSC081/PA/1993/BRA |
| *Norovirus* Hu/GII/NSC141/PA/1993/BRA |
| *Norovirus* Hu/GII/NSC183/PA/1993/BRA |
| *Norovirus* Hu/GII/NSC185/PA/1993/BRA |
| *Norovirus* Hu/GII/NSC225/PA/1993/BRA |
| *Norovirus* Hu/GII/NSC253/PA/1993/BRA |
| *Norovirus* Hu/GII/NSC281/PA/1993/BRA |
| *Norovirus* Hu/GII/Nsk-688/2005/RUS |
| *Norovirus* Hu/GII/Nsk-701/2005/RUS |
| *Norovirus* Hu/GII/Nsk-K14/2006/RUS |
| *Norovirus* Hu/GII/Nsk-K15/2006/RUS |
| *Norovirus* Hu/GII/Nucci/2005/CO/US |
| *Norovirus* Hu/GII/nursing home flag2/Flagstaff/2004/USA |
| *Norovirus* Hu/GII/O1/JPN |
| *Norovirus* Hu/GII/O3a/JPN |
| *Norovirus* Hu/GII/O3b/JPN |
| *Norovirus* Hu/GII/Osaka659/2006/JPN |
| *Norovirus* Hu/GII/Oslo/1024/2000/NOR |
| *Norovirus* Hu/GII/Oslo/148/2005/NOR |
| *Norovirus* Hu/GII/Oslo/164/2004/NOR |
| *Norovirus* Hu/GII/Oslo/2202/2001/NOR |
| *Norovirus* Hu/GII/Oslo/352/2001/NOR |
| *Norovirus* Hu/GII/Oslo/477/2005/NOR |
| *Norovirus* Hu/GII/Oslo/6498/2000/NOR |
| *Norovirus* Hu/GII/Oslo/785/2005/NOR |
| *Norovirus* Hu/GII/P1.Confectionary2004/Gothenburg/Sweden |
| *Norovirus* Hu/GII/P2.Confectionary2004/Gothenburg/Sweden |
| *Norovirus* Hu/GII/P2/JPN |
| *Norovirus* Hu/GII/P3.Confectionary2004/Gothenburg/Sweden |
| *Norovirus* Hu/GII/P3/JPN |
| *Norovirus* Hu/GII/P4.Confectionary2004/Gothenburg/Sweden |
| *Norovirus* Hu/GII/P5.Confectionary2004/Gothenburg/Sweden |
| *Norovirus* Hu/GII/P5/JPN |
| *Norovirus* Hu/GII/P6.Confectionary2004/Gothenburg/Sweden |

TABLE 1-continued

| *Norovirus* Strains |
| --- |
| *Norovirus* Cor/Gunma/Dec-4/GII/2004/JP |
| *Norovirus* Cor/Gunma/Feb-1/GII/2004/JP |
| *Norovirus* Cor/Gunma/Feb-3/GII/2004/JP |
| *Norovirus* Cor/Gunma/Feb-4/GII/2004/JP |
| *Norovirus* Cor/Gunma/Feb-5/GII/2004/JP |
| *Norovirus* Cor/Gunma/Jan-1/GII/2004/JP |
| *Norovirus* Cor/Gunma/Jan-2/GII/2004/JP |
| *Norovirus* Cor/Gunma/Jul-1/GII/2004/JP |
| *Norovirus* Cor/Gunma/Jul-2/GII/2004/JP |
| *Norovirus* Cor/Gunma/Jul-3/GII/2004/JP |
| *Norovirus* Cor/Gunma/Jul-4/GII/2004/JP |
| *Norovirus* Cor/Gunma/Jun-1/GII/2004/JP |
| *Norovirus* Cor/Gunma/Jun-2/GII/2004/JP |
| *Norovirus* Cor/Gunma/Mar-2/GII/2004/JP |
| *Norovirus* Cor/Gunma/May-1/GII/2004/JP |
| *Norovirus* Cor/Gunma/May-2/GII/2004/JP |
| *Norovirus* Cor/Gunma/May-3/GII/2004/JP |
| *Norovirus* Cor/Gunma/May-4/GII/2004/JP |
| *Norovirus* Cor/Gunma/Nov-2/GII/2004/JP |
| *Norovirus* Cor/Gunma/Oct-1/GII/2004/JP |
| *Norovirus* Cor/Gunma/Oct-2/GII/2004/JP |
| *Norovirus* Cor/Gunma/Oct-3/GII/2004/JP |
| *Norovirus* Env/GGII/670/2006/IT |
| *Norovirus* GII/103/2005/RJ/BRA |
| *Norovirus* GII/105/2005/RJ/BRA |
| *Norovirus* GII/107/2005/RJ/BRA |
| *Norovirus* GII/58/2005/RJ/BRA |
| *Norovirus* GII/60/2005/RJ/BRA |
| *Norovirus* GII/70/2005/RJ/BRA |
| *Norovirus* GII/71/2005/RJ/BRA |
| *Norovirus* GII/Lopburi020/2006/THA |
| *Norovirus* GII/Lopburi026/2006/THA |
| *Norovirus* GII/Lopburi043/2006/THA |
| *Norovirus* GII/Lopburi084/2006/THA |
| *Norovirus* GII/Lopburi085/2006/THA |
| *Norovirus* GII/Lopburi095/2006/THA |
| *Norovirus* GII/Lopburi102/2006/THA |
| *Norovirus* GII/Lopburi103/2006/THA |
| *Norovirus* GII/Lopburi109/2006/THA |
| *Norovirus* GII/Lopburi117/2006/THA |
| *Norovirus* GII/Lopburi127/2006/THA |
| *Norovirus* GII/Lopburi146/2006/THA |
| *Norovirus* GII/Lopburi147/2006/THA |
| *Norovirus* GII/Lopburi155/2006/THA |
| *Norovirus* GII/Lopburi159/2006/THA |
| *Norovirus* groundwater/GII/Busan/BU01-04/2008/KOR |
| *Norovirus* groundwater/GII/Busan/BU01-08/2008/KOR |
| *Norovirus* groundwater/GII/Changwon/BU01-38/2008/KOR |
| *Norovirus* groundwater/GII/Cheorwon/KA01-19/2008/KOR |
| *Norovirus* groundwater/GII/Geochang/BU01-42/2008/KOR |
| *Norovirus* groundwater/GII/Goseong/KA01-28/2008/KOR |
| *Norovirus* groundwater/GII/Gyeongju/BU01-30/2008/KOR |
| *Norovirus* groundwater/GII/Gyeongsan/BU01-12/2008/KOR |
| *Norovirus* groundwater/GII/Hapcheon/BU01-45/2008/KOR |
| *Norovirus* groundwater/GII/JI-a-1/2007/KOR |
| *Norovirus* groundwater/GII/JI-a/2007/KOR |
| *Norovirus* groundwater/GII/Pohang/BU01-21/2008/KOR |
| *Norovirus* groundwater/GII/Uiryeong/BU01-15/2008/KOR |
| *Norovirus* groundwater/GII/Uiryeong/BU01-16/2008/KOR |
| *Norovirus* groundwater/GII/Uljin/BU01-23/2008/KOR |
| *Norovirus* groundwater/GII/Ulju/BU01-34/2008/KOR |
| *Norovirus* |
| *Norovirus* Hu/GII/P7.Confectionary2004/Gothenburg/Sweden |
| *Norovirus* Hu/GII/PC12/2006/Botswana |
| *Norovirus* Hu/GII/PC23/2006/Botswana |
| *Norovirus* Hu/GII/PC28/2006/Botswana |
| *Norovirus* Hu/GII/PC5/2006/Botswana |
| *Norovirus* Hu/GII/Penza/10625/2006/RUS |
| *Norovirus* Hu/GII/Penza/10630/2006/RUS |
| *Norovirus* Hu/GII/Penza/10631/2006/RUS |
| *Norovirus* Hu/GII/Podolsk/10604/2006/RUS |
| *Norovirus* Hu/GII/Podolsk/10609/2006/RUS |
| *Norovirus* Hu/GII/Podolsk/10620/2006/RUS |
| *Norovirus* Hu/GII/R1D-111206/2006/SGP |
| *Norovirus* Hu/GII/R1D-150806/2006/SGP |
| *Norovirus* Hu/GII/R1D-201106/2006/SGP |
| *Norovirus* Hu/GII/R1D-220606/2006/SGP |
| *Norovirus* Hu/GII/R1D-271206/2006/SGP |
| *Norovirus* Hu/GII/R1U-011106/2006/SGP |
| *Norovirus* Hu/GII/R1U-031006/2006/SGP |
| *Norovirus* Hu/GII/R1U-111206/2006/SGP |
| *Norovirus* Hu/GII/R1U-150806-1/2006/SGP |
| *Norovirus* Hu/GII/R1U-150806-2/2006/SGP |
| *Norovirus* Hu/GII/R1U-201106/2006/SGP |
| *Norovirus* Hu/GII/R2D-011106/2006/SGP |
| *Norovirus* Hu/GII/R2D-031006/2006/SGP |
| *Norovirus* Hu/GII/R2D-111206/2006/SGP |
| *Norovirus* Hu/GII/R2D-150806/2006/SGP |
| *Norovirus* Hu/GII/R2D-201106/2006/SGP |
| *Norovirus* Hu/GII/R2D-240706-1/2006/SGP |
| *Norovirus* Hu/GII/R2D-240706-2/2006/SGP |
| *Norovirus* Hu/GII/R2U-011106/2006/SGP |
| *Norovirus* Hu/GII/R2U-031006/2006/SGP |
| *Norovirus* Hu/GII/R2U-111206-1/2006/SGP |
| *Norovirus* Hu/GII/R2U-111206-2/2006/SGP |
| *Norovirus* Hu/GII/R2U-111206-3/2006/SGP |
| *Norovirus* Hu/GII/R2U-150806/2006/SGP |
| *Norovirus* Hu/GII/R2U-201106-1/2006/SGP |
| *Norovirus* Hu/GII/R2U-201106-2/2006/SGP |
| *Norovirus* Hu/GII/R2U-201106-3/2006/SGP |
| *Norovirus* Hu/GII/R2U-240706/2006/SGP |
| *Norovirus* Hu/GII/R2U-271206/2006/SGP |
| *Norovirus* Hu/GII/R3D-251006/2006/SGP |
| *Norovirus* Hu/GII/R3U-200607/2007/SGP |
| *Norovirus* Hu/GII/R3U-251006/2006/SGP |
| *Norovirus* Hu/GII/Ramotswa73/2006/Botswana |
| *Norovirus* Hu/GII/Ramotswa92/2006/Botswana |
| *Norovirus* Hu/GII/Rjukan/5577/2002/NOR |
| *Norovirus* Hu/GII/S10/JPN |
| *Norovirus* Hu/GII/S11/JPN |
| *Norovirus* Hu/GII/S12a/JPN |
| *Norovirus* Hu/GII/S12b/JPN |
| *Norovirus* Hu/GII/S2/JPN |
| *Norovirus* Hu/GII/S3/JPN |
| *Norovirus* Hu/GII/S4/JPN |
| *Norovirus* Hu/GII/S5/JPN |
| *Norovirus* Hu/GII/S8/JPN |
| *Norovirus* Hu/GII/S9/JPN |
| *Norovirus* Hu/GII/Salvador/B02/2006/BRA |
| *Norovirus* Hu/GII/Salvador/B07/2006/BRA |
| *Norovirus* Hu/GII/Salvador/D07/2006/BRA |
| *Norovirus* Hu/GII/Salvador/E04/2006/BRA |
| *Norovirus* Hu/GII/Salvador/F02/2006/BRA |
| *Norovirus* Hu/GII/Salvador/F05/2006/BRA |
| *Norovirus* Hu/GII/Seoul0006/2007/KR |
| *Norovirus* Hu/GII/Seoul0009/2007/KR |
| *Norovirus* Hu/GII/Seoul0012/2007/KR |
| *Norovirus* Hu/GII/Seoul0022/2007/KR |
| *Norovirus* Hu/GII/Seoul0031/2007/KR |
| *Norovirus* Hu/GII/Seoul0032/2007/KR |
| *Norovirus* Hu/GII/Seoul0033/2007/KR |
| *Norovirus* Hu/GII/Seoul0034/2007/KR |
| *Norovirus* Hu/GII/Seoul0037/2007/KR |
| *Norovirus* Hu/GII/Seoul0038/2007/KR |
| *Norovirus* Hu/GII/Seoul0042/2007/KR |
| *Norovirus* Hu/GII/Seoul0044/2007/KR |
| *Norovirus* Hu/GII/Seoul0046/2007/KR |

TABLE 1-continued

| *Norovirus* Strains |
| --- |
| groundwater/GII/Yeongcheon/BU01-19/2008/KOR |
| *Norovirus* groundwater/GII/Yeongcheon/BU01-20/2008/KOR |
| *Norovirus* Han River/GII/Dukpoong/Apr01/2006/KOR |
| *Norovirus* Han River/GII/Dukpoong/Apr02/2006/KOR |
| *Norovirus* Han River/GII/Dukpoong/Apr03/2006/KOR |
| *Norovirus* Han River/GII/Dukpoong/Aug01/2005/KOR |
| *Norovirus* Han River/GII/Dukpoong/Aug02/2005/KOR |
| *Norovirus* Han River/GII/Dukpoong/Aug03/2005/KOR |
| *Norovirus* Han River/GII/Dukpoong/Aug04/2005/KOR |
| *Norovirus* Han River/GII/Dukpoong/Aug05/2005/KOR |
| *Norovirus* Han River/GII/Dukpoong/Jan01/2006/KOR |
| *Norovirus* Han River/GII/Dukpoong/Jan02/2006/KOR |
| *Norovirus* Han River/GII/Dukpoong/Jan03/2006/KOR |
| *Norovirus* Han River/GII/Dukpoong/Jan04/2006/KOR |
| *Norovirus* Han River/GII/Dukpoong/Mar01/2006/KOR |
| *Norovirus* Han River/GII/Dukpoong/Mar02/2006/KOR |
| *Norovirus* Han River/GII/Dukpoong/May01/2006/KOR |
| *Norovirus* Han River/GII/Dukpoong/May02/2006/KOR |
| *Norovirus* Han River/GII/Dukpoong/Oct01/2005/KOR |
| *Norovirus* Han River/GII/Jamsil/Jan01/2006/KOR |
| *Norovirus* Han River/GII/Jamsil/Oct01/2005/KOR |
| *Norovirus* Han River/GII/Jamsil/Oct02/2005/KOR |
| *Norovirus* Han River/GII/Kyoungan/Apr01/2006/KOR |
| *Norovirus* Han River/GII/Kyoungan/Apr02/2006/KOR |
| *Norovirus* Han River/GII/Kyoungan/Jan01/2006/KOR |
| *Norovirus* Han River/GII/Kyoungan/Jan02/2006/KOR |
| *Norovirus* Han River/GII/Kyoungan/Mar01/2006/KOR |
| *Norovirus* Han River/GII/Kyoungan/May01/2006/KOR |
| *Norovirus* Han River/GII/Kyoungan/May02/2006/KOR |
| *Norovirus* Han River/GII/Kyoungan/May03/2006/KOR |
| *Norovirus* Han River/GII/Kyoungan/May04/2006/KOR |
| *Norovirus* Han River/GII/Kyoungan/Oct01/2005/KOR |
| *Norovirus* Han River/GII/Kyoungan/Oct02/2005/KOR |
| *Norovirus* Han River/GII/Kyoungan/Oct03/2005/KOR |
| *Norovirus* Han River/GII/Paldang/Oct01/2005/KOR |
| *Norovirus* Han River/GII/Paldang/Oct02/2005/KOR |
| *Norovirus* Han River/GII/Sungnae/Apr01/2006/KOR |
| *Norovirus* Han River/GII/Sungnae/Jan01/2006/KOR |
| *Norovirus* Han |
| *Norovirus* Hu/GII/Seoul0048/2007/KR |
| *Norovirus* Hu/GII/Seoul0049/2007/KR |
| *Norovirus* Hu/GII/Seoul0052/2007/KR |
| *Norovirus* Hu/GII/Seoul0055/2007/KR |
| *Norovirus* Hu/GII/Seoul0056/2007/KR |
| *Norovirus* Hu/GII/Seoul0058/2008/KR |
| *Norovirus* Hu/GII/Seoul0070/2008/KR |
| *Norovirus* Hu/GII/Seoul0071/2008/KR |
| *Norovirus* Hu/GII/Seoul0072/2008/KR |
| *Norovirus* Hu/GII/Seoul0073/2008/KR |
| *Norovirus* Hu/GII/Seoul0077/2008/KR |
| *Norovirus* Hu/GII/Seoul0079/2008/KR |
| *Norovirus* Hu/GII/Seoul0088/2008/KR |
| *Norovirus* Hu/GII/Seoul0089/2008/KR |
| *Norovirus* Hu/GII/Seoul0090/2008/KR |
| *Norovirus* Hu/GII/Seoul0125/2008/KR |
| *Norovirus* Hu/GII/Seoul0148/2008/KR |
| *Norovirus* Hu/GII/Seoul0150/2008/KR |
| *Norovirus* Hu/GII/Seoul0166/2008/KR |
| *Norovirus* Hu/GII/Seoul0184/2007/KR |
| *Norovirus* Hu/GII/Seoul0201/2007/KR |
| *Norovirus* Hu/GII/Seoul0203/2007/KR |
| *Norovirus* Hu/GII/Seoul0204/2007/KR |
| *Norovirus* Hu/GII/Seoul0208/2007/KR |
| *Norovirus* Hu/GII/Seoul0211/2007/KR |
| *Norovirus* Hu/GII/Seoul0212/2007/KR |
| *Norovirus* Hu/GII/Seoul0213/2007/KR |
| *Norovirus* Hu/GII/Seoul0214/2007/KR |
| *Norovirus* Hu/GII/Seoul0216/2007/KR |
| *Norovirus* Hu/GII/Seoul0219/2007/KR |
| *Norovirus* Hu/GII/Seoul0220/2007/KR |
| *Norovirus* Hu/GII/Seoul0222/2007/KR |
| *Norovirus* Hu/GII/Seoul0223/2007/KR |
| *Norovirus* Hu/GII/Seoul0224/2007/KR |
| *Norovirus* Hu/GII/Seoul0225/2007/KR |
| *Norovirus* Hu/GII/Seoul0226/2008/KR |
| *Norovirus* Hu/GII/Seoul0227/2008/KR |
| *Norovirus* Hu/GII/Seoul0231/2008/KR |
| *Norovirus* Hu/GII/Seoul0232/2008/KR |
| *Norovirus* Hu/GII/Seoul0235/2008/KR |
| *Norovirus* Hu/GII/Seoul0236/2008/KR |
| *Norovirus* Hu/GII/Seoul0238/2008/KR |
| *Norovirus* Hu/GII/Seoul0239/2008/KR |
| *Norovirus* Hu/GII/Seoul0240/2008/KR |
| *Norovirus* Hu/GII/Seoul0241/2008/KR |
| *Norovirus* Hu/GII/Seoul0242/2008/KR |
| *Norovirus* Hu/GII/Seoul0243/2008/KR |
| *Norovirus* Hu/GII/Seoul0505/2007/KR |
| *Norovirus* Hu/GII/Seoul0506/2007/KR |
| *Norovirus* Hu/GII/Seoul0507/2007/KR |
| *Norovirus* Hu/GII/Seoul0508/2007/KR |
| *Norovirus* Hu/GII/Seoul0509/2007/KR |
| *Norovirus* Hu/GII/Seoul0510/2007/KR |
| *Norovirus* Hu/GII/Seoul0511/2007/KR |
| *Norovirus* Hu/GII/Seoul0512/2007/KR |
| *Norovirus* Hu/GII/Seoul0513/2007/KR |
| *Norovirus* Hu/GII/Seoul0514/2007/KR |
| *Norovirus* Hu/GII/Seoul0515/2007/KR |
| *Norovirus* Hu/GII/Seoul0516/2007/KR |
| *Norovirus* Hu/GII/Seoul0517/2007/KR |
| *Norovirus* Hu/GII/Seoul0518/2007/KR |
| *Norovirus* Hu/GII/Seoul0519/2007/KR |
| *Norovirus* Hu/GII/Seoul0520/2007/KR |
| *Norovirus* Hu/GII/Seoul0521/2007/KR |
| *Norovirus* Hu/GII/Seoul0522/2007/KR |
| *Norovirus* Hu/GII/Seoul0523/2007/KR |
| *Norovirus* Hu/GII/Seoul0524/2007/KR |
| *Norovirus* Hu/GII/Seoul0525/2007/KR |
| *Norovirus* Hu/GII/Seoul0526/2007/KR |
| *Norovirus* Hu/GII/Seoul0527/2007/KR |
| *Norovirus* Hu/GII/Seoul0528/2007/KR |
| *Norovirus* Hu/GII/Seoul0529/2007/KR |
| *Norovirus* Hu/GII/Seoul0530/2007/KR |
| *Norovirus* Hu/GII/Seoul0531/2007/KR |
| *Norovirus* Hu/GII/Seoul0532/2007/KR |
| *Norovirus* Hu/GII/Seoul0533/2007/KR |
| *Norovirus* Hu/GII/Seoul0534/2007/KR |
| *Norovirus* Hu/GII/Seoul0535/2007/KR |

TABLE 1-continued

| *Norovirus* Strains | |
|---|---|
| River/GII/Sungnae/Jan02/2006/KOR | *Norovirus* Hu/GII/Seoul0536/2007/KR |
| *Norovirus* Han | *Norovirus* Hu/GII/Seoul0537/2007/KR |
| River/GII/Sungnae/Jan03/2006/KOR | *Norovirus* Hu/GII/Seoul0538/2007/KR |
| *Norovirus* Han | *Norovirus* Hu/GII/Seoul0539/2007/KR |
| River/GII/Sungnae/Mar01/2006/KOR | *Norovirus* Hu/GII/Seoul0540/2007/KR |
| *Norovirus* Han | *Norovirus* Hu/GII/Seoul0541/2007/KR |
| River/GII/Sungnae/Mar02/2006/KOR | *Norovirus* Hu/GII/Seoul0542/2007/KR |
| *Norovirus* Han | *Norovirus* Hu/GII/Seoul0543/2007/KR |
| River/GII/Sungnae/Mar03/2006/KOR | *Norovirus* Hu/GII/Seoul0544/2007/KR |
| *Norovirus* Han | *Norovirus* Hu/GII/Seoul0545/2007/KR |
| River/GII/Sungnae/May01/2006/KOR | *Norovirus* Hu/GII/Seoul0546/2007/KR |
| *Norovirus* Han | *Norovirus* Hu/GII/Seoul0547/2007/KR |
| River/GII/Sungnae/May02/2006/KOR | *Norovirus* Hu/GII/Seoul0548/2007/KR |
| *Norovirus* Han | *Norovirus* Hu/GII/Seoul0549/2007/KR |
| River/GII/Sungnae/Oct01/2005/KOR | *Norovirus* Hu/GII/Seoul0550/2007/KR |
| *Norovirus* Han | *Norovirus* Hu/GII/Seoul0551/2008/KR |
| River/GII/Wangsuk/Apr01/2006/KOR | *Norovirus* Hu/GII/Seoul0552/2007/KR |
| *Norovirus* Han | *Norovirus* Hu/GII/SewCCI/Caracas/2007/VEN |
| River/GII/Wangsuk/Apr02/2006/KOR | *Norovirus* Hu/GII/SewCI/2007/VEN |
| *Norovirus* Han | *Norovirus* Hu/GII/SewCIX/Caracas/2008/VEN |
| River/GII/Wangsuk/Apr03/2006/KOR | *Norovirus* Hu/GII/SewIvicI/Caracas/2007/VEN |
| *Norovirus* Han | *Norovirus* Hu/GII/SewVill/Caracas/2007/VEN |
| River/GII/Wangsuk/Aug01/2005/KOR | *Norovirus* Hu/GII/SH18/2005/CA |
| *Norovirus* Han | *Norovirus* Hu/GII/SH19/2005/CA |
| River/GII/Wangsuk/Aug02/2005/KOR | *Norovirus* Hu/GII/SH20/2005/CA |
| *Norovirus* Han | *Norovirus* Hu/GII/SH23/2005/CA |
| River/GII/Wangsuk/Jan01/2006/KOR | *Norovirus* Hu/GII/SH24/2005/CA |
| *Norovirus* Han | *Norovirus* Hu/GII/SH25/2005/CA |
| River/GII/Wangsuk/Jan02/2006/KOR | *Norovirus* Hu/GII/SH26/2005/CA |
| *Norovirus* Han | *Norovirus* Hu/GII/SH27/2005/CA |
| River/GII/Wangsuk/Jan03/2006/KOR | *Norovirus* Hu/GII/SH28/2005/CA |
| *Norovirus* Han | *Norovirus* Hu/GII/SH29/2005/CA |
| River/GII/Wangsuk/Mar01/2006/KOR | *Norovirus* Hu/GII/SH30/2005/CA |
| *Norovirus* Han | *Norovirus* Hu/GII/SH31/2005/CA |
| River/GII/Wangsuk/May01/2006/KOR | *Norovirus* Hu/GII/SH32/2005/CA |
| *Norovirus* Han | *Norovirus* Hu/GII/Shandong/TQ24/China |
| River/GII/Wangsuk/May02/2006/KOR | *Norovirus* Hu/GII/Shandong/TQ3/China |
| *Norovirus* Han | *Norovirus* Hu/GII/Shandong/TQ33/China |
| River/GII/Wangsuk/Oct01/2005/KOR | *Norovirus* Hu/GII/Shandong/TQ36/China |
| *Norovirus* Han | *Norovirus* Hu/GII/Shandong/TQ8/China |
| River/GII/Wangsuk/Oct02/2005/KOR | *Norovirus* Hu/GII/Shandong/TR28/China |
| *Norovirus* Han | *Norovirus* Hu/GII/Shandong/TR86/China |
| River/GII/Wangsuk/Oct03/2005/KOR | *Norovirus* Hu/GII/Shandong/TR88/China |
| *Norovirus* Hu/5032/2001/Bra | *Norovirus* Hu/GII/Shandong/TR92/China |
| *Norovirus* Hu/5037/2001/Bra | *Norovirus* Hu/GII/Shandong/TT138/China |
| *Norovirus* Hu/5046/2001/Bra | *Norovirus* Hu/GII/Shandong/TT147/China |
| *Norovirus* Hu/5049/2001/Bra | *Norovirus* Hu/GII/Shandong/TT170/China |
| *Norovirus* Hu/5095/2001/Bra | *Norovirus* Hu/GII/Shandong/TT19/China |
| *Norovirus* Hu/5112/2001/Bra | *Norovirus* Hu/GII/Shandong/TT197/China |
| *Norovirus* Hu/5118/2001/Bra | *Norovirus* Hu/GII/Shandong/TT37/China |
| *Norovirus* Hu/Billings/2006/USA | *Norovirus* Hu/GII/Shandong/TT40/China |
| *Norovirus* Hu/CL-CS/2006/USA | *Norovirus* Hu/GII/Shandong/TT50/China |
| *Norovirus* Hu/Cumberland/2004/USA | *Norovirus* Hu/GII/Shandong/TT62/China |
| *Norovirus* Hu/Duan/Beijing/2006/China | *Norovirus* Hu/GII/Shandong/TT66/China |
| *Norovirus* Hu/FL04/2004/USA | *Norovirus* Hu/GII/Shandong/TT7/China |
| *Norovirus* Hu/G2/1737/2006/BRA | *Norovirus* Hu/GII/Shandong/TT89/China |
| *Norovirus* Hu/G2/2762/2006/BRA | *Norovirus* Hu/GII/Shandong/TT99/China |
| *Norovirus* Hu/G2/2810/2006/BRA | *Norovirus* Hu/GII/Shizuoka/2005/JP |
| *Norovirus* Hu/G2/916/2006/BRA | *Norovirus* Hu/GII/Sinaloa/Mexico/M1/2007 |
| *Norovirus* Hu/G2/Fin-Beng/1998/Finland | *Norovirus* Hu/GII/Sinaloa/Mexico/NV1/2006 |
| *Norovirus* Hu/G2/Fin-Hank/2003/Finland | *Norovirus* Hu/GII/Sinaloa/Mexico/NV10/2007 |
| *Norovirus* Hu/G2/Fin-Jana/2002/Finland | *Norovirus* Hu/GII/Sinaloa/Mexico/NV11/2007 |
| *Norovirus* Hu/G2/Fin-Keur2/1998/Finland | *Norovirus* Hu/GII/Sinaloa/Mexico/NV12/2007 |
| *Norovirus* Hu/G2/Fin-Korp/2002/Finland | *Norovirus* Hu/GII/Sinaloa/Mexico/NV13/2007 |
| *Norovirus* Hu/G2/Fin-Nauv/2003/Finland | *Norovirus* Hu/GII/Sinaloa/Mexico/NV16/2007 |
| *Norovirus* Hu/G2/Fin-Pyha/2000/Finland | *Norovirus* Hu/GII/Sinaloa/Mexico/NV17/2007 |
| *Norovirus* Hu/G2/Fin-Pyha2/2000/Finland | *Norovirus* Hu/GII/Sinaloa/Mexico/NV19/2007 |
| *Norovirus* Hu/G2/Fin-Savi/1999/Finland | *Norovirus* Hu/GII/Sinaloa/Mexico/NV2/2007 |
| *Norovirus* Hu/GA04/2004/USA | *Norovirus* Hu/GII/Sinaloa/Mexico/NV20/2006 |
| *Norovirus* Hu/GCanyon/2002/USA | *Norovirus* Hu/GII/Sinaloa/Mexico/NV20/2007 |
| *Norovirus* Hu/GGI/Hamburg/744/2008/DEU | *Norovirus* Hu/GII/Sinaloa/Mexico/NV21/2007 |
| *Norovirus* Hu/GGII/New Delhi/209/01/IND | *Norovirus* Hu/GII/Sinaloa/Mexico/NV22/2007 |
| *Norovirus* Hu/GGII/NL19990014/1999/NL | *Norovirus* Hu/GII/Sinaloa/Mexico/NV23/2007 |
| *Norovirus* Hu/GGII/NL20000047/2000/NL | *Norovirus* Hu/GII/Sinaloa/Mexico/NV24/2007 |
| *Norovirus* Hu/GII.ne/Gothenburg/2005/SWE | *Norovirus* Hu/GII/Sinaloa/Mexico/NV25/2007 |
| *Norovirus* Hu/GII/1/JPN | *Norovirus* Hu/GII/Sinaloa/Mexico/NV3/2007 |
| *Norovirus* Hu/GII/10/JPN | *Norovirus* Hu/GII/Sinaloa/Mexico/NV4/2007 |
| *Norovirus* Hu/GII/10015/2004/BRA | *Norovirus* Hu/GII/Sinaloa/Mexico/NV5/2007 |

TABLE 1-continued

| *Norovirus* Strains |
|---|
| *Norovirus* Hu/GII/10070/2004/BRA |
| *Norovirus* Hu/GII/10076/2004/BRA |
| *Norovirus* Hu/GII/10079/2004/BRA |
| *Norovirus* Hu/GII/101/JPN |
| *Norovirus* Hu/GII/103/JPN |
| *Norovirus* Hu/GII/106/JPN |
| *Norovirus* Hu/GII/10B/2004/South Korea |
| *Norovirus* Hu/GII/11/JPN |
| *Norovirus* Hu/GII/110/JPN |
| *Norovirus* Hu/GII/111/JPN |
| *Norovirus* Hu/GII/112/JPN |
| *Norovirus* Hu/GII/114/JPN |
| *Norovirus* Hu/GII/115/JPN |
| *Norovirus* Hu/GII/118/JPN |
| *Norovirus* Hu/GII/11B/2004/South Korea |
| *Norovirus* Hu/GII/12/JPN |
| *Norovirus* Hu/GII/127/JPN |
| *Norovirus* Hu/GII/131/2004/HK |
| *Norovirus* Hu/GII/1329/2006/Ghana |
| *Norovirus* Hu/GII/1333/2006/Ghana |
| *Norovirus* Hu/GII/136/JPN |
| *Norovirus* Hu/GII/1364/2006/Ghana |
| *Norovirus* Hu/GII/1367/2006/Ghana |
| *Norovirus* Hu/GII/1407/2006/Ghana |
| *Norovirus* Hu/GII/143/JPN |
| *Norovirus* Hu/GII/1443/2006/Ghana |
| *Norovirus* Hu/GII/147/JPN |
| *Norovirus* Hu/GII/148/JPN |
| *Norovirus* Hu/GII/1495/2006/Ghana |
| *Norovirus* Hu/GII/15/JPN |
| *Norovirus* Hu/GII/150/JPN |
| *Norovirus* Hu/GII/1517/2006/Ghana |
| *Norovirus* Hu/GII/153/JPN |
| *Norovirus* Hu/GII/1559/2006/Ghana |
| *Norovirus* Hu/GII/156/JPN |
| *Norovirus* Hu/GII/1566/2006/Ghana |
| *Norovirus* Hu/GII/161/JPN |
| *Norovirus* Hu/GII/17/JPN |
| *Norovirus* Hu/GII/173/JPN |
| *Norovirus* Hu/GII/174/JPN |
| *Norovirus* Hu/GII/175/JPN |
| *Norovirus* Hu/GII/177/JPN |
| *Norovirus* Hu/GII/195/JPN |
| *Norovirus* Hu/GII/196/JPN |
| *Norovirus* Hu/GII/197/JPN |
| *Norovirus* Hu/GII/1B/2004/South Korea |
| *Norovirus* Hu/GII/2002/2064/Moscow/RUS |
| *Norovirus* Hu/GII/2002/2325/Moscow/RUS |
| *Norovirus* Hu/GII/2003/3464/Moscow/RUS |
| *Norovirus* Hu/GII/2003/3601/Moscow/RUS |
| *Norovirus* Hu/GII/2005/5844/Moscow/RUS |
| *Norovirus* Hu/GII/2005/6082/Chelyabinsk/RUS |
| *Norovirus* Hu/GII/2005/6297/St. Petersburg/RUS |
| *Norovirus* Hu/GII/2005/6300/St Petersburg/RUS |
| *Norovirus* Hu/GII/2005/6315/St. Petersburg/RUS |
| *Norovirus* Hu/GII/2005/6316/St. Petersburg/RUS |
| *Norovirus* Hu/GII/2005/6336/Moscow/RUS |
| *Norovirus* Hu/GII/2005/6373/Moscow/RUS |
| *Norovirus* Hu/GII/2005/6442/Nizhny Novgorod/RUS |
| *Norovirus* Hu/GII/2005/6451/Nizhny Novgorod/RUS |
| *Norovirus* Hu/GII/2005/6455/Nizhny Novgorod/RUS |
| *Norovirus* Hu/GII/2005/6457/Nizhny Novgorod/RUS |
| *Norovirus* Hu/GII/2005/6463/Nizhny Novgorod/RUS |
| *Norovirus* Hu/GII/2005/6640/Chelyabinsk/RUS |
| *Norovirus* Hu/GII/2005/6655/Chelyabinsk/RUS |
| *Norovirus* |
| *Norovirus* Hu/GII/Sinaloa/Mexico/NV6/2007 |
| *Norovirus* Hu/GII/Sinaloa/Mexico/NV9/2007 |
| *Norovirus* Hu/GII/Sinsiro/97/JP |
| *Norovirus* Hu/GII/SL4452/2005/Arg |
| *Norovirus* Hu/GII/Sofia166/2007/BGR |
| *Norovirus* Hu/GII/Sofia663/2007/BGR |
| *Norovirus* Hu/GII/St Petersburg/6296/2006/RUS |
| *Norovirus* Hu/GII/St Petersburg/9092/2006/RUS |
| *Norovirus* Hu/GII/St Petersburg/9102/2006/RUS |
| *Norovirus* Hu/GII/Stavanger/2851/2002/NOR |
| *Norovirus* Hu/GII/T4/JPN |
| *Norovirus* Hu/GII/Tahara/04/JP |
| *Norovirus* Hu/GII/TF4618/2006/Arg |
| *Norovirus* Hu/GII/Tianjin/1/2008/CHN |
| *Norovirus* Hu/GII/Tianjin/510/2009/CHN |
| *Norovirus* Hu/GII/Tianjin/53/2008/CHN |
| *Norovirus* Hu/GII/Toronto/SK/2002/CAN |
| *Norovirus* Hu/GII/Toronto/SK/2005/CAN |
| *Norovirus* Hu/GII/Toyama/106/2007/JP |
| *Norovirus* Hu/GII/Toyama/108/2007/JP |
| *Norovirus* Hu/GII/Toyama/114/2007/JP |
| *Norovirus* Hu/GII/Toyama/115/2007/JP |
| *Norovirus* Hu/GII/Toyama/409/2006/JP |
| *Norovirus* Hu/GII/Toyama/52/2007/JP |
| *Norovirus* Hu/GII/Toyama/54/2007/JP |
| *Norovirus* Hu/GII/Toyama/55/2007/JP |
| *Norovirus* Hu/GII/Toyama/56/2007/JP |
| *Norovirus* Hu/GII/Toyama/58/2007/JP |
| *Norovirus* Hu/GII/Toyama/59/2007/JP |
| *Norovirus* Hu/GII/Toyama/60/2007/JP |
| *Norovirus* Hu/GII/Toyama/61/2007/JP |
| *Norovirus* Hu/GII/Toyama/64/2007/JP |
| *Norovirus* Hu/GII/Toyama/93/2007/JP |
| *Norovirus* Hu/GII/Toyama/98/2007/JP |
| *Norovirus* Hu/GII/Toyama/99/2007/JP |
| *Norovirus* Hu/GII/Tromso/4266/2003/NOR |
| *Norovirus* Hu/GII/Tromso/4398/2002/NOR |
| *Norovirus* Hu/GII/Tromso/4469/2003/NOR |
| *Norovirus* Hu/GII/TSPC18/2006/Botswana |
| *Norovirus* Hu/GII/TSPC19/2006/Botswana |
| *Norovirus* Hu/GII/TSPC22/2006/Botswana |
| *Norovirus* Hu/GII/TSPC29/2006/Botswana |
| *Norovirus* Hu/GII/Tynset/4117/2003/NOR |
| *Norovirus* Hu/GII/Tyumen/9825/2006/RUS |
| *Norovirus* Hu/GII/Tyumen/9830/2006/RUS |
| *Norovirus* Hu/GII/UE/200307-1/2007/SGP |
| *Norovirus* Hu/GII/UE/200307-2/2007/SGP |
| *Norovirus* Hu/GII/UE/200307-3/2007/SGP |
| *Norovirus* Hu/GII/UE/230107-1/2007/SGP |
| *Norovirus* Hu/GII/UE/230107-2/2007/SGP |
| *Norovirus* Hu/GII/UE/230207-1/2007/SGP |
| *Norovirus* Hu/GII/UE/230207-2/2007/SGP |
| *Norovirus* Hu/GII/UE/230207-3/2007/SGP |
| *Norovirus* Hu/GII/UE/240407-1/2007/SGP |
| *Norovirus* Hu/GII/UE/240407-2/2007/SGP |
| *Norovirus* Hu/GII/UE/270607-1/2007/SGP |
| *Norovirus* Hu/GII/UE/270607-2/2007/SGP |
| *Norovirus* Hu/GII/UE/270607-3/2007/SGP |
| *Norovirus* Hu/GII/UE/290507-1/2007/SGP |
| *Norovirus* Hu/GII/UE/290507-2/2007/SGP |
| *Norovirus* Hu/GII/UE/290507-3/2007/SGP |
| *Norovirus* Hu/GII/US/200307-1/2007/SGP |
| *Norovirus* Hu/GII/US/200307-2/2007/SGP |
| *Norovirus* Hu/GII/US/200307-3/2007/SGP |
| *Norovirus* Hu/GII/US/230107-1/2007/SGP |
| *Norovirus* Hu/GII/US/230107-2/2007/SGP |
| *Norovirus* Hu/GII/US/230207-1/2007/SGP |
| *Norovirus* Hu/GII/US/230207-2/2007/SGP |
| *Norovirus* Hu/GII/US/230207-3/2007/SGP |
| *Norovirus* Hu/GII/US/240407-1/2007/SGP |
| *Norovirus* Hu/GII/US/240407-2/2007/SGP |
| *Norovirus* Hu/GII/US/270607/2007/SGP |
| *Norovirus* Hu/GII/US/290507-1/2007/SGP |
| *Norovirus* Hu/GII/US/290507-2/2007/SGP |
| *Norovirus* Hu/GII/Vagedalen/314/2004/NOR |
| *Norovirus* Hu/GII/VN10/2002/VNM |
| *Norovirus* Hu/GII/VN190/2002/VNM |
| *Norovirus* Hu/GII/VN207/2003/VNM |

TABLE 1-continued

| *Norovirus* Strains |
| --- |
| Hu/GII/2005/6667/Chelyabinsk/RUS |
| *Norovirus* Hu/GII/2005/6670/Chelyabinsk/RUS |
| *Norovirus* Hu/GII/2005/6671/Chelyabinsk/RUS |
| *Norovirus* Hu/GII/2005/6672/Chelyabinsk/RUS |
| *Norovirus* Hu/GII/2005/6675/Chelyabinsk/RUS |
| *Norovirus* Hu/GII/2005/6727/Chelyabinsk/RUS |
| *Norovirus* Hu/GII/2005/6733/Chelyabinsk/RUS |
| *Norovirus* Hu/GII/2005/6742/Chelyabinsk/RUS |
| *Norovirus* Hu/GII/2005/6743/Chelyabinsk/RUS |
| *Norovirus* Hu/GII/2005/6808/Chelyabinsk/RUS |
| *Norovirus* Hu/GII/2005/6894/Chelyabinsk/RUS |
| *Norovirus* Hu/GII/2005/7137/Moscow/RUS |
| *Norovirus* Hu/GII/2005/7579/Moscow/RUS |
| *Norovirus* Hu/GII/2005/7586/Moscow/RUS |
| *Norovirus* Hu/GII/2005/7594/Moscow/RUS |
| *Norovirus* Hu/GII/2005/7601/Nizhny Novgorod/RUS |
| *Norovirus* Hu/GII/2005/7679/Nizhny Novgorod/RUS |
| *Norovirus* Hu/GII/2005/7718/Moscow/RUS |
| *Norovirus* Hu/GII/2005/7725/Moscow/RUS |
| *Norovirus* Hu/GII/2005/7748/Moscow/RUS |
| *Norovirus* Hu/GII/2005/7749/Moscow/RUS |
| *Norovirus* Hu/GII/2005/7764/Moscow/RUS |
| *Norovirus* Hu/GII/2005/7821/Odessa/RUS |
| *Norovirus* Hu/GII/2005/8093/Chelyabinsk/RUS |
| *Norovirus* Hu/GII/2005/8159/St. Petersburg/RUS |
| *Norovirus* Hu/GII/2005/8162/St. Petersburg/RUS |
| *Norovirus* Hu/GII/2005/8254/Nizhny Novgorod/RUS |
| *Norovirus* Hu/GII/2005/8256/Nizhny Novgorod/RUS |
| *Norovirus* Hu/GII/2005/8433/Chelyabinsk/RUS |
| *Norovirus* Hu/GII/2006/10584/Moscow/RUS |
| *Norovirus* Hu/GII/2006/8292/Moscow/RUS |
| *Norovirus* Hu/GII/2006/8791/Tyumen/RUS |
| *Norovirus* Hu/GII/2006/9442/Chelyabinsk/RUS |
| *Norovirus* Hu/GII/2006/9563/Chelyabinsk/RUS |
| *Norovirus* Hu/GII/2006/9607/Chelyabinsk/RUS |
| *Norovirus* Hu/GII/2006/9895/St. Petersburg/RUS |
| *Norovirus* Hu/GII/2006/9942/Makhachkala/RUS |
| *Norovirus* Hu/GII/2007/11976/Chelyabinsk/RUS |
| *Norovirus* Hu/GII/204/JPN |
| *Norovirus* Hu/GII/209/JPN |
| *Norovirus* Hu/GII/21/JPN |
| *Norovirus* Hu/GII/210/JPN |
| *Norovirus* Hu/GII/213/JPN |
| *Norovirus* Hu/GII/224/JPN |
| *Norovirus* Hu/GII/229/JPN |
| *Norovirus* Hu/GII/233/JPN |
| *Norovirus* Hu/GII/234/JPN |
| *Norovirus* Hu/GII/235/JPN |
| *Norovirus* Hu/GII/236/JPN |
| *Norovirus* Hu/GII/237/JPN |
| *Norovirus* Hu/GII/239/JPN |
| *Norovirus* Hu/GII/241/JPN |
| *Norovirus* Hu/GII/251/JPN |
| *Norovirus* Hu/GII/256/JPN |
| *Norovirus* Hu/GII/VN3/2002/VNM |
| *Norovirus* Hu/GII/VN433/2003/VNM |
| *Norovirus* Hu/GII/VN799/2003/VNM |
| *Norovirus* Hu/GII/VN800/2003/VNM |
| *Norovirus* Hu/GII/VN862/2003/VNM |
| *Norovirus* Hu/GII/VN915/2003/VNM |
| *Norovirus* Hu/GII/VN981/2003/VNM |
| *Norovirus* Hu/GII/Water-A/2004/South Korea |
| *Norovirus* Hu/GII/Water-B/2004/South Korea |
| *Norovirus* Hu/GII/Yamaguchi/2003/JP |
| *Norovirus* Hu/GII/Yamaguchi/2005/JP |
| *Norovirus* Hu/Gunma/1/GII/JP |
| *Norovirus* Hu/Gunma/2/GII/JP |
| *Norovirus* Hu/Gunma/6/GII/JP |
| *Norovirus* Hu/Houston/1995/USA |
| *Norovirus* Hu/Lonaconing/2001/USA |
| *Norovirus* Hu/Mashhad1/GGII/Iran |
| *Norovirus* Hu/Mashhad2/GGII/Iran |
| *Norovirus* Hu/Mashhad3/GGII/Iran |
| *Norovirus* Hu/Minato/N1/10/99/JP |
| *Norovirus* Hu/Minato/N1/14/99/JP |
| *Norovirus* Hu/Minato/N1/33/99/JP |
| *Norovirus* Hu/Minato/N1/6/99/JP |
| *Norovirus* Hu/Mississip/2006/USA |
| *Norovirus* Hu/MT01/2006/USA |
| *Norovirus* Hu/NLV/GII/Neustrelitz260/2000/DE |
| *Norovirus* Hu/NLV/II/Hualien/DY/2003/TW |
| *Norovirus* Hu/NLV/VannesL169/2000/France |
| *Norovirus* Hu/OSD-CS/2006/USA |
| *Norovirus* Hu/Pune/OPD01/2007/India |
| *Norovirus* Hu/Pune/OPD02/2007/India |
| *Norovirus* Hu/Pune/OPD03/2007/India |
| *Norovirus* Hu/QM2-CS/2004/USA |
| *Norovirus* Hu/Richmond/1994/USA |
| *Norovirus* Hu/Ryndam/2005/USA |
| *Norovirus* Hu/Warren/2002/USA |
| *Norovirus* NV/GII/Chiba1/2004/JP |
| *Norovirus* NV/GII/Shizuoka31/2005/JP |
| *Norovirus* NV/GII/Yamaguchi13/2005/JP |
| *Norovirus* NV/GII/Yamaguchi17/2003/JP |
| *Norovirus* NV/GII/Yamaguchi18/2004/JP |
| *Norovirus* NV/GII/Yamaguchi21/2004/JP |
| *Norovirus* NV/GII/Yamaguchi25/2005/JP |
| *Norovirus* NV/GII/Yamaguchi9/2003/JP |
| *Norovirus* NVA1 |
| *Norovirus* NVA3 |
| *Norovirus* NVM2 |
| *Norovirus* NVM3 |
| *Norovirus* NVM5 |
| *Norovirus* NVN1 |
| *Norovirus* NVN2 |
| *Norovirus* NVN3 |
| *Norovirus* NVN5 |
| *Norovirus* NVNOV1 |
| *Norovirus* NVNOV4 |
| *Norovirus* NVO3 |
| *Norovirus* NVO5 |
| *Norovirus* oyster A clone 2/GGII.2/2006/NLD |
| *Norovirus* oyster/cultured/GII/Is/Dec05/05/JP |
| *Norovirus* oyster/cultured/GII/ISDec05b/05/JP |
| *Norovirus* oyster/cultured/GII/ISDec05d/05/JP |
| *Norovirus* oyster/cultured/GII/ISJan06a/06/JP |
| *Norovirus* oyster/cultured/GII/ISJan06b/06/JP |
| *Norovirus* oyster/cultured/GII/ISJan06c/06/JP |
| *Norovirus* oyster/cultured/GII/ISJan06d/06/JP |
| *Norovirus* oyster/cultured/GII/ISJan06e/06/JP |
| *Norovirus* oyster/cultured/GII/ISMar06a/06/JP |
| *Norovirus* oyster/cultured/GII/ISMar06b/06/JP |
| *Norovirus* oyster/cultured/GII/MAApr05a/05/JP |
| *Norovirus* oyster/cultured/GII/MAApr05b/05/JP |
| *Norovirus* oyster/cultured/GII/MADec05a/05/JP |
| *Norovirus* oyster/cultured/GII/MADec05b/05/JP |
| *Norovirus* oyster/cultured/GII/MAFeb05/05/JP |
| *Norovirus* oyster/cultured/GII/MAJan06c/06/JP |
| *Norovirus* oyster/cultured/GII/MAJan06d/06/JP |
| *Norovirus* oyster/cultured/GII/MAJan06f/06/JP |
| *Norovirus* oyster/cultured/GII/MAMar05a/05/JP |
| *Norovirus* oyster/cultured/GII/MAMar05b/05/JP |

TABLE 1-continued

| *Norovirus* Strains | |
|---|---|
| *Norovirus* Hu/GII/260/JPN | *Norovirus* oyster/cultured/GII/MAMar05d/05/JP |
| *Norovirus* Hu/GII/268/JPN | *Norovirus* oyster/cultured/GII/MAMar05f/05/JP |
| *Norovirus* Hu/GII/27/JPN | *Norovirus* oyster/cultured/GII/MAMar06a/06/JP |
| *Norovirus* Hu/GII/276/JPN | *Norovirus* oyster/cultured/GII/MAMar06b/06/JP |
| *Norovirus* Hu/GII/277/JPN | *Norovirus* oyster/cultured/GII/MAMar06c/06/JP |
| *Norovirus* Hu/GII/28/JPN | *Norovirus* oyster/cultured/GII/MAMar06e/06/JP |
| *Norovirus* Hu/GII/281/2006/HKG | *Norovirus* oyster/cultured/GII/ON/Dec05/05/JP |
| *Norovirus* Hu/GII/281/JPN | *Norovirus* oyster/cultured/GII/ON/Jan06/06/JP |
| *Norovirus* Hu/GII/283/JPN | *Norovirus* oyster/GII/Aomori/1-1/03/JP |
| *Norovirus* Hu/GII/288/JPN | *Norovirus* oyster/GII/Aomori/1-2/03/JP |
| *Norovirus* Hu/GII/290/JPN | *Norovirus* oyster/GII/Aomori/1-3/03/JP |
| *Norovirus* Hu/GII/292/JPN | *Norovirus* oyster/GII/Aomori/1-4/03/JP |
| *Norovirus* Hu/GII/293/JPN | *Norovirus* oyster/GII/Aomori/10-1/03/JP |
| *Norovirus* Hu/GII/299/JPN | *Norovirus* oyster/GII/Aomori/10-2/03/JP |
| *Norovirus* Hu/GII/2B/2004/South Korea | *Norovirus* oyster/GII/Aomori/11-3/04/JP |
| *Norovirus* Hu/GII/3/8165/2004/BRA | *Norovirus* oyster/GII/Aomori/12-1/04/JP |
| *Norovirus* Hu/GII/300/JPN | *Norovirus* oyster/GII/Aomori/12-2/04/JP |
| *Norovirus* Hu/GII/304/JPN | *Norovirus* oyster/GII/Aomori/13-1/04/JP |
| *Norovirus* Hu/GII/313/JPN | *Norovirus* oyster/GII/Aomori/13-2/04/JP |
| *Norovirus* Hu/GII/315/JPN | *Norovirus* oyster/GII/Aomori/13-3/04/JP |
| *Norovirus* Hu/GII/32/JPN | *Norovirus* oyster/GII/Aomori/18/02/JP |
| *Norovirus* Hu/GII/33/JPN | *Norovirus* oyster/GII/Aomori/2-3/03/JP |
| *Norovirus* Hu/GII/37/JPN | *Norovirus* oyster/GII/Aomori/3-3/03/JP |
| *Norovirus* Hu/GII/39/JPN | *Norovirus* oyster/GII/Aomori/4-1/03/JP |
| *Norovirus* Hu/GII/3B/2004/South Korea | *Norovirus* oyster/GII/Aomori/4-2/03/JP |
| *Norovirus* Hu/GII/4/10076/2004/BRA | *Norovirus* oyster/GII/Aomori/43/02/JP |
| *Norovirus* Hu/GII/4/10840/2005/BRA | *Norovirus* oyster/GII/Aomori/5-1/03/JP |
| *Norovirus* Hu/GII/4/10842/2005/BRA | *Norovirus* oyster/GII/Aomori/5-3/03/JP |
| *Norovirus* Hu/GII/4/9491/2004/BRA | *Norovirus* oyster/GII/Aomori/7-1/03/JP |
| *Norovirus* Hu/GII/4/9546/2004/BRA | *Norovirus* oyster/GII/Aomori/7-2/03/JP |
| *Norovirus* Hu/GII/401/JPN | *Norovirus* oyster/GII/Aomori/7-3/03/JP |
| *Norovirus* Hu/GII/402/JPN | *Norovirus* oyster/GII/Aomori/8-1/03/JP |
| *Norovirus* Hu/GII/403/JPN | *Norovirus* oyster/GII/Aomori/8-2/03/JP |
| *Norovirus* Hu/GII/404/JPN | *Norovirus* oyster/GII/FP55H/2004/CAN |
| *Norovirus* Hu/GII/407/JPN | *Norovirus* oyster/GII/FP68G/2004/CAN |
| *Norovirus* Hu/GII/410/JPN | *Norovirus* oyster/GII/FP69A/2004/CAN |
| *Norovirus* Hu/GII/411/JPN | *Norovirus* oyster/GII/Hiroshimacity/122/03/JP |
| *Norovirus* Hu/GII/413/JPN | *Norovirus* oyster/GII/Hiroshimacity/35/03/JP |
| *Norovirus* Hu/GII/419/JPN | *Norovirus* oyster/GII/Osakacity/15-3/02/JP |
| *Norovirus* Hu/GII/420/JPN | *Norovirus* oyster/GII/Osakacity/4-3/02/JP |
| *Norovirus* Hu/GII/427/JPN | *Norovirus* oyster/GII/Osakacity/OY051-2/02/JP |
| *Norovirus* Hu/GII/428/JPN | *Norovirus* oyster/GII/Osakacity/OY302-1/03/JP |
| *Norovirus* Hu/GII/430/JPN | *Norovirus* oyster/GII/Osakacity/OY319-1/03/JP |
| *Norovirus* Hu/GII/486/2004/HK | *Norovirus* oyster/GII/QingDao/CS327/China/2008 |
| *Norovirus* Hu/GII/4B/2004/South Korea | *Norovirus* oyster/GII/Saitama/S3/03/JP |
| *Norovirus* Hu/GII/52/JPN | *Norovirus* oyster/GII/Saitama/S4/03/JP |
| *Norovirus* Hu/GII/53/JPN | *Norovirus* oyster/GII/Saitama/S5/03/JP |
| *Norovirus* Hu/GII/56/JPN | *Norovirus* oyster/GII/Saitama/S7-2/03/JP |
| *Norovirus* Hu/GII/57/JPN | *Norovirus* oyster/GII/Saitama/S7/03/JP |
| *Norovirus* Hu/GII/5B/2004/South Korea | *Norovirus* oyster/GII/Saitama/S8/03/JP |
| *Norovirus* Hu/GII/6/8169/2004/BRA | *Norovirus* oyster/GII/Yamaguchi/24B/02/JP |
| *Norovirus* Hu/GII/67/JPN | *Norovirus* oyster/GII/Yamaguchi/24C/02/JP |
| *Norovirus* Hu/GII/6B/2004/South Korea | *Norovirus* oyster/GII/Yamaguchi/34A/03/JP |
| *Norovirus* Hu/GII/70/JPN | *Norovirus* oyster/GII/Yamaguchi/34C/03/JP |
| *Norovirus* Hu/GII/733/2006/HKG | *Norovirus* oyster/GII/Yamaguchi/38B/03/JP |
| *Norovirus* Hu/GII/74/JPN | *Norovirus* oyster/GII/Yamaguchi/38C/03/JP |
| *Norovirus* Hu/GII/75/JPN | *Norovirus* oyster/GII/Yamaguchi/43A/03/JP |
| *Norovirus* Hu/GII/77/JPN | *Norovirus* oyster/GII/Yamaguchi/46A/03/JP |
| *Norovirus* Hu/GII/7886/2004/BRA | *Norovirus* oyster/GII/Yamaguchi/H17-97B/05/JP |
| *Norovirus* Hu/GII/79/JPN | *Norovirus* oyster/GII/Yamaguchi/H17-97C/05/JP |
| *Norovirus* Hu/GII/7B/2004/South Korea | *Norovirus* oyster/wild/GII/SST1Mar05b/05/JP |
| *Norovirus* Hu/GII/80/JPN | *Norovirus* oyster/wild/GII/SST1Mar05c/05/JP |
| *Norovirus* Hu/GII/8040/2004/BRA | *Norovirus* oyster/wild/GII/SST1Mar05e/05/JP |
| *Norovirus* Hu/GII/81/JPN | *Norovirus* oyster/wild/GII/SST1Mar05g/05/JP |
| *Norovirus* Hu/GII/8165/2004/BRA | *Norovirus* oyster/wild/GII/SST1Mar05h/05/JP |
| *Norovirus* Hu/GII/8169/2004/BRA | *Norovirus* oyster/wild/GII/SST1Mar05i/05/JP |
| *Norovirus* Hu/GII/8187/2004/BRA | *Norovirus* oyster/wild/GII/SST2Mar05a/05/JP |
| *Norovirus* Hu/GII/8193/2004/BRA | *Norovirus* oyster/wild/GII/SST2Mar05b/05/JP |
| *Norovirus* Hu/GII/8195/2004/BRA | *Norovirus* oyster/wild/GII/SST2Mar05i/05/JP |
| *Norovirus* Hu/GII/8198/2004/BRA | *Norovirus* oyster/wild/GII/SST3Apr05a/05/JP |
| *Norovirus* Hu/GII/8211/2004/BRA | *Norovirus* oyster/wild/GII/SST3Apr05b/05/JP |
| *Norovirus* Hu/GII/83/JPN | *Norovirus* oyster/wild/GII/SST3Apr05c/05/JP |
| *Norovirus* Hu/GII/84/JPN | *Norovirus* oyster/wild/GII/SST3Apr05d/05/JP |
| *Norovirus* Hu/GII/8405/2004/BRA | *Norovirus* oyster/wild/GII/SST3Dec05a/05/JP |
| *Norovirus* Hu/GII/8489/2004/BRA | *Norovirus* oyster/wild/GII/SST3Dec05b/05/JP |
| *Norovirus* Hu/GII/85/JPN | *Norovirus* oyster/wild/GII/SST3Dec05c/05/JP |
| *Norovirus* Hu/GII/86/JPN | *Norovirus* oyster/wild/GII/SST3Feb06a/06/JP |
| *Norovirus* Hu/GII/8618/2004/BRA | *Norovirus* oyster/wild/GII/SST3Feb06b/06/JP |

TABLE 1-continued

| *Norovirus* Strains | |
|---|---|
| *Norovirus* Hu/GII/8619/2004/BRA | *Norovirus* oyster/wild/GII/SST3Feb06d/06/JP |
| *Norovirus* Hu/GII/8626/2004/BRA | *Norovirus* oyster/wild/GII/SST3Feb06e/06/JP |
| *Norovirus* Hu/GII/8632/2004/BRA | *Norovirus* oyster/wild/GII/SST3Feb06f/06/JP |
| *Norovirus* Hu/GII/8740/2004/BRA | *Norovirus* oyster/wild/GII/SST3Feb06g/06/JP |
| *Norovirus* Hu/GII/8B/2004/South Korea | *Norovirus* oyster/wild/GII/SST3Jan06a/06/JP |
| *Norovirus* Hu/GII/9/JPN | *Norovirus* oyster/wild/GII/SST3Jan06d/06/JP |
| *Norovirus* Hu/GII/90/JPN | *Norovirus* oyster/wild/GII/SST3Jan06e/06/JP |
| *Norovirus* Hu/GII/92/JPN | *Norovirus* oyster/wild/GII/SST3Jan06f/06/JP |
| *Norovirus* Hu/GII/9275/2004/BRA | *Norovirus* oyster/wild/GII/SST3Jan06g/06/JP |
| *Norovirus* Hu/GII/93/JPN | *Norovirus* oyster/wild/GII/SST3Jan06h/06/JP |
| *Norovirus* Hu/GII/94/JPN | *Norovirus* oyster/wild/GII/SST3Mar05a/05/JP |
| *Norovirus* Hu/GII/9475/2004/BRA | *Norovirus* oyster/wild/GII/SST3Mar05b/05/JP |
| *Norovirus* Hu/GII/9491/2004/BRA | *Norovirus* oyster/wild/GII/SST3Mar05c/05/JP |
| *Norovirus* Hu/GII/9546/2004/BRA | *Norovirus* oyster/wild/GII/SST3Mar05d/05/JP |
| *Norovirus* Hu/GII/9547/2004/BRA | *Norovirus* oyster/wild/GII/SST3Mar05e/05/JP |
| *Norovirus* Hu/GII/97/JPN | *Norovirus* oyster/wild/GII/SST3Mar06b/06/JP |
| *Norovirus* Hu/GII/9739/2004/BRA | *Norovirus* oyster/wild/GII/SST3Mar06d/06/JP |
| *Norovirus* Hu/GII/9740/2004/BRA | *Norovirus* razor |
| *Norovirus* Hu/GII/9B/2004/South Korea | clam/GII/LaiZhou/LZ271/China/2008 |
| *Norovirus* Hu/GII/AH040/2006/UK | *Norovirus* scallop/GII/RiZhao/RZ276/China/2008 |
| *Norovirus* Hu/GII/AH050/2006/UK | *Norovirus* sewage/GII/Toyama/Apr/2006/JP |
| *Norovirus* Hu/GII/AH097/2006/UK | *Norovirus* sewage/GII/Toyama/Apr/2007/JP |
| *Norovirus* Hu/GII/AH107/2006/UK | *Norovirus* sewage/GII/Toyama/Aug-4a/2006/JP |
| *Norovirus* Hu/GII/AH109/2006/UK | *Norovirus* sewage/GII/Toyama/Aug-6/2006/JP |
| *Norovirus* Hu/GII/AH187/2006/UK | *Norovirus* sewage/GII/Toyama/Aug/2007/JP |
| *Norovirus* Hu/GII/AH192/2006/UK | *Norovirus* sewage/GII/Toyama/Dec/2006/JP |
| *Norovirus* Hu/GII/AH225/2006/UK | *Norovirus* sewage/GII/Toyama/Dec/2007/JP |
| *Norovirus* Hu/GII/AH387/2006/UK | *Norovirus* sewage/GII/Toyama/Feb/2007/JP |
| *Norovirus* Hu/GII/AH395/2006/UK | *Norovirus* sewage/GII/Toyama/Feb/2008/JP |
| *Norovirus* Hu/GII/AH397/2006/UK | *Norovirus* sewage/GII/Toyama/Jan/2007/JP |
| *Norovirus* Hu/GII/AH402/2006/UK | *Norovirus* sewage/GII/Toyama/Jan/2008/JP |
| *Norovirus* Hu/GII/AH406/2006/UK | *Norovirus* sewage/GII/Toyama/Jul-3/2006/JP |
| *Norovirus* Hu/GII/AH408/2006/UK | *Norovirus* sewage/GII/Toyama/Jul-4a/2006/JP |
| *Norovirus* Hu/GII/AH410/2006/UK | *Norovirus* sewage/GII/Toyama/Jul-4b/2006/JP |
| *Norovirus* Hu/GII/AH448/2007/UK | *Norovirus* sewage/GII/Toyama/Jul/2006/JP |
| *Norovirus* Hu/GII/AH509/2007/UK | *Norovirus* sewage/GII/Toyama/Jul/2007/JP |
| *Norovirus* Hu/GII/AH517/2007/UK | *Norovirus* sewage/GII/Toyama/Jun-1/2006/JP |
| *Norovirus* Hu/GII/AH525/2007/UK | *Norovirus* sewage/GII/Toyama/Jun-2/2006/JP |
| *Norovirus* Hu/GII/AH551/2007/UK | *Norovirus* sewage/GII/Toyama/Jun-P1/2006/JP |
| *Norovirus* Hu/GII/AH570/2007/UK | *Norovirus* sewage/GII/Toyama/Jun/2007/JP |
| *Norovirus* Hu/GII/AH571/2007/UK | *Norovirus* sewage/GII/Toyama/Mar/2007/JP |
| *Norovirus* Hu/GII/AH579/2007/UK | *Norovirus* sewage/GII/Toyama/Mar/2008/JP |
| *Norovirus* Hu/GII/AH590/2007/UK | *Norovirus* sewage/GII/Toyama/May/2006/JP |
| *Norovirus* Hu/GII/AH602/2007/UK | *Norovirus* sewage/GII/Toyama/May/2007/JP |
| *Norovirus* Hu/GII/AH604/2007/UK | *Norovirus* sewage/GII/Toyama/Nov/2006/JP |
| *Norovirus* Hu/GII/AH611/2007/UK | *Norovirus* sewage/GII/Toyama/Nov/2007/JP |
| *Norovirus* Hu/GII/AH612/2007/UK | *Norovirus* sewage/GII/Toyama/Oct-14/2006/JP |
| *Norovirus* Hu/GII/AH616/2007/UK | *Norovirus* sewage/GII/Toyama/Oct/2006/JP |
| *Norovirus* Hu/GII/AH619/2007/UK | *Norovirus* sewage/GII/Toyama/Oct/2007/JP |
| *Norovirus* Hu/GII/AH623/2007/UK | *Norovirus* sewage/GII/Toyama/Sep-3/2006/JP |
| *Norovirus* Hu/GII/AH633/2007/UK | *Norovirus* sewage/GII/Toyama/Sep-4b/2006/JP |
| *Norovirus* Hu/GII/AH642/2007/UK | *Norovirus* sewage/GII/Toyama/Sep-7/2006/JP |
| *Norovirus* Hu/GII/AH643/2007/UK | *Norovirus* sewage/GII/Toyama/Sep/2007/JP |
| *Norovirus* Hu/GII/AH651/2007/UK | *Norovirus* spinach/GII/Hanam/2007/KOR |
| *Norovirus* Hu/GII/AH653/2007/UK | *Norovirus* sw/GII/CE-06-0036/2006/CAN |
| *Norovirus* Hu/GII/AH654/2007/UK | *Norovirus* sw/GII/CE-M-05-0047/2005/CAN |
| *Norovirus* Hu/GII/Algard/886/2001/NOR | *Norovirus* sw/GII/CE-M-05-0076/2005/CAN |
| *Norovirus* Hu/GII/AM39/2005/BRA | *Norovirus* sw/GII/CE-M-05-0108/2005/CAN |
| *Norovirus* Hu/GII/Arrowpark1B/2008/UK | *Norovirus* sw/GII/CE-M-05-0111/2005/CAN |
| *Norovirus* Hu/GII/Athlone11/2006/Botswana | *Norovirus* sw/GII/CE-M-05-0112/2005/CAN |
| *Norovirus* Hu/GII/Athlone24/2006/Botswana | *Norovirus* sw/GII/CE-M-05-0116/2005/CAN |
| *Norovirus* Hu/GII/Athlone64/2006/Botswana | *Norovirus* sw/GII/CE-M-06-0003/2006/CAN |
| *Norovirus* Hu/GII/Athlone75/2006/Botswana | *Norovirus* sw/GII/CE-M-06-0011/2006/CAN |
| *Norovirus* Hu/GII/Athlone79/2006/Botswana | *Norovirus* sw/GII/CE-M-06-0016/2006/CAN |
| *Norovirus* Hu/GII/BA4521/2005/Arg | *Norovirus* sw/GII/CE-M-06-0020/2006/CAN |
| *Norovirus* Hu/GII/BC728/07-2007/CAN | *Norovirus* sw/GII/CE-M-06-0028/2006/CAN |
| *Norovirus* Hu/GII/BCCDC03008/2003/CAN | *Norovirus* swine/GII/MI-QW48/02/US |
| *Norovirus* Hu/GII/BCCDC03013/2003/CAN | *Norovirus* swine/GII/OH-QW101/03/US |
| *Norovirus* Hu/GII/BCCDC03020/2004/CAN | *Norovirus* swine/GII/OH-QW125/03/US |
| *Norovirus* Hu/GII/BCCDC03032/2003/CAN | *Norovirus* swine/GII/OH-QW170/03/US |
| *Norovirus* Hu/GII/BCCDC04002/2004/CAN | *Norovirus* swine/GII/OH-QW218/03/US |
| *Norovirus* Hu/GII/BCCDC04006/2004/CAN | *Norovirus* swine/GII/rj14008/2007/BRA |
| *Norovirus* Hu/GII/BCCDC04007/2004/CAN | *Norovirus* Sydney 2212 |
| *Norovirus* Hu/GII/BE/200307-1/2007/SGP | *Norovirus* water/GII/Gyeonggi/A11/2002/KOR |
| *Norovirus* Hu/GII/BE/200307-2/2007/SGP | *Norovirus* water/GII/Gyeonggi/A12/2002/KOR |
| *Norovirus* Hu/GII/BE/230107-1/2007/SGP | *Norovirus* water/GII/Gyeonggi/A13/2003/KOR |
| *Norovirus* Hu/GII/BE/230107-2/2007/SGP | *Norovirus* water/GII/Gyeonggi/A14/2003/KOR |
| *Norovirus* Hu/GII/BE/230107-3/2007/SGP | *Norovirus* water/GII/Gyeonggi/A15/2003/KOR |

TABLE 1-continued

| *Norovirus* Strains | |
|---|---|
| *Norovirus* Hu/GII/BE/230207-1/2007/SGP | *Norovirus* water/GII/Gyeonggi/A8/2002/KOR |
| *Norovirus* Hu/GII/BE/230207-2/2007/SGP | *Norovirus* water/GII/Gyeonggi/A9/2002/KOR |
| *Norovirus* Hu/GII/BE/230207-3/2007/SGP | *Norovirus* water/GII/Gyeonggi/H12-1/2002/KOR |
| *Norovirus* Hu/GII/BE/240407/2007/SGP | *Norovirus* water/GII/Gyeonggi/H12-2/2002/KOR |
| *Norovirus* Hu/GII/BE/270607-1/2007/SGP | *Norovirus* water/GII/Gyeonggi/H13/2003/KOR |
| *Norovirus* Hu/GII/BE/270607-2/2007/SGP | *Norovirus* water/GII/Gyeonggi/H14/2003/KOR |
| *Norovirus* Hu/GII/BE/270607-3/2007/SGP | *Norovirus* water/GII/Gyeonggi/H15/2003/KOR |
| *Norovirus* Hu/GII/BE/290507-1/2007/SGP | *Norovirus* water/GII/Gyeonggi/H8/2002/KOR |
| *Norovirus* Hu/GII/BE/290507-2/2007/SGP | *Norovirus* water/GII/Gyeonggi/H9/2002/KOR |
| *Norovirus* Hu/GII/BE/290507-3/2007/SGP | *Norovirus* water/GII/Gyeonggi/I12/2002/KOR |
| *Norovirus* Hu/GII/BE/290507-4/2007/SGP | *Norovirus* water/GII/Gyeonggi/I14/2003/KOR |
| *Norovirus* Hu/GII/Beijing/01/2004/CHN | *Norovirus* water/GII/Gyeonggi/I15/2003/KOR |
| *Norovirus* Hu/GII/Beijing/06/2005/CHN | *Norovirus* water/GII/Gyeonggi/I5/2002/KOR |
| *Norovirus* Hu/GII/Beijing/07/2005/CHN | *Norovirus* water/GII/Gyeonggi/S10/2002/KOR |
| *Norovirus* Hu/GII/Beijing/07/2006/CHN | *Norovirus* water/GII/Gyeonggi/S11-1/2002/KOR |
| *Norovirus* Hu/GII/Beijing/10/2005/CHN | *Norovirus* water/GII/Gyeonggi/S11-2/2002/KOR |
| *Norovirus* Hu/GII/Beijing/10/2006/CHN | *Norovirus* water/GII/Gyeonggi/S12/2002/KOR |
| *Norovirus* Hu/GII/Beijing/101/2005/CHN | *Norovirus* water/GII/Gyeonggi/S14/2003/KOR |
| *Norovirus* Hu/GII/Beijing/101/2007/CHN | *Norovirus* water/GII/Gyeonggi/S15/2003/KOR |
| *Norovirus* Hu/GII/Beijing/102/2005/CHN | *Norovirus* water/GII/Gyeonggi/S4/2002/KOR |
| *Norovirus* Hu/GII/Beijing/115/2004/CHN | *Norovirus* water/GII/Gyeonggi/S5/2002/KOR |
| *Norovirus* Hu/GII/Beijing/116/2007/CHN | *Norovirus* water/GII/Gyeonggi/S8/2002/KOR |
| *Norovirus* Hu/GII/Beijing/125/2007/CHN | *Norovirus* water/GII/Gyeonggi/S9/2002/KOR |
| *Norovirus* Hu/GII/Beijing/127/2007/CHN | *Norovirus* Hu/GII/C3-040407/2007/SGP |
| *Norovirus* Hu/GII/Beijing/133/2005/CHN | *Norovirus* Hu/GII/C4-19/2005/KOR |
| *Norovirus* Hu/GII/Beijing/133/2007/CHN | *Norovirus* Hu/GII/C5-59/2006/KOR |
| *Norovirus* Hu/GII/Beijing/139/2005/CHN | *Norovirus* Hu/GII/C6-39/2005/KOR |
| *Norovirus* Hu/GII/Beijing/14/2006/CHN | *Norovirus* Hu/GII/C6-80/2006/KOR |
| *Norovirus* Hu/GII/Beijing/148/2005/CHN | *Norovirus* Hu/GII/C7-130/2005/KOR |
| *Norovirus* Hu/GII/Beijing/148/2007/CHN | *Norovirus* Hu/GII/C7-171/2005/KOR |
| *Norovirus* Hu/GII/Beijing/153/2005/CHN | *Norovirus* Hu/GII/C7-182/2005/KOR |
| *Norovirus* Hu/GII/Beijing/156/2007/CHN | *Norovirus* Hu/GII/C7-212/2005/KOR |
| *Norovirus* Hu/GII/Beijing/162/2007/CHN | *Norovirus* Hu/GII/C7-307/2006/KOR |
| *Norovirus* Hu/GII/Beijing/165/2004/CHN | *Norovirus* Hu/GII/C7-394/2006/KOR |
| *Norovirus* Hu/GII/Beijing/169/2005/CHN | *Norovirus* Hu/GII/Carlow/2002/Ire |
| *Norovirus* Hu/GII/Beijing/175/2004/CHN | *Norovirus* Hu/GII/CE-M-05-0045/2005/CAN |
| *Norovirus* Hu/GII/Beijing/178/2004/CHN | *Norovirus* Hu/GII/CE-R1-06-027/2006/CAN |
| *Norovirus* Hu/GII/Beijing/178/2005/CHN | *Norovirus* Hu/GII/Chelyabinsk/8020/2005/RUS |
| *Norovirus* Hu/GII/Beijing/19/2004/CHN | *Norovirus* Hu/GII/Chelyabinsk/8031/2005/RUS |
| *Norovirus* Hu/GII/Beijing/191/2005/CHN | *Norovirus* Hu/GII/Chelyabinsk/8361/2005/RUS |
| *Norovirus* Hu/GII/Beijing/196/2007/CHN | *Norovirus* Hu/GII/Chelyabinsk/8398/2005/RUS |
| *Norovirus* Hu/GII/Beijing/197/2005/CHN | *Norovirus* Hu/GII/Chelyabinsk/8919/2006/RUS |
| *Norovirus* Hu/GII/Beijing/208/2006/CHN | *Norovirus* Hu/GII/Chelyabinsk/9418/2006/RUS |
| *Norovirus* Hu/GII/Beijing/215/2005/CHN | *Norovirus* Hu/GII/Chelyabinsk/9425/2006/RUS |
| *Norovirus* Hu/GII/Beijing/221/2005/CHN | *Norovirus* Hu/GII/Chelyabinsk/9459/2006/RUS |
| *Norovirus* Hu/GII/Beijing/228/2005/CHN | *Norovirus* Hu/GII/Chelyabinsk/9471/2006/RUS |
| *Norovirus* Hu/GII/Beijing/229/2005/CHN | *Norovirus* Hu/GII/Chelyabinsk/9475/2006/RUS |
| *Norovirus* Hu/GII/Beijing/235/2006/CHN | *Norovirus* Hu/GII/Chelyabinsk/9479/2006/RUS |
| *Norovirus* Hu/GII/Beijing/248/2006/CHN | *Norovirus* Hu/GII/Chelyabinsk/9548/2006/RUS |
| *Norovirus* Hu/GII/Beijing/259/2005/CHN | *Norovirus* Hu/GII/Chiba/2004/JP |
| *Norovirus* Hu/GII/Beijing/26/2006/CHN | *Norovirus* Hu/GII/CL4006-1309/2006/SGP |
| *Norovirus* Hu/GII/Beijing/262/2007/CHN | *Norovirus* Hu/GII/CL4007-1409/2006/SGP |
| *Norovirus* Hu/GII/Beijing/266/2006/CHN | *Norovirus* Hu/GII/CL4008-1309/2006/SGP |
| *Norovirus* Hu/GII/Beijing/27/2004/CHN | *Norovirus* Hu/GII/CL4009-1309/2006/SGP |
| *Norovirus* Hu/GII/Beijing/271/2007/CHN | *Norovirus* Hu/GII/CL4010-1409/2006/SGP |
| *Norovirus* Hu/GII/Beijing/274/2005/CHN | *Norovirus* Hu/GII/CL4015-2909/2006/SGP |
| *Norovirus* Hu/GII/Beijing/275/2005/CHN | *Norovirus* Hu/GII/CL4016-2909/2006/SGP |
| *Norovirus* Hu/GII/Beijing/275/2007 | *Norovirus* Hu/GII/CL4018-2909/2006/SGP |
| *Norovirus* Hu/GII/Beijing/277/2005/CHN | *Norovirus* Hu/GII/CL4021-0310/2006/SGP |
| *Norovirus* Hu/GII/Beijing/282/2005/CHN | *Norovirus* Hu/GII/CL4025-0310/2006/SGP |
| *Norovirus* Hu/GII/Beijing/289/2005/CHN | *Norovirus* Hu/GII/CL4029-0310/2006/SGP |
| *Norovirus* Hu/GII/Beijing/290/2007/CHN | *Norovirus* Hu/GII/CL4031-0610/2006/SGP |
| *Norovirus* Hu/GII/Beijing/30/2004/CHN | *Norovirus* Hu/GII/CL4033-0610/2006/SGP |
| *Norovirus* Hu/GII/Beijing/300/2007/CHN | *Norovirus* Hu/GII/CL4035-0610/2006/SGP |
| *Norovirus* Hu/GII/Beijing/303/2007/CHN | *Norovirus* Hu/GII/CL4056-1110/2006/SGP |
| *Norovirus* Hu/GII/Beijing/307/2005/CHN | *Norovirus* Hu/GII/CL4095-2010/2006/SGP |
| *Norovirus* Hu/GII/Beijing/308/2005/CHN | *Norovirus* Hu/GII/CL4096-2010/2006/SGP |
| *Norovirus* Hu/GII/Beijing/310/2007/CHN | *Norovirus* Hu/GII/CL4097-2010/2006/SGP |
| *Norovirus* Hu/GII/Beijing/313/2007/CHN | *Norovirus* Hu/GII/CL4097-3108/2006/SGP |
| *Norovirus* Hu/GII/Beijing/321/2007/CHN | *Norovirus* Hu/GII/CL4098-3108/2006/SGP |
| *Norovirus* Hu/GII/Beijing/323/2007/CHN | *Norovirus* Hu/GII/CL4099-3108/2006/SGP |
| *Norovirus* Hu/GII/Beijing/33/2006/CHN | *Norovirus* Hu/GII/CUHK3020/2008/HKG |
| *Norovirus* Hu/GII/Beijing/334/2007/CHN | *Norovirus* Hu/GII/CUHK3205/2008/HKG |
| *Norovirus* Hu/GII/Beijing/34/2006/CHN | *Norovirus* Hu/GII/CUHK3214/2008/HKG |
| *Norovirus* Hu/GII/Beijing/352/2007/CHN | *Norovirus* Hu/GII/CUHK3229/2008/HKG |
| *Norovirus* Hu/GII/Beijing/352/2008 | *Norovirus* Hu/GII/CUHK3286/2008/HKG |
| *Norovirus* Hu/GII/Beijing/357/2008 | *Norovirus* Hu/GII/CUHK3330/2008/HKG |
| *Norovirus* Hu/GII/Beijing/361/2007/CHN | *Norovirus* Hu/GII/CUHK3383/2008/HKG |

TABLE 1-continued

| *Norovirus* Strains | |
|---|---|
| *Norovirus* Hu/GII/Beijing/362/2007/CHN | *Norovirus* Hu/GII/CUHK3452/2008/HKG |
| *Norovirus* Hu/GII/Beijing/371/2007/CHN | *Norovirus* Hu/GII/CUHK3469/2008/HKG |
| *Norovirus* Hu/GII/Beijing/374/2007/CHN | *Norovirus* Hu/GII/CUHK3497/2008/HKG |
| *Norovirus* Hu/GII/Beijing/375/2005/CHN | *Norovirus* Hu/GII/CUHK3540/2008/HKG |
| *Norovirus* Hu/GII/Beijing/377/2007/CHN | *Norovirus* Hu/GII/CUHK3578/2008/HKG |
| *Norovirus* Hu/GII/Beijing/38/2006/CHN | *Norovirus* Hu/GII/CUHK3723/2008/HKG |
| *Norovirus* Hu/GII/Beijing/39/2004/CHN | *Norovirus* Hu/GII/CUHK3895/2008/HKG |
| *Norovirus* Hu/GII/Beijing/398/2008 | *Norovirus* Hu/GII/CUHK3918/2008/HKG |
| *Norovirus* Hu/GII/Beijing/401/2005/CHN | *Norovirus* Hu/GII/CUHK3925/2008/HKG |
| *Norovirus* Hu/GII/Beijing/402/2005/CHN | *Norovirus* Hu/GII/CUHK4071/2008/HKG |
| *Norovirus* Hu/GII/Beijing/430/2005/CHN | *Norovirus* Hu/GII/CUHK4372/2008/HKG |
| *Norovirus* Hu/GII/Beijing/439/2005/CHN | *Norovirus* Hu/GII/CUHK4389/2008/HKG |
| *Norovirus* Hu/GII/Beijing/45/2004/CHN | *Norovirus* Hu/GII/CUHK4577/2008/HKG |
| *Norovirus* Hu/GII/Beijing/45/2005/CHN | *Norovirus* Hu/GII/CUHK4636/2008/HKG |
| *Norovirus* Hu/GII/Beijing/455/2005/CHN | *Norovirus* Hu/GII/CUHK4785/2008/HKG |
| *Norovirus* Hu/GII/Beijing/46/2005/CHN | *Norovirus* Hu/GII/CUHK4844/2008/HKG |
| *Norovirus* Hu/GII/Beijing/466/2005/CHN | *Norovirus* Hu/GII/CUHK4850/2008/HKG |
| *Norovirus* Hu/GII/Beijing/479/2005/CHN | *Norovirus* Hu/GII/CUHK4870/2008/HKG |
| *Norovirus* Hu/GII/Beijing/48/2005/CHN | *Norovirus* Hu/GII/CUHK4877/2008/HKG |
| *Norovirus* Hu/GII/Beijing/48/2007/CHN | *Norovirus* Hu/GII/CUHK5054/2008/HKG |
| *Norovirus* Hu/GII/Beijing/484/2005/CHN | *Norovirus* Hu/GII/CUHK5079/2008/HKG |
| *Norovirus* Hu/GII/Beijing/49/2007/CHN | *Norovirus* Hu/GII/CUHK5120/2008/HKG |
| *Norovirus* Hu/GII/Beijing/492/2005/CHN | *Norovirus* Hu/GII/CUHK5200/2008/HKG |
| *Norovirus* Hu/GII/Beijing/493/2005/CHN | *Norovirus* Hu/GII/CUHK5324/2008/HKG |
| *Norovirus* Hu/GII/Beijing/495/2005/CHN | *Norovirus* Hu/GII/CUHK5330/2008/HKG |
| *Norovirus* Hu/GII/Beijing/496/2005/CHN | *Norovirus* Hu/GII/CUHK5355/2008/HKG |
| *Norovirus* Hu/GII/Beijing/498/2005/CHN | *Norovirus* Hu/GII/CUHK5550/2008/HKG |
| *Norovirus* Hu/GII/Beijing/509/2005/CHN | *Norovirus* Hu/GII/CUHK5573/2008/HKG |
| *Norovirus* Hu/GII/Beijing/518/2005/CHN | *Norovirus* Hu/GII/CUHK5761/2008/HKG |
| *Norovirus* Hu/GII/Beijing/55/2004/CHN | *Norovirus* Hu/GII/CUHK5815/2008/HKG |
| *Norovirus* Hu/GII/Beijing/57/2005/CHN | *Norovirus* Hu/GII/CUHK5822/2008/HKG |
| *Norovirus* Hu/GII/Beijing/589/2008 | *Norovirus* Hu/GII/CUHK5987/2008/HKG |
| *Norovirus* Hu/GII/Beijing/63/2007/CHN | *Norovirus* Hu/GII/CUHK6075/2008/HKG |
| *Norovirus* Hu/GII/Beijing/66/2005/CHN | *Norovirus* Hu/GII/CUHK6202/2008/HKG |
| *Norovirus* Hu/GII/Beijing/71/2007/CHN | *Norovirus* Hu/GII/CUHK6252/2008/HKG |
| *Norovirus* Hu/GII/Beijing/74/2004/CHN | *Norovirus* Hu/GII/CUHK6346/2008/HKG |
| *Norovirus* Hu/GII/Beijing/74/2007/CHN | *Norovirus* Hu/GII/CUHK6412/2008/HKG |
| *Norovirus* Hu/GII/Beijing/79/2004/CHN | *Norovirus* Hu/GII/CUHK6501/2008/HKG |
| *Norovirus* Hu/GII/Beijing/82/2004/CHN | *Norovirus* Hu/GII/CUHK6518/2008/HKG |
| *Norovirus* Hu/GII/Beijing/88/2004/CHN | *Norovirus* Hu/GII/CUHK6581/2008/HKG |
| *Norovirus* Hu/GII/Beijing/90/2004/CHN | *Norovirus* Hu/GII/CUHK6766/2008/HKG |
| *Norovirus* Hu/GII/Beijing/95/2005/CHN | *Norovirus* Hu/GII/E-090507/2007/SGP |
| *Norovirus* Hu/GII/Beijing/96/2007/CHN | *Norovirus* Hu/GII/E-140307/2007/SGP |
| *Norovirus* Hu/GII/Bergen/7105/2002/NOR | *Norovirus* Hu/GII/Ehime/2005/JP |
| *Norovirus* Hu/GII/BHL44/2000/Botswana | *Norovirus* Hu/GII/Elverum/4167/2003/NOR |
| *Norovirus* Hu/GII/Brisbane/01/2004/AU | |
| *Norovirus* Hu/GII/BS/200307-1/2007/SGP | |
| *Norovirus* Hu/GII/BS/200307-2/2007/SGP | |
| *Norovirus* Hu/GII/BS/230107-1/2007/SGP | |
| *Norovirus* Hu/GII/BS/230107-2/2007/SGP | |
| *Norovirus* Hu/GII/BS/230207/2007/SGP | |
| *Norovirus* Hu/GII/BS/240407-1/2007/SGP | |
| *Norovirus* Hu/GII/BS/240407-2/2007/SGP | |
| *Norovirus* Hu/GII/BS/270607-1/2007/SGP | |
| *Norovirus* Hu/GII/BS/270607-2/2007/SGP | |
| *Norovirus* Hu/GII/BS/290507-1/2007/SGP | |
| *Norovirus* Hu/GII/BS/290507-2/2007/SGP | |
| *Norovirus* Hu/GII/C1-011106/2006/SGP | |
| *Norovirus* Hu/GII/C1-040706/2006/SGP | |
| *Norovirus* Hu/GII/C1-111206/2006/SGP | |
| *Norovirus* Hu/GII/C1-120/2006/KOR | |
| *Norovirus* Hu/GII/C1-143/2006/KOR | |
| *Norovirus* Hu/GII/C1-144/2006/KOR | |
| *Norovirus* Hu/GII/C1-149/2006/KOR | |
| *Norovirus* Hu/GII/C1-150806/2006/SGP | |
| *Norovirus* Hu/GII/C1-180706/2006/SGP | |
| *Norovirus* Hu/GII/C1-201106/2006/SGP | |
| *Norovirus* Hu/GII/C1-220606/2006/SGP | |
| *Norovirus* Hu/GII/C1-240706/2006/SGP | |
| *Norovirus* Hu/GII/C1-263/2006/KOR | |
| *Norovirus* Hu/GII/C1-271206/2006/SGP | |
| *Norovirus* Hu/GII/C1-307/2005/KOR | |
| *Norovirus* Hu/GII/C2-230507/2007/SGP | |
| *Norovirus* Hu/GII/C2-55/2006/KOR | |
| *Norovirus* genogroup GII.1 | |
| *Norovirus* env/GGI.2/958/2007/ITA | *Norovirus* Hu/GII.1/3445/2008/ZAF |
| *Norovirus* Hu/GII-1/FN1-Newc/2006/UK | *Norovirus* Hu/GII.1/8738/2008/ZAF |

TABLE 1-continued

| *Norovirus* Strains | |
|---|---|
| *Norovirus* Hu/GII-12/Inba/060839/2006/JP | *Norovirus* Hu/GII.1/CanteenA/Pirkanmaa-15/2006/FIN |
| *Norovirus* Hu/GII.1/03155665/2003/AUS | *Norovirus* Hu/GII.1/CanteenB/Pirkanmaa-19/2006/FIN |
| *Norovirus* Hu/GII.1/04113024/2004/AUS | *Norovirus* Hu/GII.1/CanteenC/Pirkanmaa-18/2006/FIN |
| *Norovirus* Hu/GII.1/04113825/2004/AUS | *Norovirus* Hu/GII.13/Miyagi/26/2006/JP |
| *Norovirus* Hu/GII.1/04116150/2004/AUS | *Norovirus* Hu/GII.13/Miyagi/4/2007/JP |
| *Norovirus* Hu/GII.1/04144544/2004/AUS | |
| *Norovirus* genogroup GII.11 | |
| *Norovirus* pig/GII-11/AB117/CAN | *Norovirus* pig/GII-11/F16-8/CAN |
| *Norovirus* pig/GII-11/F12-8/05/CAN | *Norovirus* pig/GII-11/F18-10/05/CAN |
| *Norovirus* pig/GII-11/F12-8/CAN | *Norovirus* pig/GII-11/F18-10/CAN |
| *Norovirus* genogroup GII.13 | |
| *Norovirus* Hu/GII.13/04150102/2004/AUS | *Norovirus* Hu/GII.13/8591/Maizuru/2008/JPN |
| *Norovirus* Hu/GII.13/8434/Maizuru/2007/JPN | *Norovirus* Hu/GII.13/8594/Maizuru/2008/JPN |
| *Norovirus* Hu/GII.13/8533/Maizuru/2008/JPN | *Norovirus* Hu/GII.13/8599/Maizuru/2008/JPN |
| *Norovirus* Hu/GII.13/8542/Maizuru/2008/JPN | *Norovirus* Hu/GII.13/9513/2008/ZAF |
| *Norovirus* Hu/GII.13/8559/Maizuru/2008/JPN | *Norovirus* sewage/GII.13/Toyama/SW0703-6/2007/JP |
| *Norovirus* Hu/GII.13/8560/Maizuru/2008/JPN | *Norovirus* sewage/GII.13/Toyama/SW0709-11/2007/JP |
| *Norovirus* genogroup GII.14 | |
| *Norovirus* Hu/GII-14/ES071/2003/BRA | *Norovirus* Hu/GII.14/13501/2007/BRA |
| *Norovirus* Hu/GII.14/13436/2007/BRA | *Norovirus* Hu/GII.14/3607/2008/ZAF |
| *Norovirus* Hu/GII.14/13453/2007/BRA | |
| *Norovirus* genogroup GII.16 | |
| *Norovirus* Hu/GII.16/4349b/2008/ZAF | *Norovirus* Hu/GII.16/Nsk-410/2005/RUS |
| *Norovirus* genogroup GII.17 | |
| *Norovirus* Hu/GGII.17/696Nica/2005 | |
| *Norovirus* genogroup GII.18 | |
| *Norovirus* Hu/GGII.18/166Nica/2005 | *Norovirus* Hu/GGII.18/36Nica/2005 |
| *Norovirus* Hu/GGII.18/186Nica/2005 | *Norovirus* pig/GII-18/F15-10nv/CAN |
| *Norovirus* Hu/GGII.18/213Nica/2005 | *Norovirus* swine/GII.18/rj14008/2007/BR |
| *Norovirus* Hu/GGII.18/231Nica/2005 | |
| *Norovirus* genogroup GII.2 | |
| *Norovirus* env/GGI.2/1044/2007/ITA | *Norovirus* Hu/GII-3/ES203/2003/BRA |
| *Norovirus* env/GGI.2/1046/2007/ITA | *Norovirus* Hu/GII-3/ES265/2003/BRA |
| *Norovirus* env/GGI.2/1052/2007/ITA | *Norovirus* Hu/GII-3/food handler 2/OB1/2007/UK |
| *Norovirus* env/GGI.2/1054/2007/ITA | *Norovirus* Hu/GII-3/food handler 6/OB1/2007/UK |
| *Norovirus* env/GGI.2/1056/2007/ITA | *Norovirus* Hu/GII-3/Morriston/2007/UK |
| *Norovirus* env/GGI.2/1084/2007/ITA | *Norovirus* Hu/GII-3/NMH/2007/UK |
| *Norovirus* env/GGI.2/1088/2007/ITA | *Norovirus* Hu/GII-3/Patient 1-01/2007/UK |
| *Norovirus* env/GGI.2/1092/2007/ITA | *Norovirus* Hu/GII-3/Patient 2-01/2007/UK |
| *Norovirus* env/GGI.2/1110/2007/ITA | *Norovirus* Hu/GII-3/Patient1-01/2007/UK |
| *Norovirus* env/GGI.2/1112/2007/ITA | *Norovirus* Hu/GII-3/Patient1-02/2007/UK |
| *Norovirus* env/GGI.2/1134/2007/ITA | *Norovirus* Hu/GII-3/Patient1-05/2007/UK |
| *Norovirus* env/GGI.2/1138/2007/ITA | *Norovirus* Hu/GII-3/Patient2-01/2007/UK |
| *Norovirus* env/GGI.2/1158/2007/ITA | *Norovirus* Hu/GII-3/Patient2-02/2007/UK |
| *Norovirus* env/GGI.2/950/2007/ITA | *Norovirus* Hu/GII-3/Patient2-05/2007/UK |
| *Norovirus* env/GGI.2/952/2007/ITA | *Norovirus* Hu/GII.3/02108181/2002/AUS |
| *Norovirus* env/GGI.2/954/2007/ITA | *Norovirus* Hu/GII.3/02115422/2002/AUS |
| *Norovirus* env/GGI.2/964/2007/ITA | *Norovirus* Hu/GII.3/02115428/2002/AUS |
| *Norovirus* env/GGI.2/968/2007/ITA | *Norovirus* Hu/GII.3/02115441/2002/AUS |
| *Norovirus* env/GGI.2/976/2007/ITA | *Norovirus* Hu/GII.3/03157163/2003/AUS |
| *Norovirus* env/GGI.2/980/2007/ITA | *Norovirus* Hu/GII.3/03157169/2003/AUS |
| *Norovirus* env/GGI.2/982/2007/ITA | *Norovirus* Hu/GII.3/04107624/2004/AUS |
| *Norovirus* env/GGI.2/984/2007/ITA | *Norovirus* Hu/GII.3/04155699/2004/AUS |
| *Norovirus* env/GGI.2/986/2007/ITA | *Norovirus* Hu/GII.3/05100687/2004/AUS |
| *Norovirus* env/GGI.2/992/2007/ITA | *Norovirus* Hu/GII.3/05143926/2005/AUS |
| *Norovirus* env/GGI.2/994/2007/ITA | *Norovirus* Hu/GII.3/1508/1/2008/RJ/BRA |
| *Norovirus* Hu/GGI.2/oyster8491OB/77351/FR | *Norovirus* Hu/GII.3/15645/2008/RJ/BRA |
| *Norovirus* Hu/GGII.2/32Nica/2005 | *Norovirus* Hu/GII.3/15737/2008/RJ/BRA |
| *Norovirus* Hu/GII-2/C1-263/South Korea | *Norovirus* Hu/GII.3/Cuernavaca/50317/2007/MEX |
| *Norovirus* Hu/GII-2/C1-268/South Korea | *Norovirus* Hu/GII.3/Cuernavaca/7358/2008/MEX |
| *Norovirus* Hu/GII-2/Kashiwa/060771/2006/JP | *Norovirus* Hu/GII.3/Cuernavaca/7360/2008/MEX |
| *Norovirus* Hu/GII-2/teacher 1/OB4/2007/UK | *Norovirus* Hu/GII.3/GE29/IRN |
| *Norovirus* Hu/GII.2/10488/2004/IRL | *Norovirus* Hu/GII.3/Novosibirsk/s2835/2007/Ru |
| *Norovirus* Hu/GII.2/4447/2007/IRL | *Norovirus* Hu/GII.3/Novosibirsk/s2842/2007/Ru |
| *Norovirus* Hu/GII.2/Coevorden191S/1999/NL | *Norovirus* Hu/GII.3/Novosibirsk/s890/2006/Ru |
| *Norovirus* Hu/GII.2/Cuernavaca/50031/2007/MEX | *Norovirus* Hu/GII.3/Novosibirsk/s891/2006/Ru |
| | *Norovirus* Hu/GII.3/Nsk-158/2005/RUS |

TABLE 1-continued

*Norovirus* Strains

*Norovirus* Hu/GII.2/Delft48M/2000/NL
*Norovirus* Hu/GII.2/DenHaag37/2000/NL
*Norovirus* Hu/GII.2/Esslingen/3878/05/DE
*Norovirus* Hu/GII.2/Goes28/2005/NL
*Norovirus* Hu/GII.2/Heerlen7E/2002/NL
*Norovirus* Hu/GII.2/Heidenheim/3478/05/DE
*Norovirus* Hu/GII.2/Kuenzelsau/3870/05/DE
*Norovirus* Hu/GII.2/Leeuwarden15/2001/NL
*Norovirus* Hu/GII.2/Leeuwarden71/2003/NL
*Norovirus* Hu/GII.2/Mannheim/3343/05/DE
*Norovirus* Hu/GII.2/Mussels/M12nov2004/Foto/Sweden
*Norovirus* Hu/GII.2/Mussels/M40nov2004/Foto/Sweden
*Norovirus* Hu/GII.2/OC080306/2008/JPN
*Norovirus* Hu/GII.2/Rotterdam39E/2002/NL
*Norovirus* Hu/GII.2/Sigmaringen/3669/05/DE
*Norovirus* Hu/GII.2/Vaals87/2005/NL
*Norovirus* Hu/GII.2/Waiblingen/3853/05/DE
*Norovirus* Hu/GII.2/Wertheim/3501/05/DE
*Norovirus* Hu/GII.2/Zwolle25E/2001/NL
*Norovirus* genogroup GII.3
*Norovirus* Env/GGII.3/699/2006/IT
*Norovirus* env/GGII.3/972/2007/ITA
*Norovirus* environmental/GII-3/O04-HBT/2008/UK
*Norovirus* environmental/GII-3/O18-TDH/2008/UK
*Norovirus* environmental/GII-3/O28-TFH/2008/UK
*Norovirus* environmental/GII-3/O31-HBT/2008/UK
*Norovirus* Hu/GGII.3/691/2006/IT
*Norovirus* Hu/GII-3/613104/2006/UK
*Norovirus* Hu/GII-3/6479/2007/UK
*Norovirus* Hu/GII-3/6482/2007/UK
*Norovirus* Hu/GII-3/713092-3/2007/UK
*Norovirus* Hu/GII-3/Awa/060890/2006/JP
*Norovirus* Hu/GII-3/B7316/2007/UK
*Norovirus* Hu/GII-3/Batch1-Swab10/2007/UK
*Norovirus* Hu/GII-3/Batch1-Swab19/2007/UK
*Norovirus* Hu/GII-3/Batch2-Swab06/2007/UK
*Norovirus* Hu/GII-3/Batch2-Swab12/2007/UK
*Norovirus* Hu/GII-3/Batch2-Swab16/2007/UK
*Norovirus* Hu/GII-3/Batch2-Swab20/2007/UK
*Norovirus* Hu/GII-3/Batch4-Swab03/2007/UK
*Norovirus* Hu/GII-3/Batch4-Swab10/2007/UK
*Norovirus* Hu/GII-3/Batch4-Swab15/2007/UK
*Norovirus* Hu/GII-3/Batch4-Swab16/2007/UK
*Norovirus* Hu/GII-3/Batch4-Swab20/2007/UK
*Norovirus* Hu/GII-3/Batch5-Swab14/2007/UK
*Norovirus* Hu/GII-3/Batch5-Swab15/2007/UK
*Norovirus* Hu/GII-3/Batch5-Swab20/2007/UK
*Norovirus* Hu/GII-3/Batch5-Swab23/2007/UK
*Norovirus* Hu/GII-3/Batch6-Swab03/2007/UK
*Norovirus* Hu/GII-3/Batch6-Swab10/2007/UK
*Norovirus* Hu/GII-3/Batch6-Swab13/2007/UK
*Norovirus* Hu/GII-3/C1-139/South Korea
*Norovirus* Hu/GII-3/Chosei/060920/2006/JP
*Norovirus* Hu/GII-3/customer 1/OB1/2007/UK
*Norovirus* Hu/GII-3/customer 1/OB2/2007/UK
*Norovirus* Hu/GII-3/customer 1/OB3/2007/UK
*Norovirus* Hu/GII-3/customer 2/OB1/2006/UK
*Norovirus* Hu/GII-3/ES096/2003/BRA
*Norovirus* Hu/GII-3/ES130/2003/BRA
*Norovirus* Hu/GII.3/Nsk-28/2005/RUS
*Norovirus* Hu/GII.3/Nsk-2870/2008/RUS
*Norovirus* Hu/GII.3/Nsk-2872/2008/RUS
*Norovirus* Hu/GII.3/Nsk-2877/2008/RUS
*Norovirus* Hu/GII.3/Nsk-2887/2008/RUS
*Norovirus* Hu/GII.3/Nsk-2891/2008/RUS
*Norovirus* Hu/GII.3/Nsk-2987/2008/RUS
*Norovirus* Hu/GII.3/Nsk-3018/2008/RUS
*Norovirus* Hu/GII.3/Nsk-3071/2008/RUS
*Norovirus* Hu/GII.3/Nsk-3076/2008/RUS
*Norovirus* Hu/GII.3/Nsk-3077/2008/RUS
*Norovirus* Hu/GII.3/Nsk-3203/2008/RUS
*Norovirus* Hu/GII.3/Nsk-3290/2008/RUS
*Norovirus* Hu/GII.3/Nsk-3418/2008/RUS
*Norovirus* Hu/GII.3/Nsk-3489/2008/RUS
*Norovirus* Hu/GII.3/Nsk-3501/2008/RUS
*Norovirus* Hu/GII.3/Nsk-3515/2008/RUS
*Norovirus* Hu/GII.3/Nsk-76/2005/RUS
*Norovirus* Hu/GII.3/Nsk-B69/2009/RUS
*Norovirus* Hu/GII.3/Nsk-B93/2009/RUS
*Norovirus* Hu/GII.3/Nsk-B94/2009/RUS
*Norovirus* Hu/GII.3/Nsk-D138/2009/RUS
*Norovirus* Hu/GII.3/Nsk-D175/2009/RUS
*Norovirus* Hu/GII.3/Nsk-D195/2009/RUS
*Norovirus* Hu/GII.3/Nsk-D204/2009/RUS
*Norovirus* Hu/GII.3/Nsk-D218/2009/RUS
*Norovirus* Hu/GII.3/Nsk-D219/2009/RUS
*Norovirus* Hu/GII.3/Nsk-D224/2009/RUS
*Norovirus* Hu/GII.3/Nsk-D229/2009/RUS
*Norovirus* Hu/GII.3/Nsk-D256/2009/RUS
*Norovirus* Hu/GII.3/Nsk-D277/2009/RUS
*Norovirus* Hu/GII.3/Nsk-D89/2009/RUS
*Norovirus* Hu/GII.3/Nsk-H276/2004/RUS
*Norovirus* Hu/GII.3/Nsk-H379/2004/RUS
*Norovirus* Hu/GII.3/Nsk-H418/2004/RUS
*Norovirus* Hu/GII.3/Nsk-H425/2004/RUS
*Norovirus* Hu/GII.3/Nsk-H470/2004/RUS
*Norovirus* Hu/GII.3/Nsk-H487/2004/RUS
*Norovirus* Hu/GII.3/Nsk-H538/2004/RUS
*Norovirus* Hu/GII.3/Nsk-H573/2004/RUS
*Norovirus* Hu/GII.3/Nsk-H580/2004/RUS
*Norovirus* Hu/GII.3/Nsk-H617/2004/RUS
*Norovirus* Hu/GII.3/Nsk-H677/2004/RUS
*Norovirus* Hu/GII.3/O450/2008/RUS
*Norovirus* Hu/GII.3/RotterdamP1D0/2006/NL
*Norovirus* Hu/GII.3/RotterdamP1D88/2006/NL
*Norovirus* Hu/GII.3/RotterdamP5D0/2005/NL
*Norovirus* Hu/GII.3/RotterdamP8D0/2006/NL
*Norovirus* Hu/GII.3/RotterdamP8D31/2006/NL
*Norovirus* Hu/GII.3/Salvador/B10/2006/BRA
*Norovirus* Hu/GII.3/Salvador/C08/2006/BRA
*Norovirus* Hu/GII.3/Salvador/D10/2006/BRA
*Norovirus* Hu/GII.3/Salvador/G06/2006/BRA
*Norovirus* Hu/GII.3/Salvador/G10/2006/BRA
*Norovirus* Hu/GII.3/Salvador/H02/2006/BRA
*Norovirus* Hu/GII.3/Salvador/H08/2006/BRA
*Norovirus* Hu/GII.3/Salvador/H10/2006/BRA
*Norovirus* Hu/GII3/49167/Henan/06/CHN
*Norovirus* Hu/GII3/52088/Shanghai/06/CHN
*Norovirus* Hu/GII3/52403/Jilin/07/CHN
*Norovirus* oyster/GII.3/4/Stromstad/Sweden
*Norovirus* Hu/GII-3/ES149/2003/BRA
*Norovirus* Hu/GII-3/ES180/2003/BRA
*Norovirus* Hu/GII-3/ES198/2003/BRA

*Norovirus* genogroup GII.4

*Norovirus* env/GGII.4/1034/2007/ITA
*Norovirus* env/GGII.4/1162a/2007/ITA
*Norovirus* Env/GGII.4/645/2005/IT
*Norovirus* Env/GGII.4/649/2005/IT
*Norovirus* Env/GGII.4/650/2005/IT
*Norovirus* Env/GGII.4/671/2006/IT
*Norovirus* Env/GGII.4/672/2006/IT
*Norovirus* Env/GGII.4/677/2006
*Norovirus* Env/GGII.4/677/2006/IT
*Norovirus* Env/GGII.4/680/2006/IT
*Norovirus* Env/GGII.4/704/2006/IT
*Norovirus* Hu/GII.4/Hiroshima/91/2006/JPN
*Norovirus* Hu/GII.4/Hiroshima/92/2006/JPN
*Norovirus* Hu/GII.4/HK/CU09N10/2009/CHN
*Norovirus* Hu/GII.4/HK/CU09N11/2009/CHN
*Norovirus* Hu/GII.4/HK/CU09N12/2009/CHN
*Norovirus* Hu/GII.4/HK/CU09N24/2009/CHN
*Norovirus* Hu/GII.4/HK/CU09N4/2009/CHN
*Norovirus* Hu/GII.4/HK/CU09N5/2009/CHN
*Norovirus* Hu/GII.4/HK/CU09N6/2009/CHN
*Norovirus* Hu/GII.4/HK/CU09N7/2009/CHN
*Norovirus* Hu/GII.4/HK/CU09N8/2009/CHN TABLE 1-continued

| *Norovirus* Strains |
|---|
| *Norovirus* env/GGII.4/954/2007/ITA |
| *Norovirus* env/GGII.4/956/2007/ITA |
| *Norovirus* env/GGII.4/960/2007/ITA |
| *Norovirus* env/GGII.4/968/2007/ITA |
| *Norovirus* env/GGII.4/976/2007/ITA |
| *Norovirus* env/GGII.4/980/2007/ITA |
| *Norovirus* env/GGII.4/992/2007/ITA |
| *Norovirus* env/GGII.4/994/2007/ITA |
| *Norovirus* env/GGII.4/996/2007/ITA |
| *Norovirus* environmental/GII-4/O01-FDH/2008/UK |
| *Norovirus* environmental/GII-4/O01-HBT/2008/UK |
| *Norovirus* environmental/GII-4/O04-TDH/2008/UK |
| *Norovirus* environmental/GII-4/O10-TFH/2008/UK |
| *Norovirus* environmental/GII-4/O19-HBT/2008/UK |
| *Norovirus* environmental/GII-4/O27-TFH/2008/UK |
| *Norovirus* environmental/GII-4/O31-TDH/2008/UK |
| *Norovirus* Hu/GGI.4/1735OB/77351/FR |
| *Norovirus* Hu/GGI.4/oyster1735OA/77351/FR |
| *Norovirus* Hu/GGII-4/Alzira/1695/06/Sp |
| *Norovirus* Hu/GGII-4/Badalona/1586/BNM_05/06/Sp |
| *Norovirus* Hu/GGII-4/Banyoles/1474/Gi_10/06/Sp |
| *Norovirus* Hu/GGII-4/Barcelona/1258/BNM_08/05 |
| *Norovirus* Hu/GGII-4/Benicarlo/1226/04 |
| *Norovirus* Hu/GGII-4/Benidorm/1222/05 |
| *Norovirus* Hu/GGII-4/Benidorm/1680/06 |
| *Norovirus* Hu/GGII-4/Benidorm/1707/06/Sp |
| *Norovirus* Hu/GGII-4/Blanes/1483/Gi_22/06/Sp |
| *Norovirus* Hu/GGII-4/Cabrera/1590/RCSP_01/Sp |
| *Norovirus* Hu/GGII-4/Calonge/Gi_03/1216/05 |
| *Norovirus* Hu/GGII-4/Cambrils/1105/TA_10/05 |
| *Norovirus* Hu/GGII-4/Corbera/RCSP_68/1134/04 |
| *Norovirus* Hu/GGII-4/Els_Pallers/1617/TA_02/06/Sp |
| *Norovirus* Hu/GGII-4/Peniscola/1227/05 |
| *Norovirus* Hu/GGII-4/Rosas/1078/Gi59/04 |
| *Norovirus* Hu/GGII-4/Roses/1491/Gi_23/06/Sp |
| *Norovirus* Hu/GGII-4/Sabadell/1196/RC94_04/04 |
| *Norovirus* Hu/GGII-4/Sabadell/1236/RC_08/05 |
| *Norovirus* Hu/GGII-4/Sabadell/1510/RC_02/06/Sp |
| *Norovirus* Hu/GGII-4/Sant_Cugat/1527/RC_06/06/Sp |
| *Norovirus* Hu/GGII-4/Sant_Quirze/1092/RC_80/04 |
| *Norovirus* Hu/GGII-4/Sant_Sadurni/1087/RC_84/04 |
| *Norovirus* Hu/GGII-4/Tarragona/1613/TA_01/06/Sp |
| *Norovirus* Hu/GGII-4/Tarragona/1624/TA_03/06/Sp |
| *Norovirus* Hu/GGII-4/Tarragona/1636/TA_05/06/Sp |
| *Norovirus* Hu/GGII-4/Tremp/1567/Lleida_03/06/Sp |
| *Norovirus* Hu/GGII-4/Valencia_HCUV/593/02 |
| *Norovirus* Hu/GGII-4/Vall_de_Bianya/1477/Gi_19/06/Sp |
| *Norovirus* Hu/GGII-4/Villareal/1669/06 |
| *Norovirus* Hu/GGII.4/0029A/69787/2006/NLD |
| *Norovirus* Hu/GGII.4/0029B/69787/2006/NLD |
| *Norovirus* Hu/GGII.4/0518B/68592/2006/NLD |
| *Norovirus* Hu/GII.4/HK/CU09N9/2009/CHN |
| *Norovirus* Hu/GII.4/HK/CU09S42/2009/CHN |
| *Norovirus* Hu/GII.4/HK/CU09T10/2009/CHN |
| *Norovirus* Hu/GII.4/HK/CU09T12/2009/CHN |
| *Norovirus* Hu/GII.4/HME-407/2005/TWN |
| *Norovirus* Hu/GII.4/HME-417/2005/TWN |
| *Norovirus* Hu/GII.4/HME-434/2005/TWN |
| *Norovirus* Hu/GII.4/HME-465/2005/TWN |
| *Norovirus* Hu/GII.4/HME-467/2005/TWN |
| *Norovirus* Hu/GII.4/HME-618/2006/TWN |
| *Norovirus* Hu/GII.4/HME-620/2006/TWN |
| *Norovirus* Hu/GII.4/HME-622/2006/TWN |
| *Norovirus* Hu/GII.4/HME-624/2006/TWN |
| *Norovirus* Hu/GII.4/HME-627/2006/TWN |
| *Norovirus* Hu/GII.4/HME-631/2006/TWN |
| *Norovirus* Hu/GII.4/HME-633/2006/TWN |
| *Norovirus* Hu/GII.4/HS194/2009/US |
| *Norovirus* Hu/GII.4/Hunter 284E/04O/AU |
| *Norovirus* Hu/GII.4/Hunter 532D/04O/AU |
| *Norovirus* Hu/GII.4/Hunter120A/04O/AU |
| *Norovirus* Hu/GII.4/Hunter273C/04O/AU |
| *Norovirus* Hu/GII.4/Hunter4288/04S/AU |
| *Norovirus* Hu/GII.4/Hunter504D/04O/AU |
| *Norovirus* Hu/GII.4/Hunter882M/04S/AU |
| *Norovirus* Hu/GII.4/Hunter913K/04O/AU |
| *Norovirus* Hu/GII.4/Hunter956S/04O/AU |
| *Norovirus* Hu/GII.4/Hunter990O/04O/AU |
| *Norovirus* Hu/GII.4/I/2006/FIN |
| *Norovirus* Hu/GII.4/II/2006/FIN |
| *Norovirus* Hu/GII.4/III/2006/FIN |
| *Norovirus* Hu/GII.4/Isehara1/2006/JP |
| *Norovirus* Hu/GII.4/Isehara2/2006/JP |
| *Norovirus* Hu/GII.4/Jannali611C/04O/AU |
| *Norovirus* Hu/GII.4/Jannali670H/04O/AU |
| *Norovirus* Hu/GII.4/Kobe034/2006/JP |
| *Norovirus* Hu/GII.4/Kogarah393H/04O/AU |
| *Norovirus* Hu/GII.4/Kogarah4006/04O/AU |
| *Norovirus* Hu/GII.4/Longbay/00O/AU |
| *Norovirus* Hu/GII.4/Manly388P/04O/AU |
| *Norovirus* Hu/GII.4/ManlyVale098M/04O/AU |
| *Norovirus* Hu/GII.4/Mc17/2002/Th |
| *Norovirus* Hu/GII.4/MD-2004/2004/US |
| *Norovirus* Hu/GII.4/Miyagi/1/2006/JP |
| *Norovirus* Hu/GII.4/Miyagi/1/2007/JP |
| *Norovirus* Hu/GII.4/Miyagi/10/2006/JP |
| *Norovirus* Hu/GII.4/Miyagi/11/2006/JP |
| *Norovirus* Hu/GII.4/Miyagi/12/2006/JP |
| *Norovirus* Hu/GII.4/Miyagi/13/2006/JP |
| *Norovirus* Hu/GII.4/Miyagi/14/2006/JP |
| *Norovirus* Hu/GII.4/Miyagi/15/2006/JP |
| *Norovirus* Hu/GII.4/Miyagi/16/2006/JP |
| *Norovirus* Hu/GII.4/Miyagi/17/2006/JP |
| *Norovirus* Hu/GII.4/Miyagi/18/2006/JP |
| *Norovirus* Hu/GII.4/Miyagi/19/2006/JP |
| *Norovirus* Hu/GII.4/Miyagi/2/2006/JP |
| *Norovirus* Hu/GII.4/Miyagi/2/2007/JP |
| *Norovirus* Hu/GII.4/Miyagi/20/2006/JP |
| *Norovirus* Hu/GII.4/Miyagi/21/2006/JP |
| *Norovirus* Hu/GII.4/Miyagi/22/2006/JP |
| *Norovirus* Hu/GII.4/Miyagi/23/2006/JP |
| *Norovirus* Hu/GII.4/Miyagi/24/2006/JP |
| *Norovirus* Hu/GII.4/Miyagi/3/2006/JP |
| *Norovirus* Hu/GII.4/Miyagi/3/2007/JP |
| *Norovirus* Hu/GII.4/Miyagi/4/2007/JP |
| *Norovirus* Hu/GII.4/Miyagi/5/2006/JP |
| *Norovirus* Hu/GII.4/Miyagi/5/2007/JP |
| *Norovirus* Hu/GII.4/Miyagi/6/2006/JP |
| *Norovirus* Hu/GII.4/Miyagi/6/2007/JP |
| *Norovirus* Hu/GII.4/Miyagi/7/2006/JP |
| *Norovirus* Hu/GII.4/Miyagi/7/2007/JP |
| *Norovirus* Hu/GII.4/Miyagi/8/2006/JP |
| *Norovirus* Hu/GII.4/Miyagi/8/2007/JP |
| *Norovirus* Hu/GII.4/Miyagi/9/2006/JP |
| *Norovirus* Hu/GII.4/Miyagi/9/2007/JP |
| *Norovirus* Hu/GII.4/Miyagi/HM050413/2005/JP |
| *Norovirus* Hu/GII.4/Miyagi/HM050426/2005/JP |
| *Norovirus* Hu/GII.4/Miyagi/HM050511/2005/JP |
| *Norovirus* Hu/GII.4/Miyagi/HM050525/2005/JP |

TABLE 1-continued

| *Norovirus* Strains |
|---|
| *Norovirus* Hu/GGII.4/190Nica/2005 |
| *Norovirus* Hu/GGII.4/256Nica/2005 |
| *Norovirus* Hu/GGII.4/2639B/66430/2006/NLD |
| *Norovirus* Hu/GGII.4/2936A/66430/2006/NLD |
| *Norovirus* Hu/GGII.4/322Nica/2005 |
| *Norovirus* Hu/GGII.4/324Nica/2005 |
| *Norovirus* Hu/GGII.4/330Nica/2005 |
| *Norovirus* Hu/GGII.4/3474A/2006/NLD |
| *Norovirus* Hu/GGII.4/3474Ab/2006/NLD |
| *Norovirus* Hu/GGII.4/355Nica/2005 |
| *Norovirus* Hu/GGII.4/380Nica/2005 |
| *Norovirus* Hu/GGII.4/382Nica/2005 |
| *Norovirus* Hu/GGII.4/392Nica/2005 |
| *Norovirus* Hu/GGII.4/410Nica/2005 |
| *Norovirus* Hu/GGII.4/413Nica/2005 |
| *Norovirus* Hu/GGII.4/414Nica/2005 |
| *Norovirus* Hu/GGII.4/42Nica/2005 |
| *Norovirus* Hu/GGII.4/432Nica/2005 |
| *Norovirus* Hu/GGII.4/448Nica/2005 |
| *Norovirus* Hu/GGII.4/482Nica/2005 |
| *Norovirus* Hu/GGII.4/4992A/65902/2006/NLD |
| *Norovirus* Hu/GGII.4/4992B/65902/2006/NLD |
| *Norovirus* Hu/GGII.4/5357A/67071/2006/NLD |
| *Norovirus* Hu/GGII.4/5357B/67071/2006/NLD |
| *Norovirus* Hu/GGII.4/5391A/66878/2006/NLD |
| *Norovirus* Hu/GGII.4/5391B/66878/2006/NLD |
| *Norovirus* Hu/GGII.4/567Nica/2005 |
| *Norovirus* Hu/GGII.4/577Nica/2005 |
| *Norovirus* Hu/GGII.4/586Nica/2005 |
| *Norovirus* Hu/GGII.4/593Nica/2005 |
| *Norovirus* Hu/GGII.4/623Nica/2005 |
| *Norovirus* Hu/GGII.4/6282A/69479/2006/NLD |
| *Norovirus* Hu/GGII.4/634Nica/2005 |
| *Norovirus* Hu/GGII.4/668/2006/IT |
| *Norovirus* Hu/GGII.4/669/2006/IT |
| *Norovirus* Hu/GGII.4/692/2006/IT |
| *Norovirus* Hu/GGII.4/720Nica/2006 |
| *Norovirus* Hu/GGII.4/723Nica/2006 |
| *Norovirus* Hu/GGII.4/729Nica/2006 |
| *Norovirus* Hu/GGII.4/735Nica/2006 |
| *Norovirus* Hu/GGII.4/7366A/63808/NLD |
| *Norovirus* Hu/GGII.4/7366B/63808/NLD |
| *Norovirus* Hu/GGII.4/8956A/66842/2006/NLD |
| *Norovirus* Hu/GGII.4/9893B/67814/2006/NLD |
| *Norovirus* Hu/GGII.4/Almelo039/2004/NL |
| *Norovirus* Hu/GGII.4/Apeldoorn023/2003/NL |
| *Norovirus* Hu/GGII.4/B1/2002/DNK |
| *Norovirus* Hu/GGII.4/B11/2003/DNK |
| *Norovirus* Hu/GGII.4/B12/2003/DNK |
| *Norovirus* Hu/GGII.4/B13/2002/DNK |
| *Norovirus* Hu/GGII.4/B1O/2003/DNK |
| *Norovirus* Hu/GGII.4/B2/2002/DNK |
| *Norovirus* Hu/GGII.4/B3/2002/DNK |
| *Norovirus* Hu/GGII.4/B4/2002/DNK |
| *Norovirus* Hu/GGII.4/B5/2002/DNK |
| *Norovirus* Hu/GGII.4/B6/2002/DNK |
| *Norovirus* Hu/GGII.4/B7/2003/DNK |
| *Norovirus* Hu/GGII.4/B8/2002/DNK |
| *Norovirus* Hu/GGII.4/B9/2002/DNK |
| *Norovirus* Hu/GGII.4/Cairo1/2006/EGY |
| *Norovirus* Hu/GGII.4/Cairo10/2007/EGY |
| *Norovirus* Hu/GGII.4/Cairo2/2006/EGY |
| *Norovirus* Hu/GGII.4/Cairo3/2006/EGY |
| *Norovirus* Hu/GGII.4/Cairo4/2006/EGY |
| *Norovirus* Hu/GGII.4/Cairo5/2006/EGY |
| *Norovirus* Hu/GGII.4/Cairo6/2006/EGY |
| *Norovirus* Hu/GGII.4/Cairo7/2007/EGY |
| *Norovirus* Hu/GGII.4/Cairo8/2007/EGY |
| *Norovirus* Hu/GGII.4/Cairo9/2007/EGY |
| *Norovirus* Hu/GGII.4/DenBosch028/2004/NL |
| *Norovirus* Hu/GGII.4/DenHaag001/2003/NL |
| *Norovirus* Hu/GGII.4/DenHaag015/2000/NL |
| *Norovirus* Hu/GGII.4/DenHelder003/2004/NL |
| *Norovirus* Hu/GGII.4/Dijon-E1057/2002/FRA |
| *Norovirus* Hu/GGII.4/Dijon-E1267/2006/FRA |
| *Norovirus* Hu/GGII.4/Dijon-E1501/2006/FRA |
| *Norovirus* Hu/GGII.4/Dijon-E2703/2008/FRA |
| *Norovirus* Hu/GGII.4/E1/2002/DNK |
| *Norovirus* Hu/GII.4/Mussels/M29nov2004/Foto/Sweden |
| *Norovirus* Hu/GII.4/Mussels/M33nov2004/Foto/Sweden |
| *Norovirus* Hu/GII.4/New Orleans1500/2008/USA |
| *Norovirus* Hu/GII.4/Nijmegen/2007/NL |
| *Norovirus* Hu/GII.4/Nijmegen/81230-R/2008/NLD |
| *Norovirus* Hu/GII.4/Nijmegen/90106-42472/2008/NLD |
| *Norovirus* Hu/GII.4/Nijmegen115/2006/NL |
| *Norovirus* Hu/GII.4/Novosibirsk/s1218/2006/Ru |
| *Norovirus* Hu/GII.4/Novosibirsk/s1416/2006/Ru |
| *Norovirus* Hu/GII.4/Novosibirsk/s1475/2006/Ru |
| *Norovirus* Hu/GII.4/Novosibirsk/s16/2005/Ru |
| *Norovirus* Hu/GII.4/Novosibirsk/s164/2005/Ru |
| *Norovirus* Hu/GII.4/Novosibirsk/s1640/2006/Ru |
| *Norovirus* Hu/GII.4/Novosibirsk/s1735/2006/Ru |
| *Norovirus* Hu/GII.4/Novosibirsk/s1744/2007/Ru |
| *Norovirus* Hu/GII.4/Novosibirsk/s1747/2007/Ru |
| *Norovirus* Hu/GII.4/Novosibirsk/s1764/2007/Ru |
| *Norovirus* Hu/GII.4/Novosibirsk/s1768/2007/Ru |
| *Norovirus* Hu/GII.4/Novosibirsk/s1770/2007/Ru |
| *Norovirus* Hu/GII.4/Novosibirsk/s1784/2007/Ru |
| *Norovirus* Hu/GII.4/Novosibirsk/s1792/2007/Ru |
| *Norovirus* Hu/GII.4/Novosibirsk/s1795/2007/Ru |
| *Norovirus* Hu/GII.4/Novosibirsk/s1798/2007/Ru |
| *Norovirus* Hu/GII.4/Novosibirsk/s1830/2007/Ru |
| *Norovirus* Hu/GII.4/Novosibirsk/s1837/2007/Ru |
| *Norovirus* Hu/GII.4/Novosibirsk/s1843/2007/Ru |
| *Norovirus* Hu/GII.4/Novosibirsk/s1862/2007/Ru |
| *Norovirus* Hu/GII.4/Novosibirsk/s1918/2007/Ru |
| *Norovirus* Hu/GII.4/Novosibirsk/s1925/2007/Ru |
| *Norovirus* Hu/GII.4/Novosibirsk/s1985/2007/Ru |
| *Norovirus* Hu/GII.4/Novosibirsk/s2085/2007/Ru |
| *Norovirus* Hu/GII.4/Novosibirsk/s2093/2007/Ru |
| *Norovirus* Hu/GII.4/Novosibirsk/s2184/2007/Ru |
| *Norovirus* Hu/GII.4/Novosibirsk/s23/2005/Ru |
| *Norovirus* Hu/GII.4/Novosibirsk/s2369/2007/Ru |
| *Norovirus* Hu/GII.4/Novosibirsk/s2629/2007/Ru |
| *Norovirus* Hu/GII.4/Novosibirsk/s2862/2008/Ru |
| *Norovirus* Hu/GII.4/Novosibirsk/s290/2005/Ru |
| *Norovirus* Hu/GII.4/Novosibirsk/s2980/2008/Ru |
| *Norovirus* Hu/GII.4/Novosibirsk/s317/2005/Ru |
| *Norovirus* Hu/GII.4/Novosibirsk/s345/2005/Ru |
| *Norovirus* Hu/GII.4/Novosibirsk/s383/2005/Ru |
| *Norovirus* Hu/GII.4/Novosibirsk/s416/2005/Ru |
| *Norovirus* Hu/GII.4/Novosibirsk/s625/2005/Ru |
| *Norovirus* Hu/GII.4/Nsk-1/2005/RUS |
| *Norovirus* Hu/GII.4/Nsk-1973/2007/RUS |
| *Norovirus* Hu/GII.4/Nsk-2111/2007/RUS |
| *Norovirus* Hu/GII.4/Nsk-2501/2007/RUS |
| *Norovirus* Hu/GII.4/Nsk-2518/2007/RUS |
| *Norovirus* Hu/GII.4/Nsk-2523/2007/RUS |
| *Norovirus* Hu/GII.4/Nsk-2578/2007/RUS |
| *Norovirus* Hu/GII.4/Nsk-2853/2008/RUS |
| *Norovirus* Hu/GII.4/Nsk-2862/2008/RUS |
| *Norovirus* Hu/GII.4/Nsk-2980/2008/RUS |
| *Norovirus* Hu/GII.4/Nsk-3096/2008/RUS |
| *Norovirus* Hu/GII.4/Nsk-3147/2008/RUS |
| *Norovirus* Hu/GII.4/Nsk-3175/2008/RUS |
| *Norovirus* Hu/GII.4/Nsk-3255/2008/RUS |
| *Norovirus* Hu/GII.4/Nsk-3288/2008/RUS |
| *Norovirus* Hu/GII.4/Nsk-3315/2008/RUS |
| *Norovirus* Hu/GII.4/Nsk-3363/2008/RUS |
| *Norovirus* Hu/GII.4/Nsk-3392/2008/RUS |
| *Norovirus* Hu/GII.4/Nsk-3396/2008/RUS |
| *Norovirus* Hu/GII.4/Nsk-3412/2008/RUS |
| *Norovirus* Hu/GII.4/Nsk-3445/2008/RUS |
| *Norovirus* Hu/GII.4/Nsk-3469/2008/RUS |
| *Norovirus* Hu/GII.4/Nsk-3481/2008/RUS |
| *Norovirus* Hu/GII.4/Nsk-38/2005/RUS |
| *Norovirus* Hu/GII.4/Nsk-6/2005/RUS |
| *Norovirus* Hu/GII.4/Nsk-B20/2009/RUS |
| *Norovirus* Hu/GII.4/Nsk-B30/2009/RUS |
| *Norovirus* Hu/GII.4/Nsk-B38/2009/RUS |
| *Norovirus* Hu/GII.4/Nsk-B42/2009/RUS |
| *Norovirus* Hu/GII.4/Nsk-B67/2009/RUS |
| *Norovirus* Hu/GII.4/Nsk-B8/2009/RUS |

TABLE 1-continued

| *Norovirus* Strains | |
|---|---|
| *Norovirus* Hu/GGII.4/E2/2002/DNK | *Norovirus* Hu/GII.4/Nsk-D118/2009/RUS |
| *Norovirus* Hu/GGII.4/E3/2002/DNK | *Norovirus* Hu/GII.4/Nsk-D173/2009/RUS |
| *Norovirus* Hu/GGII.4/E4/2003/DNK | *Norovirus* Hu/GII.4/Nsk-D183/2009/RUS |
| *Norovirus* Hu/GGII.4/E5/2003/DNK | *Norovirus* Hu/GII.4/Nsk-D186/2009/RUS |
| *Norovirus* Hu/GGII.4/E6/2003/DNK | *Norovirus* Hu/GII.4/Nsk-D191/2009/RUS |
| *Norovirus* Hu/GGII.4/E7/2003/DNK | *Norovirus* Hu/GII.4/Nsk-D211/2009/RUS |
| *Norovirus* Hu/GGII.4/E8/2003/DNK | *Norovirus* Hu/GII.4/Nsk-D270/2009/RUS |
| *Norovirus* Hu/GGII.4/E9/2003/DNK | *Norovirus* Hu/GII.4/Nsk-D43/2009/RUS |
| *Norovirus* Hu/GGII.4/Elsloo012/2004/NL | *Norovirus* Hu/GII.4/Nsk-D45/2009/RUS |
| *Norovirus* Hu/GGII.4/EmmenE006/2002/NL | *Norovirus* Hu/GII.4/Nsk-H445/2004/RUS |
| *Norovirus* Hu/GGII.4/Haarlem457/2003/NL | *Norovirus* Hu/GII.4/Nsk-H472/2004/RUS |
| *Norovirus* Hu/GGII.4/Heerlen003/2003/NL | *Norovirus* Hu/GII.4/Nsk-H486/2004/RUS |
| *Norovirus* | *Norovirus* Hu/GII.4/Nsk-K17/2005/RUS |
| Hu/GGII.4/Leeuwarden043/2000/NL | *Norovirus* Hu/GII.4/Nsk-K25/2005/RUS |
| *Norovirus* Hu/GGII.4/Liempde048/2004/NL | *Norovirus* Hu/GII.4/NSW001P/2008/AU |
| *Norovirus* Hu/GGII.4/Middelburg007/2004/NL | *Norovirus* Hu/GII.4/NSW017I/2008/AU |
| *Norovirus* Hu/GGII.4/New Delhi/150/02/IND | *Norovirus* Hu/GII.4/NSW023C/2008/AUS |
| *Norovirus* Hu/GGII.4/New Delhi/188/01/IND | *Norovirus* Hu/GII.4/NSW042H/2008/AU |
| *Norovirus* Hu/GGII.4/New Delhi/203/01/IND | *Norovirus* Hu/GII.4/NSW071I/2008/AU |
| *Norovirus* Hu/GGII.4/New Delhi/219/01/IND | *Norovirus* Hu/GII.4/NSW088L/2007/AUS |
| *Norovirus* Hu/GGII.4/Nijmegen083/2004/NL | *Norovirus* Hu/GII.4/NSW132C/2007/AU |
| *Norovirus* Hu/GGII.4/OA1/2002/DNK | *Norovirus* Hu/GII.4/NSW137F/2007/AU |
| *Norovirus* Hu/GGII.4/OA2/2002/DNK | *Norovirus* Hu/GII.4/NSW146P/2007/AU |
| *Norovirus* Hu/GGII.4/OA3/2002/DNK | *Norovirus* Hu/GII.4/NSW161F/2007/AU |
| *Norovirus* Hu/GGII.4/OA4/2002/DNK | *Norovirus* Hu/GII.4/NSW199U/2008/AU |
| *Norovirus* Hu/GGII.4/OC1/2002/DNK | *Norovirus* Hu/GII.4/NSW2218/2008/AU |
| *Norovirus* Hu/GGII.4/OG1/2002/DNK | *Norovirus* Hu/GII.4/NSW227C/2006/AU |
| *Norovirus* Hu/GGII.4/OG2/2002/DNK | *Norovirus* Hu/GII.4/NSW252E/2007/AU |
| *Norovirus* Hu/GGII.4/OG3/2002/DNK | *Norovirus* Hu/GII.4/NSW264P/2007/AU |
| *Norovirus* Hu/GGII.4/OG4/2002/DNK | *Norovirus* Hu/GII.4/NSW287R/2007/AUS |
| *Norovirus* Hu/GGII.4/OG5/2002/DNK | *Norovirus* Hu/GII.4/NSW3639/2008/AU |
| *Norovirus* Hu/GGII.4/OG6/2002/DNK | *Norovirus* Hu/GII.4/NSW3645/2008/AU |
| *Norovirus* Hu/GGII.4/OL1/2002/DNK | *Norovirus* Hu/GII.4/NSW3722/2008/AU |
| *Norovirus* Hu/GGII.4/OM11/2003/DNK | *Norovirus* Hu/GII.4/NSW390I/2008/AU |
| *Norovirus* Hu/GGII.4/OM12/2003/DNK | *Norovirus* Hu/GII.4/NSW401B/2008/AU |
| *Norovirus* Hu/GGII.4/OM13/2003/DNK | *Norovirus* Hu/GII.4/NSW4140/2008/AU |
| *Norovirus* Hu/GGII.4/OM14/2002/DNK | *Norovirus* Hu/GII.4/NSW422H/2008/AU |
| *Norovirus* Hu/GGII.4/OM15/2003/DNK | *Norovirus* Hu/GII.4/NSW505G/2007/AU |
| *Norovirus* Hu/GGII.4/OM2/2002/DNK | *Norovirus* Hu/GII.4/NSW515L/2007/AU |
| *Norovirus* Hu/GGII.4/OM3/2002/DNK | *Norovirus* Hu/GII.4/NSW519M/2008/AU |
| *Norovirus* Hu/GGII.4/OM4/2002/DNK | *Norovirus* Hu/GII.4/NSW522G/2008/AU |
| *Norovirus* Hu/GGII.4/OM5/2002/DNK | *Norovirus* Hu/GII.4/NSW523R/2007/AU |
| *Norovirus* Hu/GGII.4/OM6/2003/DNK | *Norovirus* Hu/GII.4/NSW536S/2008/AU |
| *Norovirus* Hu/GGII.4/OM7/2003/DNK | *Norovirus* Hu/GII.4/NSW544K/2008/AUS |
| *Norovirus* Hu/GGII.4/OM8/2003/DNK | *Norovirus* Hu/GII.4/NSW587V/2007/AU |
| *Norovirus* Hu/GGII.4/ON1/2002/DNK | *Norovirus* Hu/GII.4/NSW609H/2007/AU |
| *Norovirus* Hu/GGII.4/OO1/2002/DNK | *Norovirus* Hu/GII.4/NSW618P/2008/AU |
| *Norovirus* Hu/GGII.4/OO2/2002/DNK | *Norovirus* Hu/GII.4/NSW625N/2008/AU |
| *Norovirus* Hu/GGII.4/OO4/2002/DNK | *Norovirus* Hu/GII.4/NSW647Q/2007/AU |
| *Norovirus* Hu/GGII.4/OO5/2002/DNK | *Norovirus* Hu/GII.4/NSW682R/2007/AU |
| *Norovirus* Hu/GGII.4/patient F/2006/NLD | *Norovirus* Hu/GII.4/NSW710L/2007/AU |
| *Norovirus* Hu/GGII.4/S1/2002/DNK | *Norovirus* Hu/GII.4/NSW743L/2008/AUS |
| *Norovirus* Hu/GGII.4/S2/2003/DNK | *Norovirus* Hu/GII.4/NSW774W/2007/AU |
| *Norovirus* Hu/GGII.4/S3/2003/DNK | *Norovirus* Hu/GII.4/NSW806J/2008/AU |
| *Norovirus* Hu/GGII.4/S4/2003/DNK | *Norovirus* Hu/GII.4/NSW8891/2007/AU |
| *Norovirus* Hu/GGII.4/S5/2003/DNK | *Norovirus* Hu/GII.4/NSW889Z/2007/AU |
| *Norovirus* Hu/GGII.4/S7/2003/DNK | *Norovirus* Hu/GII.4/NSW9282/2008/AU |
| *Norovirus* Hu/GGII.4/S8/2003/DNK | *Norovirus* Hu/GII.4/NSW961W/2007/AU |
| *Norovirus* Hu/GGII.4/Schiedam018/2001/NL | *Norovirus* Hu/GII.4/OC090053/2009/JPN |
| *Norovirus* Hu/GGII.4/Tiel001/1995/NL | *Norovirus* Hu/GII.4/PA1/2004/IT |
| *Norovirus* Hu/GGII.4/Tilburg059/2004/NL | *Norovirus* Hu/GII.4/PA118/2006/IT |
| *Norovirus* Hu/GGII.4/Utrecht058/2001/NL | *Norovirus* Hu/GII.4/PA118R-/2004/IT |
| *Norovirus* Hu/GGII.4/V10/2003/DNK | *Norovirus* Hu/GII.4/PA121/2006/IT |
| *Norovirus* Hu/GGII.4/V11/2003/DNK | *Norovirus* Hu/GII.4/PA125R-/2004/IT |
| *Norovirus* Hu/GGII.4/V12/2002/DNK | *Norovirus* Hu/GII.4/PA128R-/2004/IT |
| *Norovirus* Hu/GGII.4/V13/2003/DNK | *Norovirus* Hu/GII.4/PA129R-/2004/IT |
| *Norovirus* Hu/GGII.4/V15/2002/DNK | *Norovirus* Hu/GII.4/PA130R-/2004/IT |
| *Norovirus* Hu/GGII.4/V4/2002/DNK | *Norovirus* Hu/GII.4/PA133/2006/IT |
| *Norovirus* Hu/GGII.4/V5/2003/DNK | *Norovirus* Hu/GII.4/PA134R-/2004/IT |
| *Norovirus* Hu/GGII.4/V8/2003/DNK | *Norovirus* Hu/GII.4/PA135R-/2004/IT |
| *Norovirus* Hu/GGII.4/Valencia/2004/ES | *Norovirus* Hu/GII.4/PA138R-/2004/IT |
| *Norovirus* | *Norovirus* Hu/GII.4/PA14/2006/IT |
| Hu/GGII.4/Waddinxveen016/2000/NL | *Norovirus* Hu/GII.4/PA143/2005/IT |
| *Norovirus* Hu/GGII.4/WeertE022/2002/NL | *Norovirus* Hu/GII.4/PA147/2006/IT |
| *Norovirus* Hu/GII-4 vUC/M/2006/US | *Norovirus* Hu/GII.4/PA148/2006/IT |
| *Norovirus* Hu/GII-4/10641/2005/Bra | *Norovirus* Hu/GII.4/PA15R-/2002/IT |
| *Norovirus* Hu/GII-4/10668/2005/Bra | *Norovirus* Hu/GII.4/PA163/2006/IT |
| *Norovirus* Hu/GII-4/10689/2005/Bra | *Norovirus* Hu/GII.4/PA173/2006/IT |

TABLE 1-continued

| *Norovirus* Strains | |
|---|---|
| *Norovirus* Hu/GII-4/10831/2005/Bra | *Norovirus* Hu/GII.4/PA175/2006/IT |
| *Norovirus* Hu/GII-4/10942/2005/Bra | *Norovirus* Hu/GII.4/PA178/2006/IT |
| *Norovirus* Hu/GII-4/123027/2001/UK | *Norovirus* Hu/GII.4/PA179/2006/IT |
| *Norovirus* Hu/GII-4/414055/2004/UK | *Norovirus* Hu/GII.4/PA180/2006/IT |
| *Norovirus* Hu/GII-4/422031/2004/UK | *Norovirus* Hu/GII.4/PA189/2006/IT |
| *Norovirus* Hu/GII-4/588/2008/UK | *Norovirus* Hu/GII.4/PA2/2005/IT |
| *Norovirus* Hu/GII-4/613123/2006/UK | *Norovirus* Hu/GII.4/PA29R-/2002/IT |
| *Norovirus* Hu/GII-4/614025/2006/UK | *Norovirus* Hu/GII.4/PA31/2006/IT |
| *Norovirus* Hu/GII-4/AC3-1/2006/UK | *Norovirus* Hu/GII.4/PA37/2006/IT |
| *Norovirus* Hu/GII-4/Aichi3/2006/JP | *Norovirus* Hu/GII.4/PA39/2005/IT |
| *Norovirus* Hu/GII-4/Aichi4/2006/JP | *Norovirus* Hu/GII.4/PA53/2006/IT |
| *Norovirus* Hu/GII-4/Akita1/2006/JP | *Norovirus* Hu/GII.4/PA56/2005/IT |
| *Norovirus* Hu/GII-4/Akita2/2006/JP | *Norovirus* Hu/GII.4/PA57/2004/IT |
| *Norovirus* Hu/GII-4/Akita4/2006/JP | *Norovirus* Hu/GII.4/PA58R-/2004/IT |
| *Norovirus* Hu/GII-4/Akita5/2006/JP | *Norovirus* Hu/GII.4/PA71/2006/IT |
| *Norovirus* Hu/GII-4/AN6-Newc/2005/UK | *Norovirus* Hu/GII.4/PA9R-/2004/IT |
| *Norovirus* Hu/GII-4/Aomori1/2006/JP | *Norovirus* Hu/GII.4/Parma/1875/2008/ITA |
| *Norovirus* Hu/GII-4/Aomori2/2006/JP | *Norovirus* Hu/GII.4/Parma/1896/2008/ITA |
| *Norovirus* Hu/GII-4/Aomori4/2006/JP | *Norovirus* Hu/GII.4/Picton037/03O/AU |
| *Norovirus* Hu/GII-4/Aomori5/2006/JP | *Norovirus* Hu/GII.4/Picton081/03O/AU |
| *Norovirus* Hu/GII-4/Aqualand/1015/04 | *Norovirus* Hu/GII.4/Ramsgate336I/04O/AU |
| *Norovirus* Hu/GII-4/Awa/040354/2004/JP | *Norovirus* Hu/GII.4/Rhyl440/2005/UK |
| *Norovirus* Hu/GII-4/Awa/061288/2006/JP | *Norovirus* Hu/GII.4/RIS/2006/USA |
| *Norovirus* Hu/GII-4/Barcelona/985/03 | *Norovirus* Hu/GII.4/Riviera1590/2008/US |
| *Norovirus* Hu/GII-4/Beijing/h1/2005/CHN | *Norovirus* Hu/GII.4/Riviera1635/2008/US |
| *Norovirus* Hu/GII-4/Beijing145/2007/China | *Norovirus* Hu/GII.4/RotterdamP2D0/2005/NL |
| *Norovirus* Hu/GII-4/Beijing151/2007/China | *Norovirus* Hu/GII.4/RotterdamP2D182/2005/NL |
| *Norovirus* Hu/GII-4/Beijing157/2007/China | *Norovirus* Hu/GII.4/RotterdamP3D0/2006/NL |
| *Norovirus* Hu/GII-4/Benidorm/812/02/Sp | *Norovirus* Hu/GII.4/RotterdamP3D21/2006/NL |
| *Norovirus* Hu/GII-4/Benidorm/858/02/Sp | *Norovirus* Hu/GII.4/RotterdamP4D0/2006/NL |
| *Norovirus* Hu/GII-4/Benidorm/901/03/Sp | *Norovirus* Hu/GII.4/RotterdamP4D33/2006/NL |
| *Norovirus* Hu/GII-4/Berga/759/02/Sp | *Norovirus* Hu/GII.4/RotterdamP5D36/2005/NL |
| *Norovirus* Hu/GII-4/Berga/RC69_02/926/03/Sp | *Norovirus* Hu/GII.4/RotterdamP5D51/2005/NL |
| | *Norovirus* Hu/GII.4/RotterdamP6D0/2006/NL |
| *Norovirus* Hu/GII-4/Brynhaven/2003/UK | *Norovirus* Hu/GII.4/RotterdamP6D33/2006/NL |
| *Norovirus* Hu/GII-4/C1-158/South Korea | *Norovirus* Hu/GII.4/RotterdamP7D0/2006/NL |
| *Norovirus* Hu/GII-4/C1-163/South Korea | *Norovirus* Hu/GII.4/RotterdamP7D119/2007/NL |
| *Norovirus* Hu/GII-4/C1-164/South Korea | *Norovirus* Hu/GII.4/RotterdamP8D65/2006/NL |
| *Norovirus* Hu/GII-4/C1-183/South Korea | *Norovirus* Hu/GII.4/Salvador/A01/2006/BRA |
| *Norovirus* Hu/GII-4/C1-184/South Korea | *Norovirus* Hu/GII.4/Salvador/A02/2006/BRA |
| *Norovirus* Hu/GII-4/C1-185/South Korea | *Norovirus* Hu/GII.4/Salvador/A05/2006/BRA |
| *Norovirus* Hu/GII-4/C1-186/South Korea | *Norovirus* Hu/GII.4/Salvador/A09/2006/BRA |
| *Norovirus* Hu/GII-4/C1-188/South Korea | *Norovirus* Hu/GII.4/Salvador/A10/2006/BRA |
| *Norovirus* Hu/GII-4/C1-198/South Korea | *Norovirus* Hu/GII.4/Salvador/A11/2006/BRA |
| *Norovirus* Hu/GII-4/C1-199/South Korea | *Norovirus* Hu/GII.4/Salvador/A12/2006/BRA |
| *Norovirus* Hu/GII-4/C1-200/South Korea | *Norovirus* Hu/GII.4/Salvador/B01/2006/BRA |
| *Norovirus* Hu/GII-4/C1-258/South Korea | *Norovirus* Hu/GII.4/Salvador/B06/2006/BRA |
| *Norovirus* Hu/GII-4/C1-275/South Korea | *Norovirus* Hu/GII.4/Salvador/B08/2006/BRA |
| *Norovirus* Hu/GII-4/C1-307/South Korea | *Norovirus* Hu/GII.4/Salvador/B09/2006/BRA |
| *Norovirus* Hu/GII-4/C1-308/South Korea | *Norovirus* Hu/GII.4/Salvador/B11/2006/BRA |
| *Norovirus* Hu/GII-4/C1-309/South Korea | *Norovirus* Hu/GII.4/Salvador/B12/2006/BRA |
| *Norovirus* Hu/GII-4/C3-89/South Korea | *Norovirus* Hu/GII.4/Salvador/C01/2006/BRA |
| *Norovirus* Hu/GII-4/C3-92/South Korea | *Norovirus* Hu/GII.4/Salvador/C02/2006/BRA |
| *Norovirus* Hu/GII-4/C4-26/South Korea | *Norovirus* Hu/GII.4/Salvador/C03/2006/BRA |
| *Norovirus* Hu/GII-4/C5-105/South Korea | *Norovirus* Hu/GII.4/Salvador/C04/2006/BRA |
| *Norovirus* Hu/GII-4/C5-107/South Korea | *Norovirus* Hu/GII.4/Salvador/C06/2006/BRA |
| *Norovirus* Hu/GII-4/C5-113/South Korea | *Norovirus* Hu/GII.4/Salvador/C07/2006/BRA |
| *Norovirus* Hu/GII-4/C5-150/South Korea | *Norovirus* Hu/GII.4/Salvador/C09/2006/BRA |
| *Norovirus* Hu/GII-4/C5-159/South Korea | *Norovirus* Hu/GII.4/Salvador/C10/2006/BRA |
| *Norovirus* Hu/GII-4/C5-76/South Korea | *Norovirus* Hu/GII.4/Salvador/C11/2006/BRA |
| *Norovirus* Hu/GII-4/C6-107/South Korea | *Norovirus* Hu/GII.4/Salvador/C12/2006/BRA |
| *Norovirus* Hu/GII-4/C6-108/South Korea | *Norovirus* Hu/GII.4/Salvador/D01/2006/BRA |
| *Norovirus* Hu/GII-4/C7-429/South Korea | *Norovirus* Hu/GII.4/Salvador/D02/2006/BRA |
| *Norovirus* Hu/GII-4/c7-446/South Korea | *Norovirus* Hu/GII.4/Salvador/D03/2006/BRA |
| *Norovirus* Hu/GII-4/C7-481/South Korea | *Norovirus* Hu/GII.4/Salvador/D04/2006/BRA |
| *Norovirus* Hu/GII-4/C7-486/South Korea | *Norovirus* Hu/GII.4/Salvador/D05/2006/BRA |
| *Norovirus* Hu/GII-4/C7-487/South Korea | *Norovirus* Hu/GII.4/Salvador/D08/2006/BRA |
| *Norovirus* Hu/GII-4/Can_Sans/787/02/Sp | *Norovirus* Hu/GII.4/Salvador/D09/2006/BRA |
| *Norovirus* Hu/GII-4/Centelles/RC05-03/909/03 | *Norovirus* Hu/GII.4/Salvador/D11/2006/BRA |
| *Norovirus* Hu/GII-4/Chester/2006/UK | *Norovirus* Hu/GII.4/Salvador/D12/2006/BRA |
| *Norovirus* Hu/GII-4/Chiba/040095/2003/JP | *Norovirus* Hu/GII.4/Salvador/E01/2006/BRA |
| *Norovirus* Hu/GII-4/Chiba/040974/2004/JP | *Norovirus* Hu/GII.4/Salvador/E02/2006/BRA |
| *Norovirus* Hu/GII-4/Chosei/061333/2006/JP | *Norovirus* Hu/GII.4/Salvador/E03/2006/BRA |
| *Norovirus* Hu/GII-4/CUK-3/2008/KR | *Norovirus* Hu/GII.4/Salvador/E06/2006/BRA |
| *Norovirus* Hu/GII-4/EAUS Wd/2008/UK | *Norovirus* Hu/GII.4/Salvador/E09/2006/BRA |
| *Norovirus* Hu/GII-4/Ehime1/2006/JP | *Norovirus* Hu/GII.4/Salvador/E10/2006/BRA |
| *Norovirus* Hu/GII-4/Ehime2/2006/JP | *Norovirus* Hu/GII.4/Salvador/F01/2006/BRA |
| *Norovirus* Hu/GII-4/Ehime5/2006/JP | *Norovirus* Hu/GII.4/Salvador/F06/2006/BRA |

TABLE 1-continued

| *Norovirus* Strains |
|---|
| *Norovirus* Hu/GII-4/ES001/2003/BRA |
| *Norovirus* Hu/GII-4/ES003/2003/BRA |
| *Norovirus* Hu/GII-4/ES008/2003/BRA |
| *Norovirus* Hu/GII-4/ES014/2003/BRA |
| *Norovirus* Hu/GII-4/ES017/2003/BRA |
| *Norovirus* Hu/GII-4/ES020/2003/BRA |
| *Norovirus* Hu/GII-4/ES029/2003/BRA |
| *Norovirus* Hu/GII-4/ES035/2003/BRA |
| *Norovirus* Hu/GII-4/ES040/2003/BRA |
| *Norovirus* Hu/GII-4/ES272/2003/BRA |
| *Norovirus* Hu/GII-4/FUMI/2010/JP |
| *Norovirus* Hu/GII-4/Funabashi/050601/2005/JP |
| *Norovirus* Hu/GII-4/Funabashi/060548/2006/JP |
| *Norovirus* Hu/GII-4/He Wd/2008/UK |
| *Norovirus* Hu/GII-4/Hiroshima1/2006/JP |
| *Norovirus* Hu/GII-4/Hiroshima2/2006/JP |
| *Norovirus* Hu/GII-4/Ho Wd/2008/UK |
| *Norovirus* Hu/GII-4/Hokkaido1/2006/JP |
| *Norovirus* Hu/GII-4/Hokkaido2/2006/JP |
| *Norovirus* Hu/GII-4/Hokkaido3/2006/JP |
| *Norovirus* Hu/GII-4/Hokkaido4/2006/JP |
| *Norovirus* Hu/GII-4/Hokkaido5/2006/JP |
| *Norovirus* Hu/GII-4/Ichikawa/050701/2005/JP |
| *Norovirus* Hu/GII-4/Ichikawa/060832/2006/JP |
| *Norovirus* Hu/GII-4/Ichikawa/061159/2006/JP |
| *Norovirus* Hu/GII-4/Inba/050590/2005/JP |
| *Norovirus* Hu/GII-4/Inba/060946/2006/JP |
| *Norovirus* Hu/GII-4/Inba/060966/2006/JP |
| *Norovirus* Hu/GII-4/Inba/061099/2006/JP |
| *Norovirus* Hu/GII-4/Inba/061224/2006/JP |
| *Norovirus* Hu/GII-4/Inba/061365/2006/JP |
| *Norovirus* Hu/GII-4/Inba/061367/2006/JP |
| *Norovirus* Hu/GII-4/Inba/061421/2006/JP |
| *Norovirus* Hu/GII-4/Isumi/060936/2006/JP |
| *Norovirus* Hu/GII-4/Jeju-1/2007/KOR |
| *Norovirus* Hu/GII-4/Jeju-10/2007/KOR |
| *Norovirus* Hu/GII-4/Jeju-11/2007/KOR |
| *Norovirus* Hu/GII-4/Jeju-12/2007/KOR |
| *Norovirus* Hu/GII-4/Jeju-14/2007/KOR |
| *Norovirus* Hu/GII-4/Jeju-15/2007/KOR |
| *Norovirus* Hu/GII-4/Jeju-16/2007/KOR |
| *Norovirus* Hu/GII-4/Jeju-19/2007/KOR |
| *Norovirus* Hu/GII-4/Jeju-2/2007/KOR |
| *Norovirus* Hu/GII-4/Jeju-21/2007/KOR |
| *Norovirus* Hu/GII-4/Jeju-22/2007/KOR |
| *Norovirus* Hu/GII-4/Jeju-27/2007/KOR |
| *Norovirus* Hu/GII-4/Jeju-29/2007/KOR |
| *Norovirus* Hu/GII-4/Jeju-32/2007/KOR |
| *Norovirus* Hu/GII-4/Jeju-34/2007/KOR |
| *Norovirus* Hu/GII-4/Jeju-4/2007/KOR |
| *Norovirus* Hu/GII-4/Jeju-41/2007/KOR |
| *Norovirus* Hu/GII-4/Jeju-47/2007/KOR |
| *Norovirus* Hu/GII-4/Jeju-9/2007/KOR |
| *Norovirus* Hu/GII-4/JN15-Newc/2006/UK |
| *Norovirus* Hu/GII-4/JN3-Newc/2006/UK |
| *Norovirus* Hu/GII-4/Kaiso/030556/2003/JP |
| *Norovirus* Hu/GII-4/Kaiso/060848/2006/JP |
| *Norovirus* Hu/GII-4/Kaiso/061318/2006/JP |
| *Norovirus* Hu/GII-4/Kashiwa/060802/2006/JP |
| *Norovirus* Hu/GII-4/Kashiwa/061256/2006/JP |
| *Norovirus* Hu/GII-4/Katori/041008/2004/JP |
| *Norovirus* Hu/GII-4/Katori/061002/2006/JP |
| *Norovirus* Hu/GII-4/Katori/061492/2006/JP |
| *Norovirus* Hu/GII-4/Kimitsu/041440/2005/JP |
| *Norovirus* Hu/GII-4/Kimitsu/061146/2006/JP |
| *Norovirus* Hu/GII-4/Kimitsu/061427/2006/JP |
| *Norovirus* Hu/GII-4/Kumamoto1/2006/JP |
| *Norovirus* Hu/GII-4/Kumamoto2/2006/JP |
| *Norovirus* Hu/GII-4/Kumamoto3/2006/JP |
| *Norovirus* Hu/GII-4/Kumamoto4/2006/JP |
| *Norovirus* Hu/GII-4/Kumamoto5/2006/JP |
| *Norovirus* Hu/GII-4/Lincoln House/2006/UK |
| *Norovirus* Hu/GII-4/Manresa/81_02/914/02/Sp |
| *Norovirus* Hu/GII-4/Matsudo/021071/2002/JP |
| *Norovirus* Hu/GII-4/Matsudo/060907/2006/JP |
| *Norovirus* Hu/GII-4/Matsudo/061442/2006/JP |
| *Norovirus* Hu/GII.4/Salvador/F08/2006/BRA |
| *Norovirus* Hu/GII.4/Salvador/F09/2006/BRA |
| *Norovirus* Hu/GII.4/Salvador/F10/2006/BRA |
| *Norovirus* Hu/GII.4/Salvador/F11/2006/BRA |
| *Norovirus* Hu/GII.4/Salvador/F12/2006/BRA |
| *Norovirus* Hu/GII.4/Salvador/G01/2006/BRA |
| *Norovirus* Hu/GII.4/Salvador/G02/2006/BRA |
| *Norovirus* Hu/GII.4/Salvador/G03/2006/BRA |
| *Norovirus* Hu/GII.4/Salvador/G05/2006/BRA |
| *Norovirus* Hu/GII.4/Salvador/G07/2006/BRA |
| *Norovirus* Hu/GII.4/Salvador/G08/2006/BRA |
| *Norovirus* Hu/GII.4/Salvador/G09/2006/BRA |
| *Norovirus* Hu/GII.4/Salvador/H05/2006/BRA |
| *Norovirus* Hu/GII.4/Salvador/H06/2006/BRA |
| *Norovirus* Hu/GII.4/Salvador/H07/2006/BRA |
| *Norovirus* Hu/GII.4/Salvador/H09/2006/BRA |
| *Norovirus* Hu/GII.4/Salvador/H11/2006/BRA |
| *Norovirus* Hu/GII.4/Salvador/H12/2006/BRA |
| *Norovirus* Hu/GII.4/Samokov172/2007/BGR |
| *Norovirus* Hu/GII.4/Seoul/0015/2007/KOR |
| *Norovirus* Hu/GII.4/Seoul/0017/2007/KOR |
| *Norovirus* Hu/GII.4/Seoul/0023/2007/KOR |
| *Norovirus* Hu/GII.4/Seoul/0039/2007/KOR |
| *Norovirus* Hu/GII.4/Seoul/0040/2007/KOR |
| *Norovirus* Hu/GII.4/Seoul/0045/2007/KOR |
| *Norovirus* Hu/GII.4/Seoul/0053/2007/KOR |
| *Norovirus* Hu/GII.4/Seoul/0059/2008/KOR |
| *Norovirus* Hu/GII.4/Seoul/0065/2008/KOR |
| *Norovirus* Hu/GII.4/Seoul/0066/2008/KOR |
| *Norovirus* Hu/GII.4/Seoul/0068/2008/KOR |
| *Norovirus* Hu/GII.4/Seoul/0074/2008/KOR |
| *Norovirus* Hu/GII.4/Seoul/0093/2008/KOR |
| *Norovirus* Hu/GII.4/Seoul/0097/2008/KOR |
| *Norovirus* Hu/GII.4/Seoul/0104/2008/KOR |
| *Norovirus* Hu/GII.4/Seoul/0106/2008/KOR |
| *Norovirus* Hu/GII.4/Seoul/0120/2008/KOR |
| *Norovirus* Hu/GII.4/Seoul/0134/2008/KOR |
| *Norovirus* Hu/GII.4/Seoul/0136/2008/KOR |
| *Norovirus* Hu/GII.4/Seoul/0176/2008/KOR |
| *Norovirus* Hu/GII.4/Seoul/0183/2008/KOR |
| *Norovirus* Hu/GII.4/Seoul/0199/2007/KOR |
| *Norovirus* Hu/GII.4/Seoul/0200/2007/KOR |
| *Norovirus* Hu/GII.4/Seoul/0202/2007/KOR |
| *Norovirus* Hu/GII.4/Seoul/0205/2007/KOR |
| *Norovirus* Hu/GII.4/Seoul/0206/2007/KOR |
| *Norovirus* Hu/GII.4/Seoul/0207/2007/KOR |
| *Norovirus* Hu/GII.4/Seoul/0209/2007/KOR |
| *Norovirus* Hu/GII.4/Seoul/0210/2007/KOR |
| *Norovirus* Hu/GII.4/Seoul/0215/2007/KOR |
| *Norovirus* Hu/GII.4/Seoul/0217/2007/KOR |
| *Norovirus* Hu/GII.4/Seoul/0218/2007/KOR |
| *Norovirus* Hu/GII.4/Seoul/0221/2007/KOR |
| *Norovirus* Hu/GII.4/Seoul/0228/2008/KOR |
| *Norovirus* Hu/GII.4/Seoul/0229/2008/KOR |
| *Norovirus* Hu/GII.4/Seoul/0230/2008/KOR |
| *Norovirus* Hu/GII.4/Seoul/0233/2008/KOR |
| *Norovirus* Hu/GII.4/Seoul/0234/2008/KOR |
| *Norovirus* Hu/GII.4/Seoul/0237/2008/KOR |
| *Norovirus* Hu/GII.4/Seoul/0244/2008/KOR |
| *Norovirus* Hu/GII.4/Seoul/0245/2008/KOR |
| *Norovirus* Hu/GII.4/Shenzhen104-06/2006/CHN |
| *Norovirus* Hu/GII.4/Shenzhen12-06/2006/CHN |
| *Norovirus* Hu/GII.4/Shenzhen120-06/2006/CHN |
| *Norovirus* Hu/GII.4/Shenzhen122-06/2006/CHN |
| *Norovirus* Hu/GII.4/Shenzhen124-06/2006/CHN |
| *Norovirus* Hu/GII.4/Shenzhen166-06/2006/CHN |
| *Norovirus* Hu/GII.4/Shenzhen172-06/2006/CHN |
| *Norovirus* Hu/GII.4/Shenzhen173-06/2006/CHN |
| *Norovirus* Hu/GII.4/Shenzhen176-06/2006/CHN |
| *Norovirus* Hu/GII.4/Shenzhen178-06/2006/CHN |
| *Norovirus* Hu/GII.4/Shenzhen179-06/2006/CHN |
| *Norovirus* Hu/GII.4/Shenzhen181-06/2006/CHN |
| *Norovirus* Hu/GII.4/Shenzhen196-06/2006/CHN |
| *Norovirus* Hu/GII.4/Shenzhen21-06/2006/CHN |
| *Norovirus* Hu/GII.4/Shenzhen27-06/2006/CHN |
| *Norovirus* Hu/GII.4/Shenzhen44-06/2006/CHN |
| *Norovirus* Hu/GII.4/Shenzhen63-06/2006/CHN |
| *Norovirus* Hu/GII.4/Shenzhen66-06/2006/CHN |

TABLE 1-continued

| *Norovirus* Strains |
|---|
| *Norovirus* Hu/GII-4/Matsudo/061495/2006/JP |
| *Norovirus* Hu/GII-4/Miyagi2/2006/JP |
| *Norovirus* Hu/GII-4/Miyagi4/2006/JP |
| *Norovirus* Hu/GII-4/Miyagi5/2006/JP |
| *Norovirus* Hu/GII-4/Morella/867/03/Sp |
| *Norovirus* Hu/GII-4/Narashino/060903/2006/JP |
| *Norovirus* Hu/GII-4/Narashino/061281/2006/JP |
| *Norovirus* Hu/GII-4/NFL-1602VR88/02-2005/CAN |
| *Norovirus* Hu/GII-4/NFL1903/VR13/02-2005/CAN |
| *Norovirus* Hu/GII-4/Noda/061126/2006/JP |
| *Norovirus* Hu/GII-4/OM06213/2006/UK |
| *Norovirus* Hu/GII-4/Osaka/1998/JPN |
| *Norovirus* Hu/GII-4/passenger 1/OB6/2007/UK |
| *Norovirus* Hu/GII-4/Patient1/2004/UK |
| *Norovirus* Hu/GII-4/Patient10/2007/UK |
| *Norovirus* Hu/GII-4/Patient11/2007/UK |
| *Norovirus* Hu/GII-4/Patient2-1/2006/UK |
| *Norovirus* Hu/GII-4/Patient2-4/2006/UK |
| *Norovirus* Hu/GII-4/Patient5/2006/UK |
| *Norovirus* Hu/GII-4/Patient6/2006/UK |
| *Norovirus* Hu/GII-4/Patient7-1/2006/UK |
| *Norovirus* Hu/GII-4/Patient7-2/2006/UK |
| *Norovirus* Hu/GII-4/Patient8/2006/UK |
| *Norovirus* Hu/GII-4/Patient9/2006/UK |
| *Norovirus* Hu/GII-4/Peniscola/583/02/Sp |
| *Norovirus* Hu/GII-4/Peniscola/852/02/Sp |
| *Norovirus* Hu/GII-4/Pineda_de_Mar/792/02/Sp |
| *Norovirus* Hu/GII-4/Portsmouth/2004/UK |
| *Norovirus* Hu/GII-4/Res._S.Patricio/757/02/Sp |
| *Norovirus* Hu/GII-4/Res_Enbellpuig/793/02/Sp |
| *Norovirus* Hu/GII-4/RH488/2008/UK |
| *Norovirus* Hu/GII-4/Rhyl-FCH/2008/UK |
| *Norovirus* Hu/GII-4/Rhyl440/2004/UK |
| *Norovirus* Hu/GII-4/Saga1/2006/JP |
| *Norovirus* Hu/GII-4/Saga4/2006/JP |
| *Norovirus* Hu/GII-4/Saga5/2006/JP |
| *Norovirus* Hu/GII-4/Sakai2/2006/JP |
| *Norovirus* Hu/GII-4/Sakai3/2006/JP |
| *Norovirus* Hu/GII-4/Sakai4/2006/JP |
| *Norovirus* Hu/GII-4/Sallent/RC_73_02/921/02/Sp |
| *Norovirus* Hu/GII-4/Sanbu/050878/2006/JP |
| *Norovirus* Hu/GII-4/STDGH/2008/UK |
| *Norovirus* Hu/GII-4/Tarrasa/772/02/Sp |
| *Norovirus* Hu/GII-4/Toyama1/2006/JP |
| *Norovirus* Hu/GII-4/Toyama4/2006/JP |
| *Norovirus* Hu/GII-4/Toyama5/2006/JP |
| *Norovirus* Hu/GII-4/U/2004/UK |
| *Norovirus* Hu/GII-4/Valencia/530i/01/Sp |
| *Norovirus* Hu/GII-4/Vilanova/767/02/Sp |
| *Norovirus* Hu/GII.4/10468/2005/BRA |
| *Norovirus* Hu/GII.4/10513/2005/BRA |
| *Norovirus* Hu/GII.4/10526/2004/IRL |
| *Norovirus* Hu/GII.4/10624/2005/BRA |
| *Norovirus* Hu/GII.4/10641/2005/BRA |
| *Norovirus* Hu/GII.4/10661/2005/BRA |
| *Norovirus* Hu/GII.4/10668/2005/BRA |
| *Norovirus* Hu/GII.4/10801/2005/BRA |
| *Norovirus* Hu/GII.4/10852/2005/BRA |
| *Norovirus* Hu/GII.4/10897/2005/BRA |
| *Norovirus* Hu/GII.4/10942/2005/BRA |
| *Norovirus* Hu/GII.4/10962/2005/BRA |
| *Norovirus* Hu/GII.4/11779/2005/BRA |
| *Norovirus* Hu/GII.4/11869/2006/BRA |
| *Norovirus* Hu/GII.4/11952/2006/BRA |
| *Norovirus* Hu/GII.4/12016/2006/BRA |
| *Norovirus* Hu/GII.4/12044/2006/BRA |
| *Norovirus* Hu/GII.4/12079/2006/BRA |
| *Norovirus* Hu/GII.4/12090/2006/BRA |
| *Norovirus* Hu/GII.4/12091/2006/BRA |
| *Norovirus* Hu/GII.4/12098/2006/BRA |
| *Norovirus* Hu/GII.4/12103/2006/BRA |
| *Norovirus* Hu/GII.4/Shenzhen76-06/2006/CHN |
| *Norovirus* Hu/GII.4/Shenzhen79-06/2006/CHN |
| *Norovirus* Hu/GII.4/Shenzhen85-06/2006/CHN |
| *Norovirus* Hu/GII.4/Shenzhen95-06/2006/CHN |
| *Norovirus* Hu/GII.4/SHZH004/2007/CHN |
| *Norovirus* Hu/GII.4/SHZH009/2007/CHN |
| *Norovirus* Hu/GII.4/SHZH012/2007/CHN |
| *Norovirus* Hu/GII.4/SHZH154/2007/CHN |
| *Norovirus* Hu/GII.4/SHZH166/2007/CHN |
| *Norovirus* Hu/GII.4/SHZH168/2007/CHN |
| *Norovirus* Hu/GII.4/SSCS/2005/USA |
| *Norovirus* Hu/GII.4/Stockholm/19865/2008/SE |
| *Norovirus* Hu/GII.4/Su2445/03O/AU |
| *Norovirus* Hu/GII.4/Sydney1145/98S/AU |
| *Norovirus* Hu/GII.4/Sydney1347/98S/AU |
| *Norovirus* Hu/GII.4/Sydney1696/98S/AU |
| *Norovirus* Hu/GII.4/Sydney198N/04S/AU |
| *Norovirus* Hu/GII.4/Sydney2086/98S/AU |
| *Norovirus* Hu/GII.4/Sydney2113/98S/AU |
| *Norovirus* Hu/GII.4/Sydney2145/98O/AU |
| *Norovirus* Hu/GII.4/Sydney267J/04S/AU |
| *Norovirus* Hu/GII.4/Sydney284/97S/AU |
| *Norovirus* Hu/GII.4/Sydney348/97O/AU |
| *Norovirus* Hu/GII.4/Sydney4012/02S/AU |
| *Norovirus* Hu/GII.4/Sydney4134/01S/AU |
| *Norovirus* Hu/GII.4/Sydney4136/01S/AU |
| *Norovirus* Hu/GII.4/Sydney4209/01S/AU |
| *Norovirus* Hu/GII.4/Sydney4237/01S/AU |
| *Norovirus* Hu/GII.4/Sydney4262/01S/AU |
| *Norovirus* Hu/GII.4/Sydney4264/01S/AU |
| *Norovirus* Hu/GII.4/Sydney4266/01S/AU |
| *Norovirus* Hu/GII.4/Sydney4288/02S/AU |
| *Norovirus* Hu/GII.4/Sydney4337/02S/AU |
| *Norovirus* Hu/GII.4/Sydney4360/02S/AU |
| *Norovirus* Hu/GII.4/Sydney4384/02S/AU |
| *Norovirus* Hu/GII.4/Sydney4416/02S/AU |
| *Norovirus* Hu/GII.4/Sydney4477/02S/AU |
| *Norovirus* Hu/GII.4/Sydney4480/02S/AU |
| *Norovirus* Hu/GII.4/Sydney591/97S/AU |
| *Norovirus* Hu/GII.4/Sydney625K/04O/AU |
| *Norovirus* Hu/GII.4/Sydney642/97S/AU |
| *Norovirus* Hu/GII.4/Sydney715D/04S/AU |
| *Norovirus* Hu/GII.4/Sydney740C/2006/AUS |
| *Norovirus* Hu/GII.4/Sydney755/97S/AU |
| *Norovirus* Hu/GII.4/Sydney762I/04S/AU |
| *Norovirus* Hu/GII.4/Sydney776/99O/AU |
| *Norovirus* Hu/GII.4/Sydney812J/02O/AU |
| *Norovirus* Hu/GII.4/Sydney917J/02O/AU |
| *Norovirus* Hu/GII.4/Taipei-AB/06/TW |
| *Norovirus* Hu/GII.4/Taipei-AD/06/TW |
| *Norovirus* Hu/GII.4/Taipei-AE/06/TW |
| *Norovirus* Hu/GII.4/Taipei-AN/06/TW |
| *Norovirus* Hu/GII.4/Taipei-AN1/06/TW |
| *Norovirus* Hu/GII.4/Taipei-AP/06/TW |
| *Norovirus* Hu/GII.4/Taipei-AR/06/TW |
| *Norovirus* Hu/GII.4/Taipei-AS/06/TW |
| *Norovirus* Hu/GII.4/Taipei-AW/06/TW |
| *Norovirus* Hu/GII.4/Taipei-AZ/06/TW |
| *Norovirus* Hu/GII.4/Taipei-BB/06/TW |
| *Norovirus* Hu/GII.4/Taipei-BD/06/TW |
| *Norovirus* Hu/GII.4/Taipei-BG/06/TW |
| *Norovirus* Hu/GII.4/Taipei-D/06/TW |
| *Norovirus* Hu/GII.4/Taipei-U/06/TW |
| *Norovirus* Hu/GII.4/Taipei-V/06/TW |
| *Norovirus* Hu/GII.4/Terneuzen70/2006/NL |
| *Norovirus* Hu/GII.4/Tianjin/2/2008/CHN |
| *Norovirus* Hu/GII.4/Tianjin/26/2008/CHN |
| *Norovirus* Hu/GII.4/Tianjin/27/2008/CHN |
| *Norovirus* Hu/GII.4/Tianjin/28/2008/CHN |
| *Norovirus* Hu/GII.4/Tianjin/29/2008/CHN |
| *Norovirus* Hu/GII.4/Tianjin/30/2008/CHN |
| *Norovirus* Hu/GII.4/Tianjin/31/2008/CHN |
| *Norovirus* Hu/GII.4/Tianjin/33/2008/CHN |
| *Norovirus* Hu/GII.4/Tianjin/34/2008/CHN |
| *Norovirus* Hu/GII.4/Tianjin/36/2008/CHN |
| *Norovirus* Hu/GII.4/Tianjin/42/2008/CHN |
| *Norovirus* Hu/GII.4/Tianjin/50/2008/CHN |
| *Norovirus* Hu/GII.4/Tianjin/55/2008/CHN |

TABLE 1-continued

| *Norovirus* Strains | |
|---|---|
| *Norovirus* Hu/GII.4/12155/2006/BRA | *Norovirus* Hu/GII.4/Tianjin/62/2008/CHN |
| *Norovirus* Hu/GII.4/12161/2006/BRA | *Norovirus* Hu/GII.4/Tianjin/66/2008/CHN |
| *Norovirus* Hu/GII.4/122/17/2006/RJ/BRA | *Norovirus* Hu/GII.4/Tianjin/68/2008/CHN |
| *Norovirus* Hu/GII.4/124/12/2006/RJ/BRA | *Norovirus* Hu/GII.4/Tianjin/72/2008/CHN |
| *Norovirus* Hu/GII.4/124/16/2006/RJ/BRA | *Norovirus* Hu/GII.4/Tianjin/75/2008/CHN |
| *Norovirus* Hu/GII.4/130/13/2006/RJ/BRA | *Norovirus* Hu/GII.4/Tianjin/9/2008/CHN |
| *Norovirus* Hu/GII.4/13370/2007/BRA | *Norovirus* Hu/GII.4/Tianjin/90/2008/CHN |
| *Norovirus* Hu/GII.4/13473/2007/BRA | *Norovirus* Hu/GII.4/Tianjin/91/2008/CHN |
| *Norovirus* Hu/GII.4/13504/2007/BRA | *Norovirus* Hu/GII.4/Turramurra597U/04O/AU |
| *Norovirus* Hu/GII.4/13531/2007/BRA | *Norovirus* Hu/GII.4/Turramurra604J/04O/AU |
| *Norovirus* Hu/GII.4/13563/2007/BRA | *Norovirus* Hu/GII.4/VIC0682/2007/AU |
| *Norovirus* Hu/GII.4/13693/2007/BRA | *Norovirus* Hu/GII.4/VIC3850/2007/AU |
| *Norovirus* Hu/GII.4/13707/2007/BRA | *Norovirus* Hu/GII.4/VIC3852/2007/AU |
| *Norovirus* Hu/GII.4/13822/2007/BRA | *Norovirus* Hu/GII.4/VIC3863/2007/AU |
| *Norovirus* Hu/GII.4/13827/2007/BRA | *Norovirus* Hu/GII.4/VIC4670/2007/AU |
| *Norovirus* Hu/GII.4/13930/2007/BRA | *Norovirus* Hu/GII.4/VIC4681/2007/AU |
| *Norovirus* Hu/GII.4/13945/2007/BRA | *Norovirus* Hu/GII.4/VIC4906/2007/AU |
| *Norovirus* Hu/GII.4/14/1/19/2007/RJ/BRA | *Norovirus* Hu/GII.4/VIC4911/2007/AU |
| *Norovirus* Hu/GII.4/14013/2007/BRA | *Norovirus* Hu/GII.4/VIC8188/2007/AU |
| *Norovirus* Hu/GII.4/14865/2008/RJ/BRA | *Norovirus* Hu/GII.4/VIC8193/2007/AU |
| *Norovirus* Hu/GII.4/2004/NL | *Norovirus* Hu/GII.4/WA001D/2007/AU |
| *Norovirus* Hu/GII.4/2006b/AS2/2007/CHN | *Norovirus* Hu/GII.4/WA080B/2008/AU |
| *Norovirus* Hu/GII.4/2006b/AS6/2007/CHN | *Norovirus* Hu/GII.4/WA125C/2007/AU |
| *Norovirus* Hu/GII.4/2006b/AS7/2007/CHN | *Norovirus* Hu/GII.4/WA178J/2007/AU |
| *Norovirus* Hu/GII.4/2006b/BX7/2007/CHN | *Norovirus* Hu/GII.4/WA229F/2007/AU |
| *Norovirus* Hu/GII.4/2006b/DD6/2007/CHN | *Norovirus* Hu/GII.4/WA432N/2007/AU |
| *Norovirus* Hu/GII.4/2006b/DD9/2007/CHN | *Norovirus* Hu/GII.4/WA476G/2007/AU |
| *Norovirus* Hu/GII.4/2006b/DL2/2007/CHN | *Norovirus* Hu/GII.4/WA530G/2007/AU |
| *Norovirus* Hu/GII.4/2006b/DL4/2007/CHN | *Norovirus* Hu/GII.4/WA670N/2007/AU |
| *Norovirus* Hu/GII.4/2006b/FS7/2007/CHN | *Norovirus* Hu/GII.4/WA971W/2007/AU |
| *Norovirus* Hu/GII.4/2006b/FX2/2007/CHN | *Norovirus* Hu/GII.4/WA988N/2007/AU |
| *Norovirus* Hu/GII.4/2006b/FX3/2007/CHN | *Norovirus* Hu/GII.4/Wellington/1995/USA |
| *Norovirus* Hu/GII.4/2006b/FX8/2007/CHN | *Norovirus* Hu/GII.4/Yerseke38/2006/NL |
| *Norovirus* Hu/GII.4/2006b/JZ7/2007/CHN | *Norovirus* Hu/GII.4a/Sofia367/2007/BGR |
| *Norovirus* Hu/GII.4/2006b/JZ8/2007/CHN | *Norovirus* Hu/GII4/47836/Hainan/06/CHN |
| *Norovirus* Hu/GII.4/2006b/LY10/2007/CHN | *Norovirus* Hu/GII4/47847/Hainan/06/CHN |
| *Norovirus* Hu/GII.4/2006b/LY2/2007/CHN | *Norovirus* Hu/GII4/47925/Hebei/06/CHN |
| *Norovirus* Hu/GII.4/2006b/LY4/2007/CHN | *Norovirus* Hu/GII4/48178/Shanxi/06/CHN |
| *Norovirus* Hu/GII.4/2006b/LY6/2007/CHN | *Norovirus* Hu/GII4/49613/Shaanxi/06/CHN |
| *Norovirus* Hu/GII.4/2006b/LY7/2007/CHN | *Norovirus* Hu/GII4/50143/Jilin/06/CHN |
| *Norovirus* Hu/GII.4/2006b/PJ4/2007/CHN | *Norovirus* Hu/GII4/50318/Hebei/06/CHN |
| *Norovirus* Hu/GII.4/2006b/SY2/2007/CHN | *Norovirus* Hu/GII4/50483/Jilin/06/CHN |
| *Norovirus* Hu/GII.4/4336/2007/IRL | *Norovirus* Hu/GII4/50496/Jilin/06/CHN |
| *Norovirus* Hu/GII.4/754 N.Novgorod/2008/RUS | *Norovirus* Hu/GII4/50503/Jilin/06/CHN |
| *Norovirus* Hu/GII.4/7883/2006/IRL | *Norovirus* Hu/GII4/50510/Jilin/06/CHN |
| *Norovirus* Hu/GII.4/866 N.Novgorod/2008/RUS | *Norovirus* Hu/GII4/50511/Jilin/06/CHN |
| *Norovirus* Hu/GII.4/884 N.Novgorod/2008/RUS | *Norovirus* Hu/GII4/50512/Jilin/06/CHN |
| *Norovirus* Hu/GII.4/8854/2004/IRL | *Norovirus* Hu/GII4/50514/Jilin/06/CHN |
| *Norovirus* Hu/GII.4/Apeldoorn317/2007/NL | *Norovirus* Hu/GII4/50515/Jilin/06/CHN |
| *Norovirus* Hu/GII.4/Beijing/167/2007 | *Norovirus* Hu/GII4/50516/Jilin/06/CHN |
| *Norovirus* Hu/GII.4/Beijing/170/2007 | *Norovirus* Hu/GII4/50523/Jilin/06/CHN |
| *Norovirus* Hu/GII.4/Beijing/194/2007 | *Norovirus* Hu/GII4/50524/Jilin/06/CHN |
| *Norovirus* Hu/GII.4/Beijing/212/2007 | *Norovirus* Hu/GII4/50535/Jilin/06/CHN |
| *Norovirus* Hu/GII.4/Beijing/222/2007 | *Norovirus* Hu/GII4/50540/Jilin/06/CHN |
| *Norovirus* Hu/GII.4/Beijing/225/2007 | *Norovirus* Hu/GII4/50559/Jilin/06/CHN |
| *Norovirus* Hu/GII.4/BJ172/2007/CHN | *Norovirus* Hu/GII4/50562/Jilin/06/CHN |
| *Norovirus* Hu/GII.4/BJ222/2008/CHN | *Norovirus* Hu/GII4/50564/Jilin/06/CHN |
| *Norovirus* Hu/GII.4/BJ225/2008/CHN | *Norovirus* Hu/GII4/50566/Jilin/06/CHN |
| *Norovirus* Hu/GII.4/BJ226/2008/CHN | *Norovirus* Hu/GII4/50567/Jilin/06/CHN |
| *Norovirus* Hu/GII.4/BJ228/2008/CHN | *Norovirus* Hu/GII4/50569/Jilin/06/CHN |
| *Norovirus* Hu/GII.4/BJ231/2008/CHN | *Norovirus* Hu/GII4/50580/Jilin/06/CHN |
| *Norovirus* Hu/GII.4/BJ238/2008/CHN | *Norovirus* Hu/GII4/51002/Jilin/06/CHN |
| *Norovirus* Hu/GII.4/BJ240/2008/CHN | *Norovirus* Hu/GII4/51031/Jilin/06/CHN |
| *Norovirus* Hu/GII.4/BJ244/2008/CHN | *Norovirus* Hu/GII4/51074/Jilin/06/CHN |
| *Norovirus* Hu/GII.4/BJ245/2008/CHN | *Norovirus* Hu/GII4/51078/Jilin/06/CHN |
| *Norovirus* Hu/GII.4/BJ299/2008/CHN | *Norovirus* Hu/GII4/51079/Jilin/06/CHN |
| *Norovirus* Hu/GII.4/Boxmeer/90104-42217/2009/NLD | *Norovirus* Hu/GII4/51267/Anhui/06/CHN |
| *Norovirus* Hu/GII.4/CHDC2094/1974/US | *Norovirus* Hu/GII4/51268/Anhui/06/CHN |
| *Norovirus* Hu/GII.4/CHDC3967/1988/US | *Norovirus* Hu/GII4/51270/Anhui/06/CHN |
| *Norovirus* Hu/GII.4/CHDC4108/1987/US | *Norovirus* Hu/GII4/51273/Anhui/06/CHN |
| *Norovirus* Hu/GII.4/CHDC4871/1977/US | *Norovirus* Hu/GII4/51275/Anhui/06/CHN |
| *Norovirus* Hu/GII.4/CHDC5191/1974/US | *Norovirus* Hu/GII4/51850/Hebei/07/CHN |
| *Norovirus* Hu/GII.4/Chungnam(1-32)/2008/Kor | *Norovirus* Hu/GII4/51856/Hebei/07/CHN |
| | *Norovirus* Hu/GII4/51873/Hebei/07/CHN |
| | *Norovirus* Hu/GII4/51875/Hebei/07/CHN |
| | *Norovirus* Hu/GII4/52066/Shanghai/06/CHN |
| | *Norovirus* Hu/GII4/52217/Shanghai/06/CHN |
| | *Norovirus* Hu/GII4/52240/Shanghai/06/CHN |

TABLE 1-continued

| *Norovirus* Strains |
|---|
| *Norovirus* Hu/GII.4/Chungnam(10-70)/2008/Kor |
| *Norovirus* Hu/GII.4/Chungnam(10-88)/2008/Kor |
| *Norovirus* Hu/GII.4/Chungnam(11-100)/2008/Kor |
| *Norovirus* Hu/GII.4/Chungnam(11-104)/2008/Kor |
| *Norovirus* Hu/GII.4/Chungnam(11-91)/2008/Kor |
| *Norovirus* Hu/GII.4/Chungnam(11-94)/2008/Kor |
| *Norovirus* Hu/GII.4/Chungnam(12-107)/2008/Kor |
| *Norovirus* Hu/GII.4/Chungnam(12-170)/2008/Kor |
| *Norovirus* Hu/GII.4/Chungnam(12-176)/2008/Kor |
| *Norovirus* Hu/GII.4/Chungnam(12-77)/2008/Kor |
| *Norovirus* Hu/GII.4/Chungnam(4-29)/2008/Kor |
| *Norovirus* Hu/GII.4/Chungnam(6-85)/2008/Kor |
| *Norovirus* Hu/GII.4/Chungnam(9-34)/2008/Kor |
| *Norovirus* Hu/GII.4/Chungnam(out-ag5)/2008/Kor |
| *Norovirus* Hu/GII.4/Chungnam(out-as6)/2008/Kor |
| *Norovirus* Hu/GII.4/Chungnam(out-br1)/2008/Kor |
| *Norovirus* Hu/GII.4/Chungnam(out-br15)/2008/Kor |
| *Norovirus* Hu/GII.4/Chungnam(out-br17)/2008/Kor |
| *Norovirus* Hu/GII.4/Chungnam(out-br25)/2008/Kor |
| *Norovirus* Hu/GII.4/Chungnam(out-ns9)/2008/Kor |
| *Norovirus* Hu/GII.4/Chungnam(out-sc8)/2008/Kor |
| *Norovirus* Hu/GII.4/Chungnam(out-sc9)/2008/Kor |
| *Norovirus* Hu/GII.4/Chungnam(out-ss13)/2008/Kor |
| *Norovirus* Hu/GII.4/Chungnam(out-ss20)/2008/Kor |
| *Norovirus* Hu/GII.4/Chungnam(out-ss23)/2008/Kor |
| *Norovirus* Hu/GII.4/Chungnam(out-ss33)/2008/Kor |
| *Norovirus* Hu/GII.4/Chungnam(out-ss38)/2008/Kor |
| *Norovirus* Hu/GII.4/Chungnam(out-ssh1)/2008/Kor |
| *Norovirus* Hu/GII.4/cruise ship/VS122/2006/USA |
| *Norovirus* Hu/GII.4/cruiseship/2007/ZAF |
| *Norovirus* Hu/GII.4/Cuernavaca/50318/2007/MEX |
| *Norovirus* Hu/GII.4/Cuernavaca/50320/2007/MEX |
| *Norovirus* Hu/GII.4/Cuernavaca/7366/2008/MEX |
| *Norovirus* Hu/GII.4/Cuernavaca/7366v4/2008/MEX |
| *Norovirus* Hu/GII.4/Cuernavaca/8030/2008/MEX |
| *Norovirus* Hu/GII.4/Cuernavaca/8034/2008/MEX |
| *Norovirus* Hu/GII.4/DenHaag54/2006/NL |
| *Norovirus* Hu/GII.4/DenHaag89/2006/NL |
| *Norovirus* Hu/GII.4/Dhaka8/2004/BGD |
| *Norovirus* Hu/GII.4/Dijon/E872/2002/FRA |
| *Norovirus* Hu/GII.4/DilwichHill203D/04O/AU |
| *Norovirus* Hu/GII4/52398/Jilin/07/CHN |
| *Norovirus* Hu/GII4/52415/Jilin/07/CHN |
| *Norovirus* Hu/GII4/52416/Jilin/07/CHN |
| *Norovirus* Hu/GII4/52421/Jilin/07/CHN |
| *Norovirus* Hu/GII4/52422/Jilin/07/CHN |
| *Norovirus* Hu/Houston/TCH186/2002/US |
| *Norovirus* Hu/*Norovirus*/GII-4/Cegled1603/2002/HUN |
| *Norovirus* Hu/*Norovirus*/GII-4/Dunaujvaros2477/2006/HUN |
| *Norovirus* Hu/*Norovirus*/GII-4/Gyor2872/2006/HUN |
| *Norovirus* Hu/*Norovirus*/GII-4/Kapuvar3029/2007/HUN |
| *Norovirus* Hu/*Norovirus*/GII-4/Kiskunhalas1264/2002/HUN |
| *Norovirus* Hu/*Norovirus*/GII-4/Mohacs1147/2002/HUN |
| *Norovirus* Hu/*Norovirus*/GII-4/Mosonmagyarovar2594/2006/HUN |
| *Norovirus* Hu/*Norovirus*/GII-4/Nagykoru2098/2004/HUN |
| *Norovirus* Hu/*Norovirus*/GII-4/Ocsa923/2002/HUN |
| *Norovirus* Hu/*Norovirus*/GII-4/Pecs2967/2007/HUN |
| *Norovirus* Hu/*Norovirus*/GII-4/Sopron1562/2002/HUN |
| *Norovirus* Hu/*Norovirus*/GII-4/Tiszatelek982/2002/HUN |
| *Norovirus* oyster/GII.4/2007/USA |
| *Norovirus* sea water/GII.4/HME-371/TWN |
| *Norovirus* sea water/GII.4/HME-493/TWN |
| *Norovirus* sea water/GII.4/HME-527/TWN |
| *Norovirus* sewage/GII.4/Toyama/SW0610-1/2006/JP |
| *Norovirus* sewage/GII.4/Toyama/SW0611-1/2006/JP |
| *Norovirus* sewage/GII.4/Toyama/SW0612-7/2006/JP |
| *Norovirus* sewage/GII.4/Toyama/SW0701-5/2007/JP |
| *Norovirus* sewage/GII.4/Toyama/SW0702-4/2007/JP |
| *Norovirus* sewage/GII.4/Toyama/SW0703-1/2007/JP |
| *Norovirus* sewage/GII.4/Toyama/SW0704-2/2007/JP |
| *Norovirus* sewage/GII.4/Toyama/SW0706-1/2007/JP |
| *Norovirus* sewage/GII.4/Toyama/SW0707-1/2007/JP |
| *Norovirus* sewage/GII.4/Toyama/SW0708-19/2007/JP |
| *Norovirus* sewage/GII.4/Toyama/SW0710-1/2007/JP |
| *Norovirus* sewage/GII.4/Toyama/SW0711-10/2007/JP |
| *Norovirus* sewage/GII.4/Toyama/SW0712-13/2007/JP |
| *Norovirus* Hu/GII.4/Hiroshima/115/2007/JPN |
| *Norovirus* Hu/GII.4/Hiroshima/129/2007/JPN |
| *Norovirus* Hu/GII.4/Hiroshima/134/2007/JPN |
| *Norovirus* Hu/GII.4/Hiroshima/139/2007/JPN |
| *Norovirus* Hu/GII.4/Hiroshima/151/2008/JPN |
| *Norovirus* Hu/GII.4/Hiroshima/154/2008/JPN |
| *Norovirus* Hu/GII.4/Hiroshima/19/2001/JPN |
| *Norovirus* Hu/GII.4/Hiroshima/42/2004/JPN |
| *Norovirus* Hu/GII.4/Hiroshima/44/2004/JPN |
| *Norovirus* Hu/GII.4/Hiroshima/48/2004/JPN |
| *Norovirus* Hu/GII.4/Hiroshima/55/2005/JPN |
| *Norovirus* Hu/GII.4/Hiroshima/56/2005/JPN |
| *Norovirus* Hu/GII.4/Hiroshima/57/2005/JPN |
| *Norovirus* Hu/GII.4/Hiroshima/58/2005/JPN |
| *Norovirus* Hu/GII.4/Hiroshima/59/2005/JPN |
| *Norovirus* Hu/GII.4/Hiroshima/63/2006/JPN |
| *Norovirus* Hu/GII.4/Hiroshima/67/2006/JPN |

TABLE 1-continued

| *Norovirus* Strains | |
|---|---|
| *Norovirus* Hu/GII.4/Dongen46/2006/NL | *Norovirus* Hu/GII.4/Hiroshima/68/2006/JPN |
| *Norovirus* Hu/GII.4/DulwichHill190I/04O/AU | *Norovirus* Hu/GII.4/Hiroshima/69/2006/JPN |
| *Norovirus* Hu/GII.4/DulwichHill194M/04O/AU | *Norovirus* Hu/GII.4/Hiroshima/74/2006/JPN |
| *Norovirus* Hu/GII.4/DulwichHill197P/04O/AU | |
| *Norovirus* Hu/GII.4/GE14/IRN | |
| *Norovirus* Hu/GII.4/GE28/IRN | |
| *Norovirus* Hu/GII.4/GE3/IRN | |
| *Norovirus* Hu/GII.4/GE31/IRN | |
| *Norovirus* Hu/GII.4/GE44/IRN | |
| *Norovirus* Hu/GII.4/GE8/IRN | |
| *Norovirus* Hu/GII.4/GE9/IRN | |
| *Norovirus* Hu/GII.4/Henry/2000/USA | |
| *Norovirus* Hu/GII.4/Hiroshima/108/2007/JPN | |
| *Norovirus* Hu/GII.4/Hiroshima/109/2007/JPN | |
| *Norovirus* Hu/GII.4/Hiroshima/110/2007/JPN | |
| *Norovirus* genogroup GII.5 | |
| *Norovirus* Hu/GII.5/Cuernavaca/8039/2008/MEX | *Norovirus* Hu/GII.5/Guadalajara/50051/2007/MEX |
| *Norovirus* genogroup GII.6 | |
| *Norovirus* Hu/GII-6/ES315/2003/BRA | *Norovirus* Hu/GII.6/Cuernavaca/50335/2007/MEX |
| *Norovirus* Hu/GII-6/ES332/2003/BRA | *Norovirus* Hu/GII.6/Dhaka233/2000/BGD |
| *Norovirus* Hu/GII.6/13573/2007/RJ/BRA | *Norovirus* sewage/GII.6/Toyama/SW0701-35/2007/JP |
| *Norovirus* Hu/GII.6/46048/2006/IRL | *Norovirus* sewage/GII.6/Toyama/SW0705-2/2007/JP |
| *Norovirus* Hu/GII.6/47747/2006/IRL | |
| *Norovirus* genogroup GII.7 | |
| *Norovirus* Hu/GII-8/ES343/2003/BRA | *Norovirus* Hu/GII.8/Cuernavaca/50364v2/2007/MEX |
| *Norovirus* | Hu/GII.8/Cuernavaca/50364v1/2007/MEX |
| *Norovirus* genogroup GII.8 | |
| *Norovirus* Hu/GII-8/ES343/2003/BRA | *Norovirus* Hu/GII.8/Cuernavaca/50364v2/2007/MEX |
| *Norovirus* | Hu/GII.8/Cuernavaca/50364v1/2007/MEX |
| *Norovirus* genogroup GII.9 | |
| *Norovirus* Hu/GII.9/10775/2005/BRA | *Norovirus* Hu/GII.9/Salvador/A07/2006/BRA |
| *Norovirus* Hu/GII.9/Alingsas/p1/2009/SWE | *Norovirus* Hu/GII.9/Salvador/A08/2006/BRA |
| *Norovirus* Hu/GII.9/Cuernavaca/7315/2007/MEX | *Norovirus* Hu/GII.9/Salvador/B03/2006/BRA |
| *Norovirus* Hu/GII.9/Salvador/A04/2006/BRA | *Norovirus* Hu/GII.9/Salvador/B04/2006/BRA |
| *Norovirus* Hu/GII.9/Salvador/A06/2006/BRA | *Norovirus* Hu/GII.9/Salvador/B05/2006/BRA |
| | *Norovirus* Hu/GII.9/Salvador/F03/2006/BRA |
| *Norovirus* genogroup GII.b | |
| Human calicivirus NLV/Gourdon78/2000/France | *Norovirus* Hu/GIIb/02115441/2002/AUS |
| *Norovirus* env/GGII.b/1036/2007/ITA | *Norovirus* Hu/GIIb/03155665/2003/AUS |
| *Norovirus* env/GGII.b/1161a/2007/ITA | *Norovirus* Hu/GIIb/03157163/2003/AUS |
| *Norovirus* env/GGII.b/1161b/2007/ITA | *Norovirus* Hu/GIIb/03157169/2003/AUS |
| *Norovirus* env/GGII.b/1162b/2007/ITA | *Norovirus* Hu/GIIb/04107624/2004/AUS |
| *Norovirus* Env/GGII.b/678/2006/IT | *Norovirus* Hu/GIIb/04113824/2004/AUS |
| *Norovirus* Env/GGII.b/679/2006/IT | *Norovirus* Hu/GIIb/04113843/2004/AUS |
| *Norovirus* Hu/GGII.b/670/2006/IT | *Norovirus* Hu/GIIb/04114779/2004/AUS |
| *Norovirus* Hu/GGIIb/oyster1735OA/77351/FR | *Norovirus* Hu/GIIb/04121605/2004/AUS |
| *Norovirus* Hu/GGIIb/oyster1786OA/77351/FR | *Norovirus* Hu/GIIb/04134701/2004/AUS |
| *Norovirus* Hu/GII.b/50602/2006/IRL | *Norovirus* Hu/GIIb/04144544/2004/AUS |
| *Norovirus* Hu/GII.b/8503/2007/IRL | *Norovirus* Hu/GIIb/04150102/2004/AUS |
| *Norovirus* Hu/GII.b/9590/2004/IRL | *Norovirus* Hu/GIIb/04155699/2004/AUS |
| *Norovirus* Hu/GII.b/9614/2004/IRL | *Norovirus* Hu/GIIb/05100687/2004/AUS |
| *Norovirus* Hu/GIIb/02106590/2002/AUS | *Norovirus* Hu/GIIb/05143926/2005/AUS |
| *Norovirus* Hu/GIIb/02115422/2002/AUS | |
| Snow Mountain virus | |
| *Norovirus* genogroup 3 | |
| *Norovirus* Bo/GIII.1/Aba-Z5/2002/HUN | *Norovirus* bovine/GIII.2/541_0448/2005/NOR |
| *Norovirus* Bo/GIII.1/Norsewood/2006/NZL | *Norovirus* bovine/GIII.2/584_3248/2005/NOR |
| *Norovirus* Bo/GIII.2/Aba-4736/2008/HUN | *Norovirus* bovine/GIII.2/670_0799/2006/NOR |
| *Norovirus* Bo/GIII.2/Aba-Z2/2002/HUN | *Norovirus* bovine/GIII.2/718_0785/2006/NOR |
| *Norovirus* bovine/GIII.2/216_0114/2006/NOR | *Norovirus* bovine/GIII/chimeric/107_0485/2005/NOR |
| *Norovirus* bovine/GIII.2/240_0243/2005/NOR | *Norovirus* |
| *Norovirus* bovine/GIII.2/300_0250/2006/NOR | |

TABLE 1-continued

| *Norovirus* Strains | |
|---|---|
| *Norovirus* bovine/GIII.2/312_0529/2006/NOR | bovine/GIII/chimeric/661_1570/2006/NOR |
| *Norovirus* bovine/GIII.2/340_1235/2006/NOR | *Norovirus* bovine/GIII/chimeric/752_3024/2006/NOR |
| *Norovirus* bovine/GIII.2/471_0790/2005/NOR | *Norovirus* bovine/GIII/chimeric/785_0449/2006/NOR |
| | *Norovirus* Hu/G3/C5-106/South Korea |
| *Norovirus* genogroup 4 | |
| Human calcivirus NV/GIV/Stockholm/IV1680/2002/SE | *Norovirus* dog/GIV.2/Bari/91/2007/ITA |
| *Norovirus* dog/170/07/Ita | *Norovirus* Hu/GIV.1/Italy/980/2007/ITA |
| | *Norovirus* lion/GGIV.2/Pistoia/387/06/ITA |
| *Norovirus* isolates | |
| Human calicivirus Hu/NLV/Berlin/226/01/DE | *Norovirus* Hu/NFLV4641/Terre-Neuve/06-2004/CAN |
| Human calicivirus Hu/NLV/Bitburg/289/01/DE | *Norovirus* Hu/NLV/BA4231/2004/Arg |
| Human calicivirus Hu/NLV/Leverkusen451/2000/DE | *Norovirus* Hu/NLV/Banbury/B9S23/2003/UK |
| Human calicivirus Hu/NLV/Leverkusen476/2000/DE | *Norovirus* Hu/NLV/ChippingNorton/2003/UK |
| Human calicivirus Hu/NLV/Oxford/B5S22/2003/UK | *Norovirus* Hu/NLV/Didcot/B9S2/2003/UK |
| Human calicivirus Hu/NLV/Queen's Arms/Leeds/92/UK | *Norovirus* Hu/NLV/DjiboutiVdG5/2003/Djibouti |
| Human calicivirus Hu/SaV4895/2001/Bra | *Norovirus* Hu/NLV/DjiboutiVdG50/2003/Djibouti |
| Human calicivirus Mc10 | *Norovirus* Hu/NLV/DjiboutiVdG66/2003/Djibouti |
| Human calicivirus NLV/1157-01/SWE | *Norovirus* Hu/NLV/Dresden174/pUS-NorII/1997/GE |
| Human calicivirus NLV/1312-01/SWE | *Norovirus* Hu/NLV/E3/1997/Crete |
| Human calicivirus NLV/1464-01/SWE | *Norovirus* Hu/NLV/ER4424/2004/Arg |
| Human calicivirus NLV/1581-00/SWE | *Norovirus* Hu/NLV/ER4426/2004/Arg |
| Human calicivirus NLV/1581-01/SWE | *Norovirus* Hu/NLV/II/Hualien/2004/TW |
| Human calicivirus NLV/186-01/SWE | *Norovirus* Hu/NLV/LP4392/2004/Arg |
| Human calicivirus NLV/1937-00/SWE | *Norovirus* Hu/NLV/LP4395/2004/Arg |
| Human calicivirus NLV/2004-00/SWE | *Norovirus* Hu/NLV/NE4208/2004/Arg |
| Human calicivirus NLV/2102-00/SWE | *Norovirus* Hu/NLV/Oxford/B1S1/2002/UK |
| Human calicivirus NLV/2115-00/SWE | *Norovirus* Hu/NLV/Oxford/B1S11/2002/UK |
| Human calicivirus NLV/2197-00/SWE | *Norovirus* Hu/NLV/Oxford/B1S12/2002/UK |
| Human calicivirus NLV/2366-00/SWE | *Norovirus* Hu/NLV/Oxford/B1S16/2002/UK |
| Human calicivirus NLV/500-01/SWE | *Norovirus* Hu/NLV/Oxford/B1S2/2002/UK |
| Human calicivirus NLV/Albacete70/01/SP | *Norovirus* Hu/NLV/Oxford/B1S21/2002/UK |
| Human calicivirus NLV/Altenkirchen 140/01/DE | *Norovirus* Hu/NLV/Oxford/B1S4/2002/UK |
| Human calicivirus NLV/Avila112/02/SP | *Norovirus* Hu/NLV/Oxford/B2S10/2002/UK |
| Human calicivirus NLV/BA1026 | *Norovirus* Hu/NLV/Oxford/B2S11/2002/UK |
| Human calicivirus NLV/Bacsborsod/1542/2002/HUN | *Norovirus* Hu/NLV/Oxford/B2S14/2002/UK |
| Human calicivirus NLV/Bad Berleburg/477/01 | *Norovirus* Hu/NLV/Oxford/B2S15/2002/UK |
| Human calicivirus NLV/Balatonlelle/680/2001/HUN | *Norovirus* Hu/NLV/Oxford/B2S16/2002/UK |
| Human calicivirus NLV/Basel/2001/CH | *Norovirus* Hu/NLV/Oxford/B2S17/2002/UK |
| Human calicivirus NLV/Batonyterenye/1436/2002/HUN | *Norovirus* Hu/NLV/Oxford/B2S18/2002/UK |
| Human calicivirus NLV/Beijing/cr840/China | *Norovirus* Hu/NLV/Oxford/B2S20/2002/UK |
| Human calicivirus NLV/Benetusser/453/2002/Sp | *Norovirus* Hu/NLV/Oxford/B2S23/2002/UK |
| Human calicivirus NLV/Berlin 146/2000/DE | *Norovirus* Hu/NLV/Oxford/B2S24/2002/UK |
| Human calicivirus NLV/Berlin 210-1/1999/DE | *Norovirus* Hu/NLV/Oxford/B2S25/2002/UK |
| Human calicivirus NLV/Berlin 210-2/1999/DE | *Norovirus* Hu/NLV/Oxford/B2S26/2002/UK |
| Human calicivirus NLV/Berlin 211-1/1999/DE | *Norovirus* Hu/NLV/Oxford/B3S16/2003/UK |
| Human calicivirus NLV/Berlin 211-2/1999/DE | *Norovirus* Hu/NLV/Oxford/B3S18/2003/UK |
| Human calicivirus NLV/Berlin 248/1999/DE | *Norovirus* Hu/NLV/Oxford/B3S19/2003/UK |
| Human calicivirus NLV/Berlin 348/2000/DE | *Norovirus* Hu/NLV/Oxford/B3S20/2003/UK |
| Human calicivirus NLV/Berlin 363/2000/DE | *Norovirus* Hu/NLV/Oxford/B3S4/2003/UK |
| Human calicivirus NLV/Berlin 385/2000/DE | *Norovirus* Hu/NLV/Oxford/B4S1/2002/UK |
| Human calicivirus NLV/Berlin/159/98/DE | *Norovirus* Hu/NLV/Oxford/B4S2/2002/UK |
| Human calicivirus NLV/Berlin/238/98/DE | *Norovirus* Hu/NLV/Oxford/B4S4/2002/UK |
| Human calicivirus NLV/Berne/2001/CH | *Norovirus* Hu/NLV/Oxford/B4S5/2002/UK |
| Human calicivirus NLV/Bicske/1225/2002/HUN | *Norovirus* Hu/NLV/Oxford/B4S6/2002/UK |
| Human calicivirus NLV/Boxer/2001/US | *Norovirus* Hu/NLV/Oxford/B4S7/2002/UK |
| Human calicivirus NLV/Brandenburg 40/1999/DE | *Norovirus* Hu/NLV/Oxford/B5S1/22002/UK |
| Human calicivirus NLV/Budapest/1095/2002/HUN | *Norovirus* Hu/NLV/Oxford/B5S10/2002/UK |
| Human calicivirus NLV/Budapest/HUNs1/1997/HUN | *Norovirus* Hu/NLV/Oxford/B5S13/2002/UK |
| Human calicivirus NLV/C59/99 | *Norovirus* Hu/NLV/Oxford/B5S19/2002/UK |
| Human calicivirus NLV/Castell/2001/Sp | *Norovirus* Hu/NLV/Oxford/B5S23/2003/UK |
| | *Norovirus* Hu/NLV/Oxford/B5S7/2002/UK |
| | *Norovirus* Hu/NLV/Oxford/B5S8/2002/UK |
| | *Norovirus* Hu/NLV/Oxford/B5S9/2002/UK |
| | *Norovirus* Hu/NLV/Oxford/B6S2/2003/UK |
| | *Norovirus* Hu/NLV/Oxford/B6S3/2003/UK |
| | *Norovirus* Hu/NLV/Oxford/B6S4/2003/UK |
| | *Norovirus* Hu/NLV/Oxford/B6S5/2003/UK |
| | *Norovirus* Hu/NLV/Oxford/B6S6/2003/UK |
| | *Norovirus* Hu/NLV/Oxford/B8S5/2002/UK |
| | *Norovirus* Hu/NLV/Pont de Roide 671/2004/France |
| | *Norovirus* Hu/NLV/Pont de Roide 673/2004/France |
| | *Norovirus* Hu/NLV/RN4372/2004/Arg |

TABLE 1-continued

| *Norovirus* Strains |
|---|
| Human calicivirus NLV/Coruna90/02/SP |
| Human calicivirus NLV/Csakvar/877/2001/HUN |
| Human calicivirus NLV/Csanadapaca/1868/2003/HUN |
| Human calicivirus NLV/Debrecen/1721/2003/HUN |
| Human calicivirus NLV/Debrecen/897/2001/HUN |
| Human calicivirus NLV/Dillingen 259/01/DE |
| Human calicivirus NLV/Dillingen 391/01/DE |
| Human calicivirus NLV/Egeln 399/1999/DE |
| Human calicivirus NLV/Eger/1650/2002/HUN |
| Human calicivirus NLV/Eger/HUNs19/2000/HUN |
| Human calicivirus NLV/Eger/HUNs6/2000/HUN |
| Human calicivirus NLV/Erd/967/2002/HUN |
| Human calicivirus NLV/Erfurt 007/2000/DE |
| Human calicivirus NLV/Erfurt 232/2000/DE |
| Human calicivirus NLV/Erlangen 155/2000/DE |
| Human calicivirus NLV/Frankfurt(Oder) 168/1999/DE |
| Human calicivirus NLV/Frankfurt(Oder) 170/1999/DE |
| Human calicivirus NLV/Frankfurt(Oder) 176/1999/DE |
| Human calicivirus NLV/FrankfurtO.386/1999/DE |
| Human calicivirus NLV/Fuzesabony/1253/2002/HUN |
| Human calicivirus NLV/Geesthacht 410/2000/DE |
| Human calicivirus NLV/Gelsenkirchen 468/2000/DE |
| Human calicivirus NLV/GGII/NDV1/99/IND |
| Human calicivirus NLV/GGII/NDV2/99/IND |
| Human calicivirus NLV/GGII/NDV3/99/IND |
| Human calicivirus NLV/GII/Langen1061/2002/DE |
| Human calicivirus NLV/Gothenburg1/2001/Sweden |
| Human calicivirus NLV/Granada60i/02/SP |
| Human calicivirus NLV/Gyongyos/1255/2002/HUN |
| Human calicivirus NLV/Gyongyos/1467/2002/HUN |
| Human calicivirus NLV/Gyor/1734/2003/HUN |
| Human calicivirus NLV/Hajmasker/487/2001/HUN |
| Human calicivirus NLV/Halle 445/1999/DE |
| Human calicivirus NLV/Hamburg 347/2000/DE |
| Human calicivirus NLV/Herzberg 385/01/DE |
| Human calicivirus NLV/Ibiza67/01/SP |
| Human calicivirus NLV/Intahaza/1621/2003/HUN |
| Human calicivirus NLV/J23/1999/US |
| Human calicivirus NLV/Kaposvar/1505/2002/HUN |
| Human calicivirus NLV/Kecskemet/1657/2003/HUN |
| Human calicivirus NLV/Kiskunhalas/HUNo2/1999/HUN |
| Human calicivirus NLV/Kisujbanya/650/2001/HUN |
| Human calicivirus NLV/Koblenz 229/2000/DE |
| Human calicivirus NLV/Laucha 403/1999/DE |
| Human calicivirus NLV/Leon55/00/SP |
| Human calicivirus NLV/LesBorges/319/2001/Sp |
| Human calicivirus NLV/Lleida/327/2001/Sp |
| Human calicivirus NLV/Lugo37i/00/SP |
| Human calicivirus NLV/Lugo73i/02/SP |
| Human calicivirus NLV/M7/1999/US |
| Human calicivirus NLV/Madrid106/02/SP |
| Human calicivirus NLV/Madrid33/00/SP |
| *Norovirus* Hu/NLV/RN4379/2004/Arg |
| *Norovirus* Hu/NLV/S63/1999/France |
| *Norovirus* Hu/NLV/SAG4237/2004/Arg |
| *Norovirus* Hu/NLV/SAG4238/2004/Arg |
| *Norovirus* Hu/NLV/SAG4241/2004/Arg |
| *Norovirus* Hu/NLV/SF4413/2004/Arg |
| *Norovirus* Hu/NLV/SF4420/2004/Arg |
| *Norovirus* Hu/NLV/VannesL23/1999/France |
| *Norovirus* Hu/NLV/Witney/B7S2/2003/UK |
| *Norovirus* Hu/Noguchi-1/2000/GH |
| *Norovirus* Hu/Noguchi-10/2000/GH |
| *Norovirus* Hu/Noguchi-2/2000/GH |
| *Norovirus* Hu/Noguchi-3/2000/GH |
| *Norovirus* Hu/Noguchi-4/2000/GH |
| *Norovirus* Hu/Noguchi-5/2000/GH |
| *Norovirus* Hu/Noguchi-6/2000/GH |
| *Norovirus* Hu/Noguchi-7/2000/GH |
| *Norovirus* Hu/Noguchi-8/2000/GH |
| *Norovirus* Hu/Noguchi-9/2000/GH |
| *Norovirus* Hu/Noshiro/1/2007/JP |
| *Norovirus* Hu/NoV/01/2004/SE |
| *Norovirus* Hu/NoV/02/2002/SE |
| *Norovirus* Hu/NoV/02/2006/SE |
| *Norovirus* Hu/NoV/03/2002/SE |
| *Norovirus* Hu/NoV/03/2004/SE |
| *Norovirus* Hu/NoV/03/2006/SE |
| *Norovirus* Hu/NoV/04/2004/SE |
| *Norovirus* Hu/NoV/04/2005/SE |
| *Norovirus* Hu/NoV/04/2006/SE |
| *Norovirus* Hu/NoV/05/2004/SE |
| *Norovirus* Hu/NoV/05/2005/SE |
| *Norovirus* Hu/NoV/05/2006/SE |
| *Norovirus* Hu/NoV/05_1/2002/SE |
| *Norovirus* Hu/NoV/05_2/2002/SE |
| *Norovirus* Hu/NoV/06/2002/SE |
| *Norovirus* Hu/NoV/06/2004/SE |
| *Norovirus* Hu/NoV/06/2005/SE |
| *Norovirus* Hu/NoV/06/2006/SE |
| *Norovirus* Hu/NoV/07/2002/SE |
| *Norovirus* Hu/NoV/07/2004/SE |
| *Norovirus* Hu/NoV/07/2006/SE |
| *Norovirus* Hu/NoV/07_1/2005/SE |
| *Norovirus* Hu/NoV/07_2/2005/SE |
| *Norovirus* Hu/NoV/08/2002/SE |
| *Norovirus* Hu/NoV/08/2003/SE |
| *Norovirus* Hu/NoV/08/2004/SE |
| *Norovirus* Hu/NoV/08/2005/SE |
| *Norovirus* Hu/NoV/08/2006/SE |
| *Norovirus* Hu/NoV/09/2002/SE |
| *Norovirus* Hu/NoV/09/2003/SE |
| *Norovirus* Hu/NoV/09/2004/SE |
| *Norovirus* Hu/NoV/09/2005/SE |
| *Norovirus* Hu/NoV/09/2006/SE |
| *Norovirus* Hu/NoV/10/2003/SE |
| *Norovirus* Hu/NoV/10/2004/SE |
| *Norovirus* Hu/NoV/10_1/2006/SE |
| *Norovirus* Hu/NoV/10_2/2006/SE |
| *Norovirus* Hu/NoV/11/2002/SE |
| *Norovirus* Hu/NoV/11/2003/SE |
| *Norovirus* Hu/NoV/11/2006/SE |
| *Norovirus* Hu/NoV/12/2002/SE |
| *Norovirus* Hu/NoV/12/2003/SE |
| *Norovirus* Hu/NoV/12/2004/SE |
| *Norovirus* Hu/NoV/13/2002/SE |
| *Norovirus* Hu/NoV/13/2004/SE |
| *Norovirus* Hu/NoV/13/2005/SE |
| *Norovirus* Hu/NoV/13_1/2006/SE |
| *Norovirus* Hu/NoV/13_2/2006/SE |
| *Norovirus* Hu/NoV/14/2002/SE |
| *Norovirus* Hu/NoV/15/2002/SE |
| *Norovirus* Hu/NoV/15/2003/SE |
| *Norovirus* Hu/NoV/15/2004/SE |
| *Norovirus* Hu/NoV/15/2006/SE |
| *Norovirus* Hu/NoV/16/2002/SE |
| *Norovirus* Hu/NoV/16/2003/SE |
| *Norovirus* Hu/NoV/17/2002/SE |
| *Norovirus* Hu/NoV/17/2006/SE |
| *Norovirus* Hu/NoV/18/2002/SE |

TABLE 1-continued

| *Norovirus* Strains | |
|---|---|
| Human calicivirus NLV/Madrid36i/01/SP | *Norovirus* Hu/NoV/18/2004/SE |
| Human calicivirus NLV/Madrid63/01/SP | *Norovirus* Hu/NoV/18/2006/SE |
| Human calicivirus NLV/Madrid79/00/SP | *Norovirus* Hu/NoV/19/2002/SE |
| Human calicivirus NLV/Madrid94/02/SP | *Norovirus* Hu/NoV/19/2006/SE |
| Human calicivirus NLV/Magdeburg | *Norovirus* Hu/NoV/21/2002/SE |
| 171/1999/DE | *Norovirus* Hu/NoV/21/2006/SE |
| Human calicivirus NLV/Magdeburg | *Norovirus* Hu/NoV/22/2002/SE |
| 225/1999/DE | *Norovirus* Hu/NoV/22_1/2006/SE |
| Human calicivirus NLV/Magdeburg | *Norovirus* Hu/NoV/22_2/2006/SE |
| 401/2000/DE | *Norovirus* Hu/NoV/23/2002/SE |
| Human calicivirus NLV/Magdeburg | *Norovirus* Hu/NoV/23_1/2006/SE |
| 460/1999/DE | *Norovirus* Hu/NoV/23_2/2006/SE |
| Human calicivirus NLV/Magdeburg | *Norovirus* Hu/NoV/24/2002/SE |
| 514/1999/DE | *Norovirus* Hu/NoV/24/2006/SE |
| Human calicivirus NLV/Magdeburg | *Norovirus* Hu/NoV/25/2002/SE |
| 548/1999/DE | *Norovirus* Hu/NoV/25/2006/SE |
| Human calicivirus NLV/Magdeburg | *Norovirus* Hu/NoV/26/2002/SE |
| 62/1999/DE | *Norovirus* Hu/NoV/26/2006/SE |
| Human calicivirus NLV/Mallorca43/00/SP | *Norovirus* Hu/NoV/27/2002/SE |
| Human calicivirus NLV/Meliana/230/2001/Sp | *Norovirus* Hu/NoV/28/2002/SE |
| Human calicivirus NLV/Mex7076/1999 | *Norovirus* Hu/NoV/29/2002/SE |
| Human calicivirus | *Norovirus* Hu/NoV/Dover/2000/UK |
| NLV/Mogyoroska/671/2001/HUN | *Norovirus* Hu/NR2176/1998/US |
| Human calicivirus NLV/MOH/99 | *Norovirus* Hu/NR2210/1998/US |
| Human calicivirus | *Norovirus* Hu/NR2225/1999/US |
| NLV/Mohacs/1064/2002/HUN | *Norovirus* Hu/NR2342/1997/US |
| Human calicivirus | *Norovirus* Hu/NR2443/1998/US |
| NLV/Montblanc/287/2001/Sp | *Norovirus* Hu/NR2459/1998/US |
| Human calicivirus NLV/Mora/97/SE | *Norovirus* Hu/NR2482/1998/US |
| Human calicivirus NLV/Murcia103/02/SP | *Norovirus* Hu/NR2486/1999/US |
| Human calicivirus NLV/Murcia60/00/SP | *Norovirus* Hu/NR2512/1999/US |
| Human calicivirus | *Norovirus* Hu/NR2531/1999/US |
| NLV/Nagykovacsi/1918/2003/HUN | *Norovirus* Hu/NR2552/1999/US |
| Human calicivirus | *Norovirus* Hu/NSW021E/2006/AUS |
| NLV/Nagykozar/623/2001/HUN | *Norovirus* Hu/NSW022G/2006/AUS |
| Human calicivirus | *Norovirus* Hu/NSW027B/2006/AUS |
| NLV/Nemesgulacs/418/2001/HUN | *Norovirus* Hu/NSW036B/2006/AUS |
| Human calicivirus NLV/Neustrelitz | *Norovirus* Hu/NSW065F/2006/AUS |
| 163/1999/DE | *Norovirus* Hu/NSW072D/2006/AUS |
| Human calicivirus | *Norovirus* Hu/NSW095B/2006/AUS |
| NLV/Nyiradony/793/2001/HUN | *Norovirus* Hu/NSW108C/2006/AUS |
| Human calicivirus | *Norovirus* Hu/NSW138H/2006/AUS |
| NLV/Nyiregyhaza/1057/2002/HUN | *Norovirus* Hu/NSW147I/2006/AUS |
| Human calicivirus NLV/Oberhausen | *Norovirus* Hu/NSW159U/2006/AUS |
| 455/01/DE | *Norovirus* Hu/NSW162I/2006/AUS |
| Human calicivirus | *Norovirus* Hu/NSW176K/2006/AUS |
| NLV/Paks/HUNo4/1999/HUN | *Norovirus* Hu/NSW182K/2006/AUS |
| Human calicivirus NLV/Palencia69i/02/SP | *Norovirus* Hu/NSW193M/2006/AUS |
| Human calicivirus NLV/Papa/1476/2002/HUN | *Norovirus* Hu/NSW195L/2006/AUS |
| Human calicivirus NLV/Papa/1576/2002/HUN | *Norovirus* Hu/NSW203I/2006/AUS |
| Human calicivirus | *Norovirus* Hu/NSW212E/2006/AUS |
| NLV/Patalom/HUNo10/2000/HUN | *Norovirus* Hu/NSW216C/2006/AUS |
| Human calicivirus | *Norovirus* Hu/NSW220I/2006/AUS |
| NLV/Patapoklosi/HUNs3/1999/HUN | *Norovirus* Hu/NSW248Q/2006/AUS |
| Human calicivirus | *Norovirus* Hu/NSW287S/2006/AUS |
| NLV/Pecel/1779/2003/HUN | *Norovirus* Hu/NSW304I/2006/AUS |
| Human calicivirus NLV/Pecs/571/2001/HUN | *Norovirus* Hu/NSW306G/2006/AUS |
| Human calicivirus | *Norovirus* Hu/NSW3137/2006/AUS |
| NLV/Pecs/HUNs4/1999/HUN | *Norovirus* Hu/NSW322H/2006/AUS |
| Human calicivirus NLV/Peleliu/1999 | *Norovirus* Hu/NSW324J/2006/AUS |
| Human calicivirus NLV/Pfaffenhofen | *Norovirus* Hu/NSW330F/2006/AUS |
| 028/2000/DE | *Norovirus* Hu/NSW340C/2006/AUS |
| Human calicivirus NLV/Potsdam 196/2000/DE | *Norovirus* Hu/NSW346E/2006/AUS |
| Human calicivirus NLV/Potsdam 384/2000/DE | *Norovirus* Hu/NSW356Q/2006/AUS |
| Human calicivirus | *Norovirus* Hu/NSW397R/2006/AUS |
| NLV/Rarospuszta/778/2001/HUN | *Norovirus* Hu/NSW4138/2006/AUS |
| Human calicivirus NLV/Rostock 039/2000/DE | *Norovirus* Hu/NSW415F/2006/AUS |
| Human calicivirus NLV/Sagunt/116/2000/Sp | *Norovirus* Hu/NSW415N/2006/AUS |
| Human calicivirus NLV/Sagunt/181/2001/Sp | *Norovirus* Hu/NSW419Q/2006/AUS |
| Human calicivirus NLV/Sagunt/222/2001/Sp | *Norovirus* Hu/NSW426I/2006/AUS |
| Human calicivirus NLV/Sagunt/258/2001/Sp | *Norovirus* Hu/NSW432F/2006/AUS |
| Human calicivirus NLV/Sagunt/364/2001/Sp | *Norovirus* Hu/NSW453O/2006/AUS |
| Human calicivirus | *Norovirus* Hu/NSW510G/2006/AUS |
| NLV/Sarospatak/1172/2002/HUN | *Norovirus* Hu/NSW517Q/2006/AUS |
| Human calicivirus NLV/Schwerin | *Norovirus* Hu/NSW527Q/2006/AUS |
| 002/2000/DE | *Norovirus* Hu/NSW555L/2006/AUS |

TABLE 1-continued

| *Norovirus* Strains |
| --- |
| Human calicivirus NLV/Schwerin 003/00/DE |
| Human calicivirus NLV/Schwerin 218/1999/DE |
| Human calicivirus NLV/Segovia53i/02/SP |
| Human calicivirus NLV/Segovia97/02/SP |
| Human calicivirus NLV/Sopron/1137/2002/HUN |
| Hurnan calicivirus NLV/Sopron/1562/2002/HUN |
| Human calicivirus NLV/Sopron/952/2002/HUN |
| Human calicivirus NLV/St.Feliu/255/2001/Sp |
| Human calicivirus NLV/Steinbach/EG/2001/CA |
| Human calicivirus NLV/Stockholm/genotype GGIIb |
| Human calicivirus NLV/Suria/312/2001/Sp |
| Human calicivirus NLV/Szava/HUNs13/2000/HUN |
| Human calicivirus NLV/Szeged-Algyo/HUNo1/1998/HUN |
| Human calicivirus NLV/Szeged/1237/2002/HUN |
| Human calicivirus NLV/Szekesfehervar/1851/2003/HUN |
| Human calicivirus NLV/Szigetvar/HUNs7/2000/HUN |
| Human calicivirus NLV/Szoc/806/2001/HUN |
| Human calicivirus NLV/Szolnok/1904/2003/HUN |
| Human calicivirus NLV/Szombathely/413/2001/HUN |
| Human calicivirus NLV/Tapioszentmarton/1909/2003/HUN |
| Human calicivirus NLV/Tarrag/238/2001/Sp |
| Human calicivirus NLV/Tata/1525/2002/HUN |
| Human calicivirus NLV/Tenerife41i/01/SP |
| Human calicivirus NLV/Tiefwarensee 304/1999/DE |
| Human calicivirus NLV/Tiefwarensee 305/1999/DE |
| Human calicivirus NLV/Toddin 242/1999/DE |
| Human calicivirus NLV/Toledo35/00/SP |
| Human calicivirus NLV/Totkomlos/1798/2003/HUN |
| Human calicivirus NLV/Utiel/371/2001/Sp |
| Human calicivirus NLV/VA497/1999/US |
| Human calicivirus NLV/VA97207/1997 |
| Human calicivirus NLV/VA98115/1998 |
| Human calicivirus NLV/VA98387/1998 |
| Human calicivirus NLV/Valencia/123/2000/Sp |
| Human calicivirus NLV/Valencia/213/2001/Sp |
| Human calicivirus NLV/Valencia/256/2001/Sp |
| Human calicivirus NLV/Valencia/261/2001/Sp |
| Human calicivirus NLV/Valencia/426/2002/Sp |
| Human calicivirus NLV/Varalja/1898/2003/HUN |
| Human calicivirus NLV/Veszprem/1023/2002/HUN |
| Human calicivirus NLV/Veszprem/HUNo11a/2000/HUN |
| Human calicivirus NLV/Veszprem/HUNo11b/2000/HUN |
| Human calicivirus NLV/Vilafranca/269/2001/Sp |
| Human calicivirus NLV/Wiesbaden 294/01/DE |
| Human calicivirus NLV/Zaragoza77/00/SP |
| Human calicivirus NLV/Zaragoza80/01/SP |
| Human calicivirus NLV/Zaragoza83/01/SP |
| Human calicivirus NV/Aubel/H252/2002/Be |
| Human calicivirus NV/Beaufays/H361/2002/Be |
| Human calicivirus NV/BQT648/2000/VE |
| Human calicivirus NV/CCS114/1996/VE |
| Human calicivirus NV/CCS14/1997/VE |
| Human calicivirus NV/CCS17/1997/VE |
| Human calicivirus NV/CCS207/1995/VE |
| Human calicivirus NV/CCS21/1997/VE |
| *Norovirus* Hu/NSW608R/2006/AUS |
| *Norovirus* Hu/NSW611K/2006/AUS |
| *Norovirus* Hu/NSW627Q/2006/AUS |
| *Norovirus* Hu/NSW629R/2006/AUS |
| *Norovirus* Hu/NSW659Y/2006/AUS |
| *Norovirus* Hu/NSW689S/2006/AUS |
| *Norovirus* Hu/NSW689Y/2006/AUS |
| *Norovirus* Hu/NSW695Q/2006/AUS |
| *Norovirus* Hu/NSW696T/2006/AUS |
| *Norovirus* Hu/NSW700I/2006/AUS |
| *Norovirus* Hu/NSW710H/2006/AUS |
| *Norovirus* Hu/NSW716H/2006/AUS |
| *Norovirus* Hu/NSW717P/2006/AUS |
| *Norovirus* Hu/NSW725O/2006/AUS |
| *Norovirus* Hu/NSW751J/2006/AUS |
| *Norovirus* Hu/NSW763N/2006/AUS |
| *Norovirus* Hu/NSW768Y/2006/AUS |
| *Norovirus* Hu/NSW776R/2006/AUS |
| *Norovirus* Hu/NSW779W/2006/AUS |
| *Norovirus* Hu/NSW779Y/2006/AUS |
| *Norovirus* Hu/NSW782O/2006/AUS |
| *Norovirus* Hu/NSW821N/2006/AUS |
| *Norovirus* Hu/NSW827U/2006/AUS |
| *Norovirus* Hu/NSW855V/2006/AUS |
| *Norovirus* Hu/NSW857X/2006/AUS |
| *Norovirus* Hu/NSW870K/2006/AUS |
| *Norovirus* Hu/NSW890Q/2006/AUS |
| *Norovirus* Hu/NSW892Q/2006/AUS |
| *Norovirus* Hu/NSW897Z/2006/AUS |
| *Norovirus* Hu/NSW944I/2006/AUS |
| *Norovirus* Hu/NSW953I/2006/AUS |
| *Norovirus* Hu/NSW974O/2006/AUS |
| *Norovirus* Hu/Nursing-home_A/28-12-2001/NL |
| *Norovirus* Hu/Nursing-home_B/05-05-2002/NL |
| *Norovirus* Hu/Nursing-home_C/06-06-2002/NL |
| *Norovirus* Hu/Nursing-home_D/19-11-2002/NL |
| *Norovirus* Hu/Nursing-home_E_pat_1/08-01-2003/NL/ |
| *Norovirus* Hu/Nursing-home_E_pat_2/10-01-2003/NL |
| *Norovirus* Hu/Nursing-home_F/22-01-2003/NL |
| *Norovirus* Hu/Nursing-home_G/27-01-2003/NL |
| *Norovirus* Hu/Nursing-home_H/03-02-2003/NL |
| *Norovirus* Hu/NV/Hokkaido/118/2002/JP |
| *Norovirus* Hu/NV/Hokkaido/127/2002/JP |
| *Norovirus* Hu/NV/Hokkaido/130/2002/JP |
| *Norovirus* Hu/NV/Hokkaido/135/2003/JP |
| *Norovirus* Hu/NV/Hokkaido/183/2004/JP |
| *Norovirus* Hu/NV/Hokkaido/186/2004/JP |
| *Norovirus* Hu/NV/Hokkaido/192/2004/JP |
| *Norovirus* Hu/NV/Hokkaido/194/2004/JP |
| *Norovirus* Hu/NV/Hokkaido/198/2004/JP |
| *Norovirus* Hu/NV/Hokkaido/222/2004/JP |
| *Norovirus* Hu/NV/Hokkaido/231/2004/JP |
| *Norovirus* Hu/NV/Hokkaido/284/2004/JP |
| *Norovirus* Hu/NV/Hokkaido/286/2005/JP |
| *Norovirus* Hu/NV/Hokkaido/300/2005/JP |
| *Norovirus* Hu/NV/Hokkaido/306/2005/JP |
| *Norovirus* Hu/NV/Hokkaido/307/2005/JP |
| *Norovirus* Hu/NV/Hokkaido/322/2005/JP |
| *Norovirus* Hu/NV/Hokkaido/332/2005/JP |
| *Norovirus* Hu/NV/Hokkaido/44/2000/JP |
| *Norovirus* Hu/NV/Hokkaido/47/2000/JP |
| *Norovirus* Hu/NV/Osaka/F140/2006/JP |
| *Norovirus* Hu/NV/Weymouth/2004/UK |
| *Norovirus* Hu/NZ176/2006/NZL |
| *Norovirus* Hu/NZ186/2006/NZL |
| *Norovirus* Hu/NZ225/2006/NZL |
| *Norovirus* Hu/NZ309/2006/NZL |
| *Norovirus* Hu/NZ313/2006/NZL |
| *Norovirus* Hu/NZ327/2006/NZL |
| *Norovirus* Hu/NZ330/2006/NZL |
| *Norovirus* Hu/NZ373/2005/NZL |
| *Norovirus* Hu/NZ460/2006/NZL |
| *Norovirus* Hu/NZ467/2006/NZL |
| *Norovirus* Hu/NZ500/2006/NZL |
| *Norovirus* Hu/NZ51/2006/NZL |
| *Norovirus* Hu/NZ530/2006/NZL |

TABLE 1-continued

| *Norovirus* Strains |
|---|
| Human calicivirus NV/CCS215/1996/VE |
| Human calicivirus NV/CCS227/1998/VE |
| Human calicivirus NV/CCS39/1998/VE |
| Human calicivirus NV/Gentbrugge/H496/2003/Be |
| Human calicivirus NV/Gentbrugge/H494/2003/Be |
| Human calicivirus NV/Gentbrugge/H497/2003/Be |
| Human calicivirus NV/Grace-Hollogne/H384/2002/Be |
| Human calicivirus NV/Grivegnee/H501/2003/Be |
| Human calicivirus NV/H011/2002/Be |
| Human calicivirus NV/H325/2002/Be |
| Human calicivirus NV/Heusden/H492/2003/Be |
| Human calicivirus NV/Kristianstad-Pat/2001/SE |
| Human calicivirus NV/Kristianstad-Ras/2001/SE |
| Human calicivirus NV/Liege/H302/2002/Be |
| Human calicivirus NV/Lontzen/H556/2003/Be |
| Human calicivirus NV/Mariakerke/H514/2003/Be |
| Human calicivirus NV/Oupeye/H007/2002/Be |
| Human calicivirus NV/Romsee/H010/2002/Be |
| Human calicivirus NV/Schoten/H473/2003/Be |
| Human calicivirus NV/Sint Amanddeg/H493/2003/Be |
| Human calicivirus NV/St Nicolas/H367/2002/Be |
| Human calicivirus NV/Tilff/H479/2003/Be |
| Human calicivirus NV/Zelzate/H495/2003/Be |
| Human calicivirus strain Arg320 |
| Human calicivirus strain BAV/2.1/98/DEU |
| Human calicivirus strain BRA/2.1/98/DEU |
| Human calicivirus strain HSS/2/98/DEU |
| Human calicivirus strain Hu/NLV/Amsterdam/98-18/1998/NET |
| Human calicivirus strain Hu/SLV/Stockholm/318/97/SE |
| Human *norovirus* CHN38109/SZ03 |
| Human *norovirus* CHN38111/SZ03 |
| Human *norovirus* CHN38112/SZ03 |
| Human *norovirus* CHN38113/SZ03 |
| Human *norovirus* CHN38114/SZ03 |
| Human *norovirus* CHN4841/SZ03 |
| Human *norovirus* Hu/NV/I/Hualien/CYC/2003/TW |
| Maryland calicivirus 6 |
| *Norovirus* Bo/Aulendorf20/2003/DE |
| *Norovirus* Bo/Aulendorf22/2003/DE |
| *Norovirus* Bo/DijonA173/2006/FR |
| *Norovirus* Bo/DijonA247/2007/FR |
| *Norovirus* Bo/DijonA273/2007/FR |
| *Norovirus* Bo/DijonA344/2007/FR |
| *Norovirus* Bo/DijonA428/2008/FR |
| *Norovirus* Bo/DijonA430/2008/FR |
| *Norovirus* Bo/Newbury2/1976/UK |
| *Norovirus* Bochum024/1998/GE |
| *Norovirus* Bochum026/1997/GE |
| *Norovirus* Bochum031/1997/GE |
| *Norovirus* Bochum108/1997/GE |
| *Norovirus* Bochum136/1998/GE |
| *Norovirus* Bochum220/1997/GE |
| *Norovirus* Bochum224/1998/GE |
| *Norovirus* Bochum272/1998/GE |
| *Norovirus* Bochum339/1997/GE |
| *Norovirus* bovine/125/2005/SVN |
| *Norovirus* bovine/Belgium/B102/2002/Be |
| *Norovirus* bovine/Belgium/B128/2002/Be |
| *Norovirus* bovine/Belgium/B164/2002/Be |
| *Norovirus* bovine/Belgium/B173/2003/Be |
| *Norovirus* bovine/Belgium/B307/2003/Be |
| *Norovirus* bovine/Belgium/B309/2003/Be |
| *Norovirus* bovine/Belgium/B52/2002/Be |
| *Norovirus* bovine/BV119/2007/BEL |
| *Norovirus* bovine/BV120/2007/BEL |
| *Norovirus* Hu/NZ535/2006/NZL |
| *Norovirus* Hu/NZ536/2006/NZL |
| *Norovirus* Hu/NZ587/2006/NZL |
| *Norovirus* Hu/O1/JPN |
| *Norovirus* Hu/O2a/JPN |
| *Norovirus* Hu/O2b/JPN |
| *Norovirus* Hu/Oberschleissheim 102/1999/DE |
| *Norovirus* Hu/Oberschleissheim 108/1999/DE |
| *Norovirus* Hu/Oberschleissheim 112/1999/DE |
| *Norovirus* Hu/Oberschleissheim 149/1999/DE |
| *Norovirus* Hu/Oberschleissheim 92/1999/DE |
| *Norovirus* Hu/OC01243/2001/JP |
| *Norovirus* Hu/OC02012/2002/JP |
| *Norovirus* Hu/OC02022/2002/JP |
| *Norovirus* Hu/OC02198/2002/JP |
| *Norovirus* Hu/OC02202/2002/JP |
| *Norovirus* Hu/OC03199-1/2003/JP |
| *Norovirus* Hu/OC03199-2/2003/JP |
| *Norovirus* Hu/OC04038/2004/JP |
| *Norovirus* Hu/OC04039/2004/JP |
| *Norovirus* Hu/OC04042/2004/JP |
| *Norovirus* Hu/OC04043/2004/JP |
| *Norovirus* Hu/OC04056-1/2004/JP |
| *Norovirus* Hu/OC04056-2/2004/JP |
| *Norovirus* Hu/OC04059/2004/JP |
| *Norovirus* Hu/OC04067/2004/JP |
| *Norovirus* Hu/OC04071/2004/JP |
| *Norovirus* Hu/OC04073/2004/JP |
| *Norovirus* Hu/OC04075/2004/JP |
| *Norovirus* Hu/OC04076/2004/JP |
| *Norovirus* Hu/OC04169/2004/JP |
| *Norovirus* Hu/OC05010/2005/JP |
| *Norovirus* Hu/OC07138/07/JP |
| *Norovirus* Hu/OC08086/08/JP |
| *Norovirus* Hu/OC97007/97/JP |
| *Norovirus* Hu/OC97049/1997/JP |
| *Norovirus* Hu/OCS000564/2001/JP |
| *Norovirus* Hu/OCS020289/2002/JP |
| *Norovirus* Hu/OCS030697/2004/JP |
| *Norovirus* Hu/OCS040035/2004/JP |
| *Norovirus* Hu/OCS040100/2004/JP |
| *Norovirus* Hu/OCS980705/1998/JP |
| *Norovirus* Hu/Odate/1/06/JP |
| *Norovirus* Hu/Odate/2/2006/JP |
| *Norovirus* Hu/Odate/3/2006/JP |
| *Norovirus* Hu/Offenburg10550/2002/DE |
| *Norovirus* Hu/Offenburg1155/2004/DE |
| *Norovirus* Hu/Offenburg216/2003/DE |
| *Norovirus* Hu/Offenburg2620/2002/DE |
| *Norovirus* Hu/Offenburg4224/2004/DE |
| *Norovirus* Hu/Offenburg726/02/DE/2002/DE |
| *Norovirus* Hu/OLHSC-1/IRL |
| *Norovirus* Hu/OLHSC-10/IRL |
| *Norovirus* Hu/OLHSC-11/IRL |
| *Norovirus* Hu/OLHSC-12/IRL |
| *Norovirus* Hu/OLHSC-13/IRL |
| *Norovirus* Hu/OLHSC-14/IRL |
| *Norovirus* Hu/OLHSC-15/IRL |
| *Norovirus* Hu/OLHSC-16/IRL |
| *Norovirus* Hu/OLHSC-2/IRL |
| *Norovirus* Hu/OLHSC-3/IRL |
| *Norovirus* Hu/OLHSC-4/IRL |
| *Norovirus* Hu/OLHSC-5/IRL |
| *Norovirus* Hu/OLHSC-6/IRL |
| *Norovirus* Hu/OLHSC-7/IRL |
| *Norovirus* Hu/OLHSC-8/IRL |
| *Norovirus* Hu/OLHSC-9/IRL |
| *Norovirus* Hu/Omonogawa/1/1993/JP |
| *Norovirus* Hu/Osaka/000321/2000/JP/3006 |
| *Norovirus* Hu/Osaka/010203/2001/JP/3611 |
| *Norovirus* Hu/Osaka/010203/2001/JP/3612 |
| *Norovirus* Hu/Osaka/010228/2001/JP/3625 |
| *Norovirus* Hu/Osaka/010314/2001/JP/3634 |
| *Norovirus* Hu/Osaka/03-132/2003/JP |
| *Norovirus* Hu/Osaka/05-1059/2006/JP |
| *Norovirus* Hu/Osaka/05-1086/2006/JP |
| *Norovirus* Hu/Osaka/05-1180/2006/JP |
| *Norovirus* Hu/Osaka/05-365/2005/JP |

TABLE 1-continued

| *Norovirus* Strains |
|---|
| *Norovirus* bovine/BV129/2007/BEL |
| *Norovirus* bovine/BV133/2007/BEL |
| *Norovirus* bovine/BV15/2007/BEL |
| *Norovirus* bovine/BV18/2007/BEL |
| *Norovirus* bovine/BV24/2007/BEL |
| *Norovirus* bovine/BV52/2007/BEL |
| *Norovirus* bovine/BV9/2007/BEL |
| *Norovirus* bovine/BV99/2007/BEL |
| *Norovirus* bovine/Corroy/B37/2002/Be |
| *Norovirus* bovine/Dalhem/B214/2003/Be |
| *Norovirus* bovine/Florennes/B242/2003/Be |
| *Norovirus* bovine/KT17/2004/SVN |
| *Norovirus* bovine/Mohiville/B123/2002/Be |
| *Norovirus* bovine/Wasma/B199/2003/Be |
| *Norovirus* bovine/Wasme/B199/2003/Be |
| *Norovirus* bovine/Wasme/B200/2003/Be |
| *Norovirus* carrot/Offenburg/2004/DE |
| *Norovirus* cattle/BV416/2008/BEL |
| *Norovirus* Chanthaburi-75/Thailand |
| *Norovirus* clam/Shimane/Asari1-DT/Jun2008/JP |
| *Norovirus* clam/Shimane/Asari1-Liquid/Jun2008/JP |
| *Norovirus* clam/Shimane/Asari3-DT/Jun2008/JP |
| *Norovirus* cleaning rag/Enzkofen40942/2007/DEU |
| *Norovirus* cow/125/2005/SVN |
| *Norovirus* cow/KT17/2004/SVN |
| *Norovirus* Dhaka/167/2004/BGD |
| *Norovirus* Dhaka/176/2004/BGD |
| *Norovirus* Dhaka/196/2004/BGD |
| *Norovirus* Dhaka/262/2004/BGD |
| *Norovirus* Dhaka/267/2004/BGD |
| *Norovirus* Dhaka/270/2004/BGD |
| *Norovirus* Dhaka/289/2005/BGD |
| *Norovirus* Dhaka/295/2005/BGD |
| *Norovirus* Dhaka/305/2005/BGD |
| *Norovirus* Dhaka/335/2005/BGD |
| *Norovirus* Dhaka/361/2005/BGD |
| *Norovirus* Dhaka/367/2005/BGD |
| *Norovirus* Dhaka/373/2005/BGD |
| *Norovirus* Dhaka/389/2005/BGD |
| *Norovirus* Dhaka/401/2005/BGD |
| *Norovirus* Dhaka/415/2005/BGD |
| *Norovirus* Dhaka/417/2005/BGD |
| *Norovirus* Dhaka/423/2005/BGD |
| *Norovirus* Dhaka/427/2005/BGD |
| *Norovirus* Dhaka/455/2005/BGD |
| *Norovirus* Dhaka/471/2005/BGD |
| *Norovirus* Dhaka/473/2005/BGD |
| *Norovirus* Dhaka/478/2005/BGD |
| *Norovirus* Dhaka/481/2005/BGD |
| *Norovirus* Dhaka/493/2005/BGD |
| *Norovirus* Dhaka/497/2005/BGD |
| *Norovirus* Dhaka/501/2005/BGD |
| *Norovirus* Dhaka/503/2005/BGD |
| *Norovirus* Dhaka/527/2005/BGD |
| *Norovirus* Dhaka/617/2005/BGD |
| *Norovirus* Dhaka/665/2005/BGD |
| *Norovirus* Dhaka/717/2005/BGD |
| *Norovirus* Dhaka/750/2005/BGD |
| *Norovirus* Dhaka/759/2005/BGD |
| *Norovirus* Dhaka/767/2005/BGD |
| *Norovirus* Dhaka/791/2005/BGD |
| *Norovirus* Dhaka/817/2005/BGD |
| *Norovirus* Dhaka/861/2005/BGD |
| *Norovirus* Dhaka/881/2005/BGD |
| *Norovirus* Dhaka/893/2005/BGD |
| *Norovirus* Dhaka/904/2005/BGD |
| *Norovirus* dog/C33/Viseu/2007/PRT |
| *Norovirus* dog/Thessaloniki/30/2008/GRC |
| *Norovirus* Dresden153/1997/GE |
| *Norovirus* Dresden245/1997/GE |
| *Norovirus* Dresden267/1997/GE |
| *Norovirus* Dresden319/1997/GE |
| *Norovirus* Erlangen195/1997/GE |
| *Norovirus* Freiburg024/1997/GE |
| *Norovirus* Hu/Osaka/101/05/JP |
| *Norovirus* Hu/Osaka/110/05/JP |
| *Norovirus* Hu/Osaka/133/05/JP |
| *Norovirus* Hu/Osaka/137/05/JP |
| *Norovirus* Hu/Osaka/146/05/JP |
| *Norovirus* Hu/Osaka/161/05/JP |
| *Norovirus* Hu/Osaka/177/04/JP |
| *Norovirus* Hu/Osaka/189/04/JP |
| *Norovirus* Hu/Osaka/337/04/JP |
| *Norovirus* Hu/Osaka/36/05/JP |
| *Norovirus* Hu/Osaka/49/05/JP |
| *Norovirus* Hu/Osaka/52/05/JP |
| *Norovirus* Hu/Osaka/61/05/JP |
| *Norovirus* Hu/Osaka/7075/2005/JP |
| *Norovirus* Hu/Osaka/7107/2006/JP |
| *Norovirus* Hu/Osaka/724/04/JP |
| *Norovirus* Hu/Osaka/786/04/JP |
| *Norovirus* Hu/Osaka/840/04/JP |
| *Norovirus* Hu/OsakaNI/2004/JP |
| *Norovirus* Hu/oysters/CR17F2000/France |
| *Norovirus* Hu/oysters/CR91NL2000/Netherlands |
| *Norovirus* Hu/oysters/O04-16/2004/NL |
| *Norovirus* Hu/oysters/O04-45/2004/NL |
| *Norovirus* Hu/oysters/O6NL2002/Netherlands |
| *Norovirus* Hu/oysters/oes16NL2001/Netherlands |
| *Norovirus* Hu/P1-1/2000/SWE |
| *Norovirus* Hu/P1-10/2000/SWE |
| *Norovirus* Hu/P1-11/2000/SWE |
| *Norovirus* Hu/P1-12/2000/SWE |
| *Norovirus* Hu/P1-13/2000/SWE |
| *Norovirus* Hu/P1-14/2000/SWE |
| *Norovirus* Hu/P1-15/2000/SWE |
| *Norovirus* Hu/P1-16/2000/SWE |
| *Norovirus* Hu/P1-17/2000/SWE |
| *Norovirus* Hu/P1-18/2000/SWE |
| *Norovirus* Hu/P1-19/2000/SWE |
| *Norovirus* Hu/P1-20/2000/SWE |
| *Norovirus* Hu/P1-3/2000/SWE |
| *Norovirus* Hu/P1-6/2000/SWE |
| *Norovirus* Hu/P1-7/2000/SWE |
| *Norovirus* Hu/P1-8/2000/SWE |
| *Norovirus* Hu/P1-9/2000/SWE |
| *Norovirus* Hu/P10/JPN |
| *Norovirus* Hu/P11-10/2001/SWE |
| *Norovirus* Hu/P11-12/2001/SWE |
| *Norovirus* Hu/P11-13/2001/SWE |
| *Norovirus* Hu/P11-14/2001/SWE |
| *Norovirus* Hu/P11-16/2001/SWE |
| *Norovirus* Hu/P11-19/2001/SWE |
| *Norovirus* Hu/P11-2/2001/SWE |
| *Norovirus* Hu/P11-20/2001/SWE |
| *Norovirus* Hu/P11-21/2001/SWE |
| *Norovirus* Hu/P11-211/2001/SWE |
| *Norovirus* Hu/P11-23/2001/SWE |
| Norovrrus Hu/P11-24/2001/SWE |
| *Norovirus* Hu/P11-25/2001/SWE |
| *Norovirus* Hu/P11-26/2001/SWE |
| *Norovirus* Hu/P11-27/2001/SWE |
| *Norovirus* Hu/P11-3/2001/SWE |
| *Norovirus* Hu/P11-5/2001/SWE |
| *Norovirus* Hu/P11-7/2001/SWE |
| *Norovirus* Hu/P13-1/2001/SWE |
| *Norovirus* Hu/P13-10/2001/SWE |
| *Norovirus* Hu/P13-11/2001/SWE |
| *Norovirus* Hu/P13-12/2001/SWE |
| *Norovirus* Hu/P13-13/2001/SWE |
| *Norovirus* Hu/P13-14/2001/SWE |
| *Norovirus* Hu/P13-15/2001/SWE |
| *Norovirus* Hu/P13-16/2001/SWE |
| *Norovirus* Hu/P13-17/2001/SWE |
| *Norovirus* Hu/P13-19/2001/SWE |
| *Norovirus* Hu/P13-2/2001/SWE |
| *Norovirus* Hu/P13-3/2001/SWE |
| *Norovirus* Hu/P13-4/2001/SWE |
| *Norovirus* Hu/P13-6/2001/SWE |
| *Norovirus* Hu/P13-7/2001/SWE |
| *Norovirus* Hu/P13-8/2001/SWE |
| *Norovirus* Hu/P13-9/2001/SWE |

TABLE 1-continued

| *Norovirus* Strains |
|---|
| *Norovirus* Freiburg057/1997/GE |
| *Norovirus* Freiburg253/1998/GE |
| *Norovirus* Hamburg048/1997/GE |
| *Norovirus* Hamburg135/1998/GE |
| *Norovirus* Hamburg137/1997/GE |
| *Norovirus* Hamburg139/1997/GE |
| *Norovirus* Hamburg180/1997/GE |
| *Norovirus* Hamburg189/1997/GE |
| *Norovirus* Hamburg236/1997/GE |
| *Norovirus* Hamburg316/1998/GE |
| *Norovirus* Hu/01/05/DR |
| *Norovirus* Hu/0137/2004/NL |
| *Norovirus* Hu/0672HA/2004/NL |
| *Norovirus* Hu/1064A/73292/2007/NLD |
| *Norovirus* Hu/1064B/73292/2007/NLD |
| *Norovirus* Hu/1968/US |
| *Norovirus* Hu/4476A/64317/2006/NLD |
| *Norovirus* Hu/5013/JPN |
| *Norovirus* Hu/5014/JPN |
| *Norovirus* Hu/5015/JPN |
| *Norovirus* Hu/5017.34/2003/JPN |
| *Norovirus* Hu/5069/JPN |
| *Norovirus* Hu/5128/JPN |
| *Norovirus* Hu/5722/JPN |
| *Norovirus* Hu/5723/JPN |
| *Norovirus* Hu/5735/2004/JPN |
| *Norovirus* Hu/5740/JPN |
| *Norovirus* Hu/5828/JPN |
| *Norovirus* Hu/6136/JPN |
| *Norovirus* Hu/6819/2005/JPN |
| *Norovirus* Hu/6820/2005/JPN |
| *Norovirus* Hu/6822/2005/JPN |
| *Norovirus* Hu/6824/2005/JPN |
| *Norovirus* Hu/6825/2005/JPN |
| *Norovirus* Hu/6828/2005/JPN |
| *Norovirus* Hu/6892/2005/JPN |
| *Norovirus* Hu/6960/2005/JPN |
| *Norovirus* Hu/7300/2005/JPN |
| *Norovirus* Hu/771/2005/IRL |
| *Norovirus* Hu/78/04/Ru |
| *Norovirus* Hu/8533/Maizuru/08/JPN |
| *Norovirus* Hu/Aalen2506/2003/DE |
| *Norovirus* Hu/Accra/2000/GH |
| *Norovirus* Hu/Afyon/14/2007/TR |
| *Norovirus* Hu/Afyon/22/2007/TR |
| *Norovirus* Hu/Afyon/34/2007/TR |
| *Norovirus* Hu/Afyon/44/2007/TR |
| *Norovirus* Hu/Afyon/49/2007/TR |
| *Norovirus* Hu/Afyon/65/2007/TR |
| *Norovirus* Hu/Afyon/7/2007/TR |
| *Norovirus* Hu/Afyon/70/2007/TR |
| *Norovirus* Hu/Afyon/72/2007/TR |
| *Norovirus* Hu/Afyon/74/2007/TR |
| *Norovirus* Hu/Afyon/79/2007/TR |
| *Norovirus* Hu/Afyon/88/2007/TR |
| *Norovirus* Hu/Ahm/PC03/2006/India |
| *Norovirus* Hu/Akabane/990206/1999/JP/2087 |
| *Norovirus* Hu/Akabane/991130/1999/JP/2258 |
| *Norovirus* Hu/Akita-City/1/2006/JP |
| *Norovirus* Hu/Akita-City/1/2007/JP |
| *Norovirus* Hu/Akita-City/1/2008/JP |
| *Norovirus* Hu/Akita-City/2/2008/JP |
| *Norovirus* Hu/Akita-City/3/2008/JP |
| *Norovirus* Hu/Akita-City/4/2008/JP |
| *Norovirus* Hu/Aur/A822/2006/India |
| *Norovirus* Hu/Aur/A832/2006/India |
| *Norovirus* Hu/Balingen2573/2004/DE |
| *Norovirus* Hu/Balingen633/2002/DE |
| *Norovirus* Hu/Beijing/06/2005/CHN |
| *Norovirus* Hu/Beijing/148/2005/CHN |
| *Norovirus* Hu/Beijing/169/2005/CHN |
| *Norovirus* Hu/Beijing/375/2005/CHN |
| *Norovirus* Hu/Beijing/48/2005/CHN |
| *Norovirus* Hu/Beijing/BJ1/2002/CHN |
| *Norovirus* Hu/Beijing/BJ12/2002/CHN |
| *Norovirus* Hu/Beijing/BJ14/2002/CHN |
| *Norovirus* Hu/Beijing/BJ21/2002/CHN |
| *Norovirus* Hu/Beijing/CR2905/2004/CHN |
| *Norovirus* Hu/P14/JPN |
| *Norovirus* Hu/P15-1/2001/SWE |
| *Norovirus* Hu/P15-10/2001/SWE |
| *Norovirus* Hu/P15-12/2001/SWE |
| *Norovirus* Hu/P15-14/2001/SWE |
| *Norovirus* Hu/P15-15/2001/SWE |
| *Norovirus* Hu/P15-18/2001/SWE |
| *Norovirus* Hu/P15-2/2001/SWE |
| *Norovirus* Hu/P15-22/2001/SWE |
| *Norovirus* Hu/P15-25/2001/SWE |
| *Norovirus* Hu/P15-3/2001/SWE |
| *Norovirus* Hu/P15-30/2001/SWE |
| *Norovirus* Hu/P15-5/2001/SWE |
| *Norovirus* Hu/P15-6/2001/SWE |
| *Norovirus* Hu/P15-9/2001/SWE |
| *Norovirus* Hu/P17-1/2003/SWE |
| *Norovirus* Hu/P17-10/2003/SWE |
| *Norovirus* Hu/P17-11/2003/SWE |
| *Norovirus* Hu/P17-12/2003/SWE |
| *Norovirus* Hu/P17-13/2003/SWE |
| *Norovirus* Hu/P17-14/2003/SWE |
| *Norovirus* Hu/P17-15/2003/SWE |
| *Norovirus* Hu/P17-17/2003/SWE |
| *Norovirus* Hu/P17-18/2003/SWE |
| *Norovirus* Hu/P17-19/2003/SWE |
| *Norovirus* Hu/P17-2/2003/SWE |
| *Norovirus* Hu/P17-20/2003/SWE |
| *Norovirus* Hu/P17-3/2003/SWE |
| *Norovirus* Hu/P17-6/2003/SWE |
| *Norovirus* Hu/P17-8/2003/SWE |
| *Norovirus* Hu/P17-9/2003/SWE |
| *Norovirus* Hu/P1a/JPN |
| *Norovirus* Hu/P1b/JPN |
| *Norovirus* Hu/P2/JPN |
| *Norovirus* Hu/P3-10/2000/SWE |
| *Norovirus* Hu/P3-11/2000/SWE |
| *Norovirus* Hu/P3-14/2000/SWE |
| *Norovirus* Hu/P3-15/2000/SWE |
| *Norovirus* Hu/P3-16/2000/SWE |
| *Norovirus* Hu/P3-17/2000/SWE |
| *Norovirus* Hu/P3-18/2000/SWE |
| *Norovirus* Hu/P3-19/2000/SWE |
| *Norovirus* Hu/P3-2/2000/SWE |
| *Norovirus* Hu/P3-20/2000/SWE |
| *Norovirus* Hu/P3-3/2000/SWE |
| *Norovirus* Hu/P3-4/2000/SWE |
| *Norovirus* Hu/P3-5/2000/SWE |
| *Norovirus* Hu/P3-6/2000/SWE |
| *Norovirus* Hu/P3-7/2000/SWE |
| *Norovirus* Hu/P3-8/2000/SWE |
| *Norovirus* Hu/P3-9/2000/SWE |
| *Norovirus* Hu/P4a/JPN |
| *Norovirus* Hu/P4b/JPN |
| *Norovirus* Hu/P5-1/2000/SWE |
| *Norovirus* Hu/P5-11/2000/SWE |
| *Norovirus* Hu/P5-14/2000/SWE |
| *Norovirus* Hu/P5-15/2000/SWE |
| *Norovirus* Hu/P5-16/2000/SWE |
| *Norovirus* Hu/P5-18/2000/SWE |
| *Norovirus* Hu/P5-19/2000/SWE |
| *Norovirus* Hu/P5-2/2000/SWE |
| *Norovirus* Hu/P5-20/2000/SWE |
| *Norovirus* Hu/P5-3/2000/SWE |
| *Norovirus* Hu/P5-4/2000/SWE |
| *Norovirus* Hu/P5-5/2000/SWE |
| *Norovirus* Hu/P5-7/2000/SWE |
| *Norovirus* Hu/P5-8/2000/SWE |
| *Norovirus* Hu/P7-10/2001/SWE |
| *Norovirus* Hu/P7-11/2001/SWE |
| *Norovirus* Hu/P7-12/2001/SWE |
| *Norovirus* Hu/P7-14/2001/SWE |
| *Norovirus* Hu/P7-15/2001/SWE |
| *Norovirus* Hu/P7-16/2001/SWE |
| *Norovirus* Hu/P7-17/2001/SWE |
| *Norovirus* Hu/P7-18/2001/SWE |
| *Norovirus* Hu/P7-19/2001/SWE |
| *Norovirus* Hu/P7-2/2001/SWE |
| *Norovirus* Hu/P7-20/2001/SWE |

TABLE 1-continued

| *Norovirus* Strains |
|---|
| *Norovirus* Hu/Beijing/CR2932/2004/CHN |
| *Norovirus* Hu/Beijing/CR2987/2004/CHN |
| *Norovirus* Hu/Berlin/11/03/Germany |
| *Norovirus* Hu/Boeblingen13203/2002/DE |
| *Norovirus* Hu/Boeblingen13295/2002/DE |
| *Norovirus* Hu/Boeblingen2108/2003/DE |
| *Norovirus* Hu/Briancon870/2004/France |
| *Norovirus* Hu/C14/2002/AU |
| *Norovirus* Hu/Calw132712/2002/DE |
| *Norovirus* Hu/Calw13843/2002/DE |
| *Norovirus* Hu/Calw1452/2003/DE |
| *Norovirus* Hu/Calw2169/2003/DE |
| *Norovirus* Hu/Calw2563/2003/DE |
| *Norovirus* Hu/Calw3453/2002/DE |
| *Norovirus* Hu/Calw5194/2002/DE |
| *Norovirus* Hu/Caterer_Company_1_pat_1/10-04-2003/NL |
| *Norovirus* Hu/Caterer_Company_1_pat_2/10-04-2003/NL |
| *Norovirus* Hu/Caterer_Company_2_pat_1/12-04-2003/NL |
| *Norovirus* Hu/Caterer_Company_2_pat_2/12-04-2003/NL |
| *Norovirus* Hu/Caterer_personel_1/16-04-2003/NL |
| *Norovirus* Hu/Caterer_personel_2/16-04-2003/NL |
| *Norovirus* Hu/Caterer_personel_3/16-04-2003/NL |
| *Norovirus* Hu/Caterer_personel_4/16-04-2003/NL |
| *Norovirus* Hu/Caterer_personel_5/16-04-2003/NL |
| *Norovirus* Hu/Chatellerault709/2004/France |
| *Norovirus* Hu/Chiba/000010/2000/JP |
| *Norovirus* Hu/Chiba/000016G1/1999/JP |
| *Norovirus* Hu/Chiba/000016G2/1999/JP |
| *Norovirus* Hu/Chiba/000022/2000/JP |
| *Norovirus* Hu/Chiba/000325/2000/JP |
| *Norovirus* Hu/Chiba/000335/2000/JP |
| *Norovirus* Hu/Chiba/000336/2000/JP |
| *Norovirus* Hu/Chiba/000337/2000/JP |
| *Norovirus* Hu/Chiba/000344/2000/JP |
| *Norovirus* Hu/Chiba/000459/2000/JP |
| *Norovirus* Hu/Chiba/000468/2000/JP |
| *Norovirus* Hu/Chiba/000485/2000/JP |
| *Norovirus* Hu/Chiba/000516/2000/JP |
| *Norovirus* Hu/Chiba/000520/2000/JP |
| *Norovirus* Hu/Chiba/000600/2000/JP |
| *Norovirus* Hu/Chiba/000661/2000/JP |
| *Norovirus* Hu/Chiba/000782/2000/JP |
| *Norovirus* Hu/Chiba/001049/2000/JP |
| *Norovirus* Hu/Chiba/001080/2000/JP |
| *Norovirus* Hu/Chiba/010006/2001/JP |
| *Norovirus* Hu/Chiba/010045/2001/JP |
| *Norovirus* Hu/Chiba/010105/2001/JP |
| *Norovirus* Hu/Chiba/010108/2001/JP |
| *Norovirus* Hu/Chiba/010390/2001/JP |
| *Norovirus* Hu/Chiba/010433/2001/JP |
| *Norovirus* Hu/Chiba/010442/2001/JP |
| *Norovirus* Hu/Chiba/010465/2001/JP |
| *Norovirus* Hu/Chiba/010510/2001/JP |
| *Norovirus* Hu/Chiba/010522/2001/JP |
| *Norovirus* Hu/Chiba/010526/2001/JP |
| *Norovirus* Hu/Chiba/010539/2001/JP |
| *Norovirus* Hu/Chiba/010587/2001/JP |
| *Norovirus* Hu/Chiba/010621/2001/JP |
| *Norovirus* Hu/Chiba/010751/2001/JP |
| *Norovirus* Hu/Chiba/010998/2001/JP |
| *Norovirus* Hu/Chiba/020015/2002/JP |
| *Norovirus* Hu/Chiba/020040/2002/JP |
| *Norovirus* Hu/Chiba/020042/2002/JP |
| *Norovirus* Hu/Chiba/020062/2002/JP |
| *Norovirus* Hu/Chiba/020096G1/2002/JP |
| *Norovirus* Hu/Chiba/020096G2/2002/JP |
| *Norovirus* Hu/Chiba/020097/2002/JP |
| *Norovirus* Hu/Chiba/020198/2002/JP |
| *Norovirus* Hu/Chiba/020247/2002/JP |
| *Norovirus* Hu/P7-3/2001/SWE |
| *Norovirus* Hu/P7-4/2001/SWE |
| *Norovirus* Hu/P7-5/2001/SWE |
| *Norovirus* Hu/P7-6/2001/SWE |
| *Norovirus* Hu/P7-7/2001/SWE |
| *Norovirus* Hu/P9-1/2001/SWE |
| *Norovirus* Hu/P9-10/2001/SWE |
| *Norovirus* Hu/P9-11/2001/SWE |
| *Norovirus* Hu/P9-12/2001/SWE |
| *Norovirus* Hu/P9-18/2001/SWE |
| *Norovirus* Hu/P9-2/2001/SWE |
| *Norovirus* Hu/P9-21/2001/SWE |
| *Norovirus* Hu/P9-23/2001/SWE |
| *Norovirus* Hu/P9-24/2001/SWE |
| *Norovirus* Hu/P9-26/2001/SWE |
| *Norovirus* Hu/P9-27/2001/SWE |
| *Norovirus* Hu/P9-30/2001/SWE |
| *Norovirus* Hu/P9-5/2001/SWE |
| *Norovirus* Hu/P9-6/2001/SWE |
| *Norovirus* Hu/P9-7/2001/SWE |
| *Norovirus* Hu/P9-8/2001/SWE |
| *Norovirus* Hu/P9-9/2001/SWE |
| *Norovirus* Hu/Picton/2003/AU |
| *Norovirus* Hu/PontdeRoide682/2004/France |
| *Norovirus* Hu/ptAdam/64815/2006/NLD |
| *Norovirus* Hu/ptAdam/64815b/2006/NLD |
| *Norovirus* Hu/Pune/OPD04/2007/India |
| *Norovirus* Hu/Pune/OPD05/2007/India |
| *Norovirus* Hu/Pune/PC01/2005/India |
| *Norovirus* Hu/Pune/PC02/2006/India |
| *Norovirus* Hu/Pune/PC04/2005/India |
| *Norovirus* Hu/Pune/PC05/2005/India |
| *Norovirus* Hu/Pune/PC06/2005/India |
| *Norovirus* Hu/Pune/PC07/2005/India |
| *Norovirus* Hu/Pune/PC08/2005/India |
| *Norovirus* Hu/Pune/PC09/2005/India |
| *Norovirus* Hu/Pune/PC10/2005/India |
| *Norovirus* Hu/Pune/PC11/2006/India |
| *Norovirus* Hu/Pune/PC12/2006/India |
| *Norovirus* Hu/Pune/PC13/2006/India |
| *Norovirus* Hu/Pune/PC14/2006/India |
| *Norovirus* Hu/Pune/PC15/2006/India |
| *Norovirus* Hu/Pune/PC16/2006/India |
| *Norovirus* Hu/Pune/PC17/2006/India |
| *Norovirus* Hu/Pune/PC18/2006/India |
| *Norovirus* Hu/Pune/PC19/2006/India |
| *Norovirus* Hu/Pune/PC20/2006/India |
| *Norovirus* Hu/Pune/PC21/2006/India |
| *Norovirus* Hu/Pune/PC22/2006/India |
| *Norovirus* Hu/Pune/PC23/2006/India |
| *Norovirus* Hu/Pune/PC24/2006/India |
| *Norovirus* Hu/Pune/PC25/2006/India |
| *Norovirus* Hu/Pune/PC26/2006/India |
| *Norovirus* Hu/Pune/PC27/2006/India |
| *Norovirus* Hu/Pune/PC28/2006/India |
| *Norovirus* Hu/Pune/PC29/2006/India |
| *Norovirus* Hu/Pune/PC30/2007/India |
| *Norovirus* Hu/Pune/PC31/2007/India |
| *Norovirus* Hu/Pune/PC32/2007/India |
| *Norovirus* Hu/Pune/PC33/2007/India |
| *Norovirus* Hu/Pune/PC34/2007/India |
| *Norovirus* Hu/Pune/PC35/2007/India |
| *Norovirus* Hu/Pune/PC36/2007/India |
| *Norovirus* Hu/Pune/PC37/2007/India |
| *Norovirus* Hu/Pune/PC38/2007/India |
| *Norovirus* Hu/Pune/PC39/2007/India |
| *Norovirus* Hu/Pune/PC40/2007/India |
| *Norovirus* Hu/Pune/PC41/2007/India |
| *Norovirus* Hu/Pune/PC42/2007/India |
| *Norovirus* Hu/Pune/PC43/2007/India |
| *Norovirus* Hu/Pune/PC44/2007/India |
| *Norovirus* Hu/Pune/PC45/2007/India |
| *Norovirus* Hu/Pune/PC46/2007/India |
| *Norovirus* Hu/Pune/PC47/2007/India |
| *Norovirus* Hu/Pune/PC48/2007/India |
| *Norovirus* Hu/Pune/PC49/2007/India |
| *Norovirus* Hu/Pune/PC50/2007/India |
| *Norovirus* Hu/Pune/PC51/2007/India |

TABLE 1-continued

| *Norovirus* Strains | |
|---|---|
| *Norovirus* Hu/Chiba/020250/2002/JP | *Norovirus* Hu/Pune/PC52/2007/India |
| *Norovirus* Hu/Chiba/020251/2002/JP | *Norovirus* Hu/Pune/PC53/2007/India |
| *Norovirus* Hu/Chiba/020267/2002/JP | *Norovirus* Hu/Pune/PC54/2007/India |
| *Norovirus* Hu/Chiba/020301/2002/JP | *Norovirus* Hu/Pune/PC55/2007/India |
| *Norovirus* Hu/Chiba/020475/2002/JP | *Norovirus* Hu/Pune/PC56/2007/India |
| *Norovirus* Hu/Chiba/020555/2002/JP | *Norovirus* Hu/Pune/PC57/2007/India |
| *Norovirus* Hu/Chiba/020984/2002/JP | *Norovirus* Hu/Pune/PC58/2007/India |
| *Norovirus* Hu/Chiba/021022/2002/JP | *Norovirus* Hu/QLD059/2006/AUS |
| *Norovirus* Hu/Chiba/021026/2002/JP | *Norovirus* Hu/QLD466/2006/AUS |
| *Norovirus* Hu/Chiba/021050/2002/JP | *Norovirus* Hu/QLD497/2006/AUS |
| *Norovirus* Hu/Chiba/021068/2002/JP | *Norovirus* Hu/QLD900/2006/AUS |
| *Norovirus* Hu/Chiba/021071/2002/JP | *Norovirus* Hu/QLD946/2006/AUS |
| *Norovirus* Hu/Chiba/030100/2003/JP | *Norovirus* Hu/QLD987/2006/AUS |
| *Norovirus* Hu/Chiba/030305/2003/JP | *Norovirus* Hu/R1/JPN |
| *Norovirus* Hu/Chiba/030308/2003/JP | *Norovirus* Hu/R2/JPN |
| *Norovirus* Hu/Chiba/030322/2003/JP | *Norovirus* Hu/R3/JPN |
| *Norovirus* Hu/Chiba/030335/2003/JP | *Norovirus* Hu/Rastatt724/2003/DE |
| *Norovirus* Hu/Chiba/030358/2003/JP | *Norovirus* Hu/Ravensburg12859/2001/DE |
| *Norovirus* Hu/Chiba/030360/2003/JP | *Norovirus* Hu/Ravensburg6690/2001/DE |
| *Norovirus* Hu/Chiba/030399/2003/JP | *Norovirus* Hu/reference/2000/SWE |
| *Norovirus* Hu/Chiba/030403/2003/JP | *Norovirus* Hu/RemsMurr3910/2002/DE |
| *Norovirus* Hu/Chiba/030412/2003/JP | *Norovirus* Hu/Reutlingen1302/2002/DE |
| *Norovirus* Hu/Chiba/030429/2003/JP | *Norovirus* Hu/Reutlingen1402/2002/DE |
| *Norovirus* Hu/Chiba/030474/2003/JP | *Norovirus* Hu/Reutlingen2844/2002/DE |
| *Norovirus* Hu/Chiba/030486/2003/JP | *Norovirus* Hu/River_Cruising_ship_1/16-05-2001/NL |
| *Norovirus* Hu/Chiba/030510/2003/JP | |
| *Norovirus* Hu/Chiba/030517/2003/JP | *Norovirus* Hu/River_Cruising_Ship_2/08-04-2003/NL |
| *Norovirus* Hu/Chiba/030522/2003/JP | |
| *Norovirus* Hu/Chiba/030541/2003/JP | *Norovirus* Hu/S1/JPN |
| *Norovirus* Hu/Chiba/030542/2003/JP | *Norovirus* Hu/S10/JPN |
| *Norovirus* Hu/Chiba/030546/2003/JP | *Norovirus* Hu/S12a/JPN |
| *Norovirus* Hu/Chiba/030547G1/2003/JP | *Norovirus* Hu/S12b/JPN |
| *Norovirus* Hu/Chiba/030547G2/2003/JP | *Norovirus* Hu/S14/JPN |
| *Norovirus* Hu/Chiba/030556/2003/JP | *Norovirus* Hu/S2/JPN |
| *Norovirus* Hu/Chiba/030603/2003/JP | *Norovirus* Hu/S4/JPN |
| *Norovirus* Hu/Chiba/030654/2003/JP | *Norovirus* Hu/S6/JPN |
| *Norovirus* Hu/Chiba/030658/2003/JP | *Norovirus* Hu/S7/JPN |
| *Norovirus* Hu/Chiba/030910/2003/JP | *Norovirus* Hu/S8/JPN |
| *Norovirus* Hu/Chiba/030968/2003/JP | *Norovirus* Hu/Saarbruecken/04/03/Germany |
| *Norovirus* Hu/Chiba/030981/2003/JP | *Norovirus* Hu/Saga/000313/2000/JP/2876 |
| *Norovirus* Hu/Chiba/031038/2003/JP | *Norovirus* Hu/Saga/001215/2000/JP/3101 |
| *Norovirus* Hu/Chiba/04-1008/2004/JP | *Norovirus* Hu/Saga/5424/03/JP |
| *Norovirus* Hu/Chiba/04-1050/2005/JP | *Norovirus* Hu/Sakai/04-179/2005/JP |
| *Norovirus* Hu/Chiba/04-899/2004/JP | *Norovirus* Hu/Samokov414/2007/BGR |
| *Norovirus* Hu/Chiba/04-974/2004/JP | *Norovirus* Hu/SchwaebischHall11120/2002/DE |
| *Norovirus* Hu/Chiba/040001/2004/JP | *Norovirus* Hu/Serian/GE0241/2001/MYS |
| *Norovirus* Hu/Chiba/040002/2004/JP | *Norovirus* Hu/Serian/GE0431/2001/MYS |
| *Norovirus* Hu/Chiba/040003/2004/JP | *Norovirus* Hu/Serian/GE0433/2001/MYS |
| *Norovirus* Hu/Chiba/040045/2004/JP | *Norovirus* Hu/Serian/GE0861/2001/MYS |
| *Norovirus* Hu/Chiba/040092/2004/JP | *Norovirus* Hu/Shaanxi/49576/2006/CHN |
| *Norovirus* Hu/Chiba/040096/2004/JP | *Norovirus* Hu/Shaanxi/49586/2006/CHN |
| *Norovirus* Hu/Chiba/040110/2004/JP | *Norovirus* Hu/Shaanxi/49595/2006/CHN |
| *Norovirus* Hu/Chiba/040140/2004/JP | *Norovirus* Hu/Shaanxi/49596/2006/CHN |
| *Norovirus* Hu/Chiba/040230/2004/JP | *Norovirus* Hu/Shaanxi/49597/2006/CHN |
| *Norovirus* Hu/Chiba/040252/2004/JP | *Norovirus* Hu/Shaanxi/49598/2006/CHN |
| *Norovirus* Hu/Chiba/040277/2004/JP | *Norovirus* Hu/Shaanxi/49599/2006/CHN |
| *Norovirus* Hu/Chiba/040300/2004/JP | *Norovirus* Hu/Shaanxi/49600/2006/CHN |
| *Norovirus* Hu/Chiba/040309/2004/JP | *Norovirus* Hu/Shaanxi/49601/2006/CHN |
| *Norovirus* Hu/Chiba/040311/2004/JP | *Norovirus* Hu/Shaanxi/49606/2006/CHN |
| *Norovirus* Hu/Chiba/040493/2004/JP | *Norovirus* Hu/Shaanxi/49607/2006/CHN |
| *Norovirus* Hu/Chiba/040500/2004/JP | *Norovirus* Hu/Shaanxi/49610/2006/CHN |
| *Norovirus* Hu/Chiba/040501/2004/JP | *Norovirus* Hu/Shaibah-1/2007/IRQ |
| *Norovirus* Hu/Chiba/040502/2004/JP | *Norovirus* Hu/Shaibah-2/2007/IRQ |
| *Norovirus* Hu/Chiba/040545/2004/JP | *Norovirus* Hu/Shanghai/49798/2006/CHN |
| *Norovirus* Hu/Chiba/040554/2004/JP | *Norovirus* Hu/Shanghai/49800/2006/CHN |
| *Norovirus* Hu/Chiba/040589/2004/JP | *Norovirus* Hu/Shanghai/49803/2006/CHN |
| *Norovirus* Hu/Chiba/990897/1999/JP | *Norovirus* Hu/Shanxi/49709/2006/CHN |
| *Norovirus* Hu/Chiba/990900/1999/JP | *Norovirus* Hu/Shanxi/49716/2006/CHN |
| *Norovirus* Hu/Chiba/990969/1999/JP | *Norovirus* Hu/Shanxi/50106/2006/CHN |
| *Norovirus* Hu/Chiba/991012/1999/JP | *Norovirus* Hu/Shimane/D1712-A-a/Jun2008/JP |
| *Norovirus* Hu/Chiba/991013/1999/JP | *Norovirus* Hu/Shimane/D1712-A-b/Jun2008/JP |
| *Norovirus* Hu/Chiba/991118/1999/JP | *Norovirus* Hu/Shimane/D1714-B/Jun2008/JP |
| *Norovirus* Hu/Chiba/991120/1999/JP | *Norovirus* Hu/Shimane/D1715-B-a/Jun2008/JP |
| *Norovirus* Hu/Chiba/991173/1999/JP | *Norovirus* Hu/Shimane/D1715-B-b/Jun2008/JP |
| *Norovirus* Hu/Chiba/991180/1999/JP | *Norovirus* Hu/Shimane/D1716-B/Jun2008/JP |
| *Norovirus* Hu/CHN2119/CC99 | *Norovirus* Hu/Shimane/D1725/Jun2008/JP |
| *Norovirus* Hu/CHN2121/CC99 | *Norovirus* Hu/Shimane/D1730-A/Jun2008/JP |
| *Norovirus* Hu/CHN2122/CC99 | *Norovirus* Hu/Shimane/D1731-A/Jun2008/JP |

TABLE 1-continued

| *Norovirus* Strains | |
|---|---|
| *Norovirus* Hu/CHN2127/CC99 | *Norovirus* Hu/Shimane/D1734-D/Jun2008/JP |
| *Norovirus* Hu/CHN2136/CC99 | *Norovirus* Hu/Shimane/D1739-A/Jun2008/JP |
| *Norovirus* Hu/CHN2139/CC99 | *Norovirus* Hu/Shimane/D1741-D-a/Jun2008/JP |
| *Norovirus* Hu/CHN2140/CC99 | *Norovirus* Hu/Shimane/D1741-D-b/Jun2008/JP |
| *Norovirus* Hu/CHN2168/LL99 | *Norovirus* Hu/Shimane/D1742-D/Jun2008/JP |
| *Norovirus* Hu/CHN2183/LL99 | *Norovirus* Hu/Shimane/D1743-D/Jun2008/JP |
| *Norovirus* Hu/CHN2514/HN99 | *Norovirus* Hu/Shinshiro/1/2006/JP |
| *Norovirus* Hu/CHN2553/HN99 | *Norovirus* Hu/Showa/1/05/JP |
| *Norovirus* Hu/CHN2576/HN99 | *Norovirus* Hu/SI001386/Slovenia |
| *Norovirus* Hu/CHN2625/GZH99 | *Norovirus* Hu/Sigmaringen13187/2002/DE |
| *Norovirus* Hu/CHN2749/GZH99 | *Norovirus* Hu/Sigmaringen4557/2001/DE |
| *Norovirus* Hu/CHN2792/LZH99 | *Norovirus* Hu/Sigmaringen687/2003/DE |
| *Norovirus* Hu/CHN2799/LZH99 | *Norovirus* Hu/Sofia156/2007/BGR |
| *Norovirus* Hu/CHN2807/KM00 | *Norovirus* Hu/Sofia578/2007/BGR |
| *Norovirus* Hu/CHN2809/KM00 | *Norovirus* Hu/Sofia661/2007/BGR |
| *Norovirus* Hu/CHN2841/KM99 | *Norovirus* Hu/Sommieres1203/2006/France |
| *Norovirus* Hu/CHN2842/KM99 | *Norovirus* Hu/SteColette658/2004/France |
| *Norovirus* Hu/CHN2844/KM99 | *Norovirus* Hu/Stuttgart02184/2002/DE |
| *Norovirus* Hu/CHN2851/KM99 | *Norovirus* Hu/Stuttgart7528/2002/DE |
| *Norovirus* Hu/CHN2929/GZH00 | *Norovirus* Hu/T2a/JPN |
| *Norovirus* Hu/CHN302/BJ99 | *Norovirus* Hu/T2b/JPN |
| *Norovirus* Hu/CHN3055/FJ99 | *Norovirus* Hu/T3/JPN |
| *Norovirus* Hu/CHN3111/FJ99 | *Norovirus* Hu/T4/JPN |
| *Norovirus* Hu/CHN3156/FJ99 | *Norovirus* Hu/Taipei-1/04/TW |
| *Norovirus* Hu/CHN3181/HZH99 | *Norovirus* Hu/Taipei-11/04/TW |
| *Norovirus* Hu/CHN3191/HZH99 | *Norovirus* Hu/Taipei-24/04/TW |
| *Norovirus* Hu/CHN3198/HZH99 | *Norovirus* Hu/Taipei-32/04/TW |
| *Norovirus* Hu/CHN3202/HZH99 | *Norovirus* Hu/Taipei-33/04/TW |
| *Norovirus* Hu/CHN3241/HZH99 | *Norovirus* Hu/Taipei-52/04/TW |
| *Norovirus* Hu/CHN3256/HZH99 | *Norovirus* Hu/Taipei-53/04/TW |
| *Norovirus* Hu/CHN3258/HZH99 | *Norovirus* Hu/Taipei-57/04/TW |
| *Norovirus* Hu/CHN3263/HZH99 | *Norovirus* Hu/Taipei-63/04/TW |
| *Norovirus* Hu/CHN3275/HZH99 | *Norovirus* Hu/Taipei-69/04/TW |
| *Norovirus* Hu/CHN3298/HZH99 | *Norovirus* Hu/Taipei-70/04/TW |
| *Norovirus* Hu/CHN3299/HZH99 | *Norovirus* Hu/Taipei-73/04/TW |
| *Norovirus* Hu/CHN3309/HZH99 | *Norovirus* Hu/Taipei-76/04/TW |
| *Norovirus* Hu/CHN3477/LL00 | *Norovirus* Hu/Taipei-78/04/TW |
| *Norovirus* Hu/CHN360/BJ99 | *Norovirus* Hu/Taipei-81/04/TW |
| *Norovirus* Hu/CHN3755/CC00 | *Norovirus* Hu/Taipei-82/04/TW |
| *Norovirus* Hu/CHN3786/CC00 | *Norovirus* Hu/Taipei-84/04/TW |
| *Norovirus* Hu/CHN3787/CC00 | *Norovirus* Hu/Taipei-91/04/TW |
| *Norovirus* Hu/CHN3822/CC00 | *Norovirus* Hu/Taipei-93GI/04/TW |
| *Norovirus* Hu/CHN3824/CC99 | *Norovirus* Hu/Taipei-93GII/04/TW |
| *Norovirus* Hu/CHN3826/CC99 | *Norovirus* Hu/Takanosu/1/2008/JP |
| *Norovirus* Hu/CHN3838/LL00 | *Norovirus* Hu/Tamagawa/1/05/JP |
| *Norovirus* Hu/CHN38456/BJ04 | *Norovirus* Hu/Tamagawa/1/06/JP |
| *Norovirus* Hu/CHN3852/LL00 | *Norovirus* Hu/Tamagawa/2/05/JP |
| *Norovirus* Hu/CHN38588/BJ04 | *Norovirus* Hu/Tamagawa/2/2006/JP |
| *Norovirus* Hu/CHN38791/XJ04 | *Norovirus* Hu/Tauberbischofsheim14175/2001/DE |
| *Norovirus* Hu/CHN388/BJ00 | *Norovirus* Hu/Tauberbischofsheim6245/2002/DE |
| *Norovirus* Hu/CHN38812/XJ04 | *Norovirus* Hu/TE5/2003/ITA |
| *Norovirus* Hu/CHN38816/XJ04 | *Norovirus* Hu/Texas/TCH04-577/2004/US |
| *Norovirus* Hu/CHN3898/KM00 | *Norovirus* Hu/TL206/1999/MEX |
| *Norovirus* Hu/CHN39186/CC04 | *Norovirus* Hu/TL24/1998/MEX |
| *Norovirus* Hu/CHN39240/CC04 | *Norovirus* Hu/TL354/2000/MEX |
| *Norovirus* Hu/CHN39246/CC04 | *Norovirus* Hu/Tokyo/1Se/2005/JPN |
| *Norovirus* Hu/CHN39280/CC04 | *Norovirus* Hu/Tokyo/216DCC/2005/JPN |
| *Norovirus* Hu/CHN3931/KM00 | *Norovirus* Hu/Tokyo/272DCC/2006/JPN |
| *Norovirus* Hu/CHN39386/SZ04 | *Norovirus* Hu/Tokyo/276DCC/2006/JPN |
| *Norovirus* Hu/CHN39428/SZ04 | *Norovirus* Hu/Tokyo/285DCC/2006/JPN |
| *Norovirus* Hu/CHN39462/SZ04 | *Norovirus* Hu/Tokyo/286DCC/2006/JPN |
| *Norovirus* Hu/CHN39540/SZ04 | *Norovirus* Hu/Tokyo/2Se/2006/JPN |
| *Norovirus* Hu/CHN3963/LL00 | *Norovirus* Hu/Tokyo/306DCC/2006/JPN |
| *Norovirus* Hu/CHN3973/LL00 | *Norovirus* Hu/Tokyo/390DCC/2006/JPN |
| *Norovirus* Hu/CHN40048/KM04 | *Norovirus* Hu/Tokyo/391DCC/2006/JPN |
| *Norovirus* Hu/CHN40078/KM04 | *Norovirus* Hu/Tokyo/392DCC/2006/JPN |
| *Norovirus* Hu/CHN40092/KM04 | *Norovirus* Hu/Tokyo/393DCC/2006/JPN |
| *Norovirus* Hu/CHN401/BJ00 | *Norovirus* Hu/Tokyo/396DCC/2006/JPN |
| *Norovirus* Hu/CHN40182/KM04 | *Norovirus* Hu/Tokyo/398DCC/2006/JPN |
| *Norovirus* Hu/CHN40482/SH04 | *Norovirus* Hu/Tokyo/3Se/2006/JPN |
| *Norovirus* Hu/CHN40496/SH04 | *Norovirus* Hu/Tokyo/400DCC/2006/JPN |
| *Norovirus* Hu/CHN40538/SH04 | *Norovirus* Hu/Tokyo/401DCC/2006/JPN |
| *Norovirus* Hu/CHN40600/SH04 | *Norovirus* Hu/Tokyo/402DCC/2006/JPN |
| *Norovirus* Hu/CHN40656/CZ04 | *Norovirus* Hu/Tokyo/403DCC/2006/JPN |
| *Norovirus* Hu/CHN40685/CZ04 | *Norovirus* Hu/Tokyo/405DCC/2006/JPN |
| *Norovirus* Hu/CHN40737/CZ04 | *Norovirus* Hu/Tokyo/406DCC/2006/JPN |
| *Norovirus* Hu/CHN40763/CZ04 | *Norovirus* Hu/Tokyo/411DCC/2006/JPN |
| *Norovirus* Hu/CHN40896/SZ04 | *Norovirus* Hu/Tokyo/414DCC/2006/JPN |

TABLE 1-continued

| *Norovirus* Strains | |
|---|---|
| *Norovirus* Hu/CHN40998/SZ04 | *Norovirus* Hu/Tokyo/418DCC/2006/JPN |
| *Norovirus* Hu/CHN41779/XJ04 | *Norovirus* Hu/Tokyo/419DCC/2006/JPN |
| *Norovirus* Hu/CHN41808/LL04 | *Norovirus* Hu/Tokyo/51Se/2005/JPN |
| *Norovirus* Hu/CHN42018/LL05 | *Norovirus* Hu/Tokyo/56Se/2005/JPN |
| *Norovirus* Hu/CHN42164/CC04 | *Norovirus* Hu/Tokyo/61Se/2005/JPN |
| *Norovirus* Hu/CHN42224/LL05 | *Norovirus* Hu/Tokyo/6602St/2005/JPN |
| *Norovirus* Hu/CHN42269/LL05 | *Norovirus* Hu/Tokyo/6789St/2006/JPN |
| *Norovirus* Hu/CHN4253/LL01 | *Norovirus* Hu/Tokyo/6801St/2006/JPN |
| *Norovirus* Hu/CHN42548/LL05 | *Norovirus* Hu/Tokyo/7391St/2005/JPN |
| *Norovirus* Hu/CHN42572/LL05 | *Norovirus* Hu/Tokyo/7395St/2005/JPN |
| *Norovirus* Hu/CHN42814/CZ04 | *Norovirus* Hu/Tokyo/7403St/2005/JPN |
| *Norovirus* Hu/CHN42846/CZ04 | *Norovirus* Hu/Tokyo/7860/2007/JPN |
| *Norovirus* Hu/CHN42936/CZ04 | *Norovirus* Hu/Tokyo/7882/2007/JPN |
| *Norovirus* Hu/CHN42951/CZ05 | *Norovirus* Hu/Tsushima/1/2006/JP |
| *Norovirus* Hu/CHN42973/CZ05 | *Norovirus* Hu/Tuebingen4259/2002/DE |
| *Norovirus* Hu/CHN42982/XJ05 | *Norovirus* Hu/Tuebingen7827/2001/DE |
| *Norovirus* Hu/CHN4300/LL01 | *Norovirus* Hu/Tuebingen9261/2001/DE |
| *Norovirus* Hu/CHN43098/CC05 | Noroviius Hu/UK11/1998/GBR |
| *Norovirus* Hu/CHN43160/CC05 | *Norovirus* Hu/UK12/2001/GBR |
| *Norovirus* Hu/CHN43172/CC05 | *Norovirus* Hu/UK14/1998/GBR |
| *Norovirus* Hu/CHN43202/LZ04 | *Norovirus* Hu/Ulm2451/2002/DE |
| *Norovirus* Hu/CHN43262/LZ05 | *Norovirus* Hu/Ulm70/2003/DE |
| *Norovirus* Hu/CHN43266/LZ05 | *Norovirus* Hu/V1607/06/IND |
| *Norovirus* Hu/CHN43283/LZ05 | *Norovirus* Hu/V1622/06/IND |
| *Norovirus* Hu/CHN43301/LZ05 | *Norovirus* Hu/V1628/06/IND |
| *Norovirus* Hu/CHN43303/LZ05 | *Norovirus* Hu/V1656/06/IND |
| *Norovirus* Hu/CHN43320/LZ05 | *Norovirus* Hu/V1668/06/IND |
| *Norovirus* Hu/CHN43321/LZ05 | *Norovirus* Hu/V1682/07/IND |
| *Norovirus* Hu/CHN43324/LZ05 | *Norovirus* Hu/V1699/07/IND |
| *Norovirus* Hu/CHN43330/LZ05 | *Norovirus* Hu/V1702/07/IND |
| *Norovirus* Hu/CHN43332/LZ05 | *Norovirus* Hu/V1706/07/IND |
| *Norovirus* Hu/CHN43338/LZ05 | *Norovirus* Hu/V1707/07/IND |
| *Norovirus* Hu/CHN43342/LZ05 | *Norovirus* Hu/V1714/07/IND |
| *Norovirus* Hu/CHN43364/LZ04 | *Norovirus* Hu/V1737/07/IND |
| *Norovirus* Hu/CHN43367/LZ04 | *Norovirus* Hu/V1749/07/IND |
| *Norovirus* Hu/CHN43466/SH04 | *Norovirus* Hu/V1750/07/IND |
| *Norovirus* Hu/CHN43502/SH04 | *Norovirus* Hu/V1760/07/IND |
| *Norovirus* Hu/CHN43512/SH05 | *Norovirus* Hu/V1766/07/IND |
| *Norovirus* Hu/CHN43552/SH05 | *Norovirus* Hu/V1772/07/IND |
| *Norovirus* Hu/CHN43568/SH05 | *Norovirus* Hu/V1774/07/IND |
| *Norovirus* Hu/CHN4359/LL01 | *Norovirus* Hu/V1776/07/IND |
| *Norovirus* Hu/CHN43594/SH05 | *Norovirus* Hu/V1783/07/IND |
| *Norovirus* Hu/CHN4369/LL01 | *Norovirus* Hu/VC192/2000/MEX |
| *Norovirus* Hu/CHN43949/LZ04 | *Norovirus* Hu/VC193/2000/MEX |
| *Norovirus* Hu/CHN43964/LZ04 | *Norovirus* Hu/VC66/1999/MEX |
| *Norovirus* Hu/CHN43989/LZ04 | *Norovirus* Hu/Vesoul576/2003/France |
| *Norovirus* Hu/CHN4411/CC01 | *Norovirus* Hu/VIC080/2006/AUS |
| *Norovirus* Hu/CHN4412/CC01 | *Norovirus* Hu/VIC248/2006/AUS |
| *Norovirus* Hu/CHN44123/LZ05 | *Norovirus* Hu/VIC397/2006/AUS |
| *Norovirus* Hu/CHN44124/LZ05 | *Norovirus* Hu/VIC399/2006/AUS |
| *Norovirus* Hu/CHN44126/LZ05 | *Norovirus* Hu/VIC458/2006/AUS |
| *Norovirus* Hu/CHN44128/LZ05 | *Norovirus* Hu/VIC534/2006/AUS |
| *Norovirus* Hu/CHN44134/LZ05 | *Norovirus* Hu/VIC544/2006/AUS |
| *Norovirus* Hu/CHN44136/LZ05 | *Norovirus* Hu/VIC545/2006/AUS |
| *Norovirus* Hu/CHN44692/KM04 | *Norovirus* Hu/VIC584/2006/AUS |
| *Norovirus* Hu/CHN4474/CC01 | *Norovirus* Hu/VIC595/2006/AUS |
| *Norovirus* Hu/CHN44812/LZ05 | *Norovirus* Hu/VIC644/2006/AUS |
| *Norovirus* Hu/CHN44821/LZ05 | *Norovirus* Hu/VIC647/2006/AUS |
| *Norovirus* Hu/CHN44858/KM04 | *Norovirus* Hu/VIC885/2006/AUS |
| *Norovirus* Hu/CHN44898/KM04 | *Norovirus* Hu/VIC886/2006/AUS |
| *Norovirus* Hu/CHN459/BJ00 | *Norovirus* Hu/Vigneux1379/2006/France |
| *Norovirus* Hu/CHN4617/CC00 | *Norovirus* Hu/Villingen2309/2004/DE |
| *Norovirus* Hu/CHN462/BJ00 | *Norovirus* Hu/Villingen311/2003/DE |
| *Norovirus* Hu/CHN465/BJ00 | *Norovirus* Hu/VN1/2006/VNM |
| *Norovirus* Hu/CHN4709/LL01 | *Norovirus* Hu/VN26/2006/VNM |
| *Norovirus* Hu/CHN4711/LL01 | *Norovirus* Hu/VN41/2006/VNM |
| *Norovirus* Hu/CHN4748/LL01 | *Norovirus* Hu/VN59/2006/VNM |
| *Norovirus* Hu/CHN4789/LL01 | *Norovirus* Hu/VN73/2006/VNM |
| *Norovirus* Hu/CHN5450/KM01 | *Norovirus* Hu/VN74/2006/VNM |
| *Norovirus* Hu/CHN5531/KM01 | *Norovirus* Hu/VN75/2006/VNM |
| *Norovirus* Hu/CMH001/03/2003/THA | *Norovirus* Hu/VN77/2006/VNM |
| *Norovirus* Hu/CMH002/05/2005/THA | *Norovirus* Hu/VN78/2006/VNM |
| *Norovirus* Hu/CMH005/05/2005/THA | *Norovirus* Hu/VN79/2006/VNM |
| *Norovirus* Hu/CMH006/04/2004/THA | *Norovirus* Hu/VN80/2006/VNM |
| *Norovirus* Hu/CMH010/00/2000/THA | *Norovirus* Hu/VN82/2006/VNM |
| *Norovirus* Hu/CMH010/05/2005/THA | *Norovirus* Hu/VN84/2006/VNM |
| *Norovirus* Hu/CMH011/02/2002/THA | *Norovirus* Hu/VN85/2006/VNM |
| *Norovirus* Hu/CMH011/04/2004/THA | *Norovirus* Hu/VN87/2006/VNM |

TABLE 1-continued

| *Norovirus* Strains | |
|---|---|
| *Norovirus* Hu/CMH015/03/2003/THA | *Norovirus* Hu/VN88/2006/VNM |
| *Norovirus* Hu/CMH018/04/2004/THA | *Norovirus* Hu/VN89/2006/VNM |
| *Norovirus* Hu/CMH025/04/2004/THA | *Norovirus* Hu/VN9/2006/VNM |
| *Norovirus* Hu/CMH028/03/2003/THA | *Norovirus* Hu/VN95/2006/VNM |
| *Norovirus* Hu/CMH034/03/2003/THA | *Norovirus* Hu/Waiblingen26/2003/DE |
| *Norovirus* Hu/CMH034/04/2004/THA | *Norovirus* Hu/Waiblingen5141/2002/DE |
| *Norovirus* Hu/CMH037/00/2000/THA | *Norovirus* Hu/Waiblingen6509/2001/DE |
| *Norovirus* Hu/CMH037/04/2004/THA | *Norovirus* Hu/Waldshut5564/2003/DE |
| *Norovirus* Hu/CMH038/02/2002/THA | *Norovirus* Hu/Waldshut7877/2002/DE |
| *Norovirus* Hu/CMH038/04/2004/THA | *Norovirus* Hu/WKDHaussach8968/2003/DE |
| *Norovirus* Hu/CMH040/02/2002/THA | *Norovirus* Hu/Yokohama/y04-161-16/2004/JP |
| *Norovirus* Hu/CMH041/02/2002/THA | *Norovirus* Hu/Yokohama/y04-198-13/2005/JP |
| *Norovirus* Hu/CMH042/02/2002/THA | *Norovirus* Hu/Yokohama/y04-200-11/2005/JP |
| *Norovirus* Hu/CMH042/05/2005/THA | *Norovirus* Hu/Yokohama/y04-208-1/2005/JP |
| *Norovirus* Hu/CMH043/02/2002/THA | *Norovirus* Hu/Yokohama/y04-V10-1/2005/JP |
| *Norovirus* Hu/CMH043/03/2003/THA | *Norovirus* Hu/Yokohama/y05-153-40/2005/JP |
| *Norovirus* Hu/CMH045/04/2004/THA | *Norovirus* Hu/Yokohama/y05-V14-5/2005/JP |
| *Norovirus* Hu/CMH049/04/2004/THA | *Norovirus* Hu/Yokohama/y05-V17-8/2005/JP |
| *Norovirus* Hu/CMH052/01/2001/THA | *Norovirus* Hu/Yokohama/y06-V110-5/2007/JP |
| *Norovirus* Hu/CMH063/04/2004/THA | *Norovirus* Hu/Yokohama/y06-V111-3/2007/JP |
| *Norovirus* Hu/CMH064/04/2004/THA | *Norovirus* Hu/Yokohama/y06-V114-14/2007/JP |
| *Norovirus* Hu/CMH068/01/2001/THA | *Norovirus* Hu/Yokohama/y06-V117-2/2007/JP |
| *Norovirus* Hu/CMH076/04/2004/THA | *Norovirus* Hu/Yokohama/y06-V34-5/2006/JP |
| *Norovirus* Hu/CMH076/05/2005/THA | *Norovirus* Hu/Yokohama/y06-V37-21/2006/JP |
| *Norovirus* Hu/CMH079/04/2004/THA | *Norovirus* Hu/Yokohama/y06-V44-2/2006/JP |
| *Norovirus* Hu/CMH083/05/2005/THA | *Norovirus* Hu/Yokohama/y06-V55-3/2006/JP |
| *Norovirus* Hu/CMH090/04/2004/THA | *Norovirus* Hu/Yokohama/y06-V67-5/2006/JP |
| *Norovirus* Hu/CMH091/01/2001/THA | *Norovirus* Hu/Yokohama/y06-V82-2/2007/JP |
| *Norovirus* Hu/CMH091/04/2004/THA | *Norovirus* Hu/Yokote/1/2008/JP |
| *Norovirus* Hu/CMH092/04/2004/THA | *Norovirus* Hu/Yokote/2/2008/JP |
| *Norovirus* Hu/CMH096/01/2001/THA | *Norovirus* Hu/Yokote/3/2008/JP |
| *Norovirus* Hu/CMH097/01/2001/THA | *Norovirus* Hu/Yonaizawa/1/05/JP |
| *Norovirus* Hu/CMH104/05/2005/THA | *Norovirus* Hu/Yuri/1/2007/JP |
| *Norovirus* Hu/CMH112/01/2001/THA | *Norovirus* Hu/Zuerich/P3d1/2006 |
| *Norovirus* Hu/CMH113/05/2005/THA | *Norovirus* Hu/Zuerich/P3d683/2008 |
| *Norovirus* Hu/CMH120/01/2001/THA | *Norovirus* Hu/Zuerich/P4d1/2007 |
| *Norovirus* Hu/CMH126/01/2001/THA | *Norovirus* Hu/Zuerich/P4d281/2007 |
| *Norovirus* Hu/CMH133/04/2004/THA | *Norovirus* Hu/Zuerich/P5d1/2008 |
| *Norovirus* Hu/CMH138/04/2004/THA | *Norovirus* Hu/Zuerich/P5d161/2009 |
| *Norovirus* Hu/CMH139/04/2004/THA | *Norovirus* Hu/Zuerich/P7d1/2008 |
| *Norovirus* Hu/CMH140/04/2004/THA | *Norovirus* Hu/Zuerich/P7d384/2009 |
| *Norovirus* Hu/CMH142/05/2005/THA | *Norovirus* human feces/CIT N002/IRL |
| *Norovirus* Hu/CMH145/04/2004/THA | *Norovirus* human feces/CIT N005/IRL |
| *Norovirus* Hu/CMH145/05/2005/THA | *Norovirus* human feces/CIT N008/IRL |
| *Norovirus* Hu/CMH148/01/2001/THA | *Norovirus* human feces/CIT N018/IRL |
| *Norovirus* Hu/CMH153/04/2004/THA | *Norovirus* human feces/CIT N030/IRL |
| *Norovirus* Hu/CMH158/04/2004/THA | *Norovirus* human feces/CIT N032/IRL |
| *Norovirus* Hu/CMH159/04/2004/THA | *Norovirus* human feces/CIT N034/IRL |
| *Norovirus* Hu/CMH183/00/2000/THA | *Norovirus* human feces/CIT N073/IRL |
| *Norovirus* Hu/CMH241/01/2001/THA | *Norovirus* human feces/CIT N078/IRL |
| *Norovirus* Hu/CMH247/01/2001/THA | *Norovirus* Kandy/101/2005/LKA |
| *Norovirus* Hu/CMH251/01/2001/THA | *Norovirus* Kandy/108/2005/LKA |
| *Norovirus* Hu/CMH262/01/2001/THA | *Norovirus* Kandy/115/2005/LKA |
| *Norovirus* Hu/CMH298/01/2001/THA | *Norovirus* Kandy/117/2005/LKA |
| *Norovirus* Hu/CMH308/01/2001/THA | *Norovirus* Kandy/131/2005/LKA |
| *Norovirus* Hu/CMH309/01/2001/THA | *Norovirus* Kandy/133/2005/LKA |
| *Norovirus* Hu/CMH323/02/2002/THA | *Norovirus* Kandy/140/2005/LKA |
| *Norovirus* Hu/CMH329/02/2002/THA | *Norovirus* Kandy/142/2005/LKA |
| *Norovirus* Hu/CMH344/02/2002/THA | *Norovirus* Kandy/145/2005/LKA |
| *Norovirus* Hu/CMH357/00/2000/THA | *Norovirus* Kandy/148/2005/LKA |
| *Norovirus* Hu/CMH359/00/2000/THA | *Norovirus* Kandy/152/2005/LKA |
| *Norovirus* Hu/CN244/1998/US | *Norovirus* Kandy/159/2005/LKA |
| *Norovirus* Hu/CN2686/1997/US | *Norovirus* Kandy/174/2005/LKA |
| *Norovirus* Hu/CN2693/1997/US | *Norovirus* Kandy/180/2005/LKA |
| *Norovirus* Hu/CN2694/1997/US | *Norovirus* Kandy/185/2005/LKA |
| *Norovirus* Hu/CN2716/1998/US | *Norovirus* Kandy/193/2005/LKA |
| *Norovirus* Hu/CN2753/1998/US | *Norovirus* Kandy/197/2005/LKA |
| *Norovirus* Hu/CN2765/1998/US | *Norovirus* Kandy/20/2005/LKA |
| *Norovirus* Hu/CN2819/1998/US | *Norovirus* Kandy/209/2005/LKA |
| *Norovirus* Hu/CN2841/1998/US | *Norovirus* Kandy/210/2005/LKA |
| *Norovirus* Hu/CN2849/1998/US | *Norovirus* Kandy/213/2005/LKA |
| *Norovirus* Hu/CN2856/1998/US | *Norovirus* Kandy/221/2005/LKA |
| *Norovirus* Hu/CN2887/1998/US | *Norovirus* Kandy/234/2005/LKA |
| *Norovirus* Hu/CN2957/1998/US | *Norovirus* Kandy/239/2005/LKA |
| *Norovirus* Hu/CN2976/1998/US | *Norovirus* Kandy/245/2005/LKA |
| *Norovirus* Hu/CN2982/1998/US | *Norovirus* Kandy/258/2005/LKA |
| *Norovirus* Hu/CN2990/1998/US | *Norovirus* Kandy/270/2005/LKA |
| *Norovirus* Hu/CN2996/1998/US | *Norovirus* Kandy/280/2005/LKA |

TABLE 1-continued

| *Norovirus* Strains |
|---|
| *Norovirus* Hu/CN3015/1998/US |
| *Norovirus* Hu/CN3016/1998/US |
| *Norovirus* Hu/CN3038/1998/US |
| *Norovirus* Hu/CN3041/1998/US |
| *Norovirus* Hu/CN3044/1998/US |
| *Norovirus* Hu/CN3050/1998/US |
| *Norovirus* Hu/CN3052/1998/US |
| *Norovirus* Hu/CN3071/1998/US |
| *Norovirus* Hu/CN3108/1999/US |
| *Norovirus* Hu/CN3117/1999/US |
| *Norovirus* Hu/CN3135/1999/US |
| *Norovirus* Hu/CN3147/1999/US |
| *Norovirus* Hu/CN3171/1999/US |
| *Norovirus* Hu/CN3202/1999/US |
| *Norovirus* Hu/CN3204/1999/US |
| *Norovirus* Hu/CN3221/1999/US |
| *Norovirus* Hu/CN3244/1999/US |
| *Norovirus* Hu/CN3246/1999/US |
| *Norovirus* Hu/CN3260/1999/US |
| *Norovirus* Hu/CN3273/1999/US |
| *Norovirus* Hu/CN3321/1999/US |
| *Norovirus* Hu/CN3341/1999/US |
| *Norovirus* Hu/CN438/1999/US |
| *Norovirus* Hu/CN88/1998/US |
| *Norovirus* Hu/cockles/KOK1QNL/2000/Netherlands |
| *Norovirus* Hu/Daycare-center_A/21-02-2002/NL |
| *Norovirus* Hu/Daycare-center_B/12-12-2002/NL |
| *Norovirus* Hu/DC2022-Madag04/2004/MDG |
| *Norovirus* Hu/DC2048-Madag04/2004/MDG |
| *Norovirus* Hu/DC2054-Madag04/2004/MDG |
| *Norovirus* Hu/DG6003-Madag04/2004/MDG |
| *Norovirus* Hu/DG6004-Madag04/2004/MDG |
| *Norovirus* Hu/DG6020-Madag04/2004/MDG |
| *Norovirus* Hu/Diner_Amsterdam/08-07-2002/NL |
| *Norovirus* Hu/DM4025-Madag05/2005/MDG |
| *Norovirus* Hu/DR0011-Madag04/2004/MDG |
| *Norovirus* Hu/DR0023-Madag04/2004/MDG |
| *Norovirus* Hu/DR0025-Madag04/2004/MDG |
| *Norovirus* Hu/DR0045-Madag04/2004/MDG |
| *Norovirus* Hu/DR0046-Madag04/2004/MDG |
| *Norovirus* Hu/DT1020-Magad04/2004/MDG |
| *Norovirus* Hu/DT1032-Madag04/2004/MDG |
| *Norovirus* Hu/Ehime/05-30/2005/JP |
| *Norovirus* Hu/Emmendingen13186/2002/DE |
| *Norovirus* Hu/Emmendingen13848/2002/DE |
| *Norovirus* Hu/Emmendingen154/2003/DE |
| *Norovirus* Hu/Esslingen5791/2003/DE |
| *Norovirus* Hu/Freiburg3308/2002/DE |
| *Norovirus* Hu/Freudenstadt13147/2001/DE |
| *Norovirus* Hu/Freudenstadt2011/2004/DE |
| *Norovirus* Hu/Friedrichshafen1104/2004/DE |
| *Norovirus* Hu/Friedrichshafen8054/2002/DE |
| *Norovirus* Hu/Fujian/49737/2006/CHN |
| *Norovirus* Hu/Fujian/49745/2006/CHN |
| *Norovirus* Hu/Fujian/49747/2006/CHN |
| *Norovirus* Hu/Fujian/50255/2006/CHN |
| *Norovirus* Hu/Fujian/50257/2006/CHN |
| *Norovirus* Hu/Fujian/50260/2006/CHN |
| *Norovirus* Hu/Fujian/50264/2006/CHN |
| *Norovirus* Hu/G2/Fin-Upinniemi/1998/Finland |
| *Norovirus* Hu/Ghana-1/2000/GH |
| *Norovirus* Hu/Ghana-2/2000/GH |
| *Norovirus* Hu/GI/New Delhi/120/IND |
| *Norovirus* Hu/GI/Otofuke/1979/JP |
| *Norovirus* Hu/GII/Hannover20132624/2006/DE |
| *Norovirus* Hu/GM245/2000/MEX |
| *Norovirus* Hu/GM260/2000/MEX |
| *Norovirus* Hu/GM268/2000/MEX |
| *Norovirus* Hu/GM272/2000/MEX |
| *Norovirus* Hu/GM93/1999/MEX |
| *Norovirus* Hu/Goeppingen12959/2002/DE |
| *Norovirus* Hu/Goeppingen4251/2003/DE |
| *Norovirus* Hu/Graz/10/03/Austria |
| *Norovirus* Kandy/298/2005/LKA |
| *Norovirus* Kandy/326/2005/LKA |
| *Norovirus* Kandy/332/2005/LKA |
| *Norovirus* Kandy/341/2005/LKA |
| *Norovirus* Kandy/353/2005/LKA |
| *Norovirus* Kandy/354/2005/LKA |
| *Norovirus* Kandy/362/2005/LKA |
| *Norovirus* Kandy/369/2005/LKA |
| *Norovirus* Kandy/370/2005/LKA |
| *Norovirus* Kandy/4/2005/LKA |
| *Norovirus* Mex7076/1999 |
| *Norovirus* minced meat/Stuttgart554/2007/DEU |
| *Norovirus* mouse/Hannover1/2007/DEU |
| *Norovirus* mouse/TW2006/TWN |
| *Norovirus* mouse/TW2007/TWN |
| *Norovirus* mussels/Korntal8335/2007/DEU |
| *Norovirus* Nagano/7-29/Apr2008/JPN |
| *Norovirus* Nagasaki/03/JP |
| *Norovirus* Nizhny Novgorod/14072/RUS/2006 |
| *Norovirus* Nizhny Novgorod/14342/RUS/2006 |
| *Norovirus* Nizhny Novgorod/14726/RUS/2007 |
| *Norovirus* Nizhny Novgorod/14780/RUS/2007 |
| *Norovirus* Nizhny Novgorod/14995/RUS/2007 |
| *Norovirus* Nizhny Novgorod/2461/RUS/2007 |
| *Norovirus* Nizhny Novgorod/2549/RUS/2007 |
| *Norovirus* Nizhny Novgorod/2557/RUS/2007 |
| *Norovirus* NLV/BUDS/2002/USA |
| *Norovirus* NLV/IF1998/2003/Iraq |
| *Norovirus* NLV/IF2036/2003/Iraq |
| *Norovirus* NLV/Paris Island/2003/USA |
| *Norovirus* NongKhai-22/Thailand |
| *Norovirus* NongKhai-51/Thailand |
| *Norovirus* noodle salad/Stuttgart21334/2006/DEU |
| *Norovirus* NV/aomori/C13/03/JP |
| *Norovirus* NV/ehime/C11/04/JP |
| *Norovirus* NV/ehime/C3/02/JP |
| *Norovirus* NV/Futatsui/1/05/JP |
| *Norovirus* NV/hiroshima/C1/03/JP |
| *Norovirus* NV/hokkaido/C37/04/JP |
| *Norovirus* NV/hokkaido/C38/04/JP |
| *Norovirus* NV/kagoshima/C20/03/JP |
| *Norovirus* NV/kagoshima/C31/03/JP |
| *Norovirus* NV/kagoshima/C6/04/JP |
| *Norovirus* NV/kanagawa/C10/03/JP |
| *Norovirus* NV/kanagawa/C36/04/JP |
| *Norovirus* NV/mie/C18/03/JP |
| *Norovirus* NV/mie/C27/04/JP |
| *Norovirus* NV/mie/C33/03/JP |
| *Norovirus* NV/mie/C4/03/JP |
| *Norovirus* NV/nagano/C14/03/JP |
| *Norovirus* NV/nagano/C17/03/JP |
| *Norovirus* NV/nagano/C22/03/JP |
| *Norovirus* NV/nagano/C5/03/JP |
| *Norovirus* NV/nagano/C9/03/JP |
| *Norovirus*NV/sediment/Maracaibo1/2003/VE |
| *Norovirus* NV/shizuoka/C30/04/JP |
| *Norovirus* NV/water/Maracaibo1/2003/VE |
| *Norovirus* NV/yamaguchi/C16/03/JP |
| *Norovirus* NV/Yuri/1/95/JP |
| *Norovirus* oyster clone A/Mannheim11815/2006/DEU |
| *Norovirus* oyster clone B/Mannheim11815/2006/DEU |
| *Norovirus* oyster/4433O/64317/2006/FR |
| *Norovirus* oyster/GII-4/BC-12/2009/CAN |
| *Norovirus* oyster/GII-4/BC-13/2009/CAN |
| *Norovirus* oyster/GII-4/H-149/2008/CAN |
| *Norovirus* oyster/Guangzhou 2/CHN |
| *Norovirus* oyster/oes7/64815b/2006/FR |
| *Norovirus* oyster/oes8a/64815/2006/FR |
| *Norovirus* oyster/oes8b/64815/2006/FR |
| *Norovirus* oyster/Zhuhai 5/CHN |
| *Norovirus* pasta/Waldshut11487/2007/DEU |
| *Norovirus* pig/30/2004/SVN |
| *Norovirus* pig/31/2004/SVN |
| *Norovirus* pig/36/2004/SVN |
| *Norovirus* pig/AB169/CAN |
| *Norovirus* pig/AB276/CAN |

TABLE 1-continued

| *Norovirus* Strains |
|---|
| *Norovirus* Hu/Groetzingen995/2003/DE |
| *Norovirus* Hu/Guangzhou/NV-VP1/2006/China |
| *Norovirus* Hu/Guangzhou/NV-VP2/2006/China |
| *Norovirus* Hu/Guangzhou/NVgz01/CHN |
| *Norovirus* Hu/Gunma/11-01/2005/JP |
| *Norovirus* Hu/Gunma/12-02/2006/JP |
| *Norovirus* Hu/Gunma/8-01/2004/JP |
| *Norovirus* Hu/Gunma/9-01/2004/JP |
| *Norovirus* Hu/H1/JPN |
| *Norovirus* Hu/H2/JPN |
| *Norovirus* Hu/H3/JPN |
| *Norovirus* Hu/Hainan/47840/2006/CHN |
| *Norovirus* Hu/Hainan/47841/2006/CHN |
| *Norovirus* Hu/HCMC131/2006/VNM |
| *Norovirus* Hu/HCMC204/2006/VNM |
| *Norovirus* Hu/HCMC298/2006/VNM |
| *Norovirus* Hu/HCMC311/2006/VNM |
| *Norovirus* Hu/HCMC318/2006/VNM |
| *Norovirus* Hu/HCMC91/2006/VNM |
| *Norovirus* Hu/Hebei/47931/2006/CHN |
| *Norovirus* Hu/Hebei/48574/2006/CHN |
| *Norovirus* Hu/Hebei/48578/2006/CHN |
| *Norovirus* Hu/Hebei/48580/2006/CHN |
| *Norovirus* Hu/Hebei/48588/2006/CHN |
| *Norovirus* Hu/Hebei/48962/2006/CHN |
| *Norovirus* Hu/Hebei/48963/2006/CHN |
| *Norovirus* Hu/Hebei/48966/2006/CHN |
| *Norovirus* Hu/Hebei/50033/2006/CHN |
| *Norovirus* Hu/Hebei/50034/2006/CHN |
| *Norovirus* Hu/Hebei/50036/2006/CHN |
| *Norovirus* Hu/Hebei/50038/2006/CHN |
| *Norovirus* Hu/Hebei/50039/2006/CHN |
| *Norovirus* Hu/Hebei/50040/2006/CHN |
| *Norovirus* Hu/Hebei/50302/2006/CHN |
| *Norovirus* Hu/Hebei/50307/2006/CHN |
| *Norovirus* Hu/Hebei/50316/2006/CHN |
| *Norovirus* Hu/Hebei/50322/2006/CHN |
| *Norovirus* Hu/Heidelberg13373/2002/DE |
| *Norovirus* Hu/Heidelberg13908/2002/DE |
| *Norovirus* Hu/Heidelberg1884/2003/DE |
| *Norovirus* Hu/Heidenheim3796/2002/DE |
| *Norovirus* Hu/Heilbronn2647/2004/DE |
| *Norovirus* Hu/Heilbronn2846/2002/DE |
| *Norovirus* Hu/Heilbronn4983/2001/DE |
| *Norovirus* Hu/Henan/49166/2006/CHN |
| *Norovirus* Hu/Henan/49189/2006/CHN |
| *Norovirus* Hu/Hiroshima/20-507/2001/JP |
| *Norovirus* Hu/Hiroshima/21-517/2002/JP |
| *Norovirus* Hu/Hiroshima/25-583/2002/JP |
| *Norovirus* Hu/Hiroshima/26-623/2002/JP |
| *Norovirus* Hu/Hiroshima/32-754/2003/JP |
| *Norovirus* Hu/Hiroshima/38-840/2003/JP |
| *Norovirus* Hu/Hiroshima/39-852/2003/JP |
| *Norovirus* Hu/Hiroshima/43-886/2004/JP |
| *Norovirus* Hu/Hiroshima/48-936/2004/JP |
| *Norovirus* Hu/Hiroshima/48-938/2004/JP |
| *Norovirus* Hu/Hiroshima/60-1015/2005/JP |
| *Norovirus* Hu/Hiroshima/62-1046/2006/JP |
| *Norovirus* Hu/Hiroshima/66-1110/2006/JP |
| *Norovirus* Hu/Hokkaido/10-13/2004/JP |
| *Norovirus* Hu/Hokkaido/109/2002/JP |
| *Norovirus* Hu/Hokkaido/110/2002/JP |
| *Norovirus* Hu/Hokkaido/111A/2002/JP |
| *Norovirus* Hu/Hokkaido/112/2002/JP |
| *Norovirus* Hu/Hokkaido/133/2003/JP |
| *Norovirus* Hu/Hokkaido/134/2003/JP |
| *Norovirus* Hu/Hokkaido/139/2003/JP |
| *Norovirus* Hu/Hokkaido/141/2003/JP |
| *Norovirus* Hu/Hokkaido/146A/2003/JP |
| *Norovirus* Hu/Hokkaido/157/2003/JP |
| *Norovirus* Hu/Hokkaido/160/2003/JP |
| *Norovirus* Hu/Hokkaido/182/2004/JP |
| *Norovirus* Hu/Hokkaido/190/2004/JP |
| *Norovirus* Hu/Hokkaido/203A/2004/JP |
| *Norovirus* Hu/Hokkaido/211/2004/JP |
| *Norovirus* Hu/Hokkaido/228/2004/JP |
| *Norovirus* pig/F15-7/CAN |
| *Norovirus* pig/F16-8/CAN |
| *Norovirus* pig/F16-9/CAN |
| *Norovirus* pig/F18-8/CAN |
| *Norovirus* pig/F18-9/CAN |
| *Norovirus* pig/KT7/2004/SVN |
| *Norovirus* pig/P15_2/2004/SVN |
| *Norovirus* pig/Vet10-S08108/DNK |
| *Norovirus* pig/Vet14-S08257/DNK |
| *Norovirus* pig/Vet18-S08131/DNK |
| *Norovirus* pig/Vet41-S08288/DNK |
| *Norovirus* pig/Vet53-S08140/DNK |
| *Norovirus* pig/ZP-0711/2007/NZL |
| *Norovirus* potato/Boeblingen/2003/DE |
| *Norovirus* raw sewage/Monastir/14/2005/TUN |
| *Norovirus* raw sewage/Monastir/15/2006/TUN |
| *Norovirus* raw sewage/Monastir/25/2004/TUN |
| *Norovirus* raw sewage/Monastir/29/2005/TUN |
| *Norovirus* raw sewage/Monastir/32/2006/TUN |
| *Norovirus* raw sewage/Monastir/64/2005/TUN |
| *Norovirus* raw sewage/Monastir/9/2006/TUN |
| *Norovirus* rice/Stuttgart7008/2006/DEU |
| *Norovirus* SaKaeo-14/Thailand |
| *Norovirus* SaKaeo-52/Thailand |
| *Norovirus* SaKaeo-53/Thailand |
| *Norovirus* SaKaeo-54/Thailand |
| *Norovirus* SaKaeo-57/Thailand |
| *Norovirus* SaKaeo-61/Thailand |
| *Norovirus* salami/Wiesental40521/2007/DEU |
| *Norovirus* schnitzel/Stuehlingen37112/2007/DEU |
| *Norovirus* shashlik/Stuttgart76/2007/DEU |
| *Norovirus* sheep/Norsewood11/2007/NZL |
| *Norovirus* sheep/Norsewood30/2007/NZL |
| *Norovirus* shellfish/Monastir/3/2003/TUN |
| *Norovirus* Songkhla-34/Thailand |
| *Norovirus* Songkhla-36/Thailand |
| *Norovirus* Songkhla-37/Thailand |
| *Norovirus* Suminoe oyster/Beibu Gulf/2004/China |
| *Norovirus* Sw/PC23/2007/BEL |
| *Norovirus* Sw/PC26/2007/BEL |
| *Norovirus* swab/Rottenburg/40728/2005/DE |
| *Norovirus* swab/Stuttgart/38663/2006/DE |
| *Norovirus* swine/IV-2/2005/HUN |
| *Norovirus* swine/K5/JP |
| *Norovirus* Tak-62/Thailand |
| *Norovirus* Tak-69/Thailand |
| *Norovirus* treated sewage/Monastir/24/2005/TUN |
| *Norovirus* treated sewage/Monastir/28/2005/TUN |
| *Norovirus* treated sewage/Monastir/48/2005/TUN |
| *Norovirus* treated sewage/Monastir/60/2005/TUN |
| Norwalk virus (Hu/NLV/OC00003/2000/JP) |
| Norwalk virus (Hu/NLV/OC00018/2000/JP) |
| Norwalk virus (Hu/NLV/OC00019/2000/JP) |
| Norwalk virus (Hu/NLV/OC96065/1996/JP) |
| Norwalk virus (Hu/NLV/OC98008/1998/JP) |
| Norwalk virus (Hu/NLV/OC99288/1999/JP) |
| Norwalk virus Hu/NV/Chiba/001049/2000/JP |
| Norwalk virus Hu/NV/Chiba/010105/2001/JP |
| Norwalk virus Hu/NV/Chiba/021071/2002/JP |
| Norwalk virus Hu/NV/Chiba/030100/2003/JP |
| Norwalk virus Hu/NV/Chiba/030556/2003/JP |
| Norwalk virus Hu/NV/Chiba/030910/2003/JP |
| Norwalk virus Hu/NV/Chiba/031038/2003/JP |
| Norwalk virus Hu/NV/Chiba/040092/2004/JP |
| Norwalk virus Hu/NV/Chiba/040110/2004/JP |
| Norwalk virus Hu/NV/Chiba/040277/2004/JP |
| Norwalk virus Hu/NV/Chiba/040502/2004/JP |
| Norwalk virus Hu/NV/Chiba/991002/1999/JP |
| Norwalk virus Hu/NV/Karachi/1001/1990 |
| Norwalk virus NLV/Carousel/1998/UK |
| Norwalk virus NLV/Driffield/1999/UK |
| Norwalk virus NLV/Luton/1999/UK |
| Norwalk virus NLV/Ramridge/1998/UK |
| Norwalk virus NLV/Windlesham/1998/UK |
| Norwalk virus NV/hokkaido/C-39/04/JP |
| Norwalk virus NV/hokkaido/C-40/04/JP |
| Norwalk-like virus Hu/NLV/GI/464/US |
| Norwalk-like virus Hu/NLV/GI/487/US |

TABLE 1-continued

| *Norovirus* Strains |
|---|
| *Norovirus* Hu/Hokkaido/28/1999/JP |
| *Norovirus* Hu/Hokkaido/34B/2000/JP |
| *Norovirus* Hu/Hokkaido/5-05/2003/JP |
| *Norovirus* Hu/Hokkaido/60/2001/JP |
| *Norovirus* Hu/Hokkaido/7-07/2004/JP |
| *Norovirus* Hu/Hokkaido/74/2001/JP |
| *Norovirus* Hu/Hokkaido/77/2001/JP |
| *Norovirus* Hu/Hokkaido/82/2001/JP |
| *Norovirus* Hu/Hokkaido/83/2001/JP |
| *Norovirus* Hu/Hokkaido/86B/2001/JP |
| *Norovirus* Hu/Hokkaido/87/2001/JP |
| *Norovirus* Hu/Hokkaido/88/2001/JP |
| *Norovirus* Hu/Hokkaido/90/2001/JP |
| *Norovirus* Hu/Hokkaido/91/2001/JP |
| *Norovirus* Hu/Hokkaido/92/2002/JP |
| *Norovirus* Hu/Hokkaido/94/2002/JP |
| *Norovirus* Hu/Hokkaido/96B/2002/JP |
| *Norovirus* Hu/Hospital_AA_ PAAZ_pat_1/15-07-2002/NL |
| *Norovirus* Hu/Hospital_AA_PAAZ_personel_1/18-07-2002/NL |
| *Norovirus* Hu/Hospital_AB_A1_pat_104-02-2003/NL |
| *Norovirus* Hu/Hospital_AB_A1_pat_205-03-2003/NL |
| *Norovirus* Hu/Hospital_AB_A3_pat_1/10-02-2003/NL |
| *Norovirus* Hu/Hospital_AB_A3_personel_1/10-02-2003/NL |
| *Norovirus* Hu/Hospital_AB_A7_pat_1/06-01-2003/NL |
| *Norovirus* Hu/Hospital_AB_A8_pat_1/21-01-2003/NL |
| *Norovirus* Hu/Hospital_AB_A9_pat_1/18-12-2002/NL |
| *Norovirus* Hu/Hospital_AB_B1_pat_1/22-01-2003/NL |
| *Norovirus* Hu/Hospital_AB_B1_pat_2/28-02-2003/NL |
| *Norovirus* Hu/Hospital_AB_B1_personel_1/27-01-2003/NL |
| *Norovirus* Hu/Hospital_AB_PAAZ_pat07-02-2003/NL2. |
| *Norovirus* Hu/Hospital_AB_PAAZ_pat_3/11-02-2003/NL |
| *Norovirus* Hu/I10a/JPN |
| *Norovirus* Hu/I10b/JPN |
| *Norovirus* Hu/I3a/JPN |
| *Norovirus* Hu/I3b/JPN |
| *Norovirus* Hu/I4/JPN |
| *Norovirus* Hu/IR-112/2006/Iran |
| *Norovirus* Hu/IR-115/2006/Iran |
| *Norovirus* Hu/IR-117/2006/Iran |
| *Norovirus* Hu/IR-186/2006/Iran |
| *Norovirus* Hu/IR-197/2006/Iran |
| *Norovirus* Hu/IR-198/2006/Iran |
| *Norovirus* Hu/IR-202/2006/Iran |
| *Norovirus* Hu/IR-240/2006/Iran |
| *Norovirus* Hu/IR-41/2006/Iran |
| *Norovirus* Hu/J1/JPN |
| *Norovirus* Hu/Jilin/48344/2006/CHN |
| *Norovirus* Hu/Jilin/48352/2006/CHN |
| *Norovirus* Hu/Jilin/48354/2006/CHN |
| *Norovirus* Hu/Jilin/48356/2006/CHN |
| *Norovirus* Hu/Jilin/48358/2006/CHN |
| *Norovirus* Hu/Jilin/49129/2006/CHN |
| *Norovirus* Hu/Jilin/49133/2006/CHN |
| *Norovirus* Hu/Jilin/49137/2006/CHN |
| *Norovirus* Hu/Jilin/49141/2006/CHN |
| *Norovirus* Hu/Jilin/50143/2006/CHN |
| *Norovirus* Hu/Jilin/50145/2006/CHN |
| *Norovirus* Hu/Jilin/50148/2006/CHN |
| *Norovirus* Hu/Jilin/50151/2006/CHN |
| *Norovirus* Hu/Jilin/50156/2006/CHN |
| *Norovirus* Hu/K13830/05/IND |
| Norwalk-like virus Hu/NLV/GI/488/US |
| Norwalk-like virus Hu/NLV/GI/560/US |
| Norwalk-like virus Hu/NLV/GI/579/US |
| Norwalk-like virus Hu/NLV/GI/611/US |
| Norwalk-like virus Hu/NLV/GI/615/US |
| Norwalk-like virus Hu/NLV/GI/629/US |
| Norwalk-like virus Hu/NLV/GI/653/US |
| Norwalk-like virus Hu/NLV/GI/661/US |
| Norwalk-like virus Hu/NLV/GI/665/US |
| Norwalk-like virus Hu/NLV/GI/684/US |
| Norwalk-like virus Hu/NLV/GI/736/US |
| Norwalk-like virus Hu/NLV/GI/772/US |
| Norwalk-like virus Hu/NLV/GII/506/US |
| Norwalk-like virus Hu/NLV/GII/514/US |
| Norwalk-like virus Hu/NLV/GII/535/US |
| Norwalk-like virus Hu/NLV/GII/542/US |
| Norwalk-like virus Hu/NLV/GII/549/US |
| Norwalk-like virus Hu/NLV/GII/562/US |
| Norwalk-like virus Hu/NLV/GII/564/US |
| Norwalk-like virus Hu/NLV/GII/565/US |
| Norwalk-like virus Hu/NLV/GII/567/US |
| Norwalk-like virus Hu/NLV/GII/577/US |
| Norwalk-like virus Hu/NLV/GII/580/US |
| Norwalk-like virus Hu/NLV/GII/586/US |
| Norwalk-like virus Hu/NLV/GII/596/US |
| Norwalk-like virus Hu/NLV/GII/604/US |
| Norwalk-like virus Hu/NLV/GII/607/US |
| Norwalk-like virus Hu/NLV/GII/634/US |
| Norwalk-like virus Hu/NLV/GII/642/US |
| Norwalk-like virus Hu/NLV/GII/643/US |
| Norwalk-like virus Hu/NLV/GII/649/US |
| Norwalk-like virus Hu/NLV/GII/654/US |
| Norwalk-like virus Hu/NLV/GII/663/US |
| Norwalk-like virus Hu/NLV/GII/668/US |
| Norwalk-like virus Hu/NLV/GII/677/US |
| Norwalk-like virus Hu/NLV/GII/682/US |
| Norwalk-like virus Hu/NLV/GII/683/US |
| Norwalk-like virus Hu/NLV/GII/691/US |
| Norwalk-like virus Hu/NLV/GII/692/US |
| Norwalk-like virus Hu/NLV/GII/707/US |
| Norwalk-like virus Hu/NLV/GII/708/US |
| Norwalk-like virus Hu/NLV/GII/710/US |
| Norwalk-like virus Hu/NLV/GII/712/US |
| Norwalk-like virus Hu/NLV/GII/715/US |
| Norwalk-like virus Hu/NLV/GII/723/US |
| Norwalk-like virus Hu/NLV/GII/733/US |
| Norwalk-like virus Hu/NLV/GII/734/US |
| Norwalk-like virus Hu/NLV/GII/737/US |
| Norwalk-like virus Hu/NLV/GII/740/US |
| Norwalk-like virus Hu/NLV/GII/741/US |
| Norwalk-like virus Hu/NLV/GII/759/US |
| Norwalk-like virus Hu/NLV/GII/762/US |
| Norwalk-like virus Hu/NLV/GIV/765/US |
| Norwalk-like virus Hu/NV/03012-2/GII/2003/JP |
| Norwalk-like virus Hu/NV/OC02065/2002/JP |
| Norwalk-like virus Hu/NV/OC02172-1/GII/2002/Japan |
| Norwalk-like virus Hu/NV/OC02172-2/GII/2002/Japan |
| Norwalk-like virus Hu/NV/OC02172-3/GII/2002/Japan |
| Norwalk-like virus Hu/NV/OC02172-4/GII/2002/Japan |
| Norwalk-like virus Hu/NV/OC02189/2002/Japan |
| Norwalk-like virus Hu/NV/OC02198-2/2002/JP |
| Norwalk-like virus Hu/NV/OC03006/2002/JP |
| Norwalk-like virus Hu/NV/OC03008/2003/JP |
| Norwalk-like virus Hu/NV/OC03009/GI/2003/JP |
| Norwalk-like virus Hu/NV/OC03009/GII/2003/JP |
| Norwalk-like virus Hu/NV/OC03011/2003/JP |
| Norwalk-like virus Hu/NV/OC03012-1/GII/2003/JP |
| Norwalk-like virus Hu/NV/OC03012-3/GII/2003/JP |
| Norwalk-like virus Hu/NV/OC03012/GI/2003/JP |
| Norwalk-like virus Hu/NV/OC03017/2003/JP |
| Norwalk-like virus Hu/NV/OC03020/2003/JP |
| Norwalk-like virus Hu/NV/OC03021-1/2003/JP |
| Norwalk-like virus Hu/NV/OC03021-2/2003/JP |
| Norwalk-like virus Hu/NV/OC03022-1/GI/2003/JP |

TABLE 1-continued

| *Norovirus* Strains | |
|---|---|
| *Norovirus* Hu/K4/JPN | Norwalk-like virus Hu/NV/OC03022-1/GII/2003/JP |
| *Norovirus* Hu/Kagoshima/6-04/2003/JP | Norwalk-like virus Hu/NV/OC03022-2/GI/2003/JP |
| *Norovirus* Hu/Kakunodate/1/2008/JP | Norwalk-like virus Hu/NV/OC03022-2/GII/2003/JP |
| *Norovirus* Hu/Karlsruhe10567/2002/DE | Norwalk-like virus Hu/NV/OC03024/2003/JP |
| *Norovirus* Hu/Karlsruhe2527/2004/DE | Norwalk-like virus Hu/NV/OC03026/GI/2003/JP |
| *Norovirus* Hu/Karlsruhe892/2002/DE | Norwalk-like virus Hu/NV/OC03026/GII/2003/JP |
| *Norovirus* Hu/Kawabe/1/05/JP | Norwalk-like virus Hu/NV/OC03027/2003/JP |
| *Norovirus* Hu/Kazuno/1/2007/JP | Norwalk-like virus Hu/NV/OC03028/2003/JP |
| *Norovirus* Hu/KL1009/1998/US | Norwalk-like virus Hu/NV/OC03034-1/GI/2003/JP |
| *Norovirus* Hu/KL1327/1999/US | Norwalk-like virus Hu/NV/OC03034-1/GII/2003/JP |
| *Norovirus* Hu/KL1353/1998/US | Norwalk-like virus Hu/NV/OC03034-2/GI/2003/JP |
| *Norovirus* Hu/KL1372/1999/US | Norwalk-like virus Hu/NV/OC03034-2/GII/2003/JP |
| *Norovirus* Hu/KL1404/1998/US | Norwalk-like virus Hu/NV/OC03034-3/GI/2003/JP |
| *Norovirus* Hu/KL1418/1998/US | Norwalk-like virus Hu/NV/OC03035/2003/JP |
| *Norovirus* Hu/KL1454/1999/US | Norwalk-like virus Hu/NV/OC03036/2003/JP |
| *Norovirus* Hu/KL1461/1998/US | Norwalk-like virus Hu/NV/OC03037/2003/JP |
| *Norovirus* Hu/KL1486/1998/US | Norwalk-like virus Hu/NV/OC03039-1/GII/2003/JP |
| *Norovirus* Hu/KL1494/1998/US | Norwalk-like virus Hu/NV/OC03039-2/GII/2003/JP |
| *Norovirus* Hu/KL1512/1998/US | Norwalk-like virus Hu/NV/OC03039/GI/2003/JP |
| *Norovirus* Hu/KL1522/1998/US | Norwalk-like virus Hu/NV/OC03040/2003/JP |
| *Norovirus* Hu/KL1553/1998/US | Norwalk-like virus Hu/NV/OC03042/2003/JP |
| *Norovirus* Hu/KL1574/1999/US | Norwalk-like virus Hu/NV/OC03047/GI/2003/JP |
| *Norovirus* Hu/KL1620/1998/US | Norwalk-like virus Hu/NV/OC03047/GII/2003/JP |
| *Norovirus* Hu/KL1682/1998/US | Norwalk-like virus Hu/NV/OC03048/2003/JP |
| *Norovirus* Hu/KL1733/1999/US | Norwalk-like virus Hu/NV/OC03050/2003/JP |
| *Norovirus* Hu/KL1798/1998/US | Norwalk-like virus Hu/NV/OC03053/2003/JP |
| *Norovirus* Hu/KL1823/1999/US | Norwalk-like virus Hu/NV/OC03054/2003/JP |
| *Norovirus* Hu/KL1852/1999/US | Norwalk-like virus Hu/NV/OC03055/2003/JP |
| *Norovirus* Hu/KL1872/1999/US | Norwalk-like virus NLV/Appalachicola |
| *Norovirus* Hu/KL1884/1999/US | Bay/318/1995/US |
| *Norovirus* Hu/KL1912/1999/US | Norwalk-like virus NLV/Baltimore/274/1993/US |
| *Norovirus* Hu/KL1943/1999/US | Norwalk-like virus NLV/Baltimore/277/1993/US |
| *Norovirus* Hu/KL1974/1999/US | Norwalk-like virus NLV/Brattleboro/321/1995/US |
| *Norovirus* Hu/KL2018/1999/US | Norwalk-like virus NLV/Burwash |
| *Norovirus* Hu/KL2022/1999/US | Landing/331/1995/US |
| *Norovirus* Hu/KL2030/1999/US | Norwalk-like virus NLV/Florida/269/1993/US |
| *Norovirus* Hu/KL2033/1999/US | Norwalk-like virus NLV/Fort |
| *Norovirus* Hu/KL2059/1999/US | Lauderdale/560/1998/US |
| *Norovirus* Hu/KL2089/1999/US | Norwalk-like virus NLV/Gwynedd/273/1994/US |
| *Norovirus* Hu/KL2092/1999/US | Norwalk-like virus NLV/Honolulu/219/1992/US |
| *Norovirus* Hu/KL2146/1999/US | Norwalk-like virus NLV/Honolulu/314/1994/US |
| *Norovirus* Hu/KL2162/1999/US | Norwalk-like virus NLV/Lionville/247/1993/US |
| *Norovirus* Hu/KL714/1999/US | Norwalk-like virus NLV/Little Rock/316/1994/US |
| *Norovirus* Hu/KL724/1998/US | Norwalk-like virus NLV/Miami |
| *Norovirus* Hu/KL755/1998/US | Beach/326/1995/US |
| *Norovirus* Hu/KL759/1997/US | Norwalk-like virus NLV/Miami/292/1994/US |
| *Norovirus* Hu/KL771/1998/US | Norwalk-like virus NLV/Miami/81/1986/US |
| *Norovirus* Hu/KL817/1998/US | Norwalk-like virus |
| *Norovirus* Hu/KL824/1998/US | NLV/Montgomery/312/1994/US |
| *Norovirus* Hu/KL828/1998/US | Norwalk-like virus NLV/New |
| *Norovirus* Hu/KL874/1999/US | Orleans/266/1993/US |
| *Norovirus* Hu/KL942/1998/US | Norwalk-like virus NLV/New |
| *Norovirus* Hu/Kolkata/L8775/2006/IND | Orleans/279/1994/US |
| *Norovirus* Hu/Kolkata/V1041 | Norwalk-like virus NLV/New |
| *Norovirus* Hu/Kolkata/V1370 | Orleans/306/1994/US |
| *Norovirus* Hu/Kolkata/V518 | Norwalk-like virus NLV/Port |
| *Norovirus* Hu/Komaki/1/2006/JP | Canaveral/301/1994/US |
| *Norovirus* Hu/Kuala | Norwalk-like virus NLV/Richmond/283/1994/US |
| Lumpur/NB2824/1998/MYS | Norwalk-like virus NLV/Saint Cloud/624/1998/US |
| *Norovirus* Hu/Kuala | Norwalk-like virus NLV/Towson/313/1994/US |
| Lumpur/NB2834/1998/MYS | Norwalk-like virus NLV/UK3-17/12700/1992/GB |
| *Norovirus* Hu/Kuala | Norwalk-like virus NLV/Westover/302/1994/US |
| Lumpur/NB2857/1998/MYS | Norwalk-like virus NLV/White River/290/1994/US |
| *Norovirus* Hu/Kuala | Norwalk-like virus Sw/NLV/VA34/1998/NL |
| Lumpur/NB2875/1998/MYS | Saratoga calicivirus 7 |
| *Norovirus* Hu/Kuala | Norwalk-like virus sp. |
| Lumpur/NB2895/1998/MYS | Norwalk-like virus |
| *Norovirus* Hu/Kuala | Small round structured virus |
| Lumpur/NB2922/1998/MYS | Human calicivirus SRSV-Ba/98/CH |
| *Norovirus* Hu/Kuala | Human calicivirus SRSV-Gst/98/CH |
| Lumpur/NB2969/1998/MYS | Human calicivirus SRSV/MI1/94/JP |
| *Norovirus* Hu/Kuala | Human calicivirus SRSV/SA1/89/JP |
| Lumpur/NB2978/1998/MYS | Human calicivirus SRSV/SA2/91/JP |
| *Norovirus* Hu/Kuala | Human calicivirus SRSV1-LaN/98/CH |
| Lumpur/NB4464/1999/MYS | Human calicivirus SRSV2-LaN/98/CH |
| *Norovirus* Hu/Kuala | unclassified *Norovirus* |
| Lumpur/NB4467/1999/MYS | Bovine enteric calicivirus |
| *Norovirus* Hu/Kuala | Human *norovirus* - Alphatron |

TABLE 1-continued

Norovirus Strains

Lumpur/NB4469/1999/MYS
Norovirus Hu/Kuala Lumpur/NB4492/1999/MYS
Norovirus Hu/Kuala Lumpur/NB4495/1999/MYS
Norovirus Hu/Kuala Lumpur/NB4529/1999/MYS
Norovirus Hu/Kuala Lumpur/NB4532/1999/MYS
Norovirus Hu/Kuala Lumpur/NB4540/1999/MYS
Norovirus Hu/Kuala Lumpur/NB4543/1999/MYS
Norovirus Hu/Kuala Lumpur/NB4550/1999/MYS
Norovirus Hu/Kuala Lumpur/NB4552/1999/MYS
Norovirus Hu/Kuala Lumpur/NB4577/1999/MYS
Norovirus Hu/Kuala Lumpur/NR26/1994/MYS
Norovirus Hu/Kuala Lumpur/NR94/1994/MYS
Norovirus Hu/Kuenzelsau16836/2001/DE
Norovirus Hu/Kunming/146/2004/China
Norovirus Hu/Kurume/951228/1995/JP/419
Norovirus Hu/L154/2000/France
Norovirus Hu/L1a/JPN
Norovirus Hu/L1b/JPN
Norovirus Hu/L2a/JPN
Norovirus Hu/L2b/JPN
Norovirus Hu/L2c/JPN
Norovirus Hu/L3/JPN
Norovirus Hu/L4/JPN
Norovirus Hu/Leipzig/CE1/2009/DEU
Norovirus Hu/Leipzig/CE2/2009/DEU
Norovirus Hu/Leipzig/P1-5/2009/DEU
Norovirus Hu/Lelystad_Hospital/16-01-2003/NL
Norovirus Hu/Lelystad_Nursing-home/21-07-2002/NL
Norovirus Hu/Lelystad_Nursing-home/22-07-2002/NL
Norovirus Hu/Leonberg1098/2003/DE
Norovirus Hu/Leonberg1661/2003/DE
Norovirus Hu/Loerrach11869/02/DE
Norovirus Hu/Loerrach5230/2001/DE
Norovirus Hu/Loerrach840/2002/DE
Norovirus Hu/Ludwigsburg0211/2002/DE
Norovirus Hu/Ludwigsburg13253/2002/DE
Norovirus Hu/Ludwigsburg1472/2004/DE
Norovirus Hu/Ludwigsburg7563/2002/DE
Norovirus Hu/Ludwigsburg781/2003/DE
Norovirus Hu/LuoCheng17/Sep2006/CHN
Norovirus Hu/Maastricht/03-01-2003/NL
Norovirus Hu/Maizuru/000324/2000/JP/2468
Norovirus Hu/Maizuru/000602/2000/JP/2840
Norovirus Hu/Maizuru/010426/2001/JP/3385
Norovirus Hu/Maizuru/010524/2001/JP/3229
Norovirus Hu/Maizuru/030512/2003/JP/4656
Norovirus Hu/Maizuru/5017/04/JP
Norovirus Hu/Maizuru/6448/2005/JP
Norovirus Hu/Maizuru/6449/2005/JP
Norovirus Hu/Maizuru/7179/2005/JP
Norovirus Hu/Maizuru/7297/2006/JP
Norovirus Hu/Manitoba/4205/2003/CAN
Norovirus Hu/Mannheim1265/2003/DE
Norovirus Hu/Mannheim131/2009/DE
Norovirus Hu/Mannheim1706/2003/DE
Norovirus Hu/Mannheim2491/2004/DE
Norovirus Hu/Mannheim51912/2002/DE
Norovirus Hu/Mannheim61209/2001/DE
Norovirus Hu/Mihama/1/2006/JP
Norovirus Hu/Minase/1/05/JP
Norovirus Hu/MK04/2004/JP
Norovirus Hu/Monastir 113/2003/TUN
Norovirus Hu/Monastir 127/2003/TUN
Norovirus Hu/Monastir 3968/2004/TUN
Norovirus Hu/Monastir 493/2003/TUN
Norovirus Hu/Monastir 529/2003/TUN
Human norovirus Saitama
Minireovirus
Murine norovirus
Murine norovirus 1
Murine norovirus 2
Murine norovirus 3
Murine norovirus 4
Murine norovirus 5
Murine norovirus 6
Murine norovirus 7
Norovirus Hu/Monastir/249/2003/TUN
Norovirus Hu/Monastir/273/2003/TUN
Norovirus Hu/Monastir/294/2003/TUN
Norovirus Hu/Monastir/310/2003/TUN
Norovirus Hu/Monastir/375/2003/TUN
Norovirus Hu/Monastir/389/2003/TUN
Norovirus Hu/Monastir/8655/2007/TUN
Norovirus Hu/Mougon692/2004/France
Norovirus Hu/Mum/M004/2006/India
Norovirus Hu/Mum/M633/2006/India
Norovirus Hu/Mum/M685/2006/India
Norovirus Hu/Mum/M689/2006/India
Norovirus Hu/Mum/M777/2006/India
Norovirus Hu/Mum/M780/2006/India
Norovirus Hu/Mum/M802/2006/India
Norovirus Hu/Mum/M844/2006/India
Norovirus Hu/Mum/M853/2006/India
Norovirus Hu/Mum/M860/2006/India
Norovirus Hu/mussels/Mo04-05/2004b/UK
Norovirus Hu/mussels/Mo04-07/2004/IE
Norovirus Hu/mussels/Mo04-08/2004/UK
Norovirus Hu/mussels/Mo04-10/2004b/UK
Norovirus Hu/mussels/Mo04-14/2004c/IE
Norovirus Hu/mussels/Mo04-15/2004/IE
Norovirus Hu/mussels/Mo04-21/2004b/UK
Norovirus Hu/mussels/Mo04-21/2004c/UK
Norovirus Hu/mussels/Mo04-22/2004/IE
Norovirus Hu/mussels/Mo04-22/2004b/IE
Norovirus Hu/mussels/Mo04-23/2004/UK
Norovirus Hu/mussels/Mo04-25/2004c/IE
Norovirus Hu/mussels/Mo04-32/2004b/IE
Norovirus Hu/mussels/Mo19NL2000a/Netherlands
Norovirus Hu/mussels/Mos11GB2003/United Kingdom
Norovirus Hu/mussels/Mos18I2004b/UK
Norovirus Hu/mussels/Mos2GB2003/United Kingdom
Norovirus Hu/mussels/Mos9I2003a/Ireland
Norovirus Hu/mussels/Mos9I2003b/Ireland
Norovirus Hu/mussels/Mos9I2003c/Ireland
Norovirus Hu/N1/JPN
Norovirus Hu/N2/JPN
Norovirus Hu/N3/JPN
Norovirus Hu/Nag/N230/2006/India
Norovirus Hu/Nag/N248/2006/India
Norovirus Hu/Nag/N259/2006/India
Norovirus Hu/Nag/N273/2007/India
Norovirus Hu/Nag/N363/2007/India
Norovirus Hu/Nag/N381/2007/India
Norovirus Hu/Nag/N387/2007/India
Norovirus Hu/Nag/N410/2007/India
Norovirus Hu/Nag/N416/2007/India
Norovirus Hu/Nag/N457/2007/India
Norovirus Hu/Nagano/1-01/2002/JP
Norovirus Hu/Nagano/2-01/2002/JP
Norovirus Hu/Nagano/3-01/2002/JP
Norovirus Hu/Nagano/37-3/Feb2008/JPN
Norovirus Hu/Nagano/4-04/2003/JP
Norovirus Hu/Nagano/7-19/Apr2008/JPN TABLE 1-continued

| *Norovirus* Strains | |
|---|---|
| *Norovirus* Hu/Monastir 715/2003/TUN | |
| *Norovirus* Hu/Monastir 8655/2007/TUN | |
| *Norovirus* Hu/Monastir/03/2003/TUN | |
| *Norovirus* Hu/Monastir/127/2003/TUN | |
| *Norovirus* Hu/Monastir/13562/2004/TUN | |
| *Norovirus* Hu/Monastir/17285/2004/TUN | |
| *Norovirus* Hu/Monastir/17291/2006/TUN | |
| *Norovirus* Hu/Monastir/17736/2005/TUN | |
| *Norovirus* Hu/Monastir/1795/2004/TUN | |
| *Norovirus* Hu/Monastir/18/2003/TUN | |
| *Norovirus* Hu/Monastir/39/2004/TUN | |
| *Norovirus* Hu/Monastir/430/2003/TUN | |
| *Norovirus* Hu/Monastir/4456/2005/TUN | |
| *Norovirus* Hu/Monastir/474/2003/TUN | |
| *Norovirus* Hu/Monastir/519/2003/TUN | |
| *Norovirus* Hu/Monastir/578/2003/TUN | |
| *Norovirus* Hu/Monastir/862/2003/TUN | |
| Murine *norovirus* GV | |
| Oyster *norovirus* | Oyster *norovirus* HK-W498-02 |
| Oyster *norovirus* HK-W423-02 | Oyster *norovirus* HK-W507-02 |
| Oyster *norovirus* HK-W426-02 | Oyster *norovirus* HK-W539-02 |
| Oyster *norovirus* HK-W464-02 | Swine *norovirus* |
| Oyster *norovirus* HK-W469-02 | |

What is claimed is:

1. A method of producing a chimeric norovirus VP1 protein or norovirus virus like particles (VLPs) comprising the chimeric norovirus VP1 protein, the method comprising culturing a recombinant host cell comprising a recombinant nucleic acid encoding a chimeric norovirus viral protein 1 (VP1) comprising an S-domain of the VP1 from a first norovirus strain and a P-domain of the VP1, wherein all or a portion of the P-domain is from a second norovirus strain, under conditions suitable for the expression of the recombinant nucleic acid and obtaining the chimeric VP1 protein or the VLPs from the culture, wherein the VP1 protein has the formula:

A-S-L-P-B wherein

A and B are independently absent or comprise any desired amino acid sequence;

S is the S-domain of VP1 from a first norovirus strain;

P is a norovirus VP1 P-domain; wherein at least a portion of the P-domain is from a second norovirus strain;

L is absent or a linker peptide selected from the group consisting of a linker peptide of the VP1 from the first norovirus strain, from the second norovirus strain, or from a third norovirus strain;

a polyglycine linker of formula (Gly)n wherein n=2, 3, 4, 5, 6, 7, 8, 9, 10 or more (SEQ ID NO:5);

a linker of formula (GGGS)n wherein n=1, 2, 3 or 4 (SEQ ID NO:6); and a charged linker of formula (SRSK)n wherein n=1, 2, 3 or 4 (SEQ ID NO:7).

2. The method of claim 1, wherein the culturing comprises maintaining the recombinant host cell under conditions suitable for formation of VLPs.

3. The method of claim 1, further comprising isolating the chimeric norovirus VP1 protein or VLPs from the culture media or the recombinant host cells or from both the culture media and the recombinant host cells.

4. The method of claim 3, wherein VLPs are isolated.

5. The method of claim 4, wherein the VLPs are isolated using a sucrose cushion or sucrose gradient.

6. The method of claim 1, wherein the chimeric norovirus VP1 self-assembles into virus like particles (VLPs).

7. The method of claim 1, wherein the host cell is selected from the group consisting of insect cells, mammalian cells, avian cells, bacteria, yeast cells, *Tetrahymena* cells and combinations thereof.

8. The method of claim 1, wherein the chimeric norovirus VP1 is in the form of at least 50% purified VLPs.

* * * * *